(12) United States Patent
Bouillon et al.

(10) Patent No.: US 6,548,715 B1
(45) Date of Patent: Apr. 15, 2003

(54) STRUCTURAL ANALOGUES OF VITAMIN D

(75) Inventors: Roger Bouillon, Herent; Maurits Vandewalle; Pierre Jean De Clercq, both of Ghent, all of (BE)

(73) Assignee: Laboratoire Theramex S.A. (MC)

( * ) Notice: Subject to any disclaimer, the term of this patent is extended or adjusted under 35 U.S.C. 154(b) by 0 days.

(21) Appl. No.: 09/428,927

(22) Filed: Oct. 28, 1999

Related U.S. Application Data

(63) Continuation of application No. 08/571,887, filed as application No. PCT/EP94/02294 on Jul. 7, 1994, now Pat. No. 6,017,907.

(30) Foreign Application Priority Data

Jul. 9, 1993 (EP) .............................................. 93202037

(51) Int. Cl.[7] .............................................. A61K 31/075
(52) U.S. Cl. ........................ 568/817; 568/816; 568/819; 568/664; 568/665; 514/715; 514/729; 514/738; 514/739
(58) Field of Search .......................... 552/653; 568/817, 568/816, 819, 664, 665; 514/715, 729, 738, 739

(56) References Cited

U.S. PATENT DOCUMENTS 6,017,907 A * 1/2000 Bouillon et al.

* cited by examiner

*Primary Examiner*—Samuel Barts
(74) *Attorney, Agent, or Firm*—Dennison, Schultz & Dougherty

(57) ABSTRACT

A compound of the formula I:

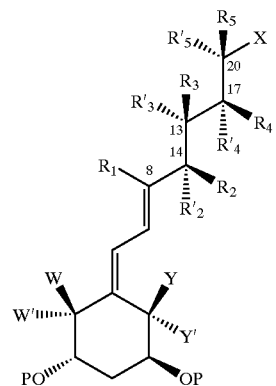

in which
P is hydrogen or alkyl;
Y and Y' are each hydrogen or, when taken together, represent a group $=CH_2$;
W and W' are each hydrogen;
X is selected from the group consisting of a hydroxyalkyl, a hydroxyalkoxy, an alkoxy optionally comprising an epoxide function, a hydroxyalkene, a hydroxyalkadiene, a hydroxyalkyne and isomeric forms thereof; and
a) either $R_1$ and $R_3$ or $R'_3$ form a saturated 5- or 6-membered carbocyclic ring and $R_2$, $R'_2$, $R_3$ or $R'_3$, $R_4$, $R'_4$, $R_5$ and $R'_5$ are each independently hydrogen or alkyl; or
b) $R_2$ or $R'_2$ and $R_4$ or $R'_4$ form a saturated 5- or 6-membered carbocyclic ring, and $R_1$, $R_2$ or $R'_2$, $R_3$, $R'_3$, $R_4$ or $R'_4$, $R_5$ and $R'_5$ are each independently hydrogen or alkyl; or
c) $R_3$ or $R'_3$ and $R_5$ or $R'_5$ form a saturated or unsaturated 5- or 6-membered carbocyclic ring, and $R_1$, $R_2$, $R'_2$, $R_3$ or $R'_3$, $R_4$, $R'_4$, and $R_5$ or $R'_5$ are each independently hydrogen or alkyl; or
d) $R_3$ or $R'_3$ taken at the same time with $R_1$ and $R_5$ or $R'_5$ form a saturated 8- or 12-membered carbobicyclic ring, and $R_2$, $R'_2$, $R_3$ or $R'_3$, $R_4$, $R'_4$, and $R_5$ or $R'_5$ are each independently hydrogen or alkyl.

15 Claims, 10 Drawing Sheets

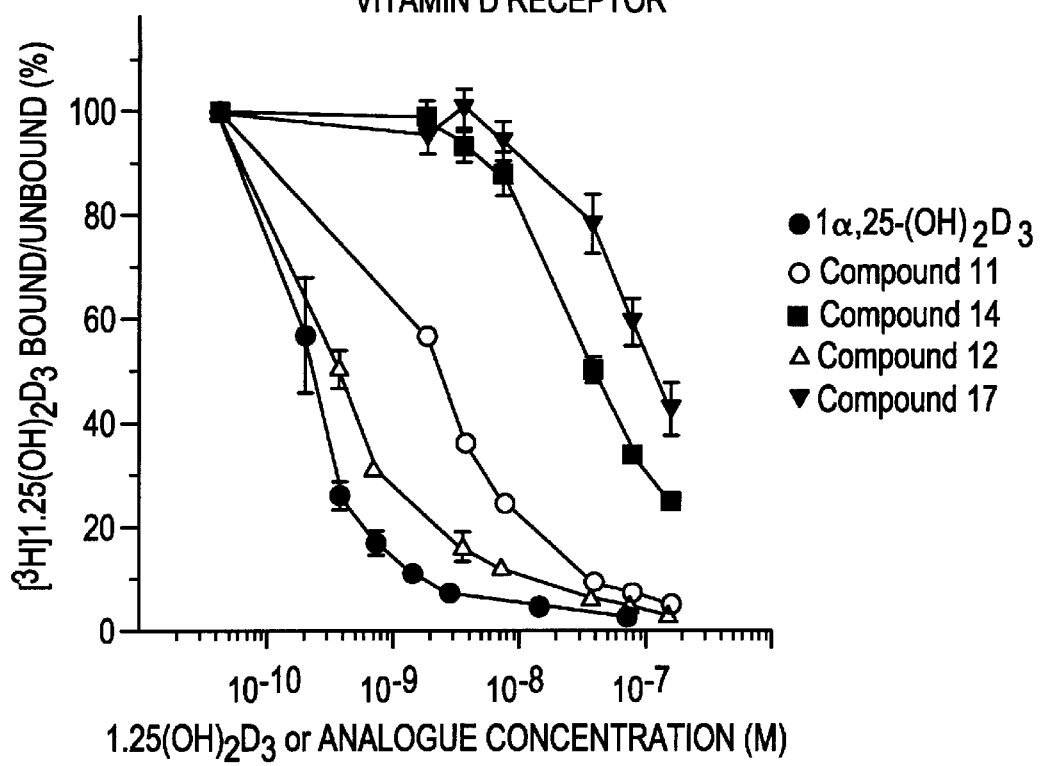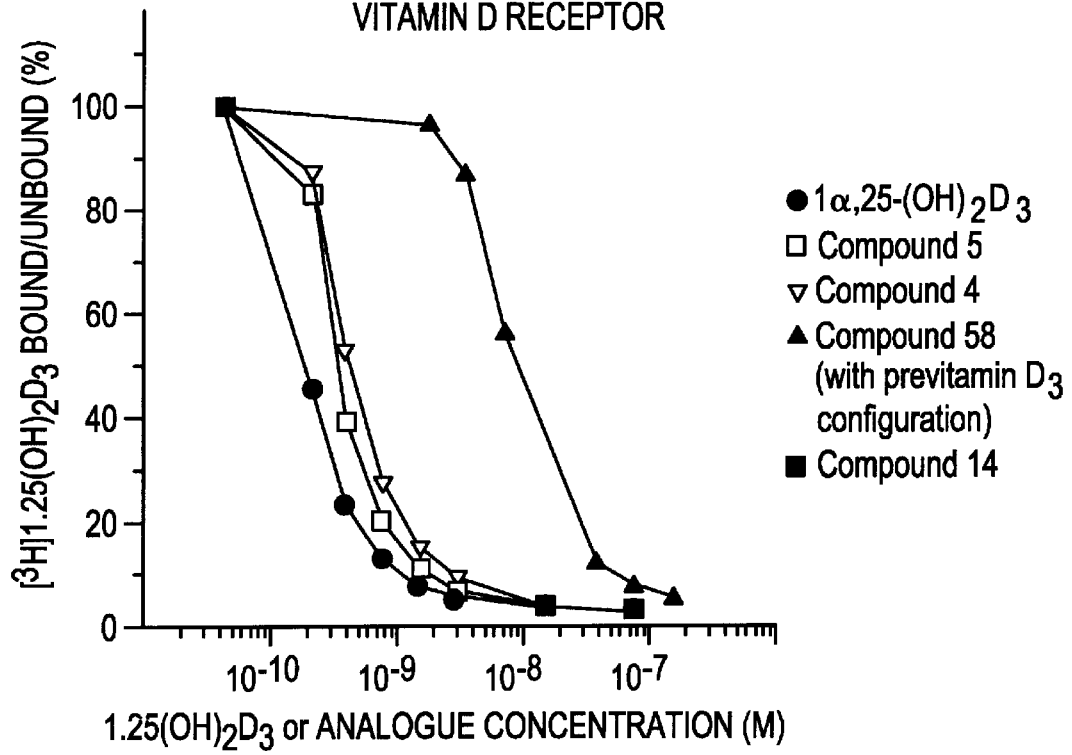

HUMAN DBP

HUMAN DBP

DIFFERENTIATING EFFECT OF ANALOGUES ON HL-60 CELLS

DIFFERENTIATING EFFECT OF ANALOGUES ON HL-60 CELLS

PRODUCTION OF OSTEOCALCIN

PRODUCTION OF OSTEOCALCIN

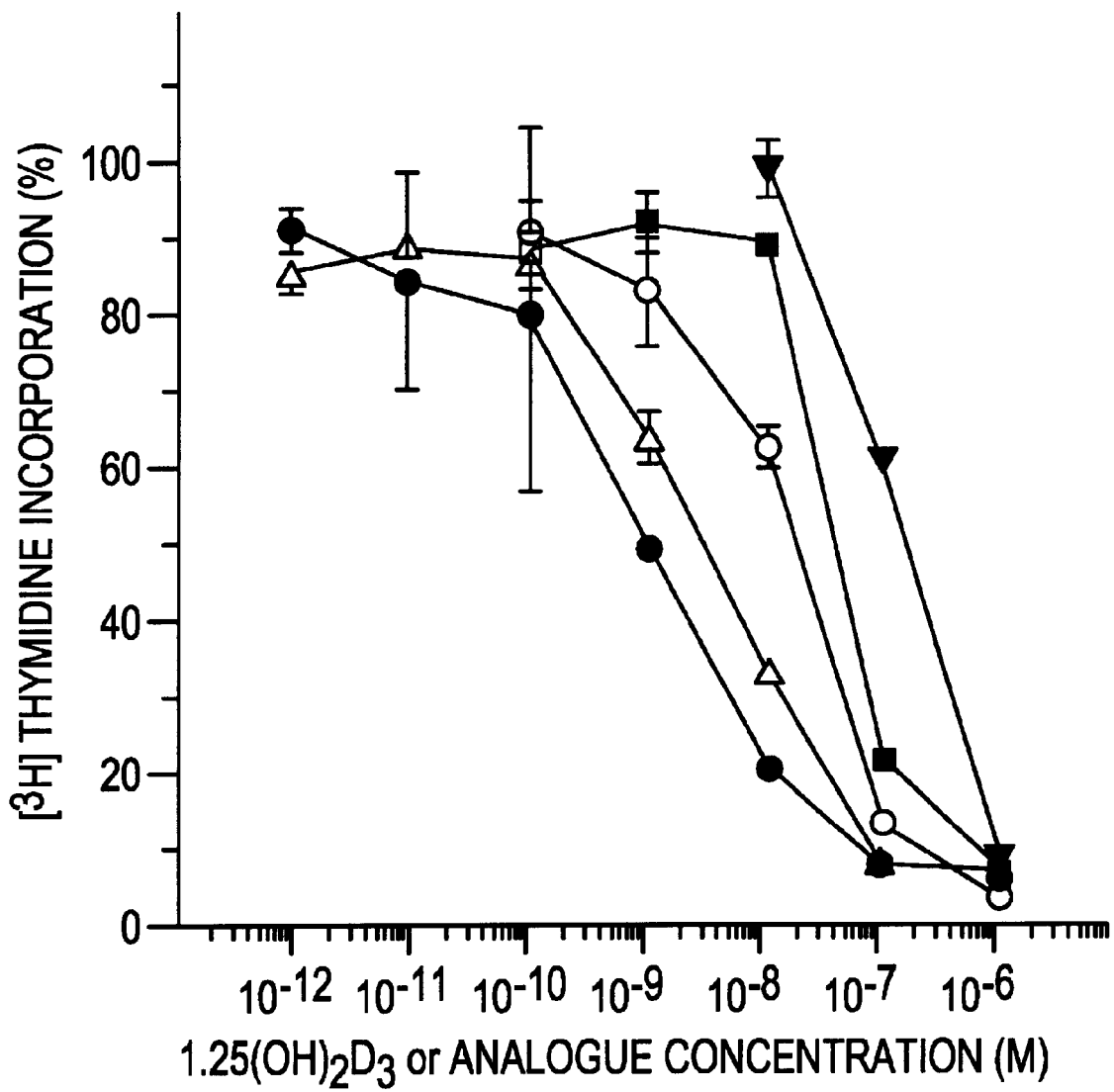

MCF-7

MCF-7

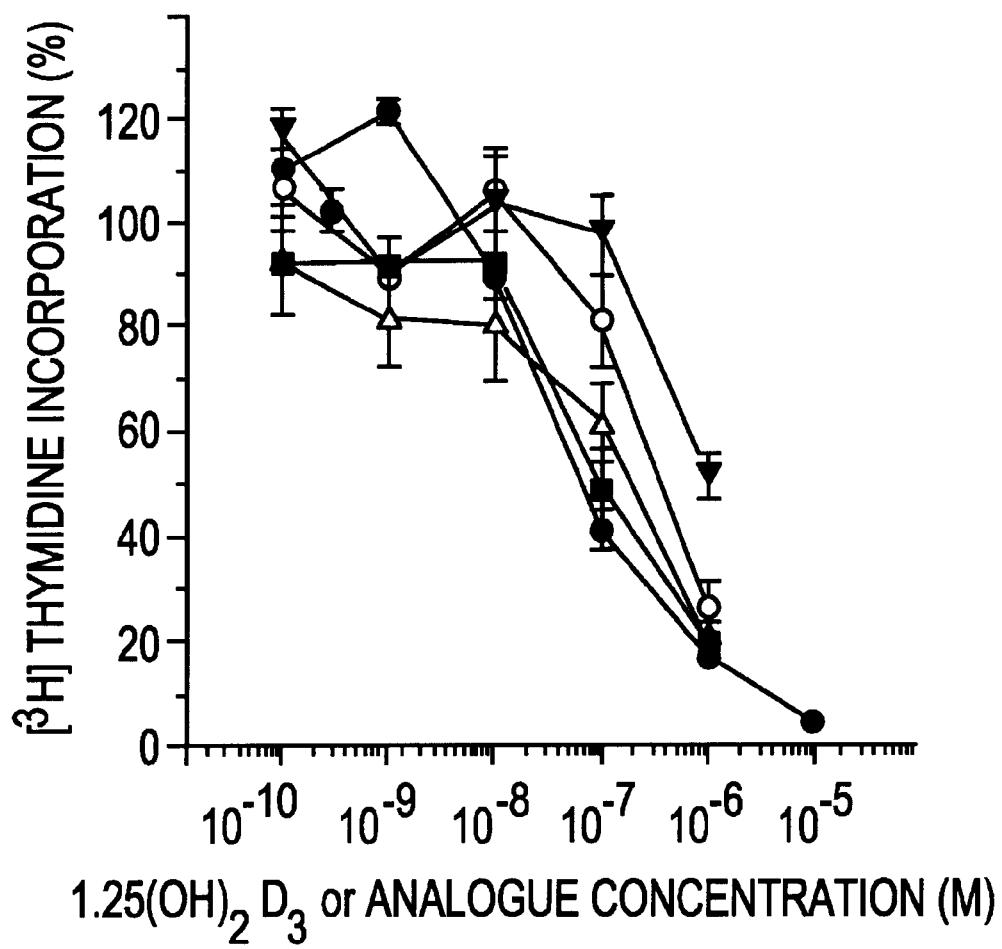

EFFECTS OF VITAMIN D ANALOGUES ON KERATINOCYTES CULTURES

EFFECTS OF VITAMIN D ANALOGUES ON KERATINOCYTES CULTURES

STRUCTURAL ANALOGUES OF VITAMIN D

The present application is a continuation of U.S. application Ser. No. 08/571,887, filed Jun. 28, 1996, now U.S. Pat. No. 6,017,907 which is a 371 of PCT/EP94/02294 filed Jul. 7, 1994.

BACKGROUND OF THE INVENTION

1. Field of the Invention

This invention describes a hitherto unknown and therefore new class of compounds which are analogues of $1\alpha,25\text{-}(OH)_2 D_3$ and show selective activity on cell functions.

2. Description of Related Art

General Introduction

Vitamin D of either nutritional (vitamin $D_2$ or $D_3$) origin or produced in the skin under the influence of ultraviolet light is metabolized in several tissues to produce firstly 25-hydroxyvitamin $D_3$ [25-$OHD_3$] and later $1\alpha,25$-dihydroxyvitamin $D_3$ [$1\alpha,25\text{-}(OH)_2 D_3$] and numerous other vitamin D metabolites (1–6). Several hydroxylases present in different tissues (e.g. liver, kidney, placenta, keratinocytes, fibroblasts, monocytes, lymphocytes, bone cells . . . ) are responsible for both the activating and inactivating pathways of the parent vitamin D molecules. $1\alpha,25\text{-}(OH)_2 D_3$ behaves as a classical steroid hormone as its synthesis is feedback controlled by several hormones, ions and humoral factors to maintain a normal body homeostasis of plasma and bone minerals. Moreover the vitamin D hormone(s) act via binding and activation of specific vitamin D receptors, present in most tissues and cells. The steroid-receptor complex then functions as a transactivating factor by binding to specific DNA sequences known as vitamin D responsive elements so that transcription of numerous genes is either activated or inactivated (7,8). This gene (in) activation occurs in collaboration with other nuclear accessory factor(s) of which the vitamin A receptor (RXR) is part of (9,10). Moreover there is some evidence for the activity of vitamin D, its metabolites and analogues to act via nongenomic mechanisms, either by activating calcium channels or other membrane or second messenger signals (11–13). Vitamin D, its metabolites and analogues have potent effects on calcium and phosphate metabolism, and therefore they can be used for prevention and therapy of vitamin D deficiency and other disorders of plasma and bone mineral homeostasis (e.g. osteomalacia, osteoporosis, renal osteodystrophy, disorders of the parathyroid function). Moreover vitamin D receptors are found in numerous tissues and cells that do not belong to the target tissues responsible for the just mentioned calcium homeostasis. Such cells include most cells belonging to the endocrine system and vitamin D, its metabolites and analogues are capable of influencing the hormonal secretion of these glands or tissues (e.g. insulin, parathyroid, calcitonin, pituitary hormones). Vitamin D receptors and vitamin D activity have also been documented in calcium transporting tissues other than the intestine and bone (e.g. placenta and mammary glands). In addition vitamin D receptors and vitamin D action have been observed in most other cells (e.g. cells belonging to the immune system, skin cells). These cells or tissues can be of a benign, adenomatous or of a malignant type. These so-called noncalcemic effects of vitamin D, its metabolites and analogues create the possibility to use such compounds for various therapeutic applications such as modification of the immune system, modification of hormone secretion, altering calcium transport in several tissues, modification of intracellular calcium concentration, induction of cell differentiation or inhibition of cell proliferation (14,15). In particular such compounds may be useful in the therapy of disorders characterized by increased cell proliferation (e.g. psoriasis, cancer) (16–18).

To increase the therapeutic potential of the natural vitamin D hormone(s), analogues can be synthesized with increased potency for a specific action and reduction of another type of action. For example to obtain an anti-psoriasis drug analogues can be synthesized with an increased activity on keratinocytes and lymphocytes present in the affected skin areas but with decreased effects on serum, urinary or bone calcium (19–23). Similarly analogues can have an increased potency to inhibit proliferation of cancer cells (e.g. leukemia or breast cancer cells) and/or increase the differentiation of such cells, either alone by their intrinsic potency or enhance such effects in combination with other drugs (e.g. growth factors or cytokines, other steroid or antisteroid hormones or retinoic acids or related compounds) and at the same time have a reduced potency to influence serum, urinary or bone calcium or phosphate homeostasis. Another such example would be analogues with increased activity on specific hormone secretion (e.g. parathyroid hormone, insulin) without the same relative potency for the other activities of the natural vitamin D hormone(s). Analogues with increased activity on non-malignant cells belonging to the immune system could be used for the treatment of immune disorders (e.g. autoimmnune disorders, AIDS, prevention of graft rejection or graft versus host reaction) especially if their effect on other systems (e.g. calcium and phosphate metabolism) would be relatively weakened. Moreover analogues can be developed with increased activity on bone forming cells without a simultaneous potency on bone resorbing cells or vice versa and such analogues could be useful in the treatment of bone disorders.

A number of vitamin D analogues with modifications in the specific action in different tissues (especially the potency ratio on cell differentiation and calcemic effects) have been described previously with variable success in such differentiation. Especially oxa analogues in the side chain (patent WO 90/09992; EP 0385 446A 2), modifications or homologation of the side chain (WO 87/00834, international patent classification C07C 172/00), changes in the stereochemistry at carbon 20 (WO 90/09991, international patent classification C07C 401/00, A61K 31/59), modifications on C11 of the C ring (EP 89/401,262–4) and epoxy analogues (PCT/EP 92/0126) of the side chain displayed interesting characteristics.

SUMMARY OF THE INVENTION

Present Invention

The present invention relates to the synthesis and biological evaluation of original compounds which still maintain some of the essential characteristics of vitamin D action but with a more selective pattern, (i.e. not all the actions of the physiological vitamin D hormone are maintained with the same relative potency) and with a structure that can be thoroughly modified in the central part. Indeed within the structure of vitamin D one may distinguish three different parts : (i) a central part consisting of the bicyclic CD-ring system; (ii) an upper part, consisting of the side-chain which is connected to position 17 of the D-ring; (iii) a lower part, consisting of the A-ring and the $\Delta(5,7)$-diene (the so-called seco B-ring), which is connected to position 8 of the C-ring. One aim of the present invention is to bring about substantial structural modifications in the central part of vitamin D.

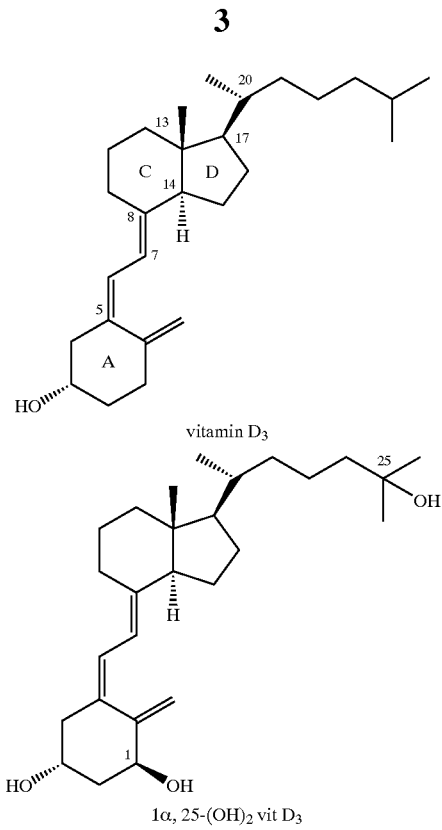

vitamin D₃

1α, 25-(OH)₂ vit D₃

In particular the present invention relates to analogues of vitamin D, which lack the combined presence of the trans-fused six-membered C-ring and of five-membered D-ring, but still possess a central part consisting of a substituted chain of five atoms, atoms which correspond to positions 8, 14, 13, 17 and 20 of vitamin D, and at the ends of which are connected, at position 20 a structural moiety representing part of the side-chain of vitamin D or of an analogue of vitamin D, and at position 8 the Δ(5,7)-diene moiety connected to the A-ring of the active 1-alpha-hydroxy metabolite or of an established vitamin D analogue.

BRIEF DESCRIPTION OF THE DRAWINGS

In the accompanying drawings, the legends correspond to those which are shown in FIGS. 1A and 1B.

FIGS. 1A and 1B are graphs of affinity for the vitamin D receptor for pig intestinal mucosa for selected vitamin D analogues;

FIG 3C is a graph of induction of cell differentiation in human osteosarcoma cells (MG-63) by selected vitamin D analogues as evaluated by potency to inhibit cell proliferation in such cells as measured by [³H]thymidine incorporation;

FIGS. 4A–4C are graphs of inhibition of cell proliferation by nonsteroidal vitamin D analogues in human breast cancer cells (MFM-223 and MCF-7) by selected vitamin D analogues as evaluated by [³H]thymidine incorporation;

DETAILED DESCRIPTION OF THE INVENTION

Figure 1C:
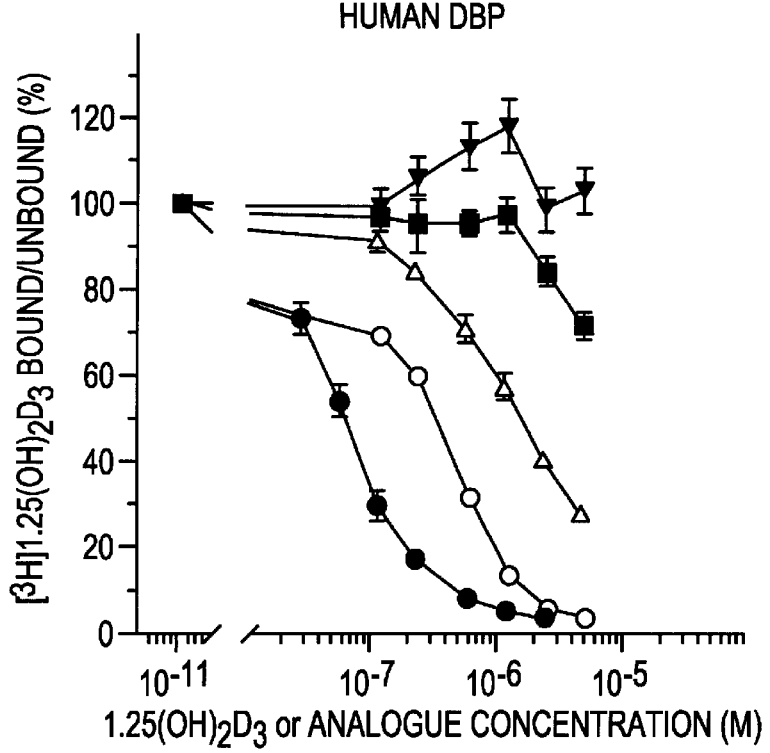
FIGS. 1C and 1D are graphs of affinity for the vitamin D receptor for human vitamin D binding protein for selected vitamin D analogues.

The compounds of the invention are represented by the general formula I, in which formula:

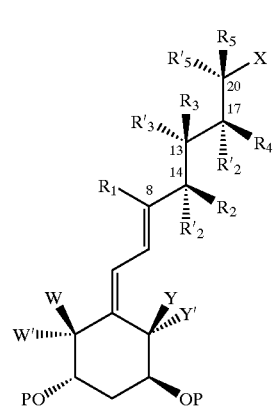

I

P stands for hydrogen, alkyl or acyl;

X represents part of the side-chain of vitamin D or of one of its established analogues;

Y and Y', which may be the same or different, stand for hydrogen or alkyl or, when taken together, represent an alkylidene group, or form a carbocyclic ring;

W and W', which may be the same or different, stand for hydrogen or alkyl or, when taken together, represent an alkylidene group, or form a carbocyclic ring;

one of the carbon atoms of the central part corresponding to positions 14, 13, 17 or 20, together with the R and R' substituents connected to it, may be replaced by an oxygen (O), a sulfur (S) or a nitrogen bearing an R substituent (NR).

R and R' (i.e., R, R₁, R₂, R'₂, R₃, R'₃, R₄, R'₄, R₅, R'₅):
when located in a relative 1,3-position along the central chain, such as R₁ and R₃ or R'₃, R₂ or R'₂ and R₄ or R'₄, R₃ or R'₃ and R₅ or R'₅, taken together with three adjacent atoms of the central chain, which correspond to positions 8, 14, 13 or 14, 13, 17 or 13, 17, 20, respectively, can form a saturated or unsaturated carbocyclic or heterocyclic 3-, 4-, 5-, 6- or 7-membered ring also including cases whereby geminal substituted R and R' taken together form a cyclic unsaturated bond, under the proviso that when R₁ and R'₃ form a 6-membered carbocyclic ring of the following nature (1) unsubstituted and saturated (2) monosubstituted at C-11 or (3) having a double bond between C-9 and C-11, R₂ and R₄ do not form a five-membered carbocyclic ring when R₃ is methyl, etnyl or ethenyl.

when located in a relative 1,2-position (i.e., vicinal) along the central chain, such as $R_1$ and $R_2$ or $R'_2$, $R_2$ or $R'_2$ and $R_3$ or $R'_3$, $R_3$ or $R'_3$ and and $R_4$ or $R'_4$, $R_4$ or $R'_4$ and $R_5$ or $R'_5$, and when not being part of a ring as described above, taken together with two adjacent atoms of the central chain, which correspond to positions 8,14 or 14,13 or 13,17 or 17,20, respectively, can form a saturated or unsaturated carbocyclic or heterocyclic 3-, 4-, 5-, 6- or 7-membered ring, also including cases whereby geminal substituted R and R' taken together form a cyclic unsaturated bond.

when located in a relative 1,1-position (i.e., geminal) along the central chain, such as $R_2$ and $R'_2$, or $R_3$ and $R'_3$, or $R_4$ and $R'_4$ or $R_5$ and $R'_5$, and when not being part of a ring as described above, taken together with the carbon bearing the R and R' substituents can form either a saturated or unsaturated carbocyclic or heterocyclic 3-, 4-, 5-, or 6-membered ring.

which may be the same or different, and when they are not forming a ring or a bond as described above, stand for hydrogen or a lower alkyl group, or when taken together in the case of geminal substitution represent a lower alkylidene group.

In the context of the invention the expression "lower alkyl group" indicates a straight or branched saturated or unsaturated carbon chain containing from 1 to 7 carbon atoms, and "lower alkylidene group" indicates a straight or branched saturated or unsaturated carbon chain containing from 1 to 7 carbon atoms, which is connected to one of the main chain atoms 14, 13, 17 and/or 20 through a double bond.

In the context of the invention part of the side-chain of vitamin D or of one of its established analogues stands for a 2 to 15 carbon atom substituted alkyl chain especially as present in vitamin $D_2$ (C-22 to C-28) or D3 (C-22 to C-27) or partially modified as shown below with the vitamin D numbering, especially:

hydroxyl substituent at one or more positions, for instance 24, 25 and/or 26 and/or methyl or ethyl substituent in one or more positions, for instance 24, 26 and/or 27 and/or halogen substituent(s) at one or more positions for instance perfluorated at positions 26 and/or 27 or difluorated at position 24 and/or additional carbon atom(s) especially $C_{24}$ between the positions 24 and 25, with the same substitution pattern mentioned above and/or esters derivatives of one or more hydroxyl substituents mentioned above and/or changing one or more carbon atoms for an oxygen, nitrogen or sulfur atom for instance at the positions 22, 23 or 24 and/or cyclized between the carbon atoms 26 and 27 by one bond (cyclopropane) or by the intermediacy of 1 to 4 carbon atoms, the ring can be saturated, unsaturated or aromatic and may optionally be substituted at any possible position(s) with the substituent mentioned above and/or cyclized between the carbon atoms 26 and 27 by 1 to 4 atoms to form a heterocyclic ring, including aromatic, which may optionally be substituted at any possible position with the substituent mentioned above and/or unsaturated with one or more double or triple C—C bond(s), these unsaturated chains may be substituted at any possible position by the substituents mentioned above and/or epoxide function can be present between carbon atoms 22,23 or 23,24 or 24,25 or 25,26; these epoxidized chains can be saturated or unsaturated and may be substituted at any possible positions with the substituents mentioned above and/or two or more of the carbon atoms of the side chain can be linked by a single bond or by the intermediacy of a one to five carbon or oxygen, nitrogen or sulfur atoms to form a 3–7 membered saturated or unsaturated carbocyclic or heterocyclic including aromatic ring which may optimally be substiuted at any possible position by substituents mentioned above and/or substituted at one or more positions by saturated, unsaturated carbocyclic, heterocyclic or aromatic ring which can be substituted at any possible position(s) with the substituents mentioned above isomeric forms of the substituted chain.

Hence the invention relates to a series of analogues with widely varying structures as exemplified in Table 1 where some specific examples of compounds with formula I are shown and which are referred to by number in the preparations and examples.

Most often the compounds of the invention are represented by one of the formulas IIa (type C), IIb (type D), IIc (type E), IId (type CD), IIe (type CE), IIf (type DE), and IIg (acyclic type):

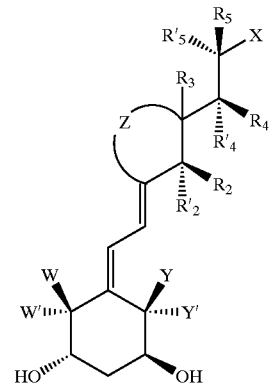

IIa

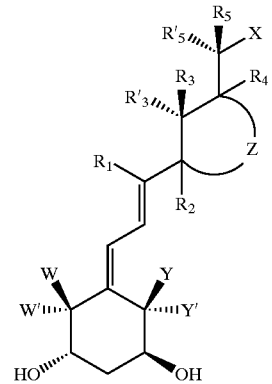

IIb

-continued

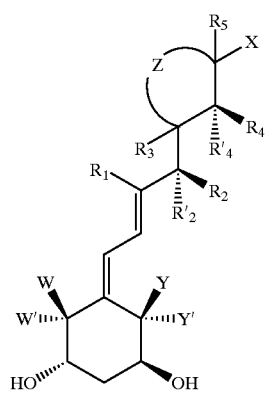
IIc

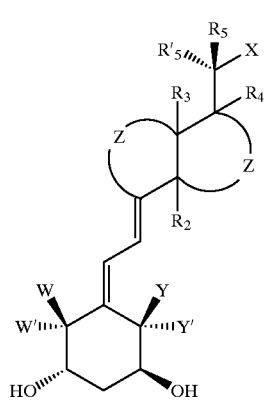
IId

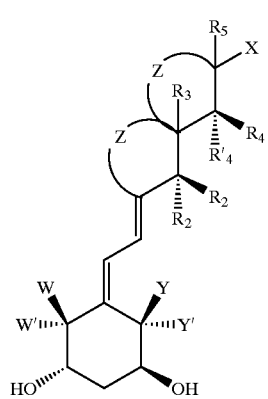
IIe

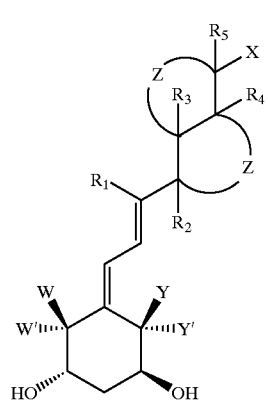
IIf

-continued

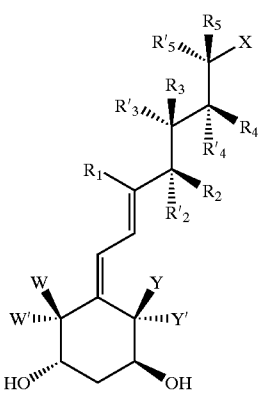
IIg where:
X, Y, Y', W and W' have the same meaning as above;
Z represents a saturated or unsaturated hydrocarbon chain consisting of zero (hence Z represents a bond between two 1,3-related carbon atoms of the central chain), one, two, three or four atoms, which may all be substituted and/or replaced by a heteroatom such as oxygen, sulfur and nitrogen.
$R_1$, $R_2$, $R'_2$, $R_3$, $R'_3$, $R_4$, $R'_4$, $R_5$, $R'_5$ which may be the same or different, stand for hydrogen or lower alkyl, such as methyl, ethyl or n-propyl.

Among those are preferred the cyclic derivatives of type C, D, E, CD, CE and DE that correspond to structures IIIa, IIIb, IIIc, IIId, IIIe, and IIIf, respectively,

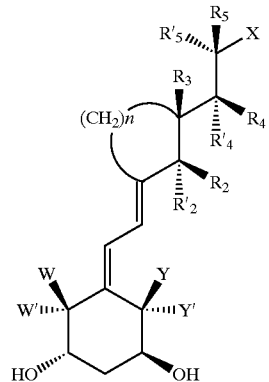
IIIa

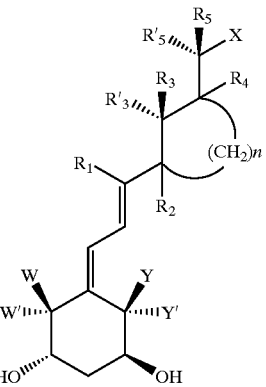
IIIb

IIIc

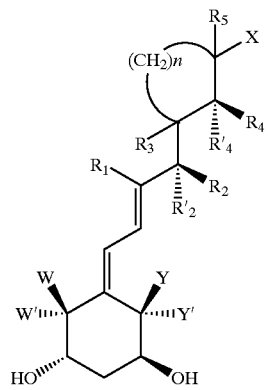

IIId

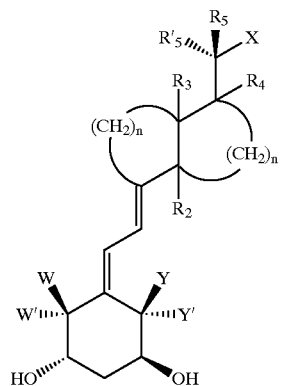

IIIe

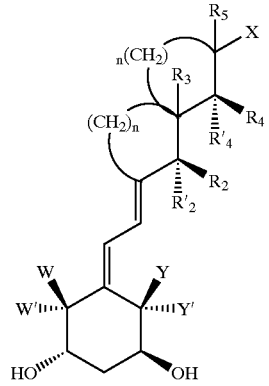

IIIf

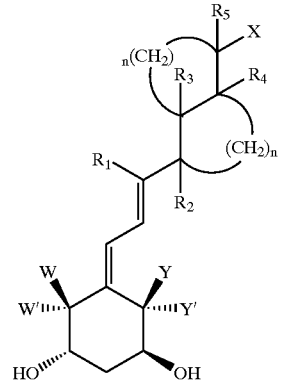

wherein n is an integer equal to 2 or 3

X represents one of the following vitamin D side-chain parts (4-hydroxy-4-methyl)pentyl, (R)- or (S)-(3-hydroxy-4-methyl)pentyl, (3'-hydroxy-3'-methyl)butyloxy, (4-hydroxy-4-ethyl)hexyl, (4-hydroxy-4-methyl)-2-pentynyl, (4'-hydroxy-4'-ethyl)hexyloxy; 4,5-epoxy, 4-methyl-2-pentynyl; 4-hydroxy-4-ethyl-2-hexynyl; (3-methyl-2,3-epoxy)-butyloxy; (3-hydroxy-3-ethyl)-pentyloxy; (4-hydroxy-4-ethyl)-hexyloxy Y, Y', W and W' are the same and represent hydrogen, or taken together represent a methylene group $=CH_2$;

$R_1$, $R_2$, $R'_2$, $R_3$, $R'_3$, $R_4$, $R'_4$, $R_5$ and $R'_5$, which may be the same or different, stand for hydrogen or methyl.

All compounds of the invention can be prepared using reactions that are well-known in the art of synthetic organic chemistry. In particular, in all cases, the lower part of the structure can be introduced following the method of Lythgoe (24) whereby the anion of a protected phosphine oxide IV is reacted with the appropriate carbonyl derivative VII, in which the various reactive functional groups are preferentially protected and in which the groups X, Y, Y', W, W', Z, P, $R_1$, $R_2$, ... $R'_5$ have the same meaning as previously, whereafter the reactive functional groups are deprotected. Also, the synthesis of derivatives as IV has been reported in the literature (25).

IV

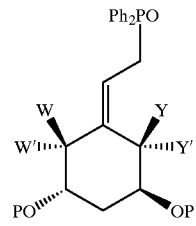

V

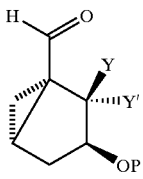

VI

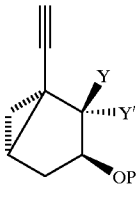

VII

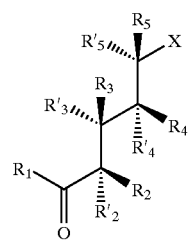

-continued

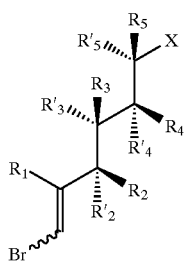

VIII

Alternative constructions involve (a) coupling of an appropriate vinylic carbanion (from VIII) with V followed by acid catalyzed solvolysis and (b) reaction of the alkynyl anion of VI with an appropriate carbonyl derivative VII followed by partial triple bond reduction and acid catalyzed solvolysis (26). It should also be possible to adapt the route so that alternative coupling methods can be used such as the sulfone way (27a) or Okamura's coupling (27b).

The compounds with structure VII can be obtained following various routes as will be shown with several examples. It is important to note that those derivatives will generally be obtained following synthetic routes that are shorter and more efficient than those that are usually used in the preparation of analogues of vitamin D.

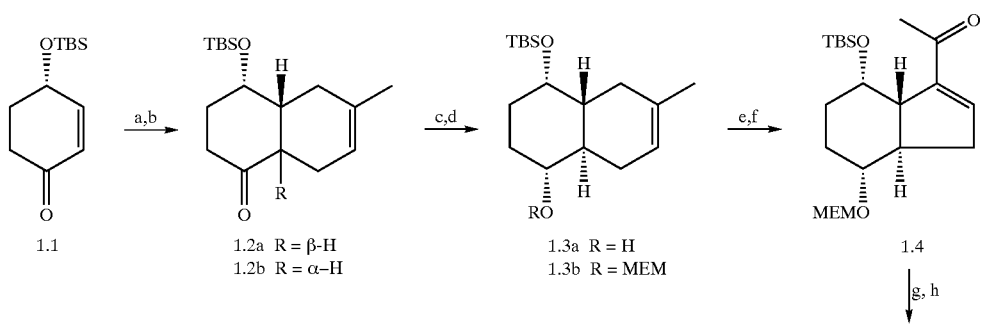

1.1

1.2a R = β-H
1.2b R = α-H 1.3a R = H
1.3b R = MEM 1.4

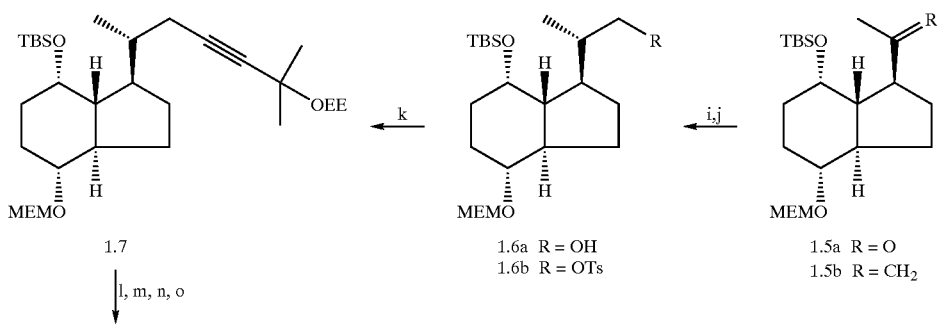

1.7

1.6a R = OH
1.6b R = OTs 1.5a R = O
1.5b R = CH$_2$

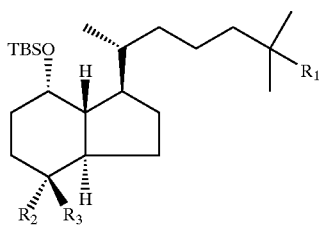

1.8a R$_1$ = OH, R$_2$ = OMEM, R$_3$ = H
1.8b R$_1$, R$_2$ = OH, R$_3$ = H
1.8c R$_1$ = OH, R$_2$, R$_3$ = O
1.8d R$_1$ = OTMS, R$_2$, R$_3$ = O p, q, r

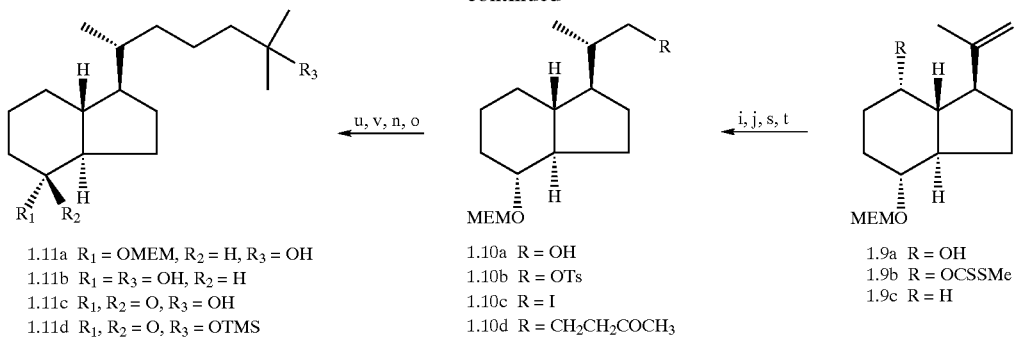

| 1.11a R₁ = OMEM, R₂ = H, R₃ = OH | 1.10a R = OH | 1.9a R = OH |
| 1.11b R₁ = R₃ = OH, R₂ = H | 1.10b R = OTs | 1.9b R = OCSSMe |
| 1.11c R₁, R₂ = O, R₃ = OH | 1.10c R = I | 1.9c R = H |
| 1.11d R₁, R₂ = O, R₃ = OTMS | 1.10d R = CH₂CH₂COCH₃ | |

(a) AlCl$_3$, isoprene, toluene, 6 h, −78° C.—r.t. (72%); (b) MeONa, MeOH, 1 h, r.t. (94%); (c) NaBH$_4$, MeOH, 12 h, 0° C.—r.t. (86%); (d) MEMCl, DIPEA, THF, 3 h, r.t. (98%); (e) (i) OsO$_4$, NMMO, Me$_2$CO:H$_2$O (3:1), 12 h, r.t. (86%); (ii) NaIO$_4$, Me$_2$CO:H$_2$O (3:1), 12 h, r.t. (98%); (f) KOH, 12 h, 60° C. (53%); (g) (i) 10% Pd/C, 1 atm H$_2$, hexane, 1.5 h, 0° C. (93%); (ii) MeONa, MeOH, 3 h, 0° C.—r.t. (97%); (h) Ph$_3$P=CH$_2$, HMPA:THF (1:1), 2 h, −20° C. (100%); (i) (i) 9-BBN, THF, 4 h, r.t.; (ii) EtOH, NaOH 6N, H$_2$O$_2$ 30%, 1 h, 60° C. (74%–91%); (j) TsCl, DMAP, Et$_3$N, CH$_2$Cl$_2$, 12 h, r.t. (91%–97%); (k) NaH, DMSO, 2-(1-ethoxy)-ethyloxy-2-methyl-3-butyne, 1.5 h. 60° C.—r.t. (70%); (l) 10% Pd/C, 4 bar H$_2$, EtOAc, 1 h, r.t. (34%); (m) Me$_2$BBr, CH$_2$Cl$_2$, 1 h, −78° C. (73%); (n) PDC, CH$_2$Cl$_2$, 4 h, r.t. (86%–99%); (o) TSIM, THF, 1 h, r.t. (94%–98%); (p) TBAF, THF, 5 days, 30° C. (99%); (q) (i) NaH, CS$_2$, 24 h, r.t.; (ii) MeI, THF, 2 h, r.t. (98%); (r) Bu$_3$SnH, AIBN, toluene, 9 h, 110° C. (92%); (s) KI, DMSO, 4 h, 60° C. (95%); (t) methylvinylketone, CuI, Zn, EtOH:H$_2$O (7:3), 3.15 h, 15° C. (83%); (u) MeMgCl, THF, 1 h, r.t. (98%); (v) Amberlyst 15, MeOH, 1 week, 30° C. (96%).

Scheme 1

The 18-nor-vitamin D skeleton is a representative of analogues of type IIId. The synthesis centers around the following steps: (a) synthesis of a transfused decalone, (b) one-ring contraction to a trans-fused hydrindane, (c) side chain construction.

The, in the literature described dienophile 1.1, is known to give Diels-Alder addition syn to the silyloxy group (28). Thus, regioselective reaction with isoprene gives 1.2a; base induced epimerization leads to 1.2b. Selective reduction of the carbonyl function and subsequent alcohol protection leads to intermediate 1.3b. Double bond cleavage and aldol reaction of the resulting dialdehyde gives trans-hydrindane 1.4. Hydrogenation of 1.4 leads to a mixture of C-17 epimers which is, upon base induced epimerization, transformed into the thermodynamically more stable 1.5a. Wittig reaction and hydroboration leads to 1.6a next to circa 20% of the C-20 epimer. After separation, the side chain is introduced via tosylate 1.6b. Finallly, catalytic hydrogenation, reintroduction of the C-8 carbonyl function and 25-hydroxyl protection afford the desired precursor 1.8d. Intermediate 1.5b also allows the removal of the C-12 oxy-function via a well established procedure, involving a radical reaction (29).

Hydroboration of 1.9c and subsequent transformation of the hydroxyl group into iodo-compound 1.10c (4:1, 20S:20R). The side chain is introduced under sonication conditions yielding 1.10d (30). This ketone gives, upon reaction with methyl magnesiumchloride, the tertiary alcohol 1.11a. Oxidation to the C-8 ketone 1.11.c and tertiary alcohol protection affords the desired precursor 1.11d.

Analogues with the six-membered structure IIIa can be synthesized according to a strategy which involves as a key-step the Ireland-Claisen rearrangement of a substrate obtained from an ester of which the alcohol part consists of (R)-3-methyl-2-cyclohexenol (31). Two examples of this strategy are shown in scheme 2.

Reaction of (R)-3-methyl-2-cyclohexenol with the homochiral acid 2.1 obtainable from (−)-menthone (32), gives the ester 2.2. After deprotonation of the ester, the enolate anion is reacted in situ with tert-butyldimethylsilyl chloride; subsequent thermolysis leads to cyclohexene 2.3 (67% after recovery of starting material) (33). The carboxygroup in 2.3 is subsequently transformed into a methylgroup, following standard conditions, yielding eventually derivative 2.4. Hydroboration of 2.4 gave a secondary alcohol which is oxidized to cyclohexanone 2.5. The latter is the required carbonyl substrate for the synthesis of analogues 4 possessing the (24S)-configuration.

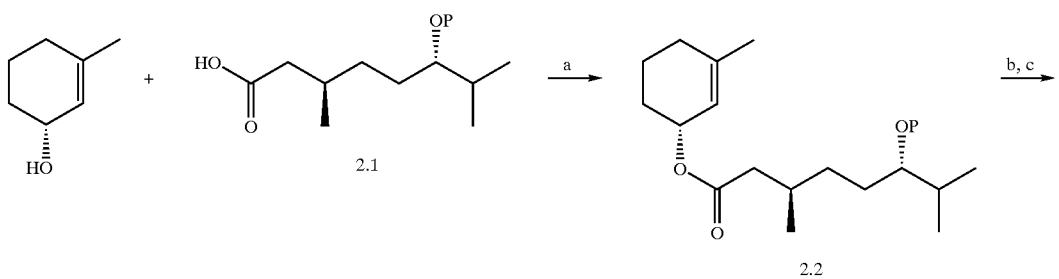

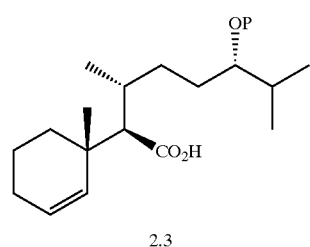
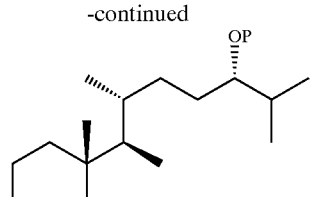
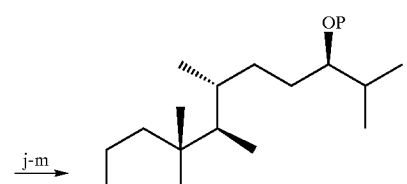
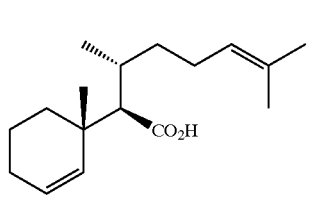

(a) DCC, DMAP, CH$_2$Cl$_2$ (91%); (b) LiCA, THF, HMPA; tBuMe$_2$SiCl; (c) Δ (67%); (d) CH$_2$N$_2$, ether (86%); (e) LAH, THF (89%); (f) TsCl, Pyridine (96%); (g) LAH, THF (91%); (h) 9-BBN, THF; NaOH, H$_2$O$_2$ (80%); (i) PDC, CH$_2$Cl$_2$ (90%); (j) TBAF, THF, 30° C. (88%); (k) PPh$_3$, DEAD, pNO$_2$PhCOOH (68%); (l) K$_2$CO$_3$, KOH; (m) TBSCl, imidazole, DMF, DMAP (97%); (n) 9-BBN, THF (92%); (o) PDC, CH$_2$Cl$_2$ (92%); (p) DCC (96%); (q) LDA, TBSCl; (r) LAH, THF, Δ (86%); (s) TsCl, py (100%); (t) LAH, THF (100%); (u) Hg(OAc)$_2$, NaOH, NaBH$_4$; (v) TESCl, DMAP, DMF, imidazole; (w) 9-BBN, H$_2$O$_2$ (95%); (x) PDC (80%).

Scheme 2

The synthesis of its (24R)-epimer is performed in a similar way after inversion at C-24. Therefore starting from intermediate 2.4, the protective group is removed and the resulting alcohol inverted via the Mitsunobu procedure (34). Repetition of the same sequence as above gives cyclohexanone 2.7. The usual coupling procedure then leads eventually to analogues 5 and 6 which possess the (24R)-hydroxy group.

The synthesis of the 25-hydroxy analogue can be performed along the same strategy. Therefore (R)-3-methyl-2-cyclohexenol is esterified with (R)-(+)-citronellic acid (2.8) to yield ester 2.9. The Ireland-Claisen rearrangement sequence then gives the acid 2.10. After transformation of the carboxygroup into a methyl group (2.11), the trisubstituted double bond is preferentially oxidized to the tertiary alcohol using mercuric acetate, NaOH and sodium borohydride. Subsequent alcohol protection and regioselective oxidation of the cyclic double bond leads to cyclohexanone 2.12, from which are obtained, using the usual coupling procedure, analogues 7 and 8.

Analogues of type IIIa with inverted configuration at C-13 can also be obtained via Ireland-Claisen strategy. This is illustrated in scheme 3. For that purpose the acetate of (S)-3-methyl-2-cyclohexenol (3.1; 86% ee) can be directly deprotonated, and the corresponding enol silylether rearranged to the acid 3.2. A further enrichment of the desired enantiomer can be realized via resolution with R-(+)-α-methylbenzyl amine. The subsequent sequence involves reduction of acid 3.2, and protection of the resulting primary alcohol to 3.3. The latter can be oxidized using 9-BBN and hydrogen peroxide to alcohol 3.4. After protection-deprotection, the primary alcohol is used to build up an oxa side-chain. This is performed by reaction of the anion with 1-chloro-3-methyl-2-butene. After hydrolysis and oxidation cyclohexanone 3.6 is obtained. The final introduction of the 25-hydroxy group involves the mercuric acetate-hydride reduction method. The obtained carbonylderivative 3.7 serves as a precursor for analogue 9 characterized by a 22-oxa sidechain and an epimeric configuration at C-13. One can further note that the usual Horner-Wittig coupling also leads in this case to the formation of the isomer with a (Z)-7,8-double bond (ratio 4:1).

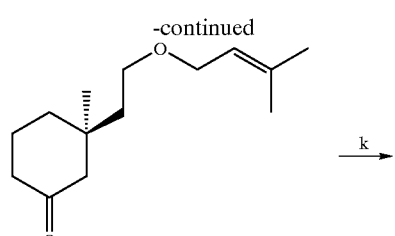

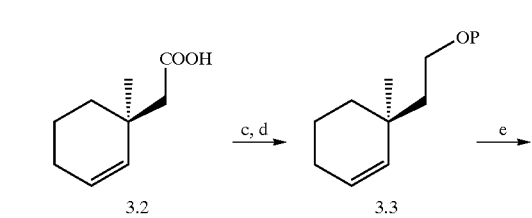

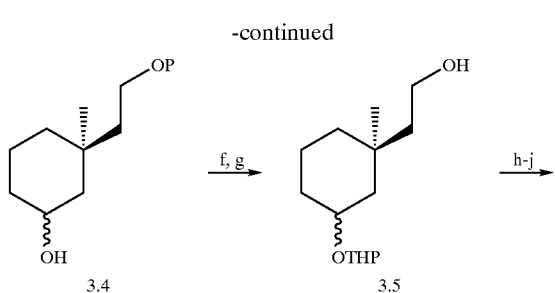

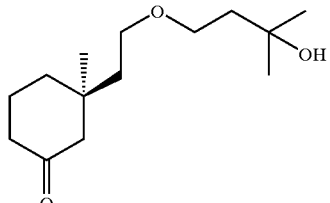

P=SiPh$_2$tBu (a) PGL, phosphate buffer (86% ee); (b) LDA, tBuMe$_2$SiCl, THF; HCl; resolution with R-(+)-α-methyl benzylamine (48%); (c) LAH, ether (95%); (d) tBuPh$_2$SiCl, DMF, imidazole (98%); (e) 9-BBN, H$_2$O$_2$ (96%); (f) DHP, CH$_2$Cl$_2$ (93%); (g) (nBu)$_4$NF, THF (91%); (h) ClCH$_2$CH=C(CH$_3$)$_2$, NaH, DMF (81%); (i) TsOH, MeOH, r.t. (98%); (j) PDC, CH$_2$Cl$_2$, r.t. (84%); (k) Hg(OAc)$_2$, NaBH$_4$ (68%).

Scheme 3

Another strategy towards the synthesis of analogues of type IIIa consists in the conjugate addition of part of the side chain involving 3-methyl-2-cyclohexenone as the substrate. An example is given in scheme 4.

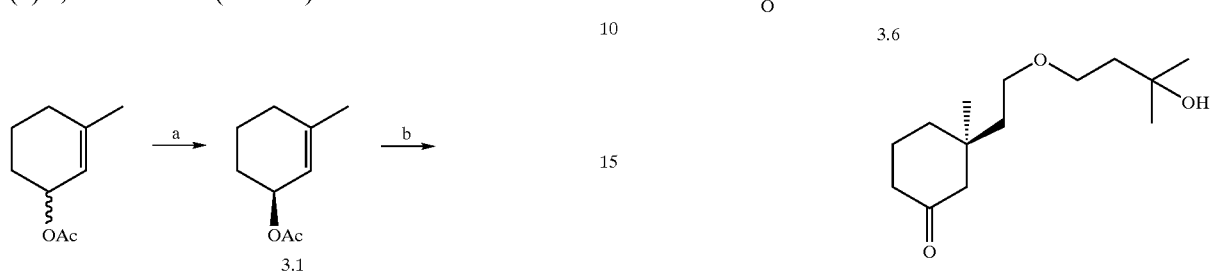

(a) tBuPh$_2$SiCl, imidazole, DMF, 36 h, r.t. (100%; (b) DIBALH, hexane, 0.5 h, −78° C.; (c) tBuOK, (MeO)$_2$P(O)CHN$_2$, THF, 20 h, −78° C., r.t. (90% overall from 4.2); (d) B—Br-9-BBN, CH$_2$Cl$_2$, 4 h, 0° C., then CH$_3$COOH, 0.5 h, 0° C., NaOH/H$_2$O$_2$, 0.5 h, r.t. (90%); (e) tBuLi, CuI/HMPT, BF$_3$—OEt$_2$, 3-methyl cyclohexenone, ether, 16 h, −120°–20° C. (40%); (f) TBAF, THF, 3 h, r.t. (90%); (g) HPLC, eluent:hexane:ethylacetate 6:4; (h) Ph$_3$P, imidazole, I$_2$, THF, 6 h, −20° C.—r.t. (88%);

Scheme 4

The necessary homochiral cuprate reagent is obtained following a sequence starting from methyl (S)-3-hydroxy-2-methylpropanoate (4.1). After protection of the alcohol, the ester is reduced and the resulting aldehyde 4.3 treated with the anion derived from methyl diazomethyl phosphonate (35). The resulting alkyne 4.4, obtained in 90% yield from 4.2, is subsequently transformed into the vinyl bromide derivative 4.5. From the latter an appropriate cuprate reagent is obtained via treatment with tert-butyllithium and CuI at −120° C. The 1,4-addition to 3-methyl-2-cyclohexenone is performed in ether in the presence of borontrifluoride (36). After usual work-up and purification cyclohexanone 4.6 is obtained together with its C13-epimer.

After hydrolysis the desired alcohol 4.7 can be separated from its C13-epimer (configurational assignment according to CD), and is further transformed into iodide 4.8. This carbonyl derivative serves as the substrate for appending the A-ring.

For the synthesis of compounds of type IIc, an example is given in. scheme 5. The starting material 5.1 is available from R-citramalic acid (37).

analogues. Transformation of the p-methoxybenzylether in 5.3 (α+β) into the ester 5.4 (α+β) and subsequent Grignard reaction leads to the side chain. Finally the aldehyde function was introduced and affords the precursor 5.6(α+β).

A group of analogues with a five-membered ring, as examples of the general formula IIIc, can readily be obtained starting from the known 6.1 (38). Cleavage of the ether bond in 6.1 with sodium iodide leads to the key-intermediate, the iodide 6.2. The synthesis centers around introduction of (a) the side chain using the iodo-function via (1) direct coupling or (2) after transforming the iodomethyl substituent to a hydroxyl substituent or (3) after inverting the orientation of the iodomethyl substituent or (4) after transformation of the iodide into a formyl group and of (b) the A-ring part after

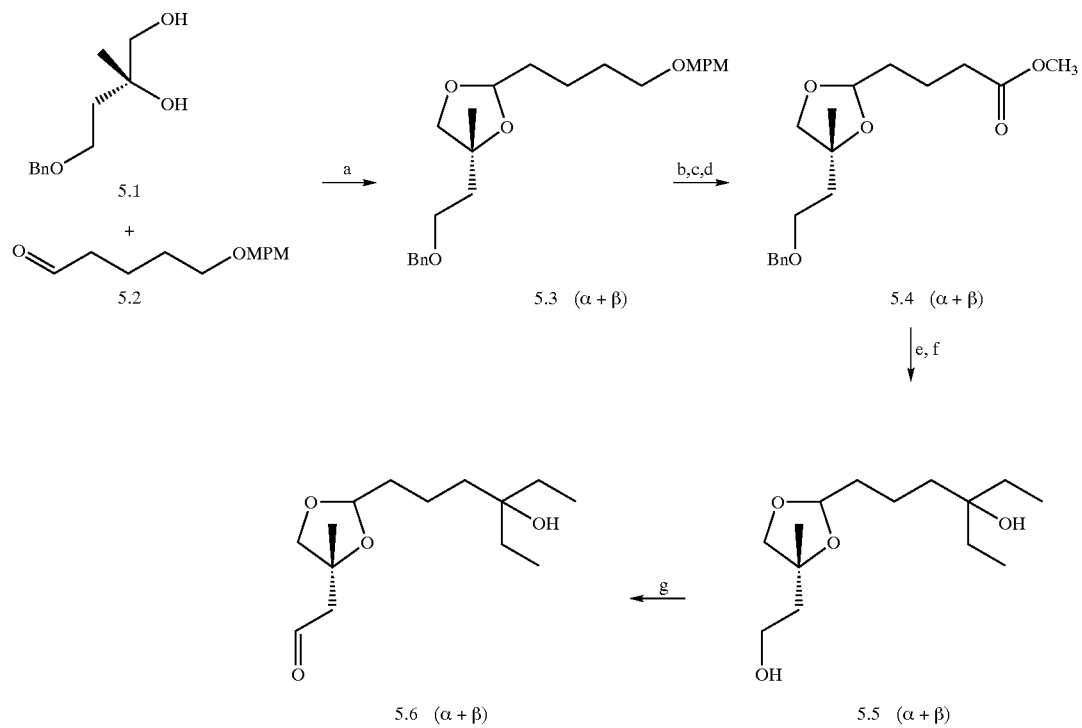

(a) TsOH, THF, 20 h, r.t. (90%); (b) DDQ, 3 h, r.t.; (c) PDC, DMF, 20 h, r.t.; (d) CH$_2$N$_2$, Et$_2$O (94%); (e) EtMgBr, 2 h, r.t.; (f) Pd/C, H$_2$ (50%); (g) TPAP, NMMO, 2 h, r.t. (70%);

Scheme 5

Construction of the heterocyclic nucleus from 5.1 and 5.2 allows assembling of the precursor skeleton in a convergent way. Both epimers of 5.3 with respectively α and β oriented side chain are obtained in a 1:1 ratio.

Further transformations are carried out on this epimeric mixture. Separation was possible on the stage of the final homologation at the hydroxymethyl substituent. Examples of this strategy are given below and are illustrated in scheme 6.

The iodo-compound 6.2 can be coupled under sonication conditions with methyl-vinyl ketone and ethyl-vinyl ketone to yield respectively 6.8 and 6.9. Ketone 6.8 upon reaction with methyl magnesiumbromide gives the corresponding tertiary alcohol. Oxidation of the primary alcohol and 1-C homologation of the resulting aldehyde 6.10 with methoxytriphenylphosphonium-methylide and subsequent hydrolysis leads to the aldehyde 6.12 required for coupling with the A ring. Similarly, reaction of 6.9 with ethyl magnesium bromide and subsequent transformation gave 6.13.

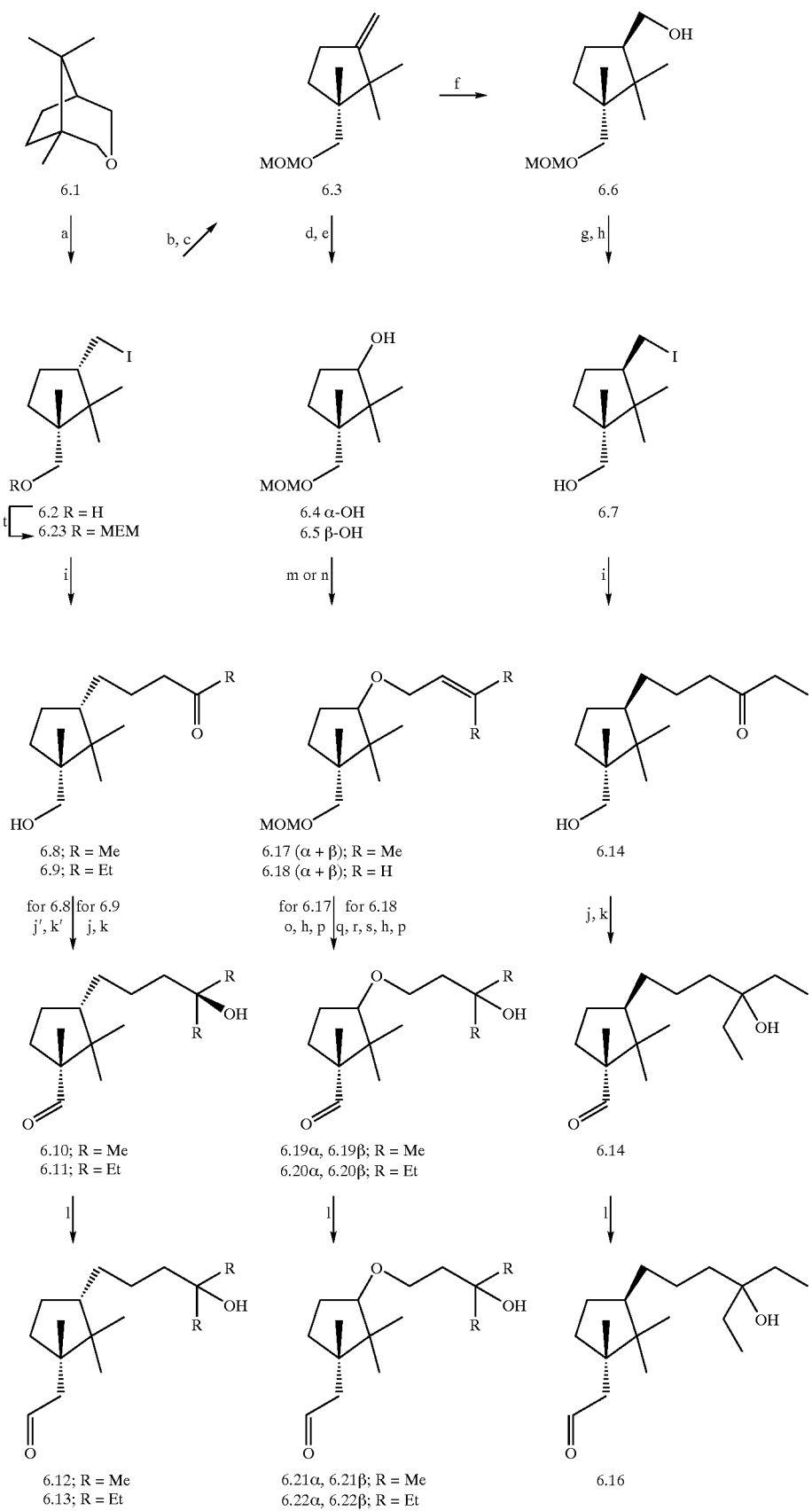

-continued

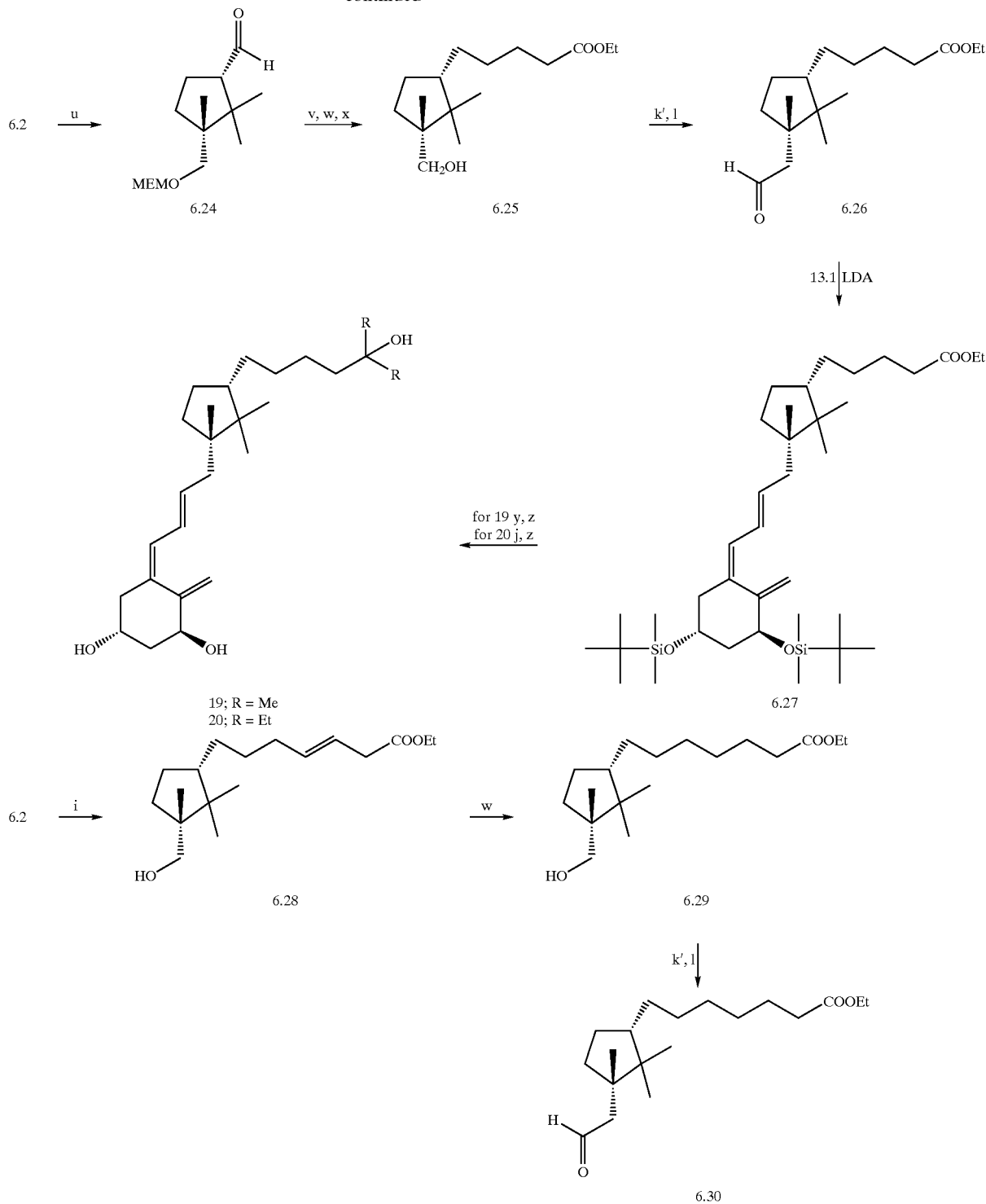

(a) Cl₃SiCH₃, NaI, CH₃CN (90%); (b) DIPEA, CH₃OCH₂Cl, CH₂Cl₂ (86%); (c) TBAF, THF (88%); (d) OsO₄, NaIO₄, THF:H₂O (65%); (e) LiAlH₄, THF, rt (95%); (f) (1) 9-BBN, THF, 60° C.; (2) H₂O₂, NaOH (87%); (g) Ph₃P, imidazol, I₂, ether:CH3CN 3:1 (93%); (h) Amberlyst-15, MeOH, THF (86%); (i) CuI, Zn, MVK, EVK, or t-2,4-pentadionic acid ethyl ester, EtOH:H₂O 7:3 (45%); (j) Mg, EtI, Et₂O, 0° C. (73%); (j') MeLi, Et₂O, −78° C. (85%); (k) TPAP, NMMO, molecular sieves 4A, CH₂Cl₂ (66%); (k') (CrO₃)Py₂ ("Collins"), CH₂Cl₂ (35%); (l) (1) [Ph₃PCH₂OCH₃]⁺Cl⁻, nBuLi, ether, −30° C., (2) HCl 2N, THF (48%); (m) KOH, isoprenylchloride, 18-Crown-6, toluene, ultrasound (40%); (n) KOH, allyl bromide, 18-Crown-6, THF (75%); (o) (1) Hg(OAc)₂, H₂O, THF; (2) NaBH₄, NaOH (94%); (p) SO₃.Py, Et₃N, CH₂Cl₂:DMSO 1:1 (71%); (q) (1) 9-BBN, THF, 60° C.; (2) H₂O₂, NaOH (95%); (r) (1) PDC, DMF, 40° C.; (2) CH₂N₂, Et₃O, 0° C. (36%); (s) Mg, EtI (2 eq), Et₂O, 0° C. (92%); (t) MEMCl, DIPEA, CH₂Cl₂ (80%); (u) (1) NaNO₂, DMF, urea, 25° C. (45%); (2) NaOMe (1.3 eq), MeOH; (3) O₃, Na₂S, −78° C. (70%); (v) (EtO)₂P(O)CH₂CH═CHCOOEt, LDA, THF (91%); (w) H₂/Pd (4 atm), 3 h (80%); (x) Me₂BBr, ClCH₂CH₂Cl:CH₂Cl₂ 1:6 (93%); (y) Mg, MeBr, THF; (z) TBAF, THF Scheme 6

On the other hand base induced elimination of iodide 6.2 after protection of the hydroxyl group gives the olefin 6.3. Hydroboration of 6.3 leads to two diastereomers in a 1:1 ratio. After separation, the isomer 6.6 was transformed into the iodide 6.7. As described for the epimer 6.2, 6.7 was used to synthesize the key-intermediate 6.16.

Oxidative cleavage of the double bond in 6.3 and reduction of the resulting ketone leads to the epimeric alcohols 6.4 and 6.5. The mixture is subjected to a Williamson ether synthesis affording the allylic ethers 6.17α and 6.17β. Water-addition to the double bond, hydrolysis of the MOM-ether and oxidation of the resulting primary alcohol gives the epimeric aldehydes 3 6.19α and 6.19β which can be separated by HPLC (hexane-aceton 9:1). The respective structures of both epimers were established by nOe measurements. 1-C homologation as already described for 6.10 leads to the intermediates 6.21α and 6.21β.

Also reaction of the mixture of the anions of 6.4 and 6.5 with allyl bromide yields the mixture of 6.18(α+β). A sequence involving hydroboration of the terminal double bond, oxidation and treatment with diazomethane leads to the corresponding carboxylic methyl ester which is reacted with ethyl magnesium bromide. Subsequent hydrolysis of the MOM ether and oxidation of the primary alcohol gives the epimeric aldehydes which are separated by HPLC. The respective structures of 6.20α and 6.20β were established by nOe measurements. 1-C homologation then gives respectively 6.22α and 6.22β. Coupling of the aldehydes 6.12, 6.13, 6.16 6.21α, 6.21β, 6.22α and 6.22β with the A-ring is described below.

Also transformation of iodide 6.2, via the corresponding nitro compound (39), into the aldehyde 6.24 allows introduction of the side chain. This can be performed by a Horner-Wittig type reaction involving a phosphonocrotonate followed by catalytic hydrogenation. The 1-C homologation is then carried out as described for 6.12. Coupling (24) of the resulting 6.26 with the anion of 13.1 leads to intermediate 6.27. Subsequently the ester function can be transformed into tertiary alcohols. This sequence is an example of construction of analogues where the required side chain is formed subsequent to the Lythgoe coupling.

In another example of this series the iodo-compound 6.2 is coupled under sonication conditions with the ethyl ester of trans-2,4-pentadionic acid. Subsequent to hydrogenation of 6.28, the resulting alcohol 6.29 is homologated to precursor 6.30 as already described.

Another example of analogues of type IIIc has an aromatic ring and can easily be constructed from 3-hydroxyphenethyl alcohol 7.1 (scheme 7) and involves construction of the side chain via the phenolic hydroxyl group and oxidation of the primary alcohol to an aldehyde function suitable for coupling with the A ring part. Ether formation with the tosylate 7.2 gives 7.3.

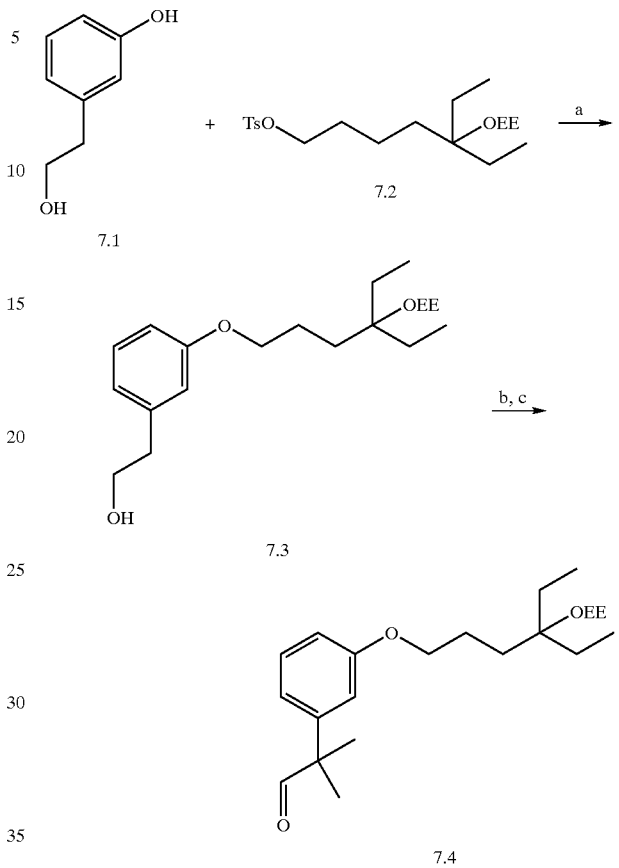

(a) KOH, DMSO, 4 h, r.t. (85%); (b) Et₃N, SO₃·C₅H₅N, 15 min (48%); (c) CH₃I, KO-t.Bu (55%).

Scheme 7

After oxidation of the primary alcohol in 7.3, the resulting aldehyde is bis-methylated affording the precursor 7.4.

Again several methods are possible for the synthesis of analogues with the general structure IIIc. A few possibilities are shown in scheme 8.

In a first approach the previously described compound 3.4 (scheme 3) is etherified as before; after deprotection to the alcohol the two diastereomers of 8.1 can be separated. Both separated alcohols 8.1α and 8.1β are treated with mercuric acetate/sodium borohydride, and are subsequently oxidized yielding the aldehydes 8.2 and 8.3, which after the usual coupling sequence give the analogues 22 and 23, respectively.

The β-epimer 8.1β can also be converted to a diastereomeric mixture of epoxides which after oxidation lead to aldehyde 8.4. This is the substrate for coupling to analogue 24.

Finally 8.4 can also lead to en epimeric mixture of primary alcohols via oxidation to the corresponding ketone, Wittig reaction with methylene triphenylphosphorane and 9-BBN oxidation. After tosylation of the primary alcohol the side chain is introduced via displacement with the anion of 3-ethoxyethyl-3-methyl-1-butyne; deprotection gives 8.5 as a mixture of epimers which can now be separated. Oxidation of the α-epimer 8.5α with PDC leads to aldehyde 8.6, the precursor of analogue 25.
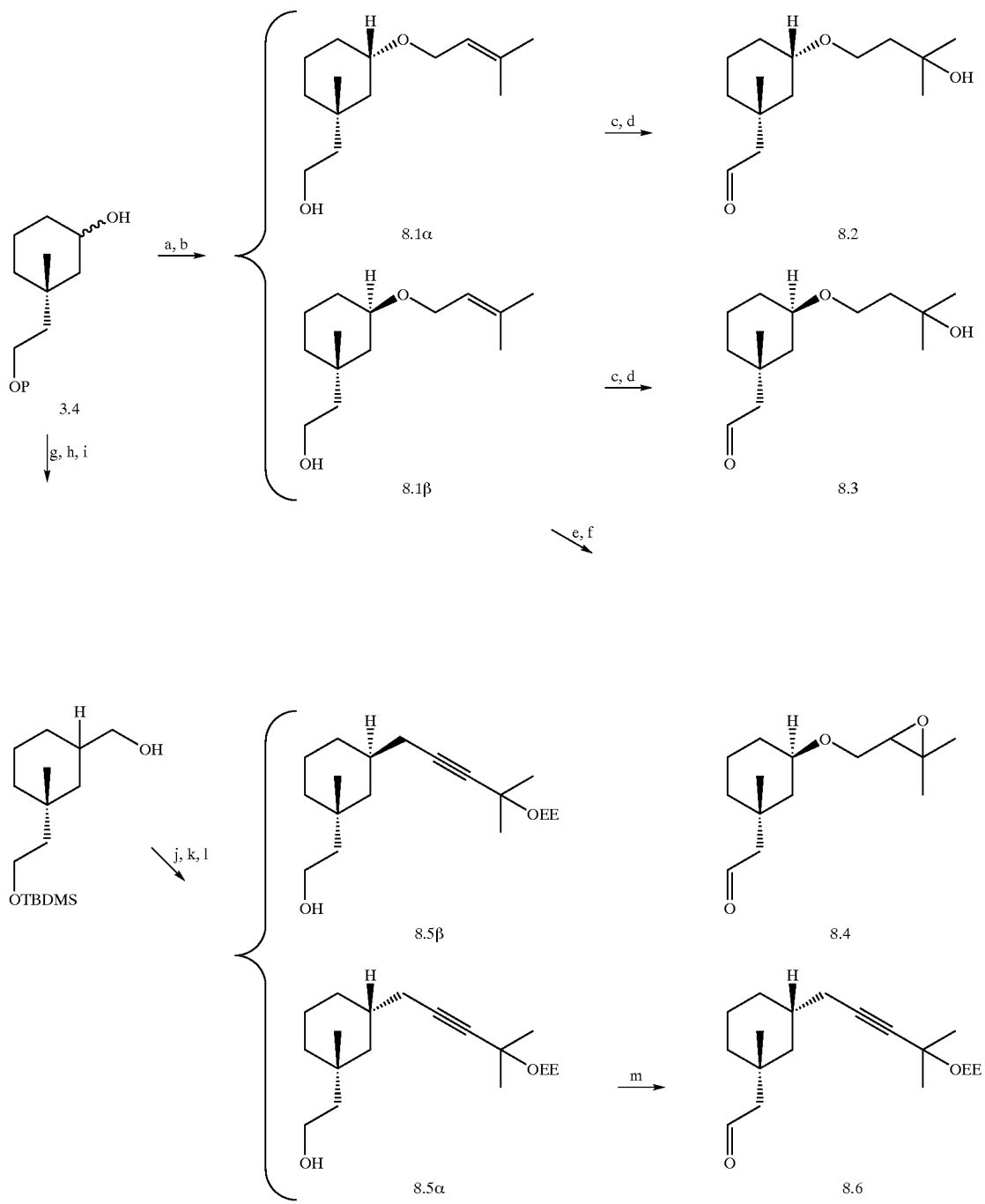

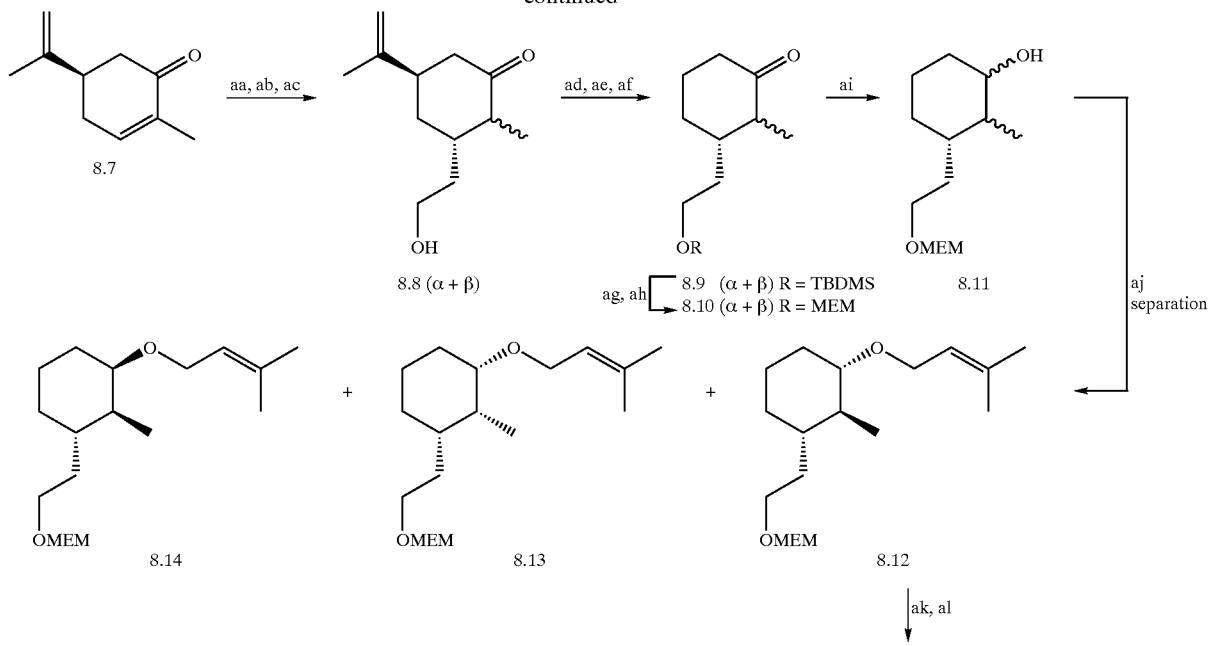
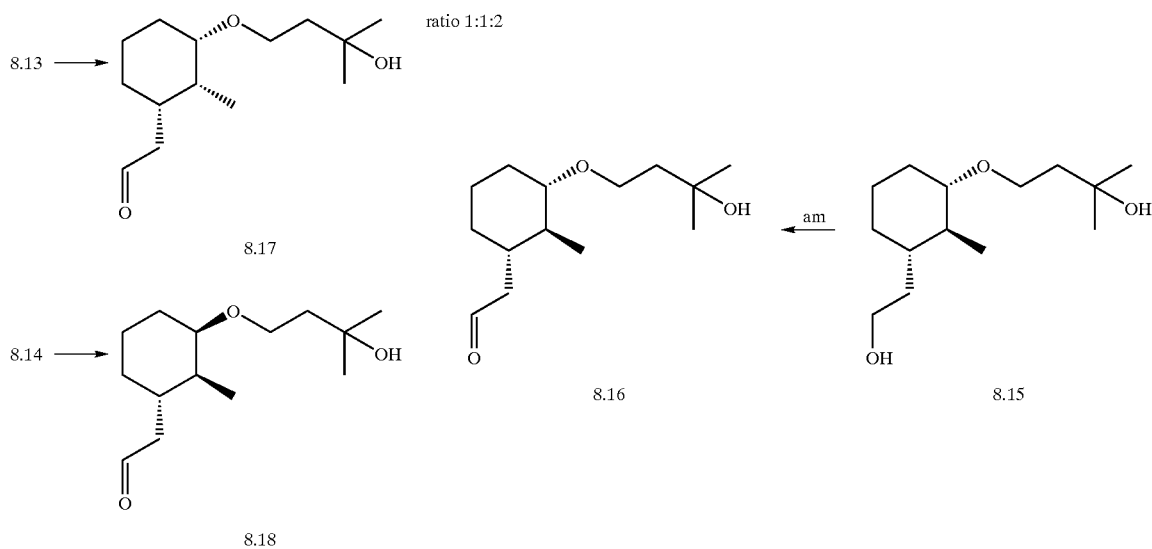
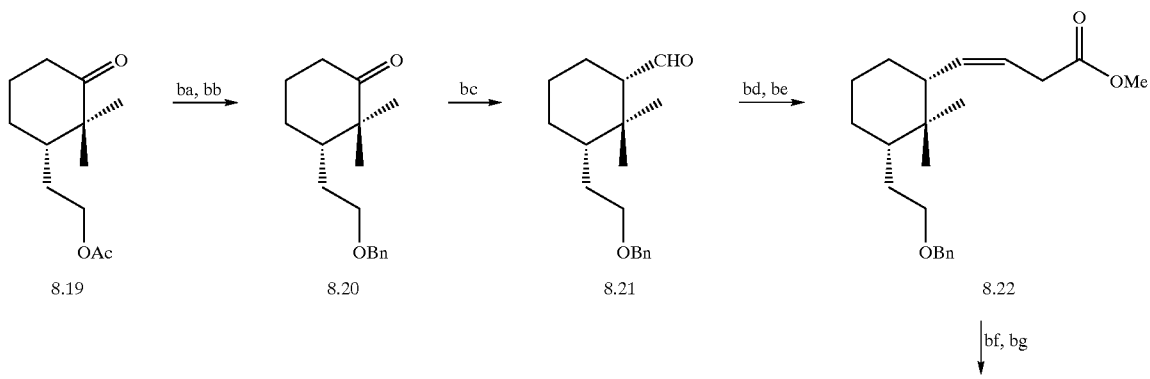

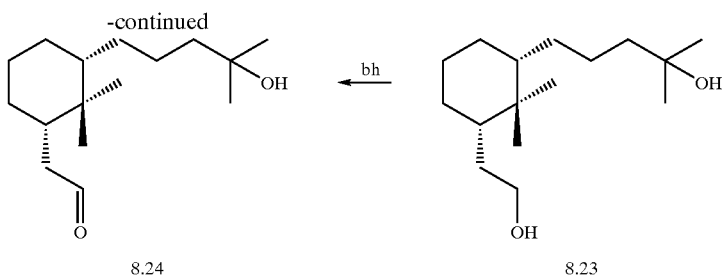

8.24        8.23

(a) ClCH$_2$CH=C(CH$_3$)$_2$, NaH (89%); (b) (nBu)$_4$NF (81%); (c) Hg(OAc)$_2$; NaOH, NaBH$_4$ (76%) 2:1 mixt.; (d) PDC, CH$_2$Cl$_2$, r.t. (80%); (e) mCPBA, CH$_2$Cl$_2$, 0° C. (86%); (f) PDC, CH$_2$Cl$_2$ (73%); (g) PDC, CH$_2$Cl$_2$ (96%); (h) Ph$_3$P$^+$CH$_3$Br$^-$, nBuLi, THF (83%); (i) 9-BBN (90%); (j) TsCl, pyridine (95%); (k) HC≡CC(Me)$_2$OEE, NaH, DMSO (62%); (l) (nBu)$_4$NF, THF (92%); (m) PDC, CH$_2$Cl$_2$ (71%).

(aa) t.butyldimethylsilyl ethyl ketene acetal, HgI$_2$, CH$_2$Cl$_2$; (ab) LiAlH$_4$, Et$_2$O; (ac) TBAF, THF (61% from 8.1); (ad) TBDMSCl, imidazole, DMF (99%); (ae) O$_3$, MeOH, −30° C., FeSO$_4$, Cu(OAc)$_2$; (af) Pd, H$_2$ (4 atm) (61% from 8.2); (ag) TBAF, THF (100%); (ah) MEMCl, EtiPr$_2$N, CH$_2$Cl$_2$ (99%); (ai) NaBH$_4$, MeOH (70%); (aj) KOH, 18-crown-6, chloro-3-methyl-2-butene, toluene, ultrasound (43%); (ak) Hg(OAc)$_2$/NaOH, NaBH$_4$ (78%); (al) Amberlyst-15, MeOH:THF 1:1 (100%); (am) CH$_2$Cl$_2$:DMSO 1:2, pyridinesulfurtrioxide complex, Et$_3$N (69%).

(ba) K$_2$CO$_3$, MeOH, 1 h, r.t. (55%); (bb) BnO—C(=NH)CCl$_3$, CF$_3$SO$_3$H, CH$_2$Cl$_2$/c.hexane, 90 min, 0° C. (60%); (bc) (i) FOSMIC, BuLi, Et$_2$O, 2 hrs, 0° C.; (ii) HCl (37% soln), 12 hr, r.t. (67%); (bd) Ø$_3$P=CH—CH$_2$—COO—, THF, 2 h, r.t.; (be) CH$_2$N$_2$, Et$_2$O (28% overall); (bf) MeLi, LiBr, diethyl ether, 2 hr, 0° C.; (bg) Pd/C 10%, EtOAc, H$_2$, 6 hr, r.t. (53%); (bh) NMMO, TPAP, CH$_2$Cl$_2$, 2 h, r.t. (85%).

Scheme 8

An example of the synthesis of analogues of general formula IIIc starting from R-carvone (8.7) is also shown in scheme 8. The strategy centers around (a) diastereoselective 1,4-addition (b) removal of the isopropylidene group (40) (c) introduction of an oxa-side chain. This route leads to separable diastereoisomers.

The 1,4-addition involving a silylated ketene acetal on 8.7 leads to an enol silyl ether. The ester function in this intermediate is conveniently reduced to a hydroxyl function prior to hydrolysis. Ozonolysis of 8.8 and subsequent treatment with iron and copper salts allows cleavage of the isopropylidene substituent. Catalytic hydrogenation of the resulting double bond and changing the protective group gives the MEM ether 8.10. Subsequently sodium borohydride reduction leads to isomeric alcohols 8.11. This mixture is subjected to ether formation with isoprenylchloride. The ethers 8.12, 8.13 and 8.14 can be separated. Each is individually transformed in the tertiary alcohols 8.16, 8.17 and 8.18 respectively.

Still another method for obtaining analogues of general formula IIIc can be illustrated starting from compound 8.19, a ketone described in the literature (41). It involves side chain construction making use of the carbonyl function.

Reaction with diethyl(isocyanomethyl)phosphonate followed by acid hydrolysis gives the aldehyde 8.21. Wittig homologation introduces the side chain. Reaction of methyllithium on 8.22 leads to the tertiary alcohol. The double bond is hydrogenated with concomitant cleavage of the benzyl ether. Finally oxidation of the primary hydroxyl group in 8.23 gives the precursor aldehyde 8.24.

An example of the synthesis of an analogue of general formula IIIe is shown in scheme 9. Starting from the known homochiral enone 9.1 (42) a dissolving metal ammonia reduction leads to the trans-fused decalone 9.2. The introduction of the side chain involves reaction with the sodium salt of protected 2-methyl-3-butyn-2-ol, followed by dehydration to 9.3. Catalytic hydrogenation eventually leads to decalone 9.4, the precursor of analogue 31.

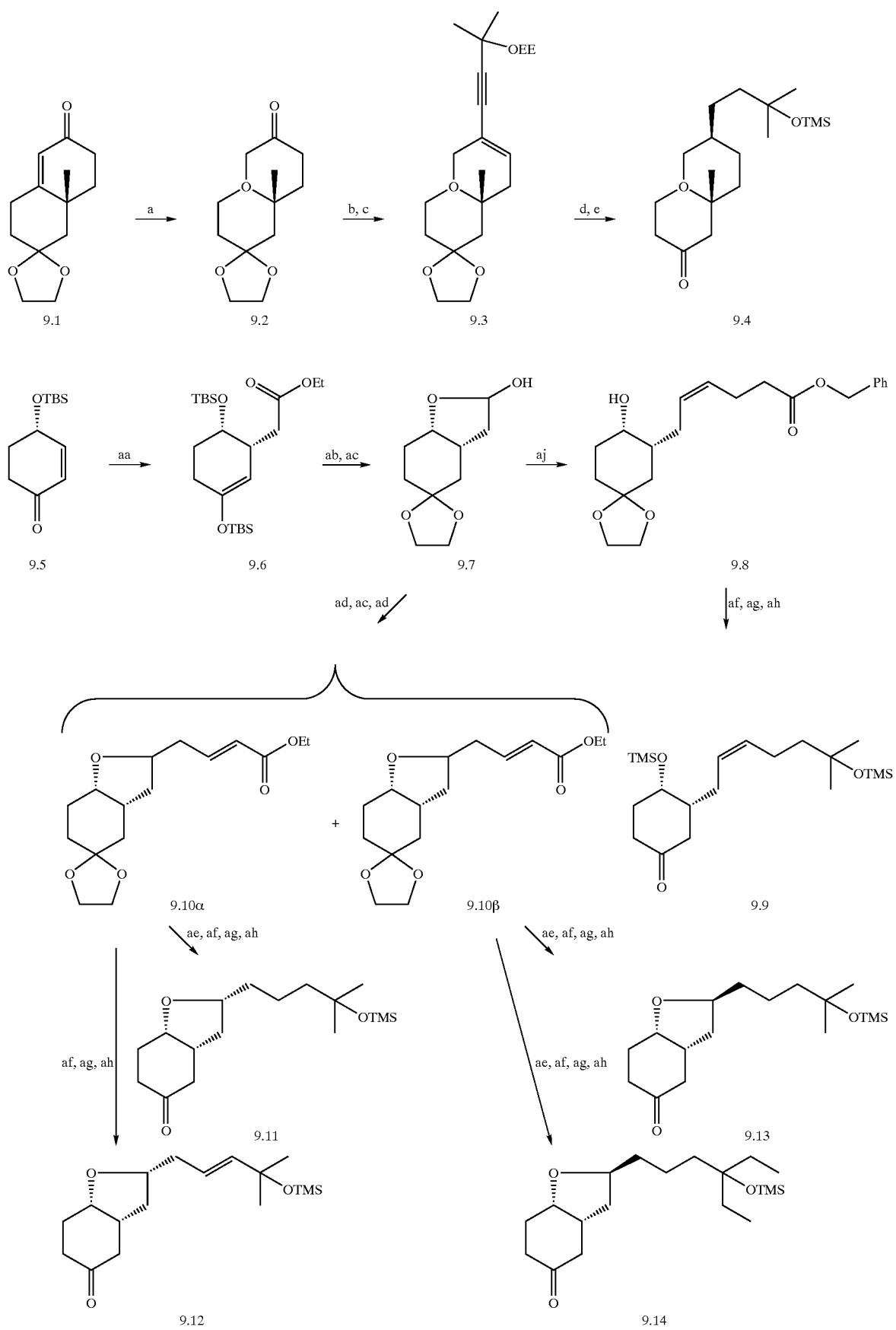

(a) Li, I.NH$_3$, (56%); (b) NaC≡C—C(Me)$_2$OEE, DMSO (74%); (c) Tf$_2$O, CH$_2$Cl$_2$, py, DMAP (25%); (d) H$_2$, Pd, EtOAc (65%); (e) TMS, imidazole;
(aa) HgI$_2$, CH$_2$(OTBAS)(OEt), Et$_3$N, CH$_2$Cl$_2$, 3 h, −78° C.—r.t. (97%); (ab) toluene, glycol, H$_2$SO$_4$, molecular sieves 3 Å, 10 h, reflux (75%); (ac) DIBAH, toluene, 4 h, −78° C. (93%); (ad) triethylphosphonoacetate, BuLi, THF, 17 h, −78° C.—r.t. (88%); (ae) 10% Pd/C, hexane, 1 atm H$_2$, 1.5 h, 0° C. (99%); (af) MeMgI, diethylether, 5 h, r.t. (85%); (ag) Amberlyst-15, THF:water 2:1, 12 h, r.t.

starting material for these particular examples is the known 10.1 (43); the ester function is the handle for the side chain construction while the carbonyl function can be transformed into a formyl group. Alkylation of 10.2 leads to 10.3 as the major (95%) epimer in accordance with literature precedents (44). After transformation of the ester function to a methyl group, following a classical procedure, the terminal double bond in 10.6 is cleaved by ozonolysis. Finally deprotection leads to ketone 10.7.

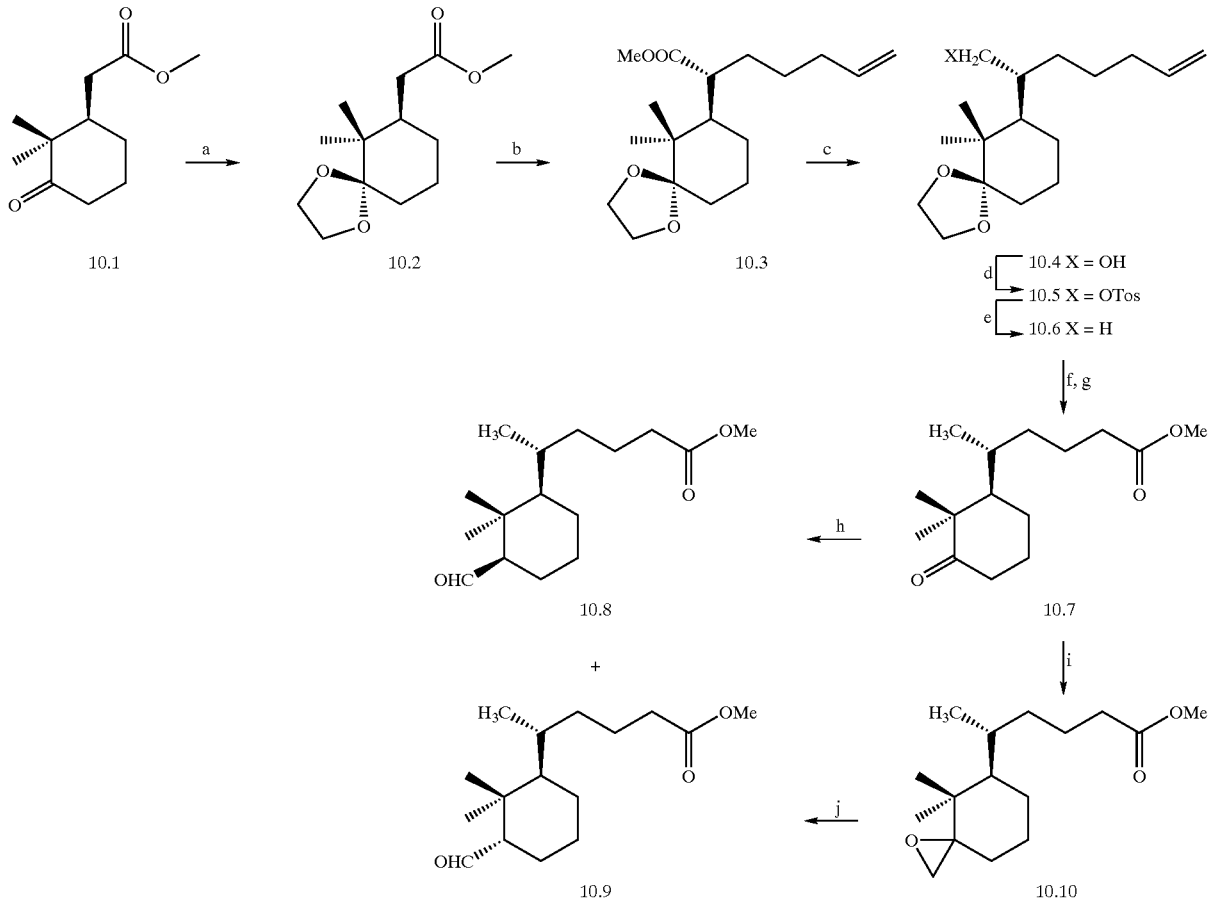

(99%); (ah) TSIM, THF, 2 h, r.t. (97%); (ai) EtMgI, diethylether, 2 h, r.t. (89%); (aj) Ph$_3$P$^+$(CH$_2$)$_3$COOBzBr—, LDA, HMPA:THF 1:1, 2 h, −20° C. (21%);

Scheme 9

Further examples of analogues of general formula IIIe whereby one of the rings of the bicyclic system is a heterocyclic ring are also shown in scheme 9. The synthesis starts from the known enone 9.5 (28) and proceeds via conjugate addition, heterocyclic ring formation and Wittig condensation as shown in the scheme. Various carbonyl derivatives were obtained that were condensed with the A-ring in the usual way.

Examples of precursors for analogues of type IIIb, with a cyclohexanoic D-ring, are described in scheme 10. The (a) PPTS, acetone, 2 h, reflux (86%); (b) LDA, THF, 1 h, −30° C.; 5-Br-1-pentene, HMPA, 3 h, −78° C. (93%); (c) LiAlH$_4$, Et$_2$O (99.8%); (d) TosCl, TEA, DMAP, DCM, 20 h, r.t. (95%); (e) LiAlH$_4$, Et$_2$O, 5 h, reflux (88%); (f) O$_3$, DCM:2.5M NaOH in MeOH 4:1 (v/v), 45 min, −78° C. (64%); (g) PPTS, acetone, H$_2$O (cat), 3 h, reflux (75%); (h) FOSMIC, BuLi, Et$_2$O, 15 min, −60° C.; HCl 37%, 12 h, r.t. (64%); (i) Me$_2$S=CH$_2$, THF, 2 h, r.t. (33%); (j) BF$_3$.OEt$_2$, Et$_2$O, 12 h, r.t. (65%).

Scheme 10

The formation of a formyl substituent from a ketone is well known. Two methods are used here; one of which involving reaction with diethyl (isocyanomethyl) phosphonate (45). The epimeric aldehydes 10.8 and 10.9 can be separated. Also base catalyzed epimerization of 10.9 gives the thermodynamically more stable 10.8. Both precursors 10.8 and 10.9 can be transformed into analogues via coupling with 13.1 and organometallic reactions under conditions similar to the synthesis of 19 from 6.27. The other method involves the intermediacy of the epoxide 10.10 which is then transformed into the mixture of 10.8 and 10.9.

Examples of precursors for compounds of type IIb with a 5-membered D-ring are described in scheme 11.

In one case the synthesis starts from the t-butyldimethylsilyl ether 11.1 of the commercially available 5-(hydroxymethyl)furfural. Wittig reaction with the ylid 11.2 yields the ester 11.3 which is easily transformed into the tertiary alcohol 11.4. Finally deprotection and oxidation of the primary hydroxyl group affords the precursor 11.5.

The precursor 11.11 can be obtained from the known 11.6 (46) and involves hydroboration of the double bond after reductive removal of the bromo-atom and formation of the tosylate. The epimers 11.9 are then coupled with the side chain. Oxidation yields the epimeric aldehydes 11.11α+ 11.11β.

A closely related precursor can be obtained from (−)-camphoric acid (11.12). Subsequent to reduction, SAM II lipase catalyzed mono-ester formation allows for the requisite differentiation of the two hydroxyl functions. From 11.13, subsequent to oxidation to the corresponding aldehyde, the side chain can be introduced. This leads to intermediate 11.14.

On the one hand, Grignard reaction and oxidation of the primary alcohol leads to precursor 11.21. On the other hand 11.14 can easily be transformed into precursors 11.19 and 11.20; now an additional catalytic hydrogenation step is involved.

Another D-ring analogue of type IIb, namely 8,9-seco-1α,25-(OH)$_2$ vitamin D$_3$ is available from 11.22 (from 12.1). Formation of an enol derivative (e.g. the triflate) via the kinetically produced enolate anion and subsequent ozonolysis gives 11.24. Reduction of the corresponding tosylate 11.25 and subsequent oxidation of the primary hydroxyl group in 11.26 affords the 8,9-seco C/D ring precursor 11.27.

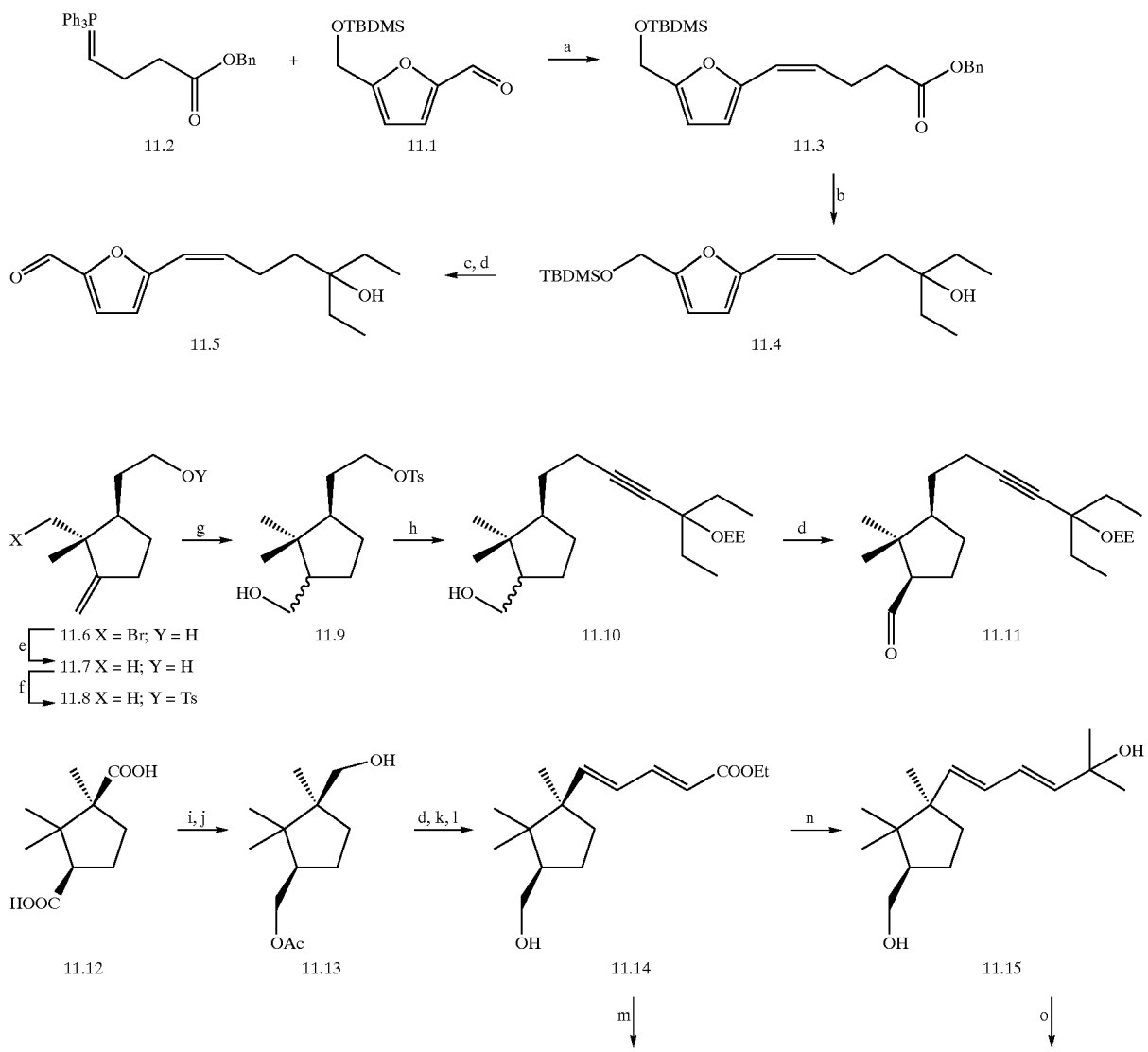

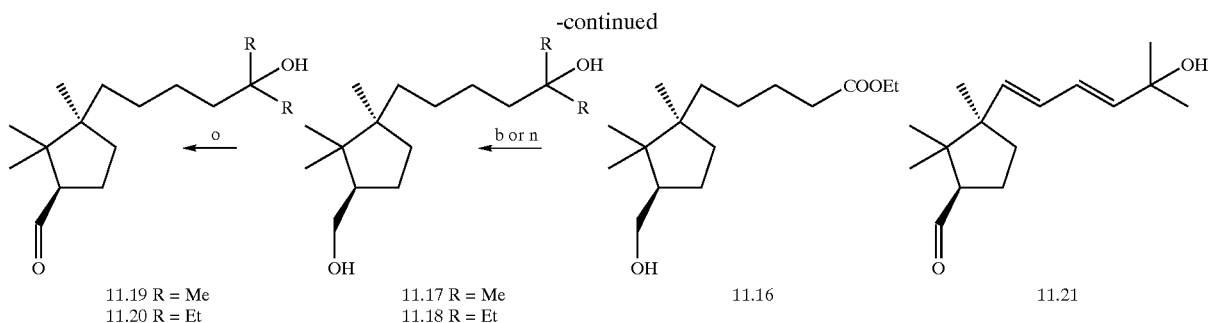

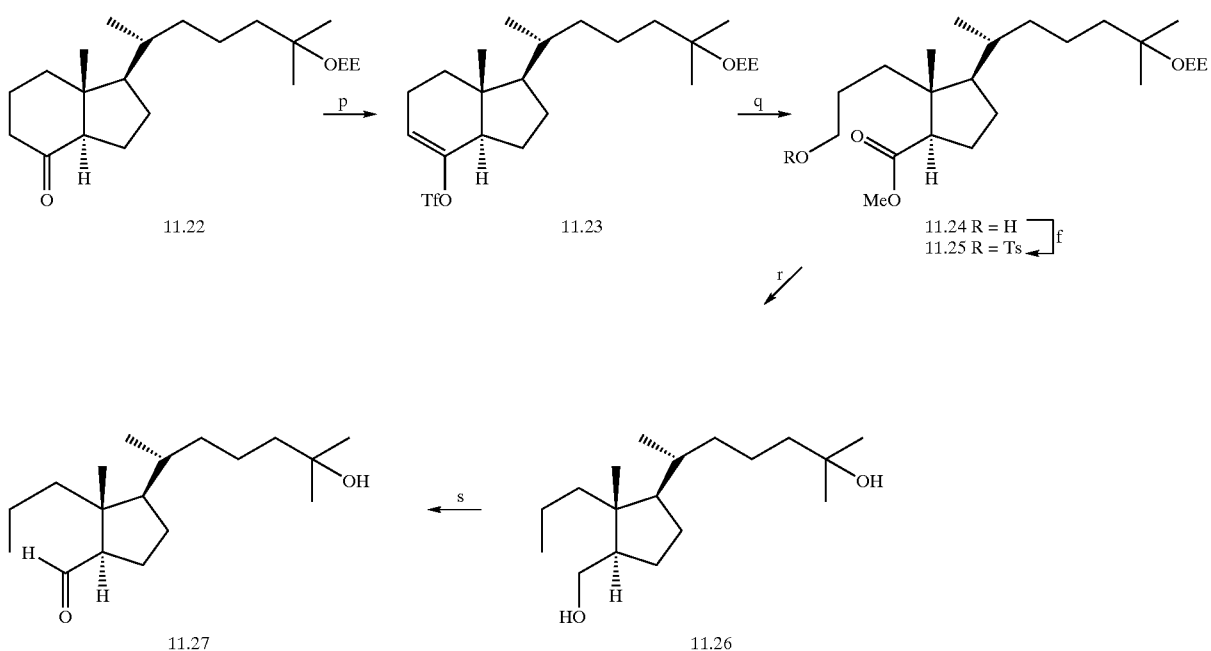

(a) THF, HMPA, 2 h, −20° C. (62%); (b) EtMgBr, Et2O, 5 h, −10° C. (86% for 11.14; 75% for 11.17); (c) TBAF, THF, 1 h, r.t.; (d) SO$_3$-pyridine, CH$_2$Cl$_2$, DMSO, 3 h, −10° C. (40% from 11.4; 63% from 11.10; 80% from 11.13); (e) nBu$_3$SnH, 100° C.; (f) TsCl, Et$_3$N, CH$_2$Cl$_2$, DMAP 71%; (g) (i) 9-BBN, THF, 60° C.; (ii) H$_2$O$_2$, NaOH (85%); (h) ≡—C(Et)$_2$OEE, NaH, DMSO, 90 min, 65° C. (63%); (i) LiAlH$_4$, THF, Et$_2$O, 4 h (88%); (j) vinyl acetate, SAM II, 66 h, 37° C. (60%); (k) tri-ethyl-4-phosphonoacetate, LDA, THF, 24 h. 0°→25° C.; (l) K$_2$CO$_3$, EtOH, r.t. (65% overall); (m) 5% Rh/Al$_2$O$_3$, EtOAc, H$_2$ (90%); (n) MeMgBr, Et$_2$O, 90 min, r.t. (86% for 11.18, 94% for 11.15); (o) TPAP, NMNO, CH$_2$Cl$_2$, 2 h, r.t. (80–78%); (p) LDA, THF, 15 min, −78° C., 2 h, r.t., then PhNTf$_2$, 18 h, 0° C. (65%);(q) O$_3$, NaHCO$_3$, MeOH, −78° C., then NaBH$_4$, MeOH, 18 h, −78° C. to r.t. (91% overall); (r) LiAlH$_4$, THF, Δ, 36 h (61%); (s) TPAP, NMNO, CH$_2$Cl$_{21}$, h, r.t. (50%);

Scheme 11

Examples of precursors for the synthesis of analogues of type IId and which are characterised by a cis-fused bicyclic system are shown in scheme 12. These precursors can be obtained via (a) ozonolysis of vitamin D$_2$, (b) introduction of a side chain and (c) epimerisation at C-13. Epimerisation of the known ketone 12.1 (47) leads to a circa 3:1 ratio in favour of the cis-fused isomer. The 25-hydroxyl group is protected prior to coupling with the A-ring. It is also possible to start from the known inhoffen-Lythgoe diol (48) which can easily be transformed into the monotosylate 12.3. Reaction of 12.3 with the anion of 3-ethoxyethyl-3-methyl-1-butyn leads to 12.4 an intermediate for two precursors. Oxidation and epimerisation afford the ketone 12.5.

On the other hand elimination of the 25-oxy-function leads to 12.6 in which the double bond can selectively be epoxidised. Oxidation of the hydroxyl group and subsequent DBU mediated epimerisation gives cis-fused ketone 12.7.

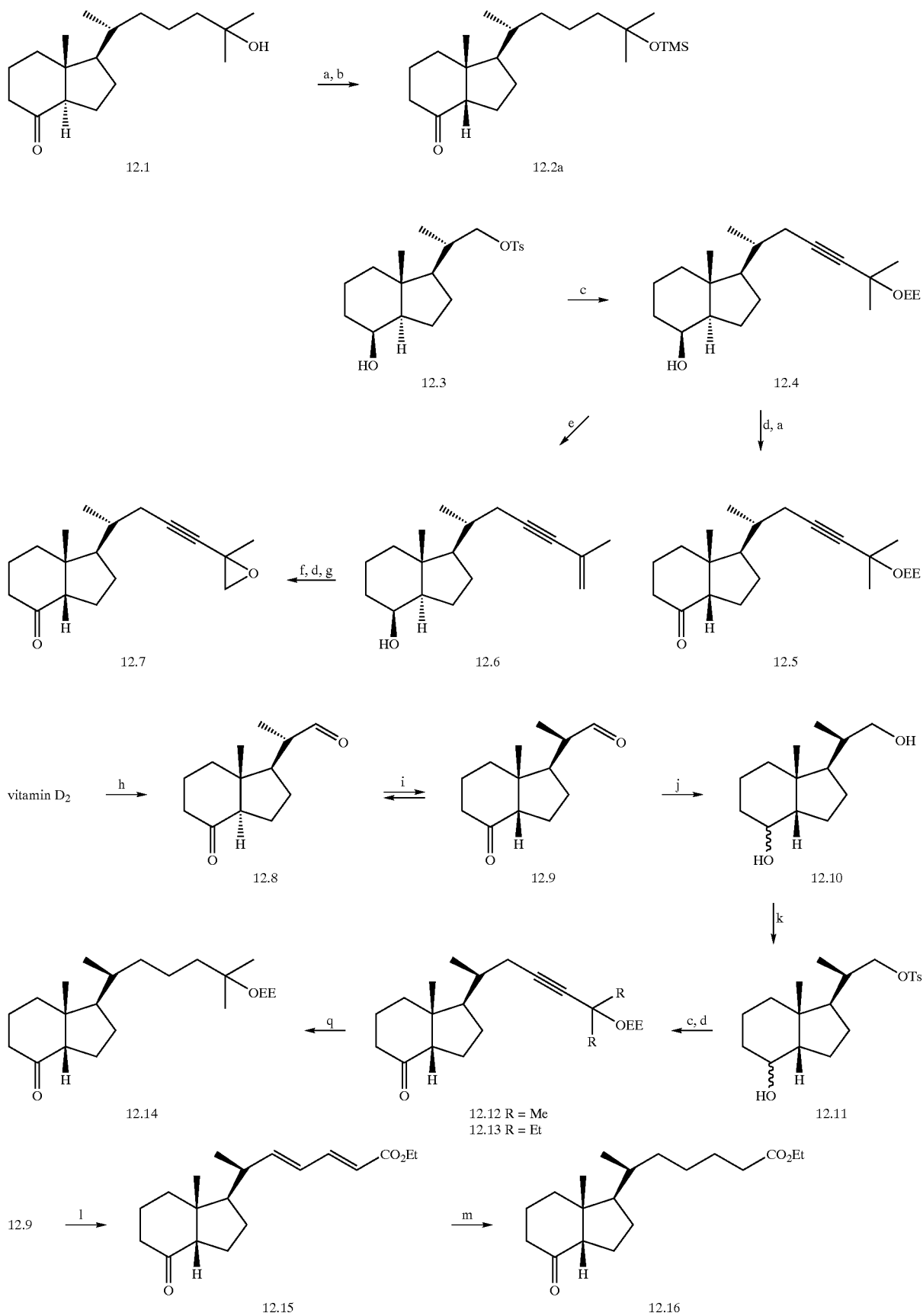

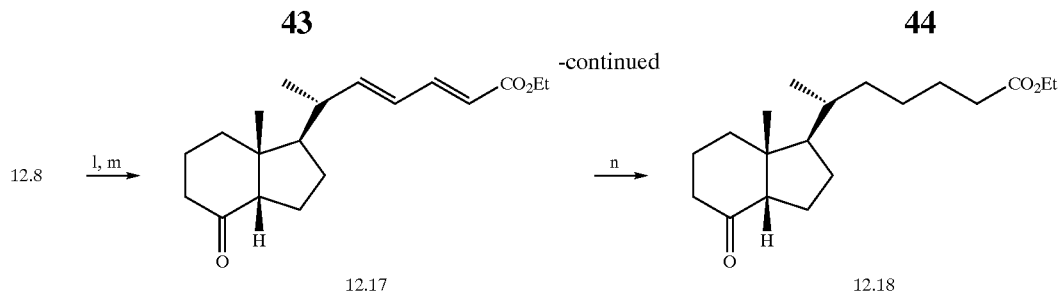

(a) NaOMe, MeOH, 24 hrs, r.t. (73% for 12.2; 65% for 12.5); (b) TMS imidazol, $CH_2Cl_2$, 3 hrs, r.t. (79%); (c) NaH, DMSO, HC≡C—C.($CH_3$)$_2$OEE (67% for 12.4; 56% for 12.12); (d) PDC, $CH_2Cl_2$, 2 hrs (84% for 12.5; 69% for 12.7; 70% for 12.12); (e) TsOH, toluene, 60° C. (74%); (f) mCPBA, $Na_2HPO_4$, THF (81%); (g) DBU, $CH_2Cl_2$, 3 d, r.t.; (h) (i) $O_3$, $CH_2Cl_2$:MeOH (1:1), −78° C.; (ii) $Me_2S$, r.t.; (i) 5% HCl, THF (1:3), 30° C., 36 hrs; (j) $NaBH_4$, MeOH, r.t. (99%); (k) TsCl, py, 0° C., 12 hrs (56%); (l) triethyl-4-phosphonocrotonate, DLA, THF, −78° C.→r.t., 3 h (85%); (m) NaOEt, EtOH, r.t., 21 h (62%); (n) $H_2$, Rh/$Al_2O_3$, EtOAc, r.t., 1.5 h (89–93%).

Scheme 12

Of importance is the fact that efficient epimerisation at C-20 and C-13 can be effected simultaneously. Ozonolysis of vitamin $D_2$ with non reductive work-up gives the keto-aldehyde 12.8 which upon acid catalysed epimerisation leads to a mixture of the four possible isomers from which the major component 12.9 can be isolated by HPLC. It is more facile to isolate the two cis fused isomers together and to reduce the carbonyl functions before separation of the C-20 epimers. The primary hydroxyl group in 12.10 can be tosylated with a sufficient selectivity. Coupling of the tosylate 12.11 with the anion of 3-ethoxyethyl-3-methyl-1-butyn and subsequent oxidation affords the precursor 12.12. An analogous coupling leads to precursor 12.13. These ketones and the tetrahydroderivative 12.14 can be coupled with the anion of 13.2 affording respectively analogues 46, 48 and 47.

Selective Horner-Wittig reaction of the aldehyde function in 12.9 with the anion of triethyl 4-phosphonocrotonate is an alternative for side chain construction. This leads to 12.15 and subsequently to 12.16. Coupling with 13.2 followed by reaction with an appropriate organometal leads to analogues 49 to 52. The same sequence, but starting from the S-epimer 12.8 leads to 12.17 and 12.18 precursors for analogues 53 to 55.

The precursor aldehydes or ketones described in schemes 1, 2, 3, 5, 6, 7, 8, 9, 10, 11 and 12 are coupled with the A-ring phosphine oxides 13.1 and 13.2 using the Lythgoe procedure (scheme 13). In this manner the vitamin $D_3$ analogues 1 to 55 shown in table I are obtained. With respect to the 5- and 6-membered rings of type C, D and E, and combinations CD, CE and DE (see table 1), it is noted that the rings may be saturated, such as cyclopentane or cyclohexane, unsaturated such as cyclopentene or cyclohexene.

Scheme 13

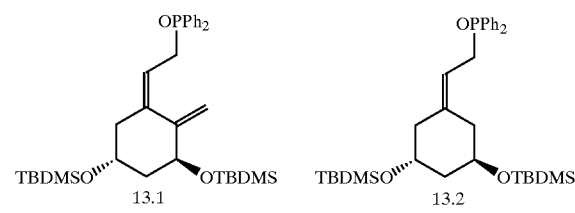

| | | |
|---|---|---|
| R—CHO + 13.1 | a.c | 1 |
| | 1.8d + 13.2 | a.c | 2 |
| 1.11d + 13.1 | a.b | 3 |
| 2.5 + 13.1 | a.b | 4 |
| 2.7 + 13.1 | a.b | 5 |
| | 2.7 + 13.2 | a.b | 6 |
| 2.12 + 13.1 | a.b | 7 |
| | 2.12 + 13.2 | a.b | 8 |
| 3.7 + 13.1 | a.b | 9 |
| 5.6 + 13.1 | a.b | 10 |
| 6.12 + 13.1 | a.b | 11 |
| 6.13 + 13.1 | a.c | 12 |
| | 6.13 + 13.2 | a.c | 13 |
| 6.21α + 13.1 | a.c | 14 |
| 6.22α + 13.1 | a.c | 15 |
| 6.16 + 13.1 | a.c | 16 |
| 6.21β + 13.1 | a.b | 17 |
| 6.22β + 13.1 | a.c | 18 |
| 6.26 + 13.1 | a.e.b | 19 |
| 6.26 + 13.1 | a.f.b | 20 |
| 6.3 + 13.1 | a.e.b | 21 |
| 8.2 + 13.1 | a.b | 22 |
| 8.3 + 13.1 | a.b | 23 |
| 8.4 + 13.1 | a.b | 24 |
| 8.6 + 13.1 | a.d.b | 25 |
| 8.18 + 13.1 | a.b | 26 |
| 8.16 + 13.1 | a.b | 27 |
| 8.17 + 13.1 | a.b | 28 |
| 8.24 + 13.1 | a.b | 29 |
| 7.4 + 13.1 | a.d.b | 30 |
| | 9.4 + 13.2 | a.b | 31 |
| 9.9 + 13.1 | a.b | 32 |
| 9.11 + 13.1 | a.b | 33 |
| | 9.12 + 13.2 | a.b | 34 |
| | 9.14 + 13.2 | a.b | 35 |
| 9.13 + 13.1 | a.b | 36 |
| 11.19 + 13.1 | a.b | 37 |
| 11.20 + 13.1 | a.b | 38 |
| 11.21 + 13.1 | a.b | 39 |
| 11.27 + 13.1 | a.b | 40 |
| 11.11 + 13.1 | a.c | 41 |
| 11.5 + 13.1 | a.b | 42 |
| | 12.2a + 13.2 | a.b | 43 |
| | 12.5 + 13.2 | a.c | 44 |
| | 12.7 + 13.2 | a.c | 45 |
| | 12.12 + 13.2 | a.c | 46 |
| | 12.14 + 13.2 | a.c | 47 |
| | 12.13 + 13.2 | a.c | 48 |
| | 12.15 + 13.2 | a.e.c | 49 |
| | 12.15 + 13.2 | a.f.c | 50 |
| | 12.16 + 13.2 | a.e.c | 51 |

Scheme 13

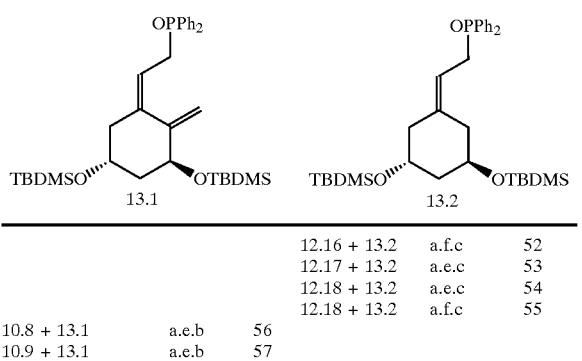

| | | |
|---|---|---|
| | 12.16 + 13.2 | a.f.c | 52 |
| | 12.17 + 13.2 | a.e.c | 53 |
| | 12.18 + 13.2 | a.e.c | 54 |
| | 12.18 + 13.2 | a.f.c | 55 |
| 10.8 + 13.1 | a.e.b | 56 |
| 10.9 + 13.1 | a.e.b | 57 |

(a) n.BuLi, THF −78° C.; (b) n.Bu₄NF, THF; (c) Amberlyst-15, MeOH; (d) PPTS, CH₂Cl₂; (e) MeMgX, THF, r.t.; (f) EtMgX, THF, r.t..

The rings may also be substituted with one or more substituents selected from the group comprising alkyl, alkenyl, alkynyl, aryl, halogen, hydroxy and functional groups derived therefrom such as ethers and esters, and amine and functional groups therefrom such as N-alkylated amines and amides.

The Horner-Wittig coupling using the classical A-ring phosphinoxide and the trans-fused CD-ring ketone leads exclusively to the E-stereochemistry at the 7,8-double bond ( ). The profound modification of the central CD-ring system in the new analogues described above can result in a change in stereoselectivity for that transformation. This is especialy true in cases where the Wittig condensation is performed on cycloalkanones of which the α-positions may be less differentiated compared to the classical example. Hence this problem may be expected especially in the case of the synthesis of analogues of type IIIa, IIId and IIIe. As an example the Wittig condensation on decalone 9.4 leads to a 2:1 mixture of E- and Z-derivatives 14.1 and 14.2 that are further hydrolyzed to analogue 31 that is isolated as a mixture of 2:1 isomers. A similar example is the reaction on 3.7 which led to a separable 4:1 mixture of E:Z-isomers 14.3 and 14.4.

Also in other cases, however, can this stereoselectivity problem occur. As an example the Wittig condensation on aldehyde 11.27 leads to a E:Z mixture of 14.5 and 14.6 that can be separated, one of which leading after hydrolysis to analogue 40.

At higher temperatures vitamin D derivatives possessing the natural triene system are known to rearrange readily into the so-called previtamin D derivatives (scheme 15). In the natural series the vitamin D structure predominates in the equilibrium (approximate ratio at 25° C.=9:1). A substantial change in the CD-ring part of the molecule may, however, affect considerably this equilibrium composition. Also, the conversion of the vitamin form into the previtamin form may occur more readily than in the natural derivatives.

Scheme 14

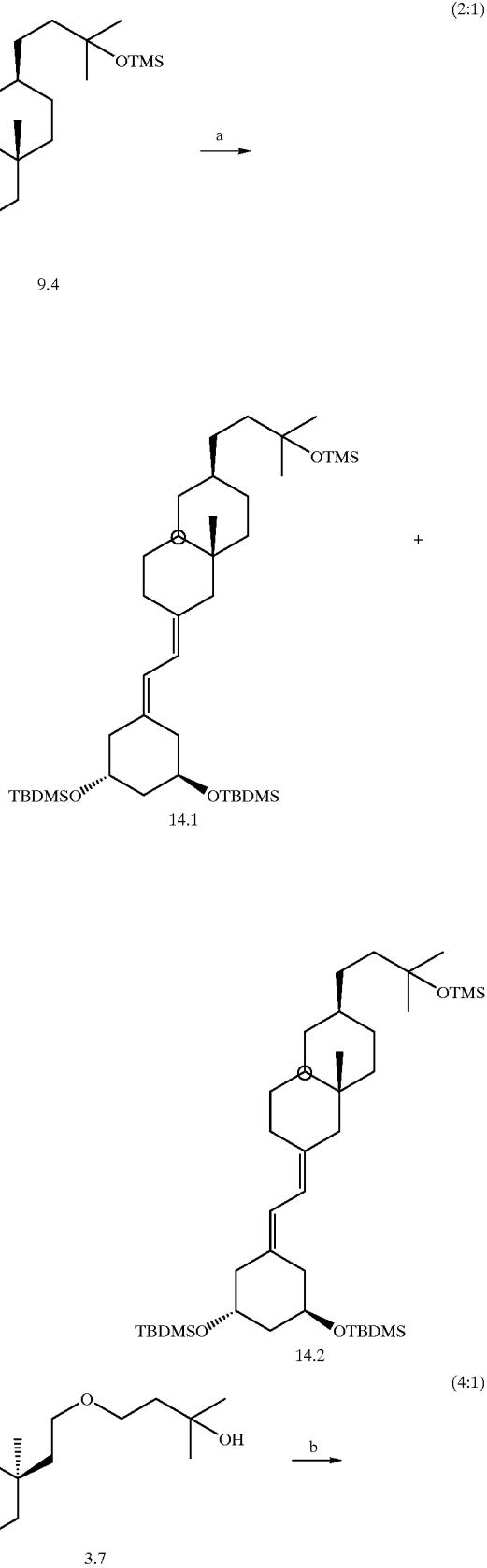

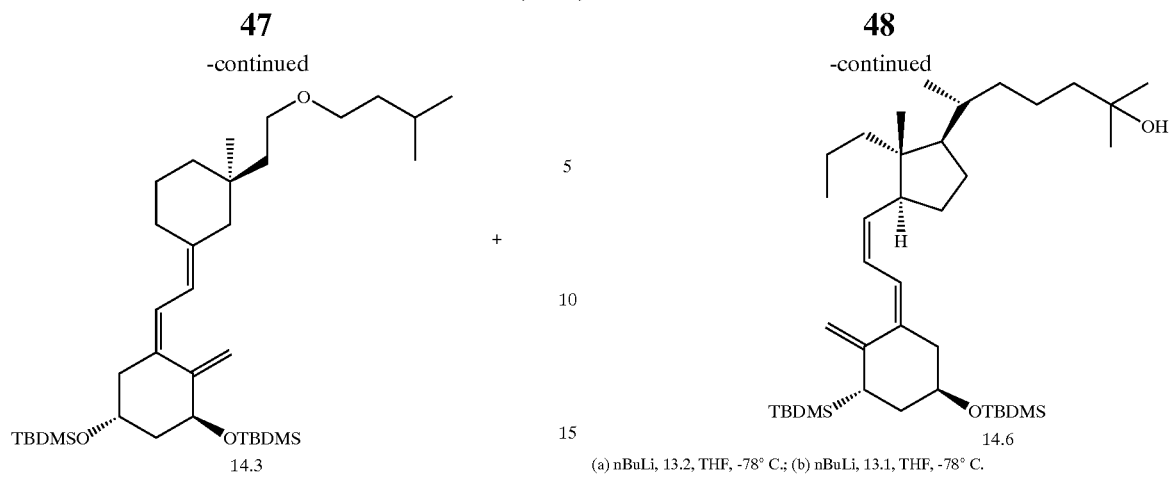
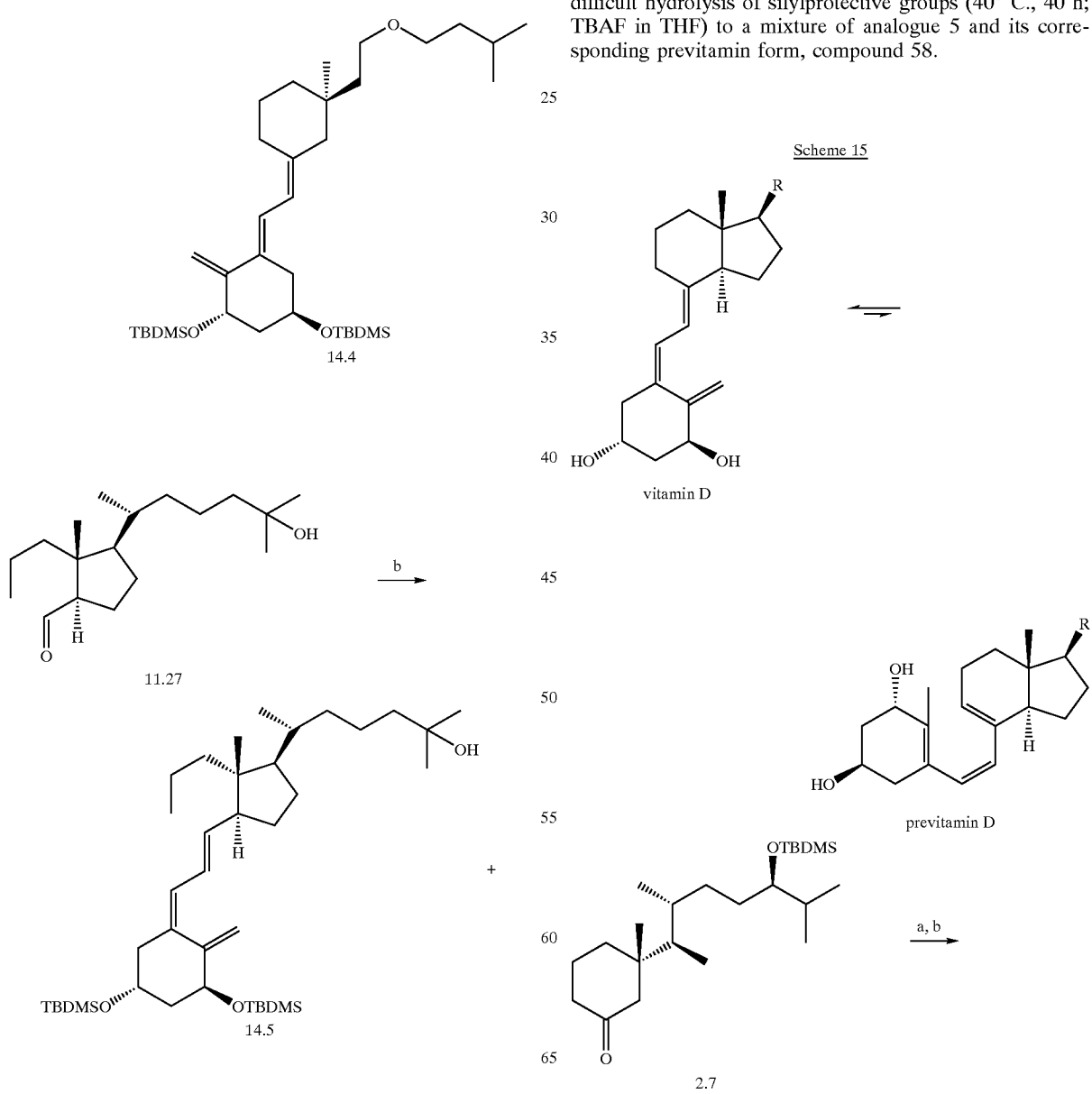
As an example the carbonyl derivative 2.7 was found to lead, after the usual Wittig-Horner coupling and a somewhat difficult hydrolysis of silylprotective groups (40° C., 40 h; TBAF in THF) to a mixture of analogue 5 and its corresponding previtamin form, compound 58.

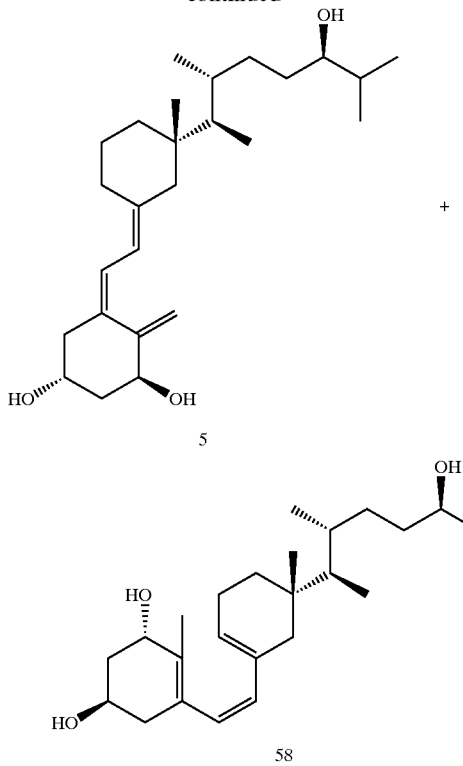

For certain types of analogues the presence of a 19-nor A-ring is mandatory. Ketones, of type VII, when used as precursors of 19-nor analogues can be coupled, using the Lythgoe procedure, with 13.2, an example of phosphine oxide IV, or alternatively with alkynes of type VI. It is also possible to transform ketones VII into vinylic bromide VII which can react with the carbonyl function in V. The 19-Nor-A ring precursors V and VI are alternatives for 13.2 can be obtained from (−)-quinic acid 16.1. The method is based on the "cyclovitamin" strategy for which there are examples in the case of the natural series (19 methylene). The two essential features are the simultaneous removal of the 1- and 4-hydroxyl functions in 16.1 and formation of the bicyclo[3.1.0]hexane skeleton. The 5-hydroxyl group in lactone 16.2 is protected, for instance as a t-butyldimethyl silyl ether; 16.3 can be separated from the minor regioisomer. The two hydroxyl groups are removed by the Barton-McCombie deoxygenation via the bis-thiocarbonyl imidazolide 16.4, as one of the several potential methods (29). Solvolysis of the resulting 16.5 gave 16.6. Transformation of the hydroxyl function into a suitable leaving group and subsequent base-induced cyclopropane formation gave ester 16.8. The two precursors 16.10 and 16.11 are now readily available; one of the possible methods for alkyne formation is reaction of aldehyde 16.10 with dimethyl diazomethylphosphonate (35). Coupling of 16.11 with an appropriate ketone of type VII (such as 12.2b) can be carried out as described in the natural series and comprises reaction of the anion of 16.11, $LiAlH_4$ reduction of the resulting propargylic alcohol unit and acid catalyzed solvolysis giving the 19-nor vitamine analogue 43.

Aldehyde 16.10 can also directly be used via reaction of a appropriate vinylic anion derived from a vinylic halide of type VII (such as 16.12). The vinylic halide is accessible from a ketone with for instance a Wittig type olefination.

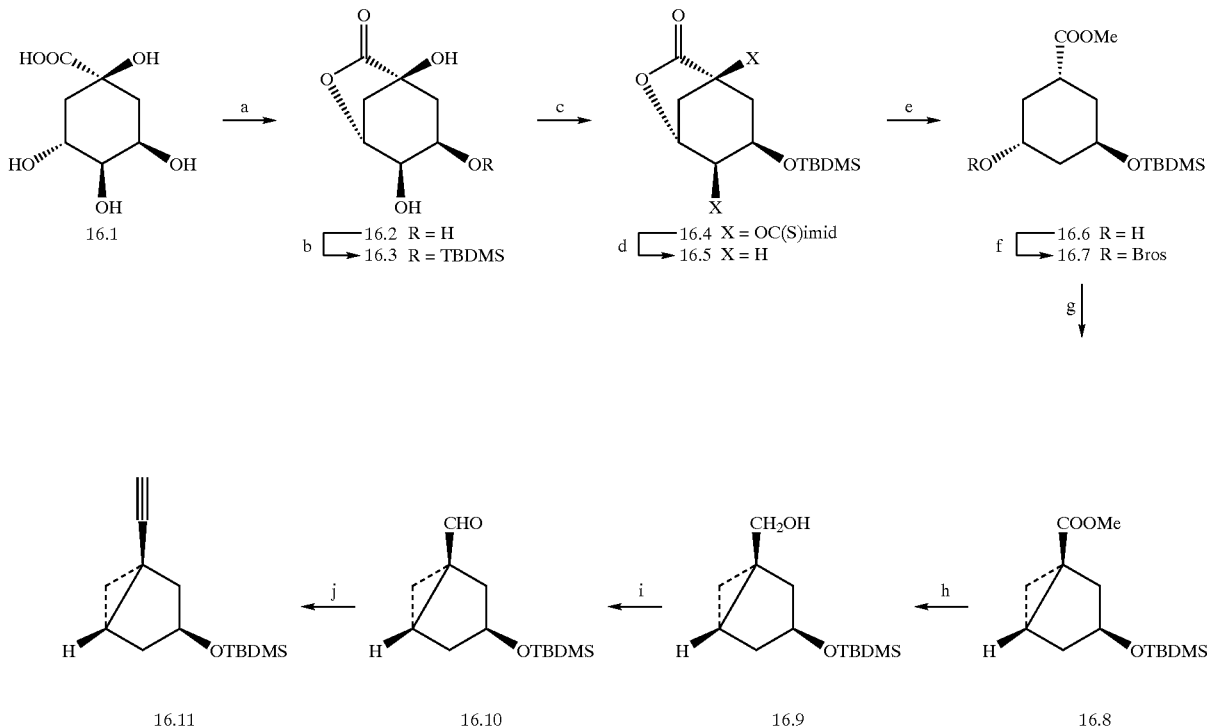

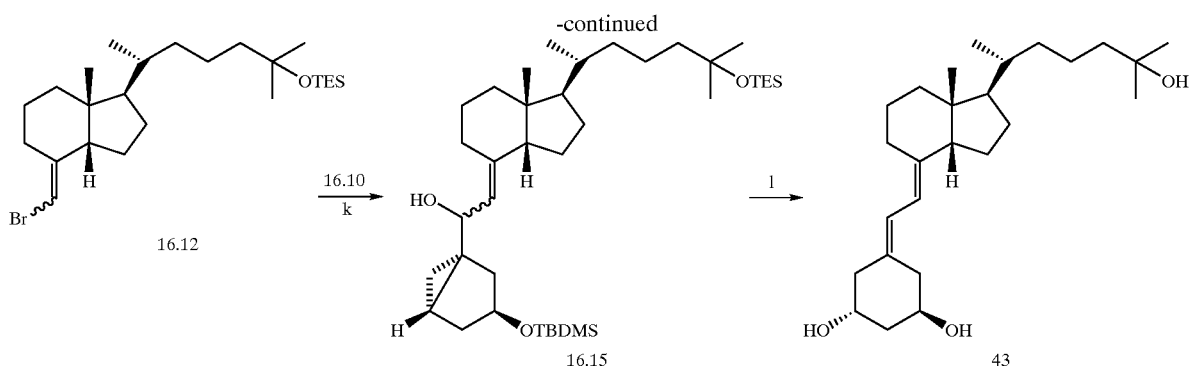

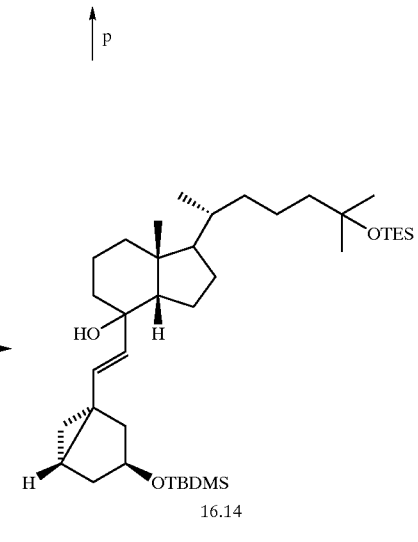

(a) TsOH, toluene, Δ, 15 h (79%); (b) TBDMSCl, imid, DMAP, DMF, r.t., 12 h (66%); (c) (imid)$_2$C=S, DMAP, Δ, 3 d (87%); (d) Bu3SnH, AIBN, toluene, Δ, 5 h (55%); (e) NaOMe, MeOH, 0° C., 1 h (100%); (f) p-BrC$_6$H$_4$SO$_2$Cl, CHCl$_3$, py, 0°—r.t., 13.5 h (100%); (g) t-BuOK, t-BuOH, Δ, 1 h (71%); (h) DIBAH, toluene, −78° C., 2 h (98%); (i) PCC, CH$_2$Cl$_2$, r.t., 2 h (90%); (j) (MeO)$_2$P(O)CHN$_2$, t-BuOK, −78° C.→r.t., 18 h (89%); (k) 16.12, t-BuLi; Et$_2$O; −78° C.; 50 min; 16.10, 1 h (46%); (l) p-TsOH, H$_2$O-dioxane (1:3), 63° C., 6 h (78%); (m) Ph$_3$P$^+$CH$_2$Br; Br$^-$; NaN(TMS)$_2$, THF, −68° C., 1 h; 12.2, −68° C., 1 h, r.t. overnight (56%); (n) 16.11, n-BuLi, THF, −50° C., 1 h, 12.2, r.t., 30 min (55%); (o) LiAlH4, NaOMe, THF, reflux, 2 h, (50%); (p) p-TsOH; H$_2$O-dioxane (1:3), 63° C.; 6 h (40%).

Scheme 16

TABLE 1

Some specific examples of compounds with formula I which are referred to by number in the preparations and examples

| | | 8 | | 14 | | 13 | | 17 | 20 | | | Sidechain: 22, 23, … | 10 | |
|---|---|---|---|---|---|---|---|---|---|---|---|---|---|---|
| # | type | $R_1$ | $R_2$ | $R'_2$ | $R_3$ | $R'_3$ | $R_4$ | $R'_4$ | $R_5$ | $R'_5$ | X | | Y | Y' |
| 1 | acyclic | —H | —H | —H | —H | —H | —H | —H | —H | —H | —CH$_2$CH$_2$CH$_2$C(CH$_3$)$_2$OH | | =CH$_2$ | |
| 2 | CD | | | | —H | —H | | | | —CH$_3$ | —CH$_2$CH$_2$CH$_2$C(CH$_3$)$_2$OH | | H | H |
| 3 | CD | | | —(CH$_2$)$_2$—(S)—CH(OH)—(CH$_2$)$_2$— | | | | | | | —CH$_2$CH$_2$CH$_2$C(CH$_3$)$_2$OH | | =CH$_2$ | |
| 4 | C | —H | —H | —(CH$_2$)$_3$— | —CH$_3$ | | —CH$_3$ | | —H | —CH$_3$ | —CH$_2$CH$_2$—(S)—CH(OH)CH(CH$_3$)$_2$ | | =CH$_2$ | |
| 5 | C | —H | —H | —(CH$_2$)$_3$— | —CH$_3$ | | —CH$_3$ | | —H | —CH$_3$ | —CH$_2$CH$_2$—(R)—CH(OH)CH(CH$_3$)$_2$ | | H | H |
| 6 | C | —H | —H | —(CH$_2$)$_3$— | —CH$_3$ | | —CH$_3$ | | —H | —CH$_3$ | —CH$_2$CH$_2$—(R)—CH(OH)CH(CH$_3$)$_2$ | | =CH$_2$ | |
| 7 | C | —H | —H | —(CH$_2$)$_3$— | —CH$_3$ | | —CH$_3$ | | —H | —CH$_3$ | —CH$_2$CH$_2$CH$_2$C(CH$_3$)$_2$OH | | =CH$_2$ | |
| 8 | C | —H | —H | —(CH$_2$)$_3$— | —CH$_3$ | | —H | | —H | —H | —CH$_2$CH$_2$CH$_2$C(CH$_3$)$_2$OH | | =CH$_2$ | |
| 9 | C | —H | —H | —(CH$_2$)$_3$— | —CH$_3$ | | —CH$_3$ | | —H | —H | —OCH$_2$CH$_2$C(CH$_3$)$_2$OH | | =CH$_2$ | |
| 10 | E | —H | —H | —(CH$_2$)$_3$— | —CH$_3$ | | CH$_2$—CH$_3$ | O O | | ,H | —CH$_2$CH$_2$CH$_2$C(Et)$_2$OH | | =CH$_2$ | |
| 11 | E | —H | —H | —H | —CH$_3$ | | —CH$_3$ | —(CH$_2$)$_2$— | —H | | —CH$_2$CH$_2$CH$_2$C(CH$_3$)$_2$OH | | =CH$_2$ | |
| 12 | E | —H | —H | —H | —CH$_3$ | | —CH$_3$ | —(CH$_2$)$_2$— | —H | | —CH$_2$CH$_2$CH$_2$C(Et)$_2$OH | | =CH$_2$ | |
| 13 | E | —H | —H | —H | —CH$_3$ | | —CH$_3$ | —(CH$_2$)$_2$— | —H | | —CH$_2$CH$_2$CH$_2$C(Et)$_2$OH | | =CH$_2$ | |
| 14 | E | —H | —H | —H | —CH$_3$ | | —CH$_3$ | —(CH$_2$)$_2$— | —H | | —CH$_2$CH$_2$CH$_2$C(Et)$_2$OH | | =CH$_2$ | |
| 15 | E | —H | —H | —H | —CH$_3$ | | —CH$_3$ | —(CH$_2$)$_2$— | —H | | —OCH$_2$CH$_2$C(CH$_3$)$_2$OH | | =CH$_2$ | |
| 16 | E | —H | —H | —H | —CH$_3$ | | —CH$_3$ | —(CH$_2$)$_2$— | —H | —H | —OCH$_2$CH$_2$C(Et)$_2$OH | | =CH$_2$ | |
| 17 | E | —H | —H | —H | —CH$_3$ | | —CH$_3$ | —(CH$_2$)$_2$— | —H | —H | —OCH$_2$CH$_2$C(CH$_3$)$_2$OH | | —H | —H |
| 18 | E | —H | —H | —H | —CH$_3$ | | —CH$_3$ | —(CH$_2$)$_2$— | —H | —H | —OCH$_2$CH$_2$C(Et)$_2$OH | | =CH$_2$ | |
| 19 | E | —H | —H | —H | —CH$_3$ | | —CH$_3$ | —(CH$_2$)$_2$— | —H | | —CH$_2$CH$_2$CH$_2$CH$_2$C(CH$_3$)$_2$OH | | =CH$_2$ | |
| 20 | E | —H | —H | —H | —CH$_3$ | | —CH$_3$ | —(CH$_2$)$_2$— | —H | | —CH$_2$CH$_2$CH$_2$CH$_2$C(Et)$_2$OH | | =CH$_2$ | |
| 21 | E | —H | —H | —H | —CH$_3$ | | —CH$_3$ | —(CH$_2$)$_2$— | —H | | —CH$_2$CH$_2$CH$_2$CH$_2$C(Me)$_2$OH | | =CH$_2$ | |
| 22 | E | —H | —H | —H | —CH$_3$ | | —H | —(CH$_2$)$_3$— | —H | | —OCH$_2$CH$_2$C(CH$_3$)$_2$OH | | =CH$_2$ | |

TABLE 1-continued

Some specific examples of compounds with formula I which are referred to by number in the preparations and examples

| | | 8 | | 14 | | 13 | | 17 | | 20 | Sidechain: 22, 23, . . . | | 10 |
|---|---|---|---|---|---|---|---|---|---|---|---|---|---|
| | type | R$_1$ | R$_2$ | R'$_2$ | R$_3$ | R'$_3$ | R$_4$ | R'$_4$ | R$_5$ | R'$_5$ | X | Y | Y' |
| 23 | E | —H | —H | —H | —CH$_3$ | | —H | —(CH$_2$)$_3$— | —H | —H | —OCH$_2$CH$_2$C(CH$_3$)$_2$OH | H | =CH$_2$ |
| 24 | E | —H | —H | —H | —CH$_3$ | | —H | —(CH$_2$)$_3$— | —H | —H | —OCH$_2$CH(—O—)C(CH$_3$)$_2$ | H | =CH$_2$ |
| 25 | E | —H | —H | —H | —CH$_3$ | | —H | —(CH$_2$)$_3$— | —H | —H | —CH$_2$C≡C—C(CH$_3$)$_2$OH | H | =CH$_2$ |
| 26 | E | —H | —H | —H | —CH$_3$ | —CH$_3$ | —H | —(CH$_2$)$_3$— | —H | —H | —OCH$_2$CH$_2$C(CH$_3$)$_2$OH | H | =CH$_2$ |
| 27 | E | —H | —H | —H | —H | —CH$_3$ | —CH$_3$ | —(CH$_2$)$_3$— | —H | —H | —OCH$_2$CH$_2$C(CH$_3$)$_2$OH | H | =CH$_2$ |
| 28 | E | —H | —H | —H | —H | | —CH$_3$ | —(CH$_2$)$_3$— | —H | —H | —OCH$_2$CH$_2$C(CH$_3$)$_2$OH | H | =CH$_2$ |
| 29 | E | —H | —H | —CH$_3$ | —CH$_3$ | | —H | —CH$_3$ | —H | —H | —CH$_2$CH$_2$CH$_2$C(CH$_3$)$_2$OH | H | =CH$_2$ |
| 30 | E | —H | —H | —H | —CH$_3$ | | —H | —(CH$_2$)$_3$— H,CH=CH—CH | —H | —H | —OCH$_2$CH$_2$C(Et)$_2$OH | H | =CH$_2$ |
| 31 | CE | | | —(CH$_2$)$_2$—(S)—CH—(OH) | —H | —(S)—CH— | —H | —CH$_2$— | —H | —H | (R)—CHCH$_2$CH$_2$C(Me)$_2$OH | H | H |
| 32 | C | | | —(CH$_2$)$_2$— | —H | —(S)—CH— | —H | | —H | —H | (Z)—CHCH$_2$CH$_2$C(Me)$_2$OH | H | =CH$_2$ |
| 33 | CE | | | —(CH$_2$)$_2$— | —H | —(S)—CH— | —H | —O— | —H | —H | —CH$_2$CH$_2$CH$_2$C(Me)$_2$OH | H | =CH$_2$ |
| 34 | CE | | | —(CH$_2$)$_2$— | —H | —(S)—CH— | —H | —O— | —H | —H | —CH$_2$—(E)—CH=CHC(Me)$_2$OH | H | H |
| 35 | CE | | | —(CH$_2$)$_2$— | —H | —(S)—CH— | —H | —O— | —H | —H | —CH$_2$CH$_2$CH$_2$C(Et)$_2$OH | H | H |
| 36 | CE | | | —(CH$_2$)$_2$— | —H | —(S)—CH— | —H | —O— | —H | —H | —CH$_2$CH$_2$CH$_2$C(CH$_3$)$_2$OH | H | H |
| 37 | D | —H | | —H | —CH$_3$ | —CH$_3$ | —H | —CH$_3$ | —H | —H | —CH$_2$CH$_2$CH$_2$C(Me)$_2$OH | H | =CH$_2$ |
| 38 | D | —H | | —H | —(CH$_2$)$_2$— | —CH$_3$ | —H | —CH$_3$ | —H | —H | —CH$_2$CH$_2$CH$_2$C(Et)$_2$OH | H | =CH$_2$ |
| 39 | D | —H | | —H | —(CH$_2$)$_2$— | —CH$_3$ | —H | —CH$_3$ | —H | —H | (E)—CH=(E)—CH=CHC(Me)$_2$OH | H | =CH$_2$ |
| 40 | D | —H | —H | —H | —CH$_3$ | —(CH$_2$)$_3$ | —H | | —H | CH$_3$ | —CH$_2$CH$_2$CH$_2$C(Me)$_2$OH | H | =CH$_2$ |
| 41 | D | —H | | —H | —(CH$_2$)$_2$— | —CH$_3$ | —H | | —H | —H | CH$_2$—C=CC(Et)$_2$OH | H | =CH$_2$ |
| 42 | D | —H | | —H | —(CH$_2$)$_2$— | O CH—CH | —H | | —H | —H, | —CHCH$_2$CH$_2$C(Et)$_2$OH | H | =CH$_2$ |
| 43 | CD | | —H —(CH$_2$)$_3$ | | —CH$_3$ (CH$_2$)$_3$—CH$_3$ | | —H | —CH$_3$ | —H | —CH$_3$ | —CH$_2$CH$_2$CH$_2$C(CH$_3$)$_2$OH | H | H |
| 44 | CD | | —H —(CH$_2$)$_3$ | | (CH$_2$)$_2$ | | —H | —H | —H | —CH$_3$ | —CH$_2$C≡C—C(CH$_3$)$_2$OH | H | H |

TABLE 1-continued

Some specific examples of compounds with formula I which are referred to by number in the preparations and examples

| | | 8 | 14 | | | 13 | | 17 | | 20 | Sidechain: 22, 23, ... | | 10 |
|---|---|---|---|---|---|---|---|---|---|---|---|---|---|
| | type | $R_1$ | $R_2$ | $R'_2$ | $R_3$ | $R'_3$ | $R_4$ | $R'_4$ | $R_5$ | $R'_5$ | X | Y | Y' |
| 45 | CD | | —H (CH$_2$)$_3$ | | (CH$_2$)$_2$—CH$_3$ | | | —H | —H | —CH$_3$ | —CH$_2$C≡C—C(O—CH$_2$)$_2$CH$_3$ | H | H |
| 46 | CD | | —H (CH$_2$)$_3$ | | (CH$_2$)$_2$—CH$_3$ | | | —H | —CH$_3$ | —H | —CH$_2$C≡C—C(CH$_3$)$_2$OH | H | H |
| 47 | CD | | —H (CH$_2$)$_3$ | | (CH$_2$)$_2$—CH$_3$ | | | —H | —CH$_3$ | —H | —CH$_2$CH$_2$CH$_2$C(Me)$_2$OH | H | H |
| 48 | CD | | —H (CH$_2$)$_3$ | | (CH$_2$)$_2$—CH$_3$ | | | —H | —CH$_3$ | —H | —CH$_2$C≡C—C(Et)$_2$OH | H | H |
| 49 | CD | | —H (CH$_2$)$_3$ | | (CH$_2$)$_2$—CH$_3$ | | | —H | —CH$_3$ | —H | (E)—CH═CH—(E)—CH═CHC(Me)$_2$OH | H | H |
| 50 | CD | | —H (CH$_2$)$_3$ | | (CH$_2$)$_2$—CH$_3$ | | | —H | —CH$_3$ | —H | (E)—CH═CH—(E)—CH═CHC(Et)$_2$OH | H | H |
| 51 | CD | | —H (CH$_2$)$_3$ | | (CH$_2$)$_2$—CH$_3$ | | | —H | —CH$_3$ | —H | —CH$_2$CH$_2$CH$_2$CH$_2$C(Me)$_2$OH | H | H |
| 52 | CD | | —H (CH$_2$)$_3$ | | (CH$_2$)$_2$—CH$_3$ | | | —H | —CH$_3$ | —H | —CH$_2$CH$_2$CH$_2$CH$_2$C(Et)$_2$OH | H | H |
| 53 | CD | | —H (CH$_2$)$_3$ | | (CH$_2$)$_2$—CH$_3$ | | | —H | —H | —CH$_3$ | (E)—CH═CH—(E)—CH═CHC(Me)$_2$OH | H | H |
| 54 | CD | | —H (CH$_2$)$_3$ | | (CH$_2$)$_2$—CH$_3$ | | | —H | —H | —CH$_3$ | —CH$_2$CH$_2$CH$_2$C(Me)$_2$OH | H | H |
| 55 | CD | | —H (CH$_2$)$_3$ | | (CH$_2$)$_2$—CH$_3$ | | | —H | —H | —CH$_3$ | —CH$_2$CH$_2$CH$_2$CH$_2$C(Et)$_2$OH | H | H |
| 56 | D | —H | —H | —H | (CH$_2$)$_2$—CH$_3$ (CH$_2$)$_3$ | —CH$_3$ | | —H | —H | —CH$_3$ | —CH$_2$CH$_2$CH$_2$C(Me)$_2$OH | H | ═CH$_2$ |
| 57 | D | —H | —H | | (CH$_2$)$_2$—CH$_3$ (CH$_2$)$_3$ | —CH$_3$ | | —H | —H | —CH$_3$ | —CH$_2$CH$_2$CH$_2$C(Me)$_2$OH | H | ═CH$_2$ |

Several analogues of vitamin D related to this invention, are characterized by a central part whose structure has been thoroughly modified, and yet maintain a biological activity similar to vitamin D. Especially those derivatives which lack the combined presence of the six- and of the five-membered ring typical of the vitamin D skeleton, and which can be considered as non steroidal analogues of vitamin D constitute the first examples of an entirely novel series of vitamin D analogues.

In particular it appears that the classical trans-fused perhydrindane CD-ring system is not in se necessary for biological activity. In this respect it was also discovered that steroidal analogues possessing the unnatural cis-fused CD-ring system were in fact active; in these cases, however, the structure of the A-ring should not allow for possible preferential rearrangement to the previtamin D form.

Finally, it also appears that the presence of certain conformationally restricting structural features, such as rings and/or alkyl substituents within the central part are necessary, since the derivative (1) with a linear unsubstituted central chain is not active.

We found that the compounds described above and belonging to a new class of drugs, including vitamin D analogues with modifications of the CD ring structure, have a selective activity on cell function, such as inhibition of cell proliferation (non-malignant cells such as keratinocytes as well as malignant cell such as breast carcinoma, osteosarcoma and leukemia cells) and also have a high potency for induction of cell differentiation (e.g. cell types as just mentioned) but on the other hand have strikingly lower effect on calcium and bone homeostasis as evaluated in rachitic chicks (by measuring serum and bone calcium, and by measurement of two vitamin D-dependent proteins, serum osteocalcin and duodenal calbindin D) as well as in vitamin D repleted normal mice (using similar end points). Thus, unlike the classical vitamin D compounds, the new drugs do not have the same toxic effect on calcium and bone homeostasis. In light of prior art and studies it was unexpected and surprising that the central part of the classical vitamin D structure, known as the CD ring, is not essential for all actions of the vitamin D hormone and that on the contrary modifications in this part express selective activities of the spectrum of vitamin D activity that can be used therapeutically for several disorders. Specifically the new drugs can be used for the therapy or prevention of immune disorders, such as autoimmune diseases (such as, but not limited to diabetes mellitus type 1, multiple sclerosis, lupus and lupus like disorders, asthma, glomerulonephritis, etc.) selective dysfunctions of the immune system (e.g. AIDS) and prevention of immune rejection [such as rejections of grafts (e.g. kidney, heart, bone marrow, liver, islets or whole pancreas, skin etc.) or prevention of graft versus host disease]. The newly invented drugs can either be used alone or in combination with other drugs known to interfere with the immune system (e.g. cyclosporin, FK 506, glucocorticoids, monoclonal antibodies, cytohines or growth factors . . . ). In analogy with the immune activity of the new compounds, similar effects can be expected in other inflammatory diseases (e.g. rheumatoid arthritis).

skin disorders either characterized by hyperproliferation and/or inflammation and/or (auto)immune reaction (e.g. psoriasis, dyskeratosis, acne). Moreover since these drugs can stimulate the differentiation of skin cells they can be used for the treatment or prevention of alopecia of different origin including alopecia due to chemotherapy or irradiation.

hyperproliferative disorders and cancer such as hyperproliferative skin diseases (e.g. psoriasis) and several types of cancers and their metastases (all types of cancer which have or can be induced to have vitamin D receptors such as but not limited to breast cancer, leukemia, myelo-dysplastic syndromes and lymphomas, squamous cell carcinomas and gastrointestinal cancers, melanomas, osteosarcoma . . . ). The newly invented drugs can, again as for the other indications, be used alone in the appropriate form and route of administration or used in combination with other drugs known to be of therapeutic value in such disorders. These new drugs may be particularly advantageous for such diseases as they can, in contrast to classical chemotherapeutic agents, also stimulate cell differentiation.

endocrine disorders since vitamin D analogues can modulate hormone secretion, such as increased insulin secretion or selective suppression of parathyroid hormone secretion (e.g. in chronic renal failure and secondary hyperparathyroidism).

diseases characterized by abnormal intracellular calcium handling since the new drugs have favourable effects in cells whose functions depend largely on intracellular calcium movements (e.g. endocrine cells, muscle . . . ).

The use of the new compounds can find application as well in human disorders as in veterinary medicine.

The amount of the new compounds necessary for their therapeutic effect can vary according to its indication, route of administration and species (animal/man) treated. The compounds can be administered by enteral, parenteral or local topical route. In the treatment of dermatological disorders a topical application as ointment, cream or lotion is to be preferred over systemic treatment, preferably in a dose of 0.1 to 500 $\mu$g/g. The systemic administration as tablets, capsules, liquid or as sterile preparation in an appropriate carrier, diluent and/or solvent for parenteral injection will use microgram quantities of the compounds per day depending on the indication and the clinical/veterinary situation.

The advantage of the new compounds over the natural or existing vitamin D metabolites or analogues is due to their intrinsic activity in induction of cell differentiation, inhibition of cell proliferation and modulation of the cellular activity in general, while nevertheless displaying reduced calcemic effects in vivo. Indeed such calcemic effects, present in other vitamin D metabolites or analogues are to be considered as undesired side effects since the doses required for to above mentioned indications are sometimes supraphysiologic and would result in serious calcemic abnormalities when other vitamin D metabolites or analogues would be used.

Biological Evaluation of the Novel Vitamin D Analogues

1. Binding Properties of the New Novel Vitamin D Analogues

The methods used to evaluate the binding properties of the new analogues are examples of the state of the art techniques used for steroid hormone (including vitamin D) binding assays as described previously.

The affinity of the analogues of 1$\alpha$,25-(OH)$_2$D$_3$ to the vitamin D receptor was evaluated by their ability to compete with [$^3$H]1α,25-(OH)$_2$D$_3$ (specific activity 180 Ci/mmol Amersham, Buckinghamshire, UK) for binding to the high speed supernatant from intestinal mucosa homogenates obtained from normal pigs (22,23). The incubation was performed at 4° C. for 20 h and phase separation was obtained by addition of dextranoated charcoal. The affinity for 1α,25-(OH)$_2$D$_3$ was $1.06 \pm 0.38 \times 10^{10}$ M$^{-1}$ (M±SD, n=10). The relative affinity of the analogues was calculated from their concentration needed to displace 50% of [$^3$H]1α,25-(OH)$_2$D$_3$ from its receptor compared with 1α,25-(OH)$_2$D$_3$ (assigned a 100% value). (Table 2).

The relative affinity for hDBP was measured by incubating [$^3$H]1α,25-(OH)$_2$D$_3$ and increasing concentrations of 1α,25-(OH)$_2$D$_3$ or its anologues with purified hDBP (0.2 μM) in 1 ml (0.01 M Tris-HCl, 0.154 M NaCl, pH 7.4) for 3 h at 4° C., followed by phase separation by addition of cold dextran-coated charcoal (2,23).

The results obtained with some examples of the new analogues are given in Table 2. These data clearly show a binding to the vitamin D receptor, necessary for their biological activity, while their binding for the vitamin D binding protein, known as DBP, is decreased in comparison with 1α,25-(OH)$_2$D$_3$. We and others have previously demonstrated for other vitamin D analogues that such reduced binding to DBP enhances its ratio of cell differentiating over calcemic effects (23,37).

2. Effects of the Novel Vitamin D Analogues on Cell Proliferation and Cell Differentiation The cell culture systems were used according to the state of the art to evaluate the effects on cell proliferation of non-malignant cells and especially to evaluate their potential for use for dermatological disorders, the new compounds were tested in cultures of human normal keratinocytes.

Human skin keratinocytes were isolated and cultured using a modification of the method of Kitano and Okada (38).

Briefly, the skin from biopsies of patients with breast tumors, was cutted into pieces measuring 3–5 mm and soaked overnight at 4° C. in a solution of dispase (20 Boehringer units/ml). The epidermis was peeled from the dermis, washed with calcium- and magnesium-free phosphate buffered saline and incubated and shaked in a 0.25% trypsin solution for 10 min at room temperature. The reaction was then stopped by addition of PBS containing 10% FCS. The cells were collected after centrifugation at 4° C. for 10 min at 800 rpm. After an additional washing with PBS, the pellet was suspended in culture medium into 25 cm$^2$ primaria flasks from Becton Dickinson. The keratinocytes were cultivated at 37° C. in an atmosphere of 5% CO$_2$ in air. A few hours later, the medium was replaced by new one. The medium [Keratinocyte Medium from Gibco containing Epidermal Growth Factor (5 ng/ml), Bovine Pituitary Extract (35–50 μg/ml) and antibiotics] was renewed every other day until confluency.

Keratinocytes were cultured in 96-well plate and, after 24 hours, were treated with various concentrations of vitamin D analogues, followed by pulse labelling with 1 μCi of [$^3$H] thymidine for 3 hours. Cultures were washed 3 times with PBS and twice with 10% (v/v) ice cold trichloroacetic acid. Cells were solubilized with 1 M NaOH and radioactivity was counted in a scintillation counter.

to evaluate the effect on cell proliferation and induction of cell differentiation, malignant cells were grown in vitro and their proliferation was evaluated by measuring cell number, protein content and the incorporation of radioactive thymidine. As examples of malignant cell human leukemia cells (HL 60), human osteosarcoma cells (MG 63 cells) and both murine and human breast cancer cells (MCF 7, MFM223 and GR cells) were used. In addition the effect of the new drugs showed additive effects when tested in combination with other anticancer drugs (e.g. retinoic acids, anti-estrogens . . . ).

HL-60 cells were seeded at $1.2 \times 10^5$ cells/ml and 1α,25-(OH)$_2$D$_3$ or its anologs were added in ethanol (final concentration <0.2%) in RPMI 1640 medium supplemented with 10% heat-inactivated fetal calf serum (FCS) for 4 d at 37° C. Cells were then assayed for maturation by NBT reduction assay as described (22) using a hemacytometer, or for proliferation by cell counting and [$^3$H] thymidine incorporation. MG 63 cells, seeded at $5 \times 10^3$ cells/ml in 96 well flat bottomed culture plates (Falcon, Becton Dickinson, N.J.) in a volume of 0.2 ml of DMEM and 2% FCS, were incubated with 1α,25-(OH)$_2$D$_3$ or its analogues for 72 h. Osteocalcin was then measured in the culture medium using a homologous human osteocalcin RIA (39). Breast carcinoma cells (MCF-7 or GR) were grown in DMEM/nut.mix F-12 (HAM) medium supplemented with 10% FCS. Cells (5000/Well) were incubated during 24 h in 96 well tissue culture plates (Falcon 3072) followed by a 72 h incubation with/without 1α,25-(OH)$_2$D$_3$ or analogues. The cells were then incubated with [$^3$H]thymidine (1 μCi/well) for 4 h and harvested thereafter in NaOH (0.1 M) and the radioactivity counted. The protein content of the cells was measured by the Pierce BCA protein assay (Rockford, Ill.).

Figure 1D:
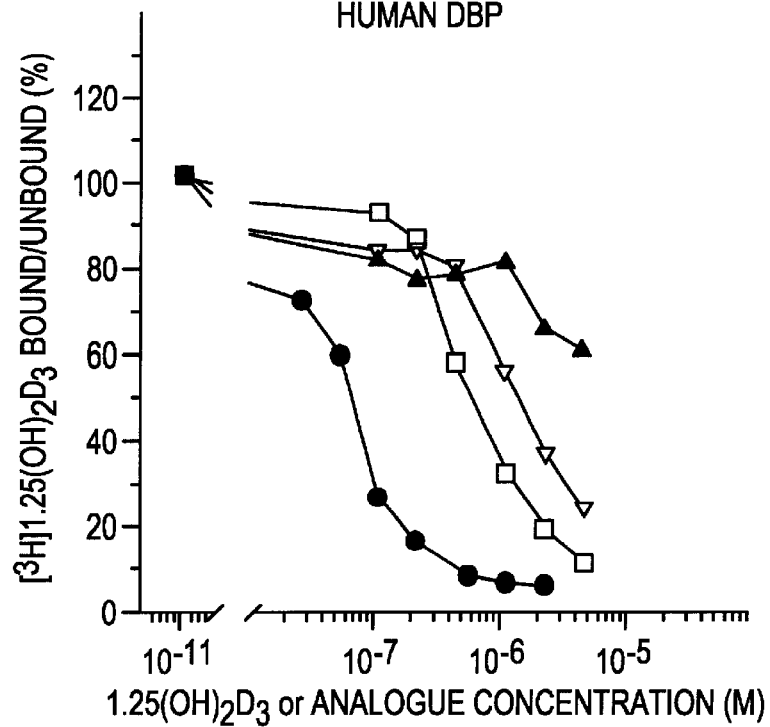
Figure 2A:
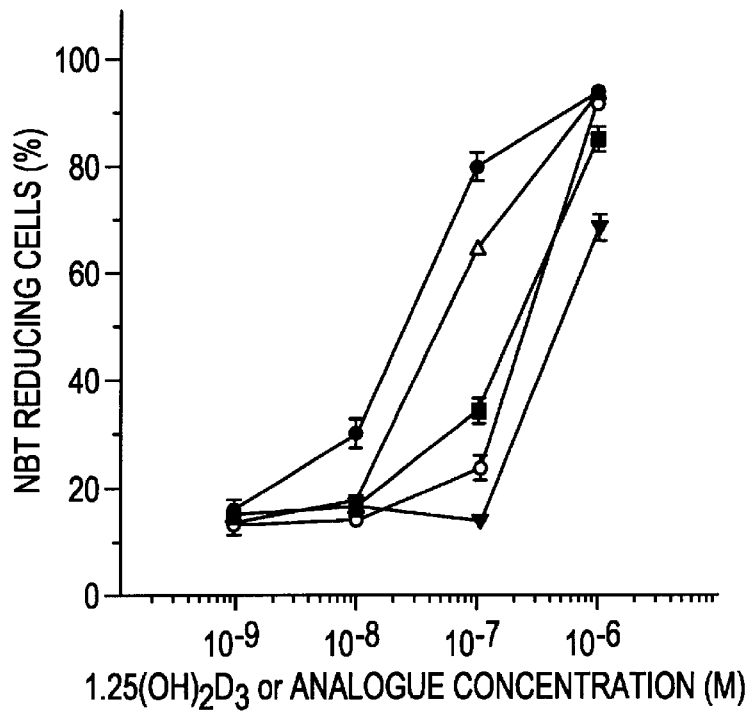
FIGS. 2A and 2B are graphs of induction of cell differentiation in human promyeloid leukemia cells (HL-60) by selected vitamin D analogues as evaluated by potency to induce superoxide production measured by NBT reduction.
Figure 2B:
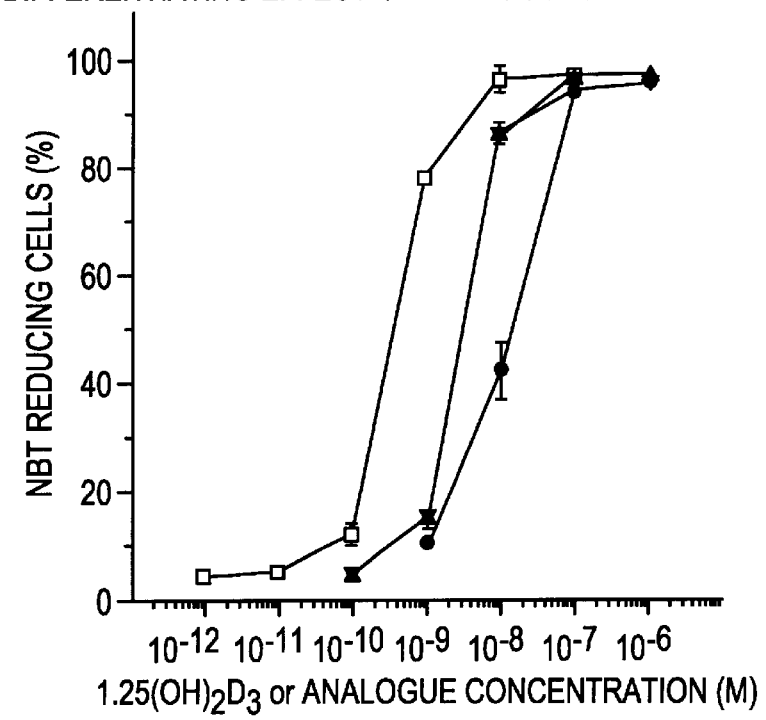
Figure 3A:
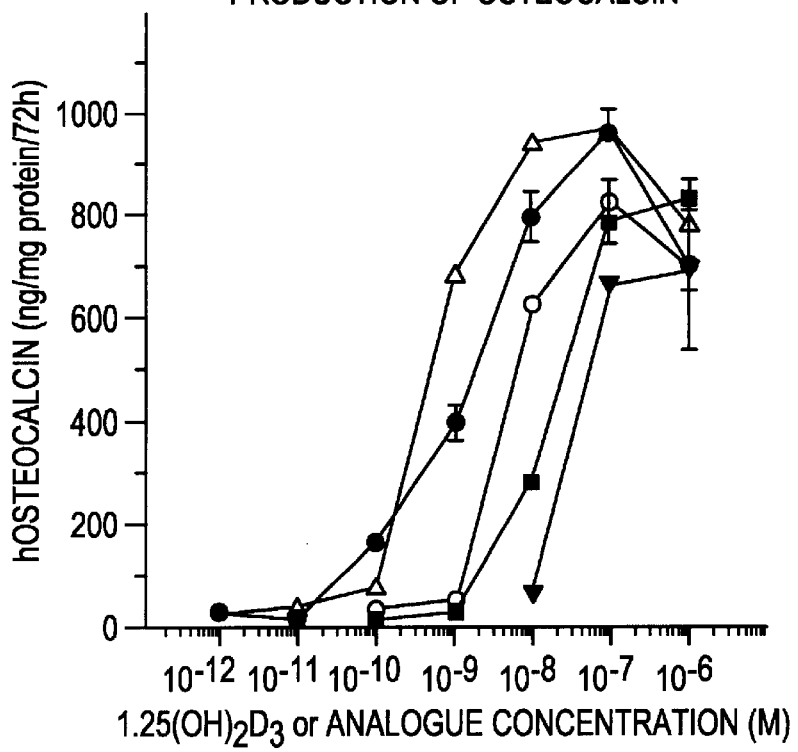
FIGS. 3A and 3B are graphs of induction of cell differentiation in human osteosarcoma cells (MG-63) by selected vitamin D analogues as evaluated by potency to induce ostecalcin secretion.
Figure 3B:
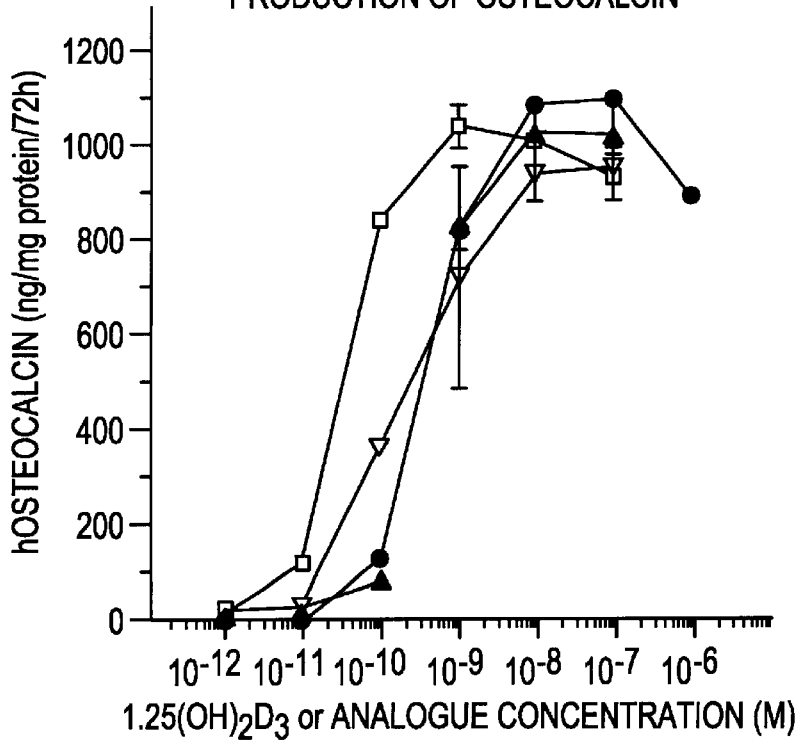
Figure 4A:
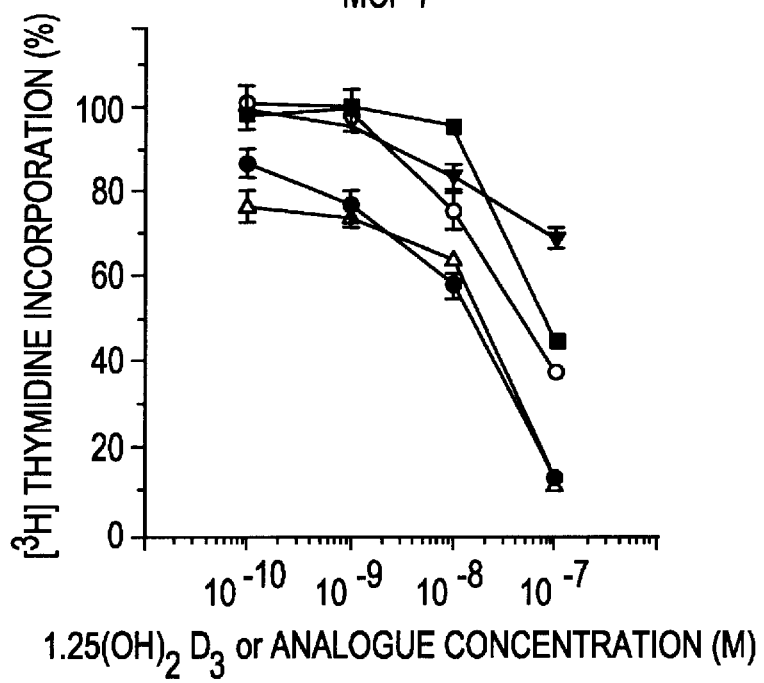
Figure 4B:
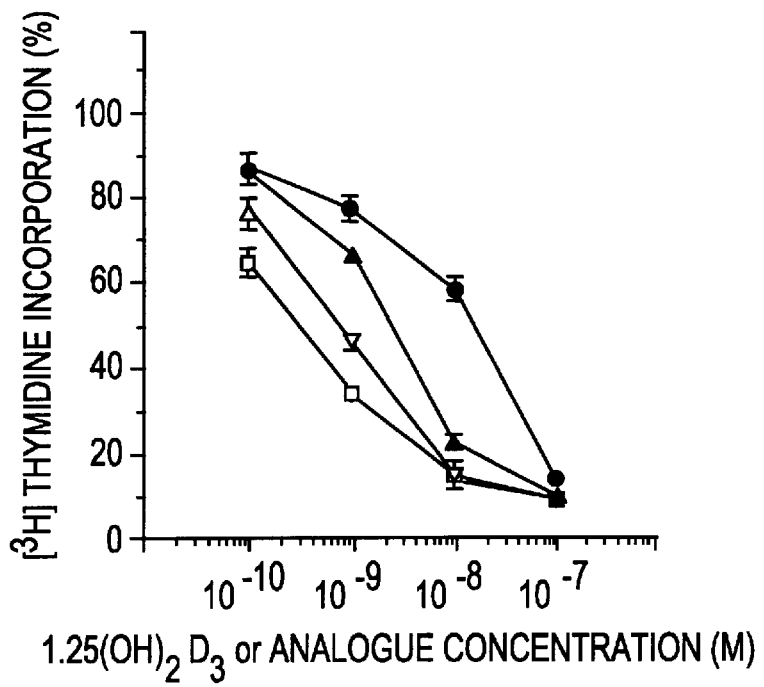
Figure 5A:
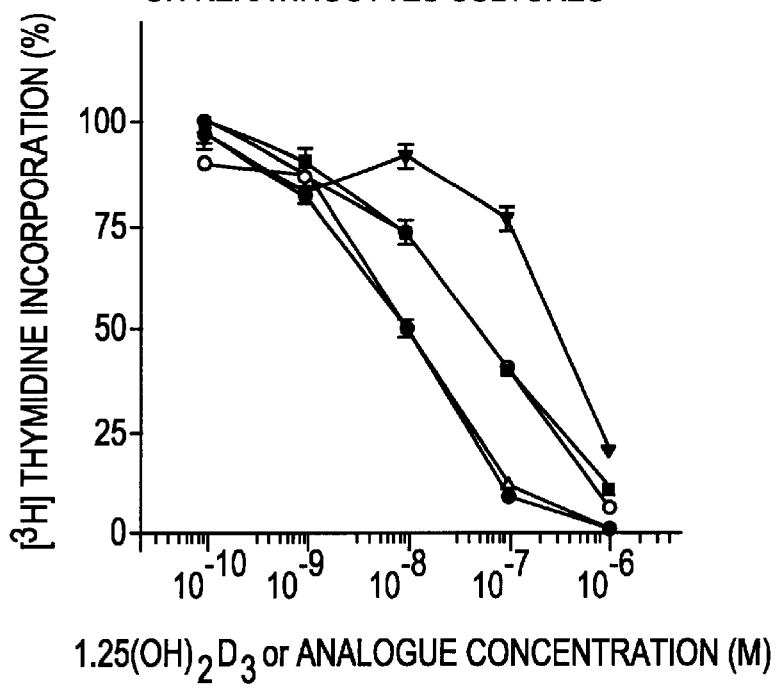
FIGS. 5A and 5B are graphs of inhibition of human keratinocyte cell proliferation by selected vitamin D analogues as evaluated by potency to inhibit [³H]thymidine incorporation in vitro.
Figure 5B:
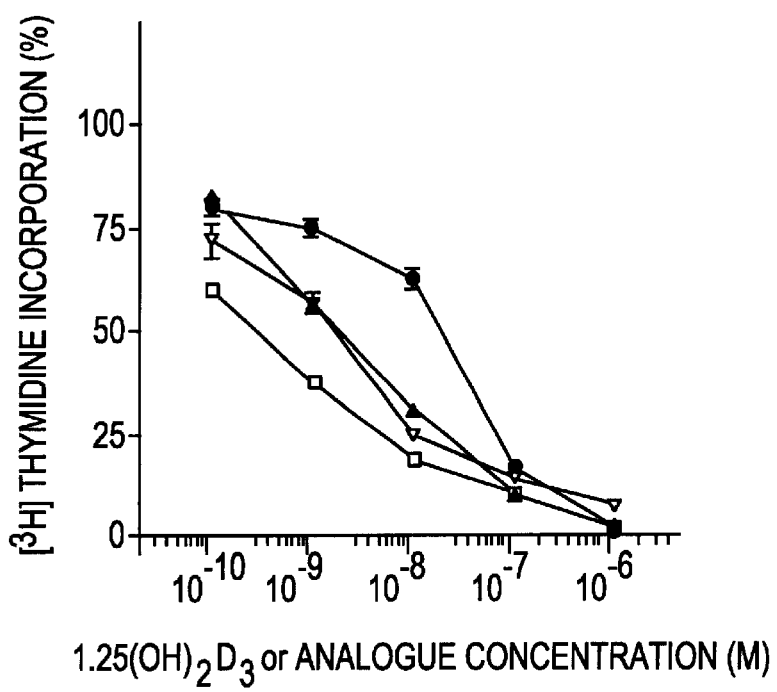

Results obtained with some of the new analogues are presented in Table 2 and FIGS. 1–5.

to evaluate the immune potential of the new drugs their biological activity was tested in a mixed lymphocyte test in vitro according to state of the art procedures; in addition the effects of the analogues for induction of differentiation of HL 60 cells into mature monocytes was tested in vitro. Moreover their immune potential was demonstrated in vivo by their potency to decrease the graft versus host reaction in mice and to prevent the neurological events in a mice model of experimental allergic encephalitis.

The capability of the novel analogues to activate the genomic pathway normally used by natural vitamin D metabolites was demonstrated by transfection studies using a construct of several direct repeats of vitamin D responsive elements (using the mouse osteopontin or rat osteocalcin VDRE sequence coupled to a CAT or hGH reporter gene (constructs made by J. White and G. N. Hendy, Montreal, Canada and M. R. Haussler, Tucson, Ariz.).

TABLE 2

Summary of the biological properties of some selected new vitamin D analogues: affinity for the vitamin D receptor/plasma vitamin D-binding protein, their potency to induce cell differentiation/inhibition of cell proliferation in human leukemia (HL-60), osteosarcoma (MG-63), human breast cancer (MCF-7) cells and human keratinocytes.

| Compound | Affinity for | | Cell differentation/cell proliferation | | | | Ca serum |
|---|---|---|---|---|---|---|---|
| number | pig receptor | human DBP | HL-60 | MG-63 | MCF-7 | keratinocytes | chick |
| 1 | 0.1 | 0.1 | 0.1 | 0.2 | / | / | / |
| 2 | 0 | 0 | 75 | 4.5 | / | / | / |
| 3 | 100 | 10 | 720 | 75 | / | / | / |
| 4 | 60 | 5 | 500 | 100 | 2000 | 2000 | <1 |
| 5 | 80 | 10 | 4000 | 1000 | 6000 | 5000 | 9 |
| 6 | 35 | 2 | 3000 | 1000 | 1000 | / | 18 |
| 7 | 60 | 20 | 1000 | 700 | 6000 | / | 5 |
| 8 | 45 | 3 | >1000 | 300 | 3000 | / | <0.1 |
| 11 | 8 | 19 | 30 | 35 | 30 | 10 | <0.1 |
| 12 | 45 | 5 | 250 | 135 | 80 | 100 | <0.1 |
| 16 | 15 | 0 | 12 | 10 | / | 30 | 0.2 |
| 18 | 4 | 0 | 10 | / | 40 | 35 | <0.1 |
| 19 | 13 | 50 | 10 | 30 | / | / | / |
| 20 | 28 | 8 | 75 | 30 | / | / | / |
| 38 | 80 | 2 | 100 | / | / | / | 2 |
| 43 | 25 | 7 | 40 | 100 | 20 | 100 | 0.1 |
| 44 | 26 | 2 | 320 | 150 | 1000 | 700 | 0.1 |
| 45 | 2.5 | 1.5 | 80 | 10 | 20 | / | 1 |
| 46 | 30 | <0.5 | 1650 | 500 | 1950 | 1000 | 2 |
| 47 | 80 | <0.5 | 500 | 450 | 1050 | 1000 | 10 |
| 48 | 40 | 0.3 | 2200 | 800 | 1500 | 350 | 1 |
| 50 | 9 | 0 | 40 | / | 100 | 60 | 0.1 |
| 51 | 100 | 2 | 600 | 400 | 600 | 400 | 0.8 |
| 52 | 100 | 0 | 600 | 900 | 2000 | 300 | 1.6 |
| 54 | 20 | 1 | 30 | 10 | / | / | 0.4 |
| 55 | 30 | 0 | 65 | 3 | / | / | 0.3 |
| 56 | / | 70 | 100 | / | / | / | / |
| 58 | 3 | 1 | 650 | 115 | 700 | 1000 | <1 |

Biological values are expressed as % of the activity of $1\alpha,25\text{-}(OH)_2D_3$ at 50% of its activity (B50).
For detail of the methods see text.
The numbering of the compounds is identical to the numbers used for the description of their chemical structure in Table 1.

3. In vivo Evaluation of the Immune Potential

To evaluate the immune potential of the analogues the well known model of prevention of autoimmune disease recurrence in the spontaneously diabetic NOD mice was used. When syngeneic NOD islets are transplanted under the kidney capsule of spontaneously diabetic NOD mice, diabetes is only cured for some days, since in the absence of immunomodulatory treatment, the newly transplanted islets are destroyed within 14 days. Cyclosporin A, a well known immunosuppressant, can only delay recurrence at near toxic doses (15 mg/kg/d). Combination of subtherapeutical doses of CyA (7.5 mg/kg/d) with low, noncalcemic dosis of one of the new analogues (number 46, from table 1) (10 μg/kg/2d) a spectacular prolongation of graft survival is observed, with survival of the graft even after discontinuation of therapy (day 60). (Table 3)

TABLE 3

| | Mean survival of islets and range (d) | Calcemia (mg/dl) |
|---|---|---|
| Control | 8 (5–13) | 9.7 |
| CyA 7.5 mg/kg/d | 15 (4–42) | 10.1 |
| CyA 15 mg/kg/d | >58 (22 –> 90) | 10.1 |
| Nr 46 10 μg/kg/2d | 19 (6–51) | 8.5 |

TABLE 3-continued

| | Mean survival of islets and range (d) | Calcemia (mg/dl) |
|---|---|---|
| Nr 46 10 μg/kg/2d + CyA 7.5 mg/kg/d | >69 (23 –> 90) | 9.1 |

4. Calcemic Effects of Novel Vitamin D Analogues

To evaluate calcemic effects in vivo tests were performed using chicks and mice.

The antirachitic activity of the analogues was tested in 3 weeks old vitamin D-deficient chicks injected for 10 consecutive days with $1\alpha,25\text{-}(OH)_2D_3$ or its analogues (22,23). Serum calcium (by atomic absorptiometry) and osteocalcin (by specific RIA), duodenal calbindin D-28K (by RIA) and bone calcium content were measured. The hypercalcemic effect of the most interesting anologues was also tested in vitamin D-replete normal NMRI mice by daily sc injection of $1\alpha,25\text{-}(OH)_2D_3$, its analogues or the solvent for 7 consecutive days, using serum, bone and urinary calcium excretion and serum osteocalcin (by specific mouse RIA) as parameters (40).

Figure 6A:
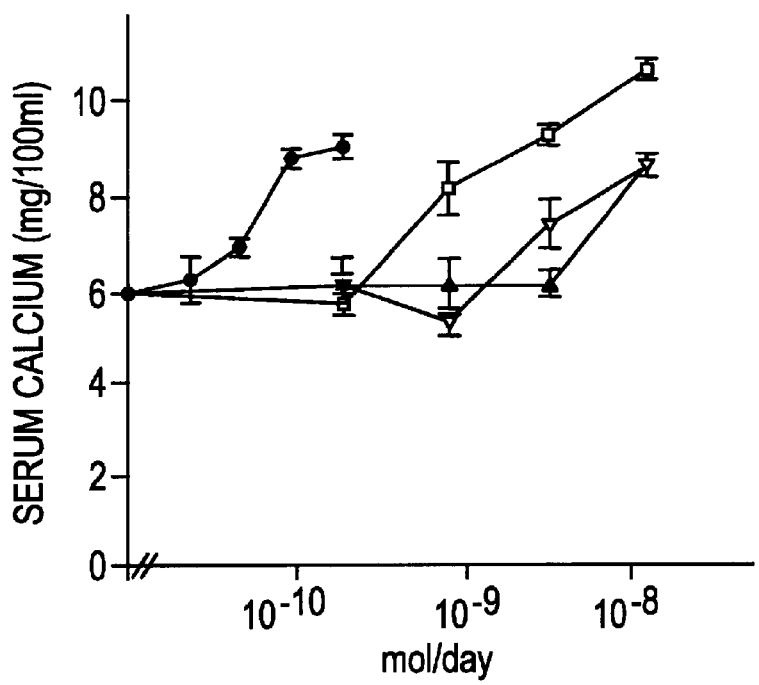
FIGS. 6A–6D are graphs of calcemic effects of selected vitamin D analogues as evaluated in vitamin D deficient chicks after i.m. treatment for ten consecutive days, with serum and bone calcium serum osteocalcin and duodenal calbindin concentration measured to evaluate the calcemic potency.
Figure 6B:
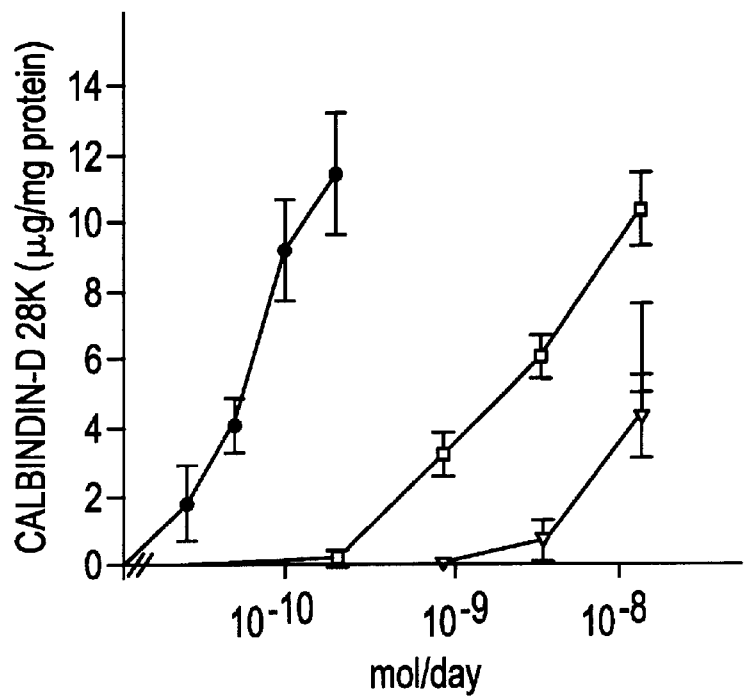
Figure 6C:
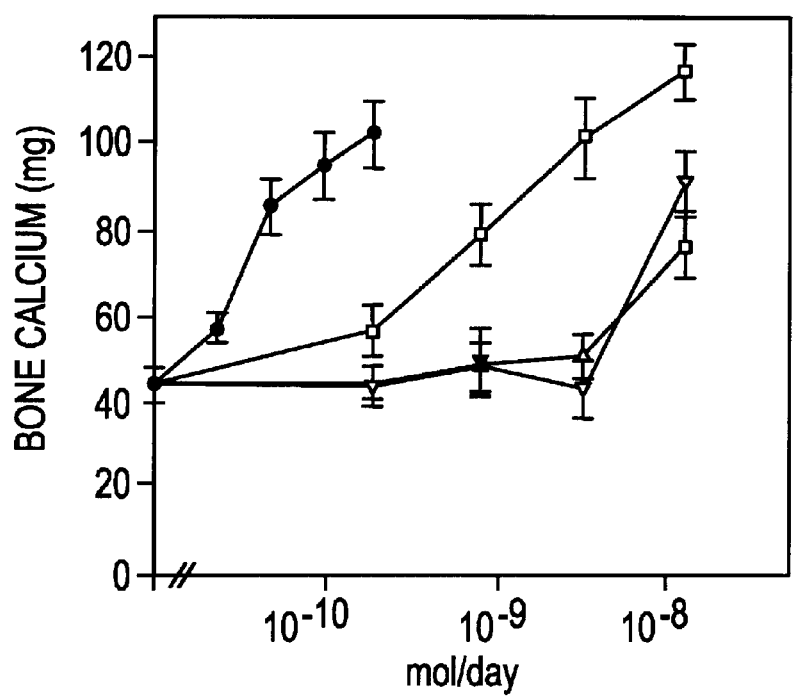
Figure 6D:
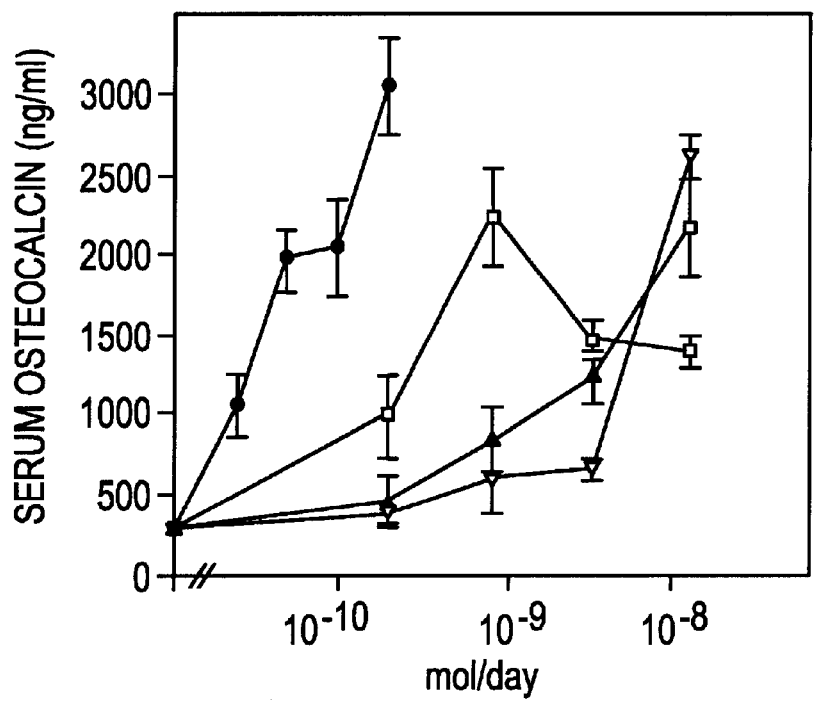

The representative data obtained with some of the new analogues are presented in FIG. 6.

1. Haussler M R, McCain T A. N Engl J Med 1977;297:974–983.

2. Haussler M R, McCain T A. N Engl J Med 1977;297:1041–1050.
3. Kanis J A. J Bone J Surg 1982;64B:542–560.
4. Henry H L, Norman A W. Disorders of Bone and Mineral Metabolism 1992;149–162.
5. Bouillon R, Van Baelen H. Saudi Med J 1989;10:260–266.
6. DeLuca H F. Endocrinology 1992;130:1763–1763.
7. Haussler M R, Mangelsdorf D J, Komm B S, Terpenning C M, Yamaoka K, Allegretto E A, Baker A R, Shine J, McDonnell D P, Hughes M, Weigel N L, O'Malley B W, Pike J W. Recent Prog Horm R 1988,44:263–305.
8. Ozono K, Sone T, Pike J W. J Bone Miner Res 1991;6:1021–1027.
9. Carlberg C, Bendik I, Wyss A, Meier E, Sturzenbecker J, Grippo J F, Hunziker W. Nature 1993;361:657–660.
10. Ross T K, Moss V E, Prahl J M, DeLuca H F. Proc Natl Acad Sci USA 1992;89:256–260.
11. Zhou L-X, Nemere I, Norman A W. J Bone Min Res 1992;7:457–463.
12. Baran D T, Sorensen A M, Honeyman R W, Ray R, Holick M F. J Bone Min Res 1990;5:517–524.
13. Lieberherr M, Grosse B, Duchambon P, Drüeke T. J Biol Chem 1989;264:20404–20406.
14. Binderup L. Biochem Pharmacol 1992;43:1885–1892.
15. Manolagas S C, Hustmyer F G, Yu X-P. Kidney Intl 1990;38,Supp.29:S9–S16.
16. Kragballe K. Arch Dermatol Res 1992;284:S30–S36.
17. Colston K W, Mackay A G, James S Y, Binderup L, Chander S, Coombes R C. Biochem Pharmacol 1992;44:2273–2280.
18. Zhou J Y, Norman A W, Chen D, Sun G, Uskokovic M R, Koeffler H P. Proc Natl Acad Sci USA 1990;87(10): 3929–3932.
19. Binderup L, Latini S, Binderup E, Bretting C, Calverley M, Hansen K. Biochem Pharmacol 1991;42:1569–1575.
20. Okamura W H, Palenzuela J A, Plumet J, Midland M M. J Cell Biochem 1992;49:10–18.
21. Ikekawa N. Med Res Rev 1987;7 no.3:333–366.
22. Bouillon R, Allewaert K, Vanleeuwen J P T M, Tan B-K, Xiang D-Z, Declercq P, Vandewalle M, Pols H A P, Bos M P, Van Baelen H, Birkenhager J C. J Biol Chem 1992;267:3044–3051.
23. Bouillon R, Allewaert K, Xiang D-Z, Tan B-K, Van Baelen H. J Bone Min Res 1991;6:1051–1057.
24.
  a. Lythgoe B, Moran T A, Nambudiry M E N, Fideswell J, Wright P W. J Chem Soc Perkin Trans I 1978;590.
  b. Lythgoe B. Chem Soc Rev 1981:449–475.
25.
  a. Baggiolini E, Lacobelli J, Henessy B, Batcho A, Gereno I, Uskokovic M. J Org chem 1986;51:3098–3108.
  b. Perlman K L, Swenson R E, Paaren H E, Schnoes H K, DeLuca H F. Tetrahedron Lett 1991;32:7663–7666.
26.
  a. Nemoto H, Kimura T, Kuroba H, Fukumoto K. J Chem Soc Perkin trans I 1986:1777–1780.
  b. Wilson S R, Venkatesan A M, Augelli-Szafran C E, Yasmin A. Tetrahedron Lett 1991;32:2339–2342.
27.
  a. Kocienski P J, Lythgoe B, Ruston S. J Chem Soc Perkin Trans I 1979:1290.
  b. Okamura W H. Acc Chem Res 1983;16:81.
28. Audia J E, Boisvert L, Danishefsky S J, Patten A D, Villalobos A, J Org Chem 1989;54:3738–3740.
29. Barton D H, McCombie S W. J Chem Soc Perkin Trans I 1975;16:1574–1585.
30. Castedo L, Mascarenas J C, Mourino A, Perez-Sestelo J. Tetrahedron Lett 1991;32:2813–2816.
31. Lam L, Hui R, Jones J P; J Org Chem 1986;51:2047.
32. Grieco P, Yokoyama Y, Gilman S, Ohfune Y. J Chem Soc 1977:870.
33. Ireland R E, Mueller R H, Willard A K. J Am Chem Soc 1976;98:1868.
34. Mitsunobu O. Synthesis 1981:1.
35. Gilbert J C, Weerasooriya U. J Org Chem 1982;47:1837–1845.
36. Rossiter B E, Swingle N M. Chem Rev 1992:771–806.
37. Yamada S, Nakayama K, Takayama H. Tetrahedron Lett 1981;22:2591.
38. Erickson G W, Fry J L. J Org Chem 1980;45:970–972.
39. McMurry J E, Melton J, Padgett H. J Org Chem 1974;39:259–260.
40. Solladié G, Hutt J. J Org Chem 1987;52:3560.
41. Chapuis C, Brauchlo R. Helv Chim Acta 1992;75:1527.
42. Pfan M, Jabin I, Revial G. J Chem Soc Perkin Trans I 1993:1935.
43. Liu H-J, Ralitsch M. J Chem Soc Chem Commun 1990:997–998.
44. Wicha J, Bal K. J Chem Soc Perkin Trans I 1978:1282–1288.
45. Moskal J, Van Leusen A. Recl Trav Chim Pays-Bas 1987;106:137–141.
46. Hutchinson J H, Money T. Can J Chem 1985;63:3182.
47. Bovicelli P, Lupattelli P, Mincione E. J Org Chem 1992;57:5052–554.
48. Dusso A S, Negrea L, Gunawardhana S, Lopez-Hilker S, Finch J, Mori T. Nishii Y, Slatopolsky E, Brown A J. Endocrinology 1991;128:1687–1692.

EXAMPLE 1

Synthesis of the cis-decalone 1.2b

To a suspension of $AlCl_3$ (2 g, 14.99 mmol) in toluene (250 ml) at −78° C., is added 1.1. The solution was stirred for 1 h under Ar, while the temperature raised to r.t. At a ratio of 2 ml/15 min, isoprene (11 ml; 0.11 mol) in toluene (80 ml) is added with a motor driven syringe. After 6 h the mixture is poured into an ice cooled saturated $NaHCO_3$ solution. The solution is exracted with $Et_2O$ and the combined organic layers are dried ($NaSO_4$). Partial solvent evaporation and filtration through a short silica gel path eluted with $Et_2O$ and HPLC (silica gel; EtOAc:isooctane 4:96) gives 1.2a (3.27 g, 74%).

To a solution of 1.2a (1.3 g, 4.5 mmol) in MeOH (94 ml), is added dropwise a 2M NaOH in MeOH (67 ml, 139.14 mmol). After 2 h solid $CO_2$ is added and the solution is concentrated. The residue is poured into water and extracted with $Et_2O$. The combined organic layers are washed with brine, dried ($NaSO_4$) and after evaporation filtered through a short path of silica gel, eluted with $Et_2O$. HPLC purification (silica gel; EtOAc:isooctane 4:96) gives 1.2b (1.25 g,94%).

Rf: 0.52 (isooctane:acetone 90:10).

IR (KBr): 1712, 1469, 1443, 1366, 1254 $cm^{-1}$.

$^1$H NMR: (500 MHz, $CDCl_3$): δ: 5.34 (1H, b s); 3.91 (1H, s); 2.83 (1H, td, J=5.81, 14.1); 2.58 (1H, dt, J=19.2, 26.45); 2.33 (1H, tm, J=15.07); 2.22 (1H, ddd, J=13.9, 4.25, 2.4); 2.17 (1H, m); 2.09 (1H, dddd, J=13.9, 5.9, 3.4, 2.5); 1.84 (1H, ddd, J=1.18, 4.28,14.1); 1.8 (1H, m); 1.74 (1H, dd, J=16.6, 5.0); 0.94 (9H, s); 0.12 (6H, s); 0.65 (3H, s) ppm.

EXAMPLE 2

Synthesis of 1.3b

To a solution of 1.2b (1.1 g, 3.74 mmol) in MeOH (60 ml) solid $NaBH_4$ (0.7 g, 18.67 mmol) is added in small portions at 0° C. The solution was stirred overnight at r.t. The solution was concentrated and the residue was dissolved in water. Extraction with $CH_2Cl_2$, washing of the combined organic layers with brine, drying ($MgSO_4$) solvent evaporation and HPLC purification (silica gel; acetone:hexane 8:2) gives 1.3a (954 g, 86% with Rf 0.36; acetone:hexane 1:9).

To a cooled (0° C.) solution of 1.3a (800 mg, 2.7 mmol) and DIPEA (6 ml, 65.61 mmol) in $CH_2Cl_2$ (30 ml), is added dropwise MEMCl (2.75 ml, 24.08 mmol). The solution is stirred during 3 h at r.t. and is then diluted with $Et_2O$ (100 ml). The mixture is washed with a 0.1 N HCl solution (30 ml), saturated $NaHCO_3$ (30 ml) and brine. The organic layer is dried ($MgSO_4$) and concentrated. Column chromatography (silica gel; acetone:hexane 1:9), affords 1.3b (1.02 g, 98%).

Rf: 0.72 (acetone:hexane 1:9).

$^1$H NMR: (360 MHz, $CDCl_3$): δ: 5.3 (1H, m); 4.86 (1H, d, J=7.12); 4.69 (1H, d, J=7.12); 3.67–3.79 (3H, m); 3.55 (2H,t,J=7.3); 3.38 (3H, s); 3.22 (1H, dt, J=4.75, 10.1); 2.4–2.48 (1 H, m); 2.16 (1H,t, J=13.5); 1.84–1.60 (5H, m); 1.63 (3H, s); 1.47–1.37 (3H, m); 0.9 (9H, s); 0.05 (6H, s) ppm.

EXAMPLE 3

Synthesis of 1.4

To a solution of 1.3b (1 g, 2.6 mmol) in acetone:water 3:1 (20 ml), is added NMMO (335 mg, 2.9 ml) and $OsO_4$ (100 mg, 0.39 mmol) and the solution is stirred overnight at r.t. Solid $Na_2S_2O_3$ is added and the mixture is extracted with $CH_2Cl_2$. The organic layers are dried (MgSO4), concentrated and filtered through a short path of silica gel (eluted with $Et_2O$). The α-diol (86%) is dissolved in acetone:water 3:1 (24 ml) and the solution is cooled (0° C.). $NaIO_4$ (1.132 g, 5.294 mmol) is added in small portions to the solution. The mixture was stirred overnight under Ar at r.t. The solution was then filtered, concentrated and the residue taken up in water. The solution is extracted with $CH_2Cl_2$ (3×), the organic layers are washed with brine and dried ($MgSO_4$).

After evaporation of the solvent, a colourless oil is obtained (98%). It (650 mg, 1.56 mmol) is dissolved in a degassed solution of KOH (2 g) in water (100 ml). The mixture is stirred overnight at 60° C.–80° C. under Ar-flow. The solution was then extracted with $CH_2Cl_2$ and the organic layers dried ($Na_2SO_4$). Filtration through a short path of silica gel (eluted with $Et_2O$) and HPLC purification (silica gel; acetone:hexane 5:95), affords 1.4 (436 mg, 53%).

Rf: 0.81 (EtOAc).

IR (film): 1669; 1560; 1458; 1376; 1235; 1035 $cm^{-1}$.

$^1$H NMR: (500 MHz, $CDCl_3$): δ: 6.70 (1H, dd, J=5.25, 2.40); 4.83 (1H, d, J=7.07); 4.73 (1H, d, J=7.07); 4.72 (1H, m); 3.76–3.67 (2H, m); 3.64 (1H, dt, J=10.36, 4.35); 3.55 (2H, dt, J=4.7); 3.38 (3H,s); 2.64 (1H, ddd, J=16.8, 6.6, 3.2); 2.45 (1H, ddd, J=22.4, 6.6); 2.35 (1H, dm, J=12); 2.24 (3H, s); 2.02 (1H, dddd, J=2.02, 3.98, 11.3, 16.8); 1.87 (1H, m); 1.73 (1H, ddd, J=13.3, 6.03, 2.9); 1.60–1.43 (2H, m); 0.80 (9H, s); 0.01 (3H, s); –0.1 (3H, s) ppm.

EXAMPLE 4

Synthesis of 1.5a

A cooled (0° C.) solution of 1.4 (320 mg, 0.80 mmol) in hexane (3 ml), is stirred for 1.5 hour under 1 atm $H_2$ in the presence of 10% Pd/C (20 mg) and is then filtered through a short path of silica gel (eluted with $Et_2O$). The solution is evaporated and the residue is dissolved in MeOH (10 ml). NaOMe (40 mg) is added at 0° C. and the solution is stirred for 3 h while the temperature raised to r.t. The mixture is concentrated and the residue is dissolved in saturated $NH_4Cl$ solution. Extraction with $Et_2O$, drying ($MgSO_4$) and HPLC purification (silica gel; acetone:hexane 1:9), affords 1.5a (311 mg, 97%).

Rf: 0.15 (acetone:petr.ether 1:9).

IR (film) 1709; 1471; 1357; 1253; 1201 $cm^{-1}$.

$^1$H NMR: (500 MHz, $CDCl_3$): δ: 4.77 (1H, d, J=7.08); 4.64 (1H, d, J=7.09); 3.88 (1H, ppd, J=2.46); 3.68–3.59 (2H, m); 4.49 (2H, t, J=4.7); 3.32 (3H, s); 3.31 (1H, dt, J=4.3, 10.5); 2.77 (1H, dt, J=10.6, 8.0); 2.06 (3H, s); 1.99–1.89 (2H, m); 1.88–1.80 (1H, m); 1.76 (1H, ddd, J=11.4, 3.7, 7.1); 1.69 (1H, ddd, J=13.7, 6.1, 3.0); 1.62–1.52 (2H, m); 1.51–1.43 (1H, m); 1.38 (1H, ddt, J=13.7, 3.7, 2.3); 1.24–1.17 (1H, m); 0.82 (9H, s); –0.05 (3H, s); –0.10 (3H, s) ppm.

EXAMPLE 5

Synthesis of 1.6a

To a cooled (0° C.) solution of $Ph_3P^+CH_3Br^-$ (112 mg, 0.31 mmol) in THF (1 ml) and HMPA (1 ml) under Ar, is added BuLi in THF (0.116 ml, 0.289 mmol) followed after 1 h by 1.5a (48 mg, 0.12 mmol) in THF (1 ml). The solution is stirred for 3 h under Ar, while the temperature raised to r.t. Concentration and column chromatographic purification (silica gel; acetone:hexane 1:9), gives 1.5b (48 mg, 100% with Rf 0.47; acetone:hexane 1:9).

To a stirred solution of 1.5b (48 mg, 0.12 mmol) in THF (0.5 ml) under Ar at r.t. is added a 0.5 M solution of 9-BBN in THF (1 ml, 0.5 mmol). After 4 h EtOH (0.1 ml), NaOH 6N (0.125 ml) and 30% $H_2O_2$ (0.25 ml) are added, and the solution stirred under Ar for 1 h at 60° C. The mixture is poured into brine and extracted with $Et_2O$ (3×). Drying ($MgSO_4$), solvent evaporation and HPLC purification (silica gel; acetone:hexane 15:85) gives 1.6a (37 mg, 74%).

Rf: 0.24 (acetone:hexane 2:8).

IR (film): 3445; 2930; 2878; 1469; 1364; 1252 $cm^{-1}$.

$^1$H NMR: (500 MHz, $CDCl_3$): δ: 4.82 (1H, d, J=7.1); 4.71 (1H, d, J=7.1); 3.99 (1H, s); 3.75–3.63 (3H, m); 3.54 (2H, t, J=4.64); 3.4–3.32 (2H, m); 3.38 (3H, s); 1.95–1.15 (12H, m); 1.10 (1H, t, J=9.81); 0.97 (3H, d, J=6.85); 0.88 (9H, s); 0.04 (3H, s); 0.02 (3H, s) ppm.

EXAMPLE 6

Synthesis of 1.8a

To a stirred solution at 0° C. of the alcohol 1.6a (35 mg, 0.083 mmol) in $CH_2Cl_2$ (2 ml) and $Et_3N$ (0.5 ml), is added TsCl (32 mg, 0.168 mmol) at 0° C. and the solution is stirred 12 h at r.t. The mixture is filtered through a short path of silica gel (eluted with acetone:hexane 15:85). HPLC purification (silica gel; acetone:hexane 15:85) gives 1.6b (43 mg, 91% with Rf 0.26; acetone:hexane 15:85).

NaH (15 mg, 0.38 mmol) in DMSO (1.5 ml) is stirred for 2 h at 60° C. under Ar, the solution was then stirred at r.t. 2-(1-ethoxy)-ethyloxy-2-methyl-3-butyne (547 mg, 3.5 mmol) is then added dropwise at r.t. After 30 min 1.6b (200 mg, 0.35 mmol) in DMSO (1.3 ml) is added and the mixture stirred for 1.5 h at r.t. The mixture was then poured in saturated NaHCO$_3$ solution and extracted with Et$_2$O. Drying (MgSO$_4$), solvent evaporation and HPLC purification (silica gel; acetone:hexane 1:9) gives 1.7 (136 mg, 70% with Rf 0.38; acetone:hexane 1:9).

1.7 (40 mg, 0.0721 mmol) is dissolved in EtOAc (3 ml) and 10% Pd/C (3 mg) is added. The suspension was shacked under 4 bar H2 for 1 h at r.t. The mixture is then filtered through a short path of silica gel (eluted with EtOAc) giving 1.8a (12 mg, 34%).

Rf: 0.20 (acetone:hexane 15:85).

IR (film): 3456; 2932; 2861; 1368; 1251 cm$^{-1}$.

$^1$H NMR: (500 MHz, CDCl$_3$): δ: 4.83 (1H, d, J=7.1); 4.71 (1H, d, J=7.1); 3.92 (1H, s); 3.76–3.68 (2H, m); 3.56 (2H, t, J=4.7); 3.39 (3H, s); 3.35 (1H, dt, J=10.3, 4.0); 1.96–1.73 (5H, m); 1.61–1.22 (10H, m); 1.21 (6H, s); 1.14–0.98 (4H, m); 0.88 (12H, m); 0.03 (3H, s); 0.01 (3H, s) ppm.

EXAMPLE 7
Synthesis of 1.8d

To a cooled (–78° C.) and stirred solution of 1.8a (10 mg, 0.02054 mmol) in CH$_2$Cl$_2$ (1 ml), is added 1.5 M Me$_2$BBr in CH$_2$Cl$_2$ (0.034 ml, 0.05 mmol). The mixture is stirred for 3 h at –78° C. and is then added dropwise to a vigorously stirred solution of saturated NaHCO$_3$ and THF. The mixture was extracted with Et$_2$O. Drying (MgSO$_4$), solvent evaporation and HPLC purification (silica gel; acetone:hexane 2:8), gives 1.8b (6 mg, 73%).

To a solution of diol 1.8b (5 mg, 0.0125 mmol) in CH$_2$Cl$_2$ (2 ml) at r.t. is added PDC (14 mg, 0.0376 mmol). The solution is stirred for 4 h and is then filtered through a short path of silica gel (acetone:hexane 3:7) giving 1.8c (5 mg, 99%).

Rf: 0.21 (acetone:hexane 2:8).

$^1$H NMR: (500 MHz, CDCl$_3$): δ: 3.93 (1H, br s); 3.35 (1H, dt, J=4.0, 10.1); 1.96–1.15 (17H, m); 1.21 (6H, s); 1.12–0.99 (3H, m); 0.9–0.88 (12H, m); 0.05 (3H, s); 0.02 (3H, s) ppm.

The ketone 1.8c (5 mg, 0.0126 mmol) was dissolved in THF (1 ml) and TSIM (0.5 ml, 3.41 mmol) is added. The mixture is stirred for 1 h at r.t. and is then purified by chromatography (silica gel; acetone:hexane 1:9) giving 1.8d (5.8 mg, 98% with Rf 0.55; acetone:hexane 1:9).

EXAMPLE 8
Synthesis of 1.9c

Alkene 1.5b (105 mg, 0.264 mmol) is stirred with 1M TBAF (1 ml, 1 mmol) in THF (1.5 ml) for 10 d at 30° C. The mixture is concentrated and purified by chromatography (silica gel; acetone:hexane 3:7) giving 1.9a (5.8 mg, 99%).

To a suspension of NaH (70 mg, 2.92 mmol) in THF (5 ml) is added dropwise 1.9a (32 mg, 0.113 mmol) in THF (2 ml). After stirring for 0.5 h and cooling (0° C.) CS$_2$ (0.349 ml, 5.8 mmol) is added dropwise and the stirring is continued for 24 h while the temperature raised to r.t. MeI (0.375 ml, 6 mmol) is added dropwise and the solution is stirred for 2 h. The mixture is poured in a 0.1 N HCl solution. Extraction with Et$_2$O, drying (MgSO$_4$), evaporation and HPLC purification (silica gel; acetone:hexane 2:8), gives 1.9b (41 mg, 97%).

To a solution of Bu$_3$SnH (1 ml, 1.08 mmol) and AIBN (2 mg) in toluene (5 ml) at 110° C., is added dropwise (0.5 h) 1.9b (41 mg, 0.11 mmol) in toluene (2 ml). The mixture is stirred for 8 h at 110° C. Column chromatography (silica gel; acetone:hexane 1:9), followed by HPLC (silica gel; acetone: hexane 3:7), gives 1.9c (27 mg, 92%).

Rf: 0.3 (acetone:hexane 5:95).

IR (film): 2927; 2872; 1447; 1113; 1043 cm$^{-1}$.

$^1$H NMR: (500 MHz, CDCl$_3$): δ: 4.83 (1H, d, J=7.1); 4.71 (1H, d, J=7.1); 4.7–4.67 (2H, m); 3.77–3.66 (2H, m); 3.57 (2H, t, J=4.8); 3.4 (3H, s); 3.38 (1H, dt, J=4.2, 9.9); 2.16 (1H, m); 2.08 (1H, m); 1.99 (1H, m); 1.88–1.76 (2H, m); 1.67 (3H, s); 1.57–1.46 (2H, m); 1.36–1.1 (6H, m); 0.90–0.80 (2H, m) ppm.

EXAMPLE 9
Synthesis of 1.10b

From 1.9c as described for 1.6b from 1.5b. Overall yield of the epimeric mixture 20-S, 20-R (ratio 8:2) is 82%.

Rf: 0.35 (acetone:hexane 15:85).

IR (film): 2931; 2876; 1458; 1362; 1189 cm$^{-1}$.

$^1$H NMR: (500 MHz, CDCl$_3$): δ: 7.78 (2H, d, J=8.3); 7.35 (2H, d, J=8.3); 4.80 (1H, d, J=7.1); 4.68 (1H, d, J=7.1); 3.97 (1H, dd, J=9.5, 5.0); 3.83 (1H, m); 3.73–3.64 (2H, m); 3.54 (3H, t, J=4.7); 3.39 (3H, s); 3.38 (3H, s); 3.28 (1H, dt, J=10.1, 4.3); 2.54 (3H, s); 2.03 (1H, m); 1.91–1.81 (2H, m); 1.78–1.47 (4H, m); 1.3–1.03 (5H, m); 0.95–0.79 (2H, m); 0.91 (3H, d, J=6.9); 0.78 (3H, d, J=6.9) ppm.

EXAMPLE 10
Synthesis of 1.10d

To a solution of 1.10b (40 mg, 0.091 mmol) in DMSO (1.5 ml), is added KI (150 mg, 0.91 mmol). The mixture is stirred for 4 h at 60° C. and is then poured out in brine. The solution was extracted. Extraction with Et$_2$O, drying (MgSO$_4$), solvent evaporation and flash chromatography gives 1.10c (34.3 mg, 95%). 1.10c (5 mg, 0.0126 mmol) is dissolved in EtOH:water 7:3 (0.5 ml). CuI (20 mg, 0.105 mmol), Zn powder (30 mg, 0.458 mmol) and methylvinylketone (0.150 ml, 1.81 mmol) are added and the solution is stirred for 35 minutes at 15° C. in a sonoficator (Banson 220). The sonofication process is stopped in order to cool down the liquid in the sonoficator and the process is repeated for 40 minutes. Extra CuI (10 mg, 0.105 mmol), Zn (14 mg, 0.23 mmol) and methylvinylketone (0.075 ml, 0.95 mmol) are added and the sonofication process is continued for 2 h. The mixture is then filtered through a short path of silica gel (eluted with Et$_2$O) and dried (MgSO$_4$). HPLC purification (acetone:hexane 15:85), gives 1.10d (3.6 mg, 83%).

Rf: 0.18 (acetone:hexane 5:95).

IR (film): 2928; 2871; 1716; 1459 cm$^{-1}$.

$^1$H NMR: (500 MHz, CDCl$_3$): δ: 4.82 (1H, d, J=7.1); 4.7 (1H, d, J=7.1); 3.96–3.66 (2H, m); 3.56 (2H, t, J=4.7); 3.39 (3H, s); 3.33 (1H, dt, J=10.4, 4.3); 2.44–2.34 (2H, m); 2.12 (3H, s); 2.05 (1H, dm, J=12.4); 1.91 (1H, m); 1.79 (1H, dm, J=11.0); 1.7–1.4 (5H, m); 1.36–1.2 (4H, m); 1.19–0.94 (4H, m); 0.88 (3H, d, J=8.5); 0.87 (1H, m); 0.77 (3H, d, J=6.6) ppm.

EXAMPLE 11
Synthesis of 1.11d

Ketone 1.10d (10 mg, 0.0294 mmol) is dissolved in THF (1.5 ml) and 2M MeMgCl (0.4 ml, 1.2 mmol) is added. The mixture is stirred for 1 h at r.t., 0.1 N HCl is then added until the formation of gas stopped. The solution is filtered through a short path of silica gel and anhydrous MgSO$_4$ giving 1.11a (10.3 mg, 98%).

A solution of 1.11a (10 mg, 0.028 mmol) in MeOH (2 ml) is stirred togsilica gel with Amberlyst 15 (200 mg) for 1 week at 30° C. The mixture is then filtered through a short path of silica gel (eluted with Et$_2$O). HPLC purification (silica gel; acetone:hexane 3:7) gives 1.11b (7.2 mg, 96%).

Alcohol 1.11b is then transformed into 1.11d (Rf 0.58; acetone:hexane 15:85) as described for 1.8d from 1.8b (80% yield).

Rf: 0.2 (acetone:hexane 15:85).

IR (film): 3422; 2958; 2872; 1713; 1464; 1377 cm$^{-1}$.

$^1$H NMR: (500 MHz, CDCl$_3$): δ: 2.37–2.22 (3H, m); 2.13 (1H, m); 2.07 (1H, dm, J=12.4); 1.74–1.20 (15H, m); 1.21 (6H, s); 1.09 (1H, m); 0.90 (3H,d, J=6.83); 0.78 (3H, d, J=6.78) ppm.

EXAMPLE 12

Synthesis of Acid 2.1

A suspension of benzeneselenic acid (9.6 g, 0.05 mol) in a mixture of THF (50 ml) and phosphate buffer (0.1M, pH=7, 25 ml) was treated with ca. 30% hydrogen peroxide (88 g, 0.4 mol) at room temperature. A solution of menthone (6.16 g, 0.04 mol) in THF (25 ml) was added and the reaction mixture was stirred at room temperature for 17 h. Saturated NaHCO$_3$ aq. solution was added until the pH of the reaction mixture reached 9. After removal of H$_2$O$_2$ and THF under reduced pressure, the reaction mixture was acidified to pH 5. After saturation with salt, the reaction mixture was extracted with ether (250 ml, 3 times) and the combined ether phases were dried over anhydrous MgSO$_4$. After filtration, the filtrate was concentrated in vacuo. The remaining colourless liquid (14 g) was dissolved in 150 ml of methanol and 37% HCl (3.75 ml) was added. This mixture was refluxed for 3 hours. After cooling, the reaction mixture was treated with saturated NaHCO$_3$ aq. solution to pH 8. The organic solvent was removed by evaporation under reduced pressure. The remaining residue was extracted with ether (3 times). The combined ether solution was dried over anhydrous MgSO$_4$. After filtration and concentration the crude material was purified by column chromatography (EtOAc/hexane 1:4) providing pure methyl ester (7.32 g, 91%).

Rf: 0.45 (EtOAc:hexane 1:2).

IR (film): 3434 (m); 2957, 2873 (s); 1736 (s); 1461, 1437 (m); 1287, 1261, 1205, 1164 (s); 734 (s) cm$^{-1}$.

$^1$H NMR: (360 MHz, CDCl$_3$): δ: 3.68 (3H, s); 2.34 (1H, dd, J=6.1, 14.8); 2.14 (1H, dd, J=8.0, 14.8); 1.95 (1H, m); 1.65 (1H, m); 1.52 (2H, m); 1.35 (2H, m); 1.22 (1H, m); 0.96 (3H, d, J=6.8); 0.90 (6H, dd, J=7.1, 7.5) ppm.

MS (m/z): 202 (2%); 187 (1%); 184 (2%); 159 (2%); 43 (100%).

To a solution of the previous ester (5.17 g, 25.5 mmol) in DMF, tert-butyldimethylsilyl chloride (RBDMS-CI, 5.79 g, 38.4 mmol), DMAP (50 mg) and imidazole (3.92 g, 57.6 mmol) were added. The solution was stirred overnight at room temperature under nitrogen atmosphere. Diluted with ether, the reaction mixture was washed with water. The organic phase was dried over anhydrous MgSO$_4$. After filtration and concentration, the remaining crude material was purified by column chromatography (silica gel, EtOAc:hexane 1:50), yielding 7.85 g of product (98% yield).

Rf: 0.58 (EtOAc:hexane 1:2).

IR (film): 2896 (s); 2857 (s); 1743 (s); 1471; 1462, 1436, 1385 (m); 1253 (s); 1210, 1165, 1101 (m); 1057, 837, 773 cm$^{-1}$.

$^1$H NMR: (360 MHz, CDCl$_3$): δ: 3.67 (3H, s); 3.40 (1H, m); 2.30 (1H, dd, J=6.4, 14.8); 2.12 (1H, dd, J=8.0, 14.8); 1.90 (1H, m); 1.68 (1H, m); 1.40 (3H, m); 1.15 (1H, m); 0.95 (3H, d, J=6.8); 0.88 (9H, s); 0.84 (6H, dd, J=6.8, 10.5); 0.02 (6H, s) ppm.

MS (m/z): 316 (1%); 301 (2%); 249 (3%); 191 (5%); 115 (80%).

To a stirred suspension of potassium tert-butoxide (16.85 g, 165 mmol) in dry diethylether (150 ml) was added 0.752 ml of water via syringe at 0° C. The resulting slurry was stirred for 10 minutes at the same temperature and was then treated with the previous product (6 g, 19 mmol). The ice bath was removed and the reaction mixture was stirred at room temperature for 50 hours. To the reaction mixture ice was added until two clear layers are formed. This mixture was acidified with 10% HCl aq. solution till pH=1. After extraction with ether the combined ether phases were dried over MgSO$_4$. Following filtration and concentration, the crude product was purified by silica gel column chromatography 1:20 and 1:4 EtOAc:hexane) affording 5.34 g of acid 2.1 (yield: 93%).

Rf: 0.54 (EtOAc:hexane 1:").

IR (film): 3500 (m); 2958, 2857 (s); 1708 (s); 1471, 1462, 1410 (s); 1294, 1252,1226 (s) 836, 773 (s) cm$^{-1}$.

$^1$H NMR: (360 MHz, CDCl$_3$): δ: 3.40 (1H, m); 2.35 (1H, dd, J=6.0, 15.0 Hz); 2.15 (1H, dd, J=8.0, 15.0 Hz); 1.92 (1H, m); 1.70 (1H, m); 1.42 (4H, m); 1.00 (3H, d, J=6.8); 0.88 (9H, s); 0.87 (6H, dd, J=6.6, 10.5); 0.03 (6H, s) ppm.

MS (m/z) 302 (1%); 287 (1%); 258 (10%); 245 (5%); 187 (50%); 115 (80%).

EXAMPLE 13

Synthesis of Ester 2.2

To a stirred solution of (R)-3-methyl-2-cyclohexen-1-ol (0.70 g, 6.25 mmol) in methylene chloride (50 ml) was added acid 2.1 (1.51 g, 5 mmol) at 0° C. After addition of DCC (3.25 g, 15.8 mmol) and DMAP (0.732 g, 6 mmol) at the same temperature, the mixture was kept for 5 minutes at 0° C. and was then warmed till room temperature and allowed to be stirred at r.t. overnight. 2 ml of ethanol and acetic acid were added respectively and the mixture was further stirred at r.t. for 2 h. After filtration, the reaction mixture was concentrated till 20 ml. After dilution with diethyl ether (200 ml), the reaction mixture was washed with water. The ether solution was dried over anhydrous MgSO$_4$ and doncentrated in vacuo. The residual liquid was separated by silica gel column chromatography affording 1.8 g of ester 2.2 (yield: 91%).

Rf: 0.6 (EtOAc:hexane 1:20).

IR (film): 2950 (s); 2857 (s); 1730 (s); 1462, 1380 (m); 1251 (s): 1162, 1055 (m) cm$^{-1}$.

$^1$H NMR: (360 MHz, CDCl$_3$): δ: 5.45 (1H, m); 5.25 (1H, m); 3.40 (1H, m); 2.30 (1H, dd, J=8,14); 2.10 (1H, dd, J=8, 15); 1.95 (2H, m); 1.75 (3H, m); 1.70 (3H, s); 1.65 (2H, m); 1.62 (2H, m); 1.40 (4H, m); 1.10 (1H, m); 0.95 (3H, d, J=6.4); 0.88 (9H, s); 0.85 (6H, q, J=7, 14); 0.02 (6H, s) ppm.

MS (m/z): 396 (1%); 339 (1%); 267 (1%); 167 (30%); 109 (50%); 95 (80%); 75 (100%).

EXAMPLE 14
Synthesis of Acid 2.3

To a stirred solution of N-isopropyl-N-cyclohexylamine (158 mg, 1.12 mmol) in 1 ml of dry hexane, n-butyllithium (2.40M solution in hexane, 0.467 ml, 1.12 mmol) was added dropwise at −5° C. over several minutes. Following the addition, the colourless solution was stirred at −5° C. for 20 minutes. After which the hexane and excess amine was removed under vacuo at 0° C. Under argon the residual white solid was dissolved in THF (2 ml) and HMPA (0.7 ml). The mixture was cooled to −78° C. and acid 2.2 was added dropwise over 2 minutes. After 10 min following the addition, the reaction mixture was allowed to warm until −30° C. and was kept at this temperature for 1 h. The reaction mixture was cooled to −78° C. and TBDMS-CI (168 mg, 1.12 mmol) was added. The reaction mixture was stirred at −78° C. for 10 min then was warmed to room temperature very slowly within 1 hour. Finally the reaction mixture was refluxed under argon for 17 hours and was then cooled down to room temperature. After dilution with ether, the reaction mixture was washed with 2.5% HCl aq. solution and water. The organic phase was dried over anhydrous $MgSO_4$ and concentrated in vacuo. The residue was separated by silica gel column chromatography (EtOAc:hexane) affording 117 mg of acid 2.3 and 220 mg of starting material 2.2 (yield: 67% based on consumed starting material).

Rf: 0.56 (EtOAc:hexane 1:5).

IR (film): 3400 (m); 2980 (s); 1704 (s); 1462, 1381 (m); 1253, 1202 (m) $cm^{-1}$.

$^1$H NMR: (360 MHz, $CDCl_3$): δ: 5.26 (1H, m); 5.40 (1H, d, J=10.3); 3.36 (1H, m); 2.21 (1H, d, J=5.5); 1.95 (2H, m); 1.60–1.80 (6H, m); 1.42 (1H, s); 1.25 (3H, m); 1.11 (3H, s); 1.02 (3H, d, J=6.8 Hz); 0.88 (9H, s); 0.83 (3H, d, J=6.8); 0.82 (3H, d, J=6.8); 0.03 (6H, s) ppm.

MS (m/z): 396 (1%); 352 (1%); 381 (1%); 339 (1%); 281 (2%); 237 (5%); 115 (30%); 95 (80%).

EXAMPLE 15
Synthesis of Alkene 2.4

To a solution of acid 2.3 (474 mg, 1.2 mmol) in dry ether (10 ml) was added 30 ml of diazomethane (0.5M solution in ether) at 0° C. The reaction mixture was stirred at 0° C. for 1 hour. The ether and excess diazomethane were removed by evaporation under reduced pressure. The residue (425 mg, 86% yield) was dissolved in THF and added to a suspension of lithium aluminum hydride (114 mg, 3 mmol) in THF (20 ml) by syring. The reaction mixture was stirred at room temperature for 3 hours and was then refluxed for 1 hour. Excess lithium aluminum hydride was destroyed by careful addition of ethanol and was then treated with diluted HCl aq. solution. The alcohol was extracted with ether and the combined ether phases were dried over anhydrous $MgSO_4$. Crude product, after filtration and concentration, was isolated by silica gel column chromatography and purified by HPLC yielding 382 mg of alcohol (89% yield).

Rf: 0.4 (EtOAc:hexane 1:10).

IR (film): 3355 (m); 2956 (s); 1462, 1385, 1251, 1048 (s); 836, 773 (s); 941, 732, 664 (m) $cm^{-1}$.

$^1$H NMR: (360 MHz, $CDCl_3$): δ: 5.67 (1H, m); 5.53 (1H, d, br, J=10); 3.81 (1H, q, J=6.0, 11.4); 3.72 (1H, dd, J=5.5, 11.3); 3.38 (1H, m); 1.95 (2H, m); 1.70 (2H, m); 1.60 (4H, m); 1.40 (1H, m); 1.35–1.15 (4H, m); 1.03 (3H, s); 1.00 (3H, s); 0.90 (9H, s); 0.85 (6H, dd, J=6.9, 9.9); 0.05 (6H, s) ppm.

MS (m/z): 339 (M.+ -iPr, 1%); 341 (1%); 325 (1%); 251 (1%).

A solution of the alcohol (250 mg, 0.65 mmol) in pyridine (10 ml) was added p-toluenesulphonylchloride (420 mg, 2.2 mmol) at room temperature. The light yellow solution was stirred at room temperature for 18 hours, then was poured onto ice. This mixture was extracted with ether and the combined ether phases were washed with 5% HCl aq. solution until pH=3. After drying over anhydrous $MgSO_4$, the organic phase was concentrated in vacuo. The residue was filtered through a short silica gel column and purified by HPLC giving 336 mg of tosylate (yield: 96%).

Rf: 0.37 (EtOAc:hexane 1:20).

IR (film): 2958, 2857 (s); 1741, 1599 (m); 1462, 1367 (s); 1250, 1178 (s); 1047, 953 (s); 837, 773 (s) $cm^{-1}$.

$^1$H NMR: (360 MHz, $CDCl_3$): δ: 7.80 (2H, d, J=8.3); 7.33 (2H, d, J=8.4 Hz); 5.59 (1H, m); 5.32 (1H, d, br, J=10.2); 4.20 (1H, dd, J=4.7, 10.0); 4.10 (1H, dd, J=7.4, 10.0); 3.30 (1H, m); 2.46 (3H, s); 1.90 (2H, m); 1.62 (2H, m); 1.53 (3H, m); 1.45 (3H, m); 1.26 (2H, m); 1.15 (1H, m); 0.95 (3H, s); 0.90 (3H, d, J=7.1); 0.88 (9H, s); 0.82 (6H, dd, J=6.9, 8.8); 0.01 (3H, s); −0.01 (3H, s) ppm.

MS (m/z): 512 (1%); 486 (1%); 455 (1%); 426 (1%); 364 (2%); 321 (2%); 307 (5%); 229 (20%); 9.5 5 (100%).

To a suspension of lithium aluminum hydride (71 mg, 1.88 mmol) in THF (12 ml) was added the tosylate (336 mg, 0.627 mmol) as a solution in THF at r.t.

The reaction mixture was refluxed for 2 hours. Excess $LiAlH_4$ was destroyed by adding ethanol. The mixture was then treated with 5% HCl aq. solution. This mixture was extracted with diethyl ether and the combined ether phases were dried over anhydrous $MgSO_4$. Pure alkene 2.4 (234 mg) was isolated by column chromatography (fine silica gle) in 91% yield.

Rf: 0.54 (pure hexane).

IR (film): 3011 (w); 2957, 2858 s); 1462, 1383, 1386 (s); 1253, 1082, 1054 (s); 836, 772 (s); 941, 731 (w) $cm^{-1}$.

$^1$H NMR: (360 MHz, $CDCl_3$): δ: 5.58 (1H, m); 5.45 (1H, m); 3.37 (1H, m); 1.92 (2H, m); 1.70 (1H, m); 1.60 (4H, m); 1.52 (2H, m); 1.36 (1H, m); 1.28 (1H, m); 1.20 (1H, m); 0.93 (3H, s); 0.89 (9H, s); 0.87 (3H, d, J=6.8); 0.85 (3H, d, J=7;3); 0.82 (6H, q, J=6.9); 0.02 (3H, s); 0.01 (3H, s) ppm.

MS (m/z): 366 (1%); 364 (1%); 309 (10%); 287 (1%); 233 (5%); 75 (100%).

EXAMPLE 16
Synthesis of Cyclohexanone 2.5

To a solution of alkene 2.4 (60 mg, 0.164 mg) in THF (6 ml) was added 9-BBN (0.5M solution in THF, 3.3 ml, 1.04 mmol) at room temperature under nitrogen atmosphere. The solution was stirred at room temperature for 1 hour and was then refluxed for 20 hours. The organoborane was oxidized by adding, successively ethanol (0.5 ml), 6N NaOH (0.4 ml) and 30% hydrogen peroxide (0.8 ml). This mixture was heated at 50° C. for 1 hour. The reaction mixture was extracted with ether and the combined ether phases were washed with 5% HCl aq. solution. The organic phase was dried over anhydrous $MgSO_4$, filtered and the filtrate was concentrated in vacuo. The residue was purified by column chromatography (fine silica gel) affording the corresponding alcohol (51 mg) in 80% yield as a mixture of diastereomers.

A mixture of this alcohol (51 mg, 0.133 mmol) and PDC (175 mg, 0.442 mmol) in methylene chloride (4 ml) was stirred at room temperature for 15 hours and was directly purified on silica gel. Final purification by HPLC led to ketone 2.5 (46 mg) in 90% yield.

Rf: 0.4 (EtOAc:hexane 1:10).

IR (film): 2931, 2857 (s); 1715 (s); 1472, 1385 (s); 1250, 1081, 1058 (s); 941, 667 (m); 837, 773 (s) cm$^{-1}$.

$^1$H NMR: (360 MHz, CDCl$_3$): δ: 3.36 (1H, m); 2.26 (3H, m); 2.05 (1H, d, J=13.3); 1.90 (1H, m); 1.82 (1H, m); 1.65 (3H, m); 1.58 (1H, m); 1.50 (3H, m); 1.25 (1H, m); 0.92 (3H, d, J=6.9); 0.88 (9H, s); 0.85 (3H, s); 0.84 (6H, q); 0.79 (3H, d, J=7;3); 0.02 (6H, s) ppm.

MS (m/z): 382 (2%); 368 (10%); 340 (1%5); 326 (60%); 185 (60%); 95 (70%); 75 (100%).

EXAMPLE 17
Synthesis of Alkene 2.6

A solution of 2.4 (160 mg, 0.437 mmol) and TBAF (1M solution in THF, 2.18 ml, 2.18 mmol) in THF (10 ml) was heated at 30° C. with stirring for 3 days. The reaction mixture was diluted with hexane and was immediately chromatographed. The reaction mixture was diluted with hexane and was immediately chromatographed. The crude product was further purified by HPLC (1:12 EtOAc/hexane) to afford the unprotected 24S-alcohol (106 mg, 88%).

IR (film): 3378 (m); 2959, 2870 (s); 1646 (w); 1462, 1380 (s); 1060, 989 (m); 732 (m) cm$^{-1}$.

$^1$H NMR (500 MHz, CDCl$_3$): δ: 5.59 (1H, dt, J=10.2, 3.5); 5.46 (1H, dq, J=10.2, 2.0); 3.31 (1H, m); 1.92 (2H, m); 1.65 (1H, m); 1.58 (4H, m); 1.37 (2H, m); 1.30–1.20 (4H, m); 0.94 (3H, s); 0.92 (3H, d, J=6.8); 0.90 (3H, d, J=6.8); 0.88 (3H, d, J=6.8); 0.82 (3H, d, J=7.3).

MS (m/z): 252 (M.$^+$, 3); 234 (5); 149 (20); 122 (20); 95 (100) ppm.

A solution of the above alcohol (100 mg, 0.397 mmol) in THF (4 ml) was treated with triphenylphosphine (260 mg, 0.99 mmol) and 4-nitrobenzoic acid (166 mg, 0.99 mmol) under nitrogen atmosphere at r.t. Diethyl azodicarboxylate was subsequently slowly added. The reaction mixture was stirred at r.t. for 15 hours. After dilution with hexane the mixture was then filtered through a silica gel column. The further purification with HPLC afforded the corresponding inverted p-nitrobenzoate ester (100 mg, 63%).

A mixture of the latter (100 mg, 0.25 mmol) and K$_2$CO$_3$ (173 mg, 1.25 mmol) in methanol was stirred at room temperature for 0.5 h. No reaction was detected. To the reaction mixture was then added KOH (745 mg) and the mixture was stirred at room temperature for 1.5 h. Water was added and the mixture was extracted with ether. The combined ether solution was washed with water, dried over anhydrous MgSO$_4$, and concentrated in vacuo. The crude material was purified by HPLC (1:11 EtOAc/hexane) to give the 24R-alcohol (59 mg, 94%).

IR (film): 3379 (m); 2959, 2870 (s); 1644 (w); 1462, 1380 (s); 1060, 989 (m); 732 (m) cm$^{-1}$.

$^1$H NMR (500 MHz, CDCl$_3$) : δ5.59 (1H, ddd, J=3.4, 4.2, 10.2 Hz); 5.46 (1H, dq, J=10.1, 2.8); 3.3 (1H, m); 1.92 (2H, ); 1.70 (1H, m); 1.63 (1H, m); 1.58 (3H, m); 1.46 (2H, m); 1.35 (1H, m); 1.28 (2H, m); 1.10 (1H, m); 0.94 (3H, s); 0.92 (3H, d, J=6.7 Hz); 0.90 (3H, d, J=6.7); 0.87 (3H, d, J=0.87); 0.82 (3H, d, J=7.3). ppm MS (m/z): 252 (M.+, 3); 234 (5); 149 (20); 122 (20); 95 (100).

A solution of this alcohol (59 mg, 0.234 mmol), imidazole (32 mg, 0.468 mmol), TBDMS-CI (71 mg, 0.468 mmol) and DMAP (10 mg) in DMF (3 ml) was stirred at room temperature for 16 hours, and was then treated with TBDMS-CI (71 mg, 0.468 mmol), imidazole (32 mg), and DMAP (10 mg). After 5 hours stirring at room temperature the addition was repeated once more. The reaction mixture was stirred 10 hours and was then treated with 10% HCl (1 ml). After 10 min stirring the reaction mixture was extracted with ether. The combined ether solution was washed with 5% HCl and water, dried over MgSO$_4$ and concentrated in vacuo. The residual material was separated by column chromatography and purified by HPLC (pure hexane) to give 2.6 (83 mg, 97%).

IR (film): 2857 (s); 1645 (w); 1408; 1375 (m); 1289, 1156 (m); 945 cm$^{-1}$.

$^1$H NMR (500 MHz, CDCl$_3$): δ5.58 (1H, dt, J=10.2, 3.4); 5.45 (1H, dq, J=10.1, 1.8); 3.36 (1H, q, J=5.0); 1.91 (2H, m); 1.68 (1H, m); 1.58 (4H, m); 1.48 (1H, m); 1.36 (2H, m); 1.27 (2H, m); 1.22 (1H, m); 0.93 (3H, s); 0.89 (9H, s); 0.87 (3H, d, J=6.8); 0.84 (3H, d, J=6.8); 0.83 (3H, d, J=6.8); 0.80 (3H, d, J=7.3); 0.03 (3H, s); 0.02 (3H, s) ppm MS (m/z): 366 (M.$^+$, 1%).

EXAMPLE 18
Synthesis of Cyclohexanone 2.7

To a solution of 2.6 (80 mg, 0.219 mmol) in THF (8 ml) was added 9-BBN (0.5 M solution in THF, 4.37 ml, 2.19 mmol) at r.t. under nitrogen atmosphere. The reaction mixture was refluxed for 20 hours. The organoboranes were oxidized by adding, successively EtOH (0.66 ml), 6N NaOH (0.53 ml) and 30% H$_2$O$_2$ (1.06 ml). This mixture was heated at 50° C. for 1 hour. After dilution with ether the reaction mixture was washed with 5% HCl aq. solution, water and dried over MgSO$_4$. After concentration the residual oil was chromatographed and was further purified by HPLC to give the alcohol (77.3 mg, 92%).

A solution of the latter (77.3 mg, 0.2 mmol) and PDC (396 mg, 1 mmol) in CH$_2$Cl$_2$ (10 ml) was stirred at room temperature for 24 hours. Direct column chromatography of the reaction mixture followed by HPLC purification afforded the desired ketone 2.7 (71 mg, 92%).

$^1$H NMR (500 MHz, CDCl$_3$): δ3.36 (1H, dt, J=9.7, 4.8); 2.28 (1H, d, J=13.7); 2.26 (2H, m); 2.05 (1H, dt, J=13.4, 1.4); 1.90 (1H, m); 1.82 (1H, m); 1.70–1.60 (4H, m); 1.50 (1H, m); 1.34–1.20 (3H, m); 0.97 (1H, m); 0.89 (3H, d, J=6.8); 0.88 (9H, s); 0.86 (3H, s); 0.84 (3H, d, J=6.8); 0.83 (3H, d, J=6.8); 0.79 (3H, d, J=7.2); 0.02 (3H, s); 0.01 (3H, s) ppm.

EXAMPLE 19
Synthesis of Ester 2.9

To a stirred solution of (R)-(+)-citronellic acid (2.8; 0.98 g, 5.76 mmol) in methylene chloride (50 ml) was added (R)-3-methylcyclohexen-1-ol (84% e.e., 0.64 g, 5.76 mmol) at 0° C. under nitrogen atmosphere. The reaction was initiated by the addition of DCC (2.96 g, 14.4 mmol) and DMAP (0.732 g, 6 mmol). After 5 min at 0° C. the reaction mixture was warmed to room temperature and allowed to stir at r.t. overnight (18 h). Ethanol (4 ml) and acetic acid (4 ml) were added to the reaction mixture at 0° C. The mixture was stirred at 0° C. for 20 min and at room temperature for 1 hour. Ether was added and the formed white solid was removed by filtration. The filtrate was evaporated under reduced pressure and the residual liquid was dissolved in ether. The ether solution was washed with water, dried over anhydrous $MgSO_4$. Column chromatography of the crude material afforded ester 2.9 (1.521 g) in 96% yield.

Rf: 0.52 (EtOAc:hexane 1:20).

IR (film): 2931 (s); 2360 (w); 1732 (s); 1456, 1378 (m); 1150, 1071 (s); 921 (m) $cm^{-1}$.

$^1$H NMR (360 MHz, $CDCl_3$): δ5.45 (1H, m); 5.25 (1H, m); 5.07 (1H, t, J=7.1 Hz); 2.28 (1H, dd, J=6.0, 14.4 Hz); 2.10 (1H, dd, J=8.2, 14.4); 1.95 (3H, m); 1.71 (3H, s); 1.68 (3H, s); 1.58 (3H, s); 1.70 (4H, m); 1.20 (4H, m); 0.92 (3H, d, J=6.6) ppm.

MS (m/z): 264 ($M.^+$, 1%); 249 (1%); 227 (1%); 191 (1); 169 (30); 109 (30); 95 (100).

EXAMPLE 20
Synthesis of Acid 2.10

To a stirred solution of diisopropylamine (456 μl, 3.27 mmol) in THF (10 ml) was added n-butyllithium (2.45M solution in hexane, 1.33 ml, 3.27 mmol) at −15° C. under nitrogen atmosphere. The reaction mixture was stirred at the same temperature for 20 min and then HMPA (3 ml) was added. The reaction mixture was cooled to −78° C. A solution of 2.9 (0.77 g, 2.92 mmol) in THF (2 ml) was added 2.9 to the reaction mixture very slowly at −78° C. After 10 min following the addition, the formed enolate is allowed to warm to −50° C. for 20 min. TBDMS-CI (491 mg, 3.27 mmol) as solid was added at −50° C. and the reaction mixture was stirred at the same temperature for 20 min and was then warmed to room temperature. The reaction mixture was stirred at room temperature for 3 hours and was then refluxed for 16 hours. 5% HCl aq. solution (15 ml) was added and the mixture was stirred at room temperature for 60 min. The mixture was extracted with ether. The combined ether solution was washed with water, dried over anhydrous $MgSO_4$ and concentrated in vacuo. The residual oil was separated by column chromatography to afford 2.10 (448 mg, 58%).

Rf: 0.35 (EtOAc/hexane 1:5).

IR (film): 2930 (s); 1704 (s); 1462, 1381 (m); 1285, 1253, 1202 (m); 836 (m) $cm^{-1}$.

$^1$H NMR (360 MHz, $CDCl_3$): δ5.62 (1H, m); 5.41 (1H, d, J=11.0); 5.09 (1H, t, j=6.9 Hz); 2.22 (1H, d, J=5.9); 2.08 (1H, m); 1.90 (3H, m); 1.68 (3H, s); 1.58 (3H, s); 1.62 (7H, m); 1.10 (3H, s); 1.02 (3H, d, J=6.8) ppm.

MS (m/z): 264 ($M.^+$, 5%); 249 (1%); 221 (1); 208 (5); 154 (15); 109 (15); 96 (100).

EXAMPLE 21
Synthesis of Alkene 2.11

To a suspension of $LiAlH_4$ (302 mg, 7.95 mmol) in THF (10 ml) was added a solution of 2.10 (420 mg, 1.59 mmol) in THF (5 ml). The reaction mixture was refluxed for 48 hours. The excess $LiAlH_4$ was destroyed by addition of 5% HCl aq. solution. The mixture was extracted with ether. The combined ether phases were washed with water, dried over $MgSO_4$ and concentrated in vacuo. The residual material was chromatographed to give the primary alcohol (344 mg, 88%). A diastereoisomer could be removed by further HPLC purification.(EtOAclhexane 1:6).

Rf: 0.35 (EtOAc/hexane 1:5).

IR (film): 3339 (m); 2928, 2871 (s); 1454, 1376 (m); 1028 (m); 732 (m) $cm^{-1}$.

$^1$H NMR (500 MHz, $CDCl_3$): δ5.67 (1H, dt, J=10.1, 3.5 Hz); 5.53 (1H, dt, J=10.2, 1.8 Hz); 5.12 (1H, tt, J=6.8, 1.6); 3.78 (1H, m); 3.72 (1H, m); 2.06 (1H, m); 1.93 (2H, m); 1.88 (1H, tt, J=7.8. 7.8); 1.70 (2H, m); 1.68 (3H, s); 1.61 (2H, m); 1.59 (3H, s); 1.50 (1H, m); 1.40 (1H, ddd, J=1.2, 4.5, 10.5); 1.33 (1H, m); 1.28 (2H, m); 1.13 (1H, m); 1.13 (3H, d, J=7.0); 1.01 (3H, s) ppm.

MS (m/z): 250 ($M.^+$, 5); 232 3); 219 (10); 137 (40); 95 (100).

To a solution of the alcohol (250 mg, 1 mmol) in pyridine (15 mo) was added p-toluenesulfonyl chloride (572 mg, 3 mmol). The light yellow solution was stirred at r.t. for 17 hours and was then poured into ice water. The mixture was extracted with ether and the combined ether solution was washed with 5% HCl aq. solution and water. After drying over anhydrous $MgSO_4$ the ether solution was concentrated under reduced pressure. The residue was separated by column chromatography to give the corresponding tosylate.

To a suspension of $LiAlH_4$ (342 mg, 9 mmol) in THF (30 ml) was added a solution of the tosylate in THF (5 ml). This reaction mixture was refluxed for 2 hours. The excess $LiAlH_4$ was destroyed by addition of ethanol. The mixture was extracted with ether. The combined ether solution was washed with 2% HCl aq. solution and water. After drying over anhydrous $MgSO_4$ the ether solution was concentrated in vacuo. Column chromatography of the residual material afforded 2.11 (245 mg, 100% over two steps).

IR (film): 2925, 2865 (s); 1647 (w); 1453, 1378 (s); 731 (s) $cm^{-1}$.

$^1$H NMR (500 MHz, $CDCl_3$): δ5.58 (1H, dt, J=10.2, 3.5); 5.45 (1H, dm, J=10.2); 5.12 (1H, tt, J=7.0, 1.3); 2.02 (1H, m); 1.92 (2H, m); 1.85 (1H, tt, J=7.9, 15.4); 1.69 (1H, m); 1.68 (3H, s); 1.59 (3H, s); 1.56 (2H, m); 1.46 (1H, m); 1.35 (1H, m); 1.25 (3H, m); 0.93 (3H, s); 0.88 (3H, d, J=6.8); 0.78 (3H, d, J=7.1) ppm.

MS (m/z): 234 (1%); 57 (100%).

EXAMPLE 22
Synthesis of Ketone 2.12

To a colourless solution of $Hg(OAc)_2$ in $H_2O$ (1.25 ml) was added THF (1.25 ml). The reaction mixture became yellow and some precipitate formed. To this mixture was added a solution of 2.11 (212 mg, 0.906 mmol) in THF (2.5 ml) and the reaction mixture was stirred at room temperature for 2 hours. 3M NaOH (1.09 ml) was added and followed by addition of 1 M solution of $NaBH_4$ in 3M NaOH (1.09 ml). This mixture was stirred for 10 min. Extraction with ether followed by column chromatography afforded the 25-hydroxy derivative (154 mg) in 67% yield.

IR (film): 3364 (m); 2963, 2867 (s); 1462, 1379 (m); 1153 (m); 732 (m) $cm^{-1}$.

$^1$H NMR (500 MHz, $CDCl_3$): δ5.58 (1H, dt, J=10.3, 3.5); 5.46 (1H, dm, J=10.3); 1.93 (2H, m); 1.70 (1H, m); 1.58 (4H, m); 1.50–1.35 (5H, m); 1.26 (2H, m); 1.21 (6H, s); 0.94 (3H, s); 0.88 (3H, d, J=7.0); 0.80 (3H, d, J=7.1) ppm.

MS (m/z) :252 ($M.^+$, 1%); 95 (100).

To a solution of the latter (50 mg, 0.20 mmol) in DMF (3 ml) was added chlorotriethylsilane (90 mg, 0.60 mmol), imidazole (54 mg, 0.80 mmol) and DMAP (10 mg) successively. This solution was stirred at room temperature for 20 hours and was then diluted with ether. The ether solution was washed with 5% HCl aq. solution and water, respectively. After drying over $MgSO_4$ the solvents were removed in vacuo. The residual material was separated by column chromatography (2% EtOAc in hexane) to give the protected silyl ether (67 mg, 92%).

IR (film): 2958 (s); 1460, 1380 (m); 1235, 1156 §m); 1042 (s); 730 (s) $cm^{-1}$.

$^1$H NMR (360 MHz, $CDCl_3$): δ5.59 (1H, dt, J=10.2, 3.6); 5.46 (1H, dm, J=10.2); 1.92 (2H, m); 1.70 (1H, m); 1.79 (3H, m); 1.45–1.33 (6H, m); 1.25 (2H, m); 1.19 (6H, s); 0.94 (9H, t, J=8.0); 0.93 (3H, s); 0.88 (3H, d, J=6.8); 0.80 (3H, d, J=7.3); 0.56 (6H, q, J=8.0) ppm.

MS (m/z): 366 ($M.^+$, 1%); 337 (10%); 233 (20%); 173 (30%); 103 (100%).

To a solution of the silyl ether (121 mg, 0.33 mmol) in THF (8 ml) was added 9-BBN (0.5M solution in THF, 6.6 ml, 3.3 mmol). This solution was refluxed for 30 hours. The organoboranes were oxidized by adding successively EtOH (1 ml), 6N NaOH (0.8 ml), and 30% $H_2O_2$ (1.6 ml). This reaction mixture was heated at 50° C. for 1 hour and was then extracted with ether. The combined ether solution was washed with 5% HCl aq. solution, water and dried over $MgSO_4$. After removal of the solvents the residual material was separated by column chromatography to afford the cyclohexanol (121 mg, 95%).

A mixture of the latter (121 mg, 0.34 mmol) and PDC (480 mg, 1.2 mmol) in $CH_2Cl_2$ was stirred at room temperature for 20 hours, and was immediately filtered through a short column. Purification of the crude product by HPLC (1:20 EtOAc/hexane) furnished cyclohexanone 2.12 (97 mg, 80%).

IR (film): 2958 (s); 1722 (s); 1461, 1381 (m); 1282, 1234, 1042 (s); 742 (m) $cm^{-1}$.

$^1$H NMR (500 MHz, $CDCl_3$): δ2.28 (1H, d, J=13.2); 2.26 (2H, m); 2.06 (1H, dt, J=13.3, 1.6); 1.90 (1H, m); 1.83 (1H, m); 1.67 (3H, m); 1.18 (6H, s); 0.93 (9H, t, J=8.0); 0.90 (3H, d, J=6.9 Hz); 0.86 (3H, s); 0.79 (3H, d, J=7.2); 0.56 (6H, q, J=8.0) ppm.

MS (m/z): 354 ($M.^+$, 10%);353 (5%); 173 (30); 111 (60); 55 (100).

EXAMPLE 23
Synthesis of Alkyne 4.4

A solution of 4.1 (48 g, 0.04 mol), imidazole (6.6 g, 0.68 mol) and t-butyldiphenylchlorosilane (13.2 g, 0.048 mol) in dry DMF (16 ml) is stirred for 36 h at r.t. under nitrogen, then ether (100 ml) is added to the solution and the organic layer is washed with water (20 ml) three times dried over anhydrous $MgSO_4$ and evaporated to give 15.58 g of 4.2. Purification by column chromatography (hexane:ethylacetate 90:1) gives 14.2 g of 4.2 in 100% yield.

Rf: 0.48 (hexane:ethylacetate 5:1).

IR (film): 2932 (m); 1741 (s); 1428 (s); 1199 (s); 1111 (s); 739 (s); 702 (s) $cm^{-1}$.

$^1$H NMR (500 MHz, $CDCl_3$): δ7.65 (4H, m); 7.4 (6H, m); 3.82 (1H, dd, J=6.9, 9.7); 3.72 (1H, dd, J=5.8, 9.7); 3.68 (3H, s); 2.72 (1H, sextet, J=6.9); 1.15 (3H, d, J=6.9); 1.03 (9H, s) ppm To a solution of 4.2 (1.5 g, 4.2 mmol) in dry hexane (9 ml) is further added diisobutyl aluminum hydride (10M/hexane, 4.2 ml, 4.2 mmol) dropwise at −78° C. under nitrogen. Work-up of the reaction with 2N solution of potassium sodium tartrate in water under stirring, and subsequent extraction of the water layer with ether (200 ml), drying of the organic layer ($MgSO_4$, anhydrous) and solvent removal yield 1.32 g of aldehyde 4.3 contaminated with a small amount of 4.2, Rf: 0.32 (hexane:ethylacetate 4:1).

$^1$H NMR (500 MHz, $CDCl_3$): δ9.76 (1H, d, J=2); 7.65 (4H, m), 7.4 (6H, m), 3.87 (2H, m), 2.57 (1H, m); 1.11 (3H, d, J=6.9); 1.03 (9H, s) ppm.

To a suspension of potassium b-butoxide (0.68 g, 6.05 mm) in dry THF (14 ml) is added dropwise methyl (diazomethyl)phosphonate (0.59 g, 6.0 mmol) in one minute under nitrogen at −78° C. The resulting red solution is allowed to stir for five minutes at −78° C. and, subsequently, a solution of aldehyde 4.3 (1.78 g, 5.5 mmol) in dry THF (13 ml) is added dropwise over a one minute period.

The reaction mixture is stirred for 18 h at −78° C. and for 2 h at room temperature, and then water (200 ml) is added, the resulting solution is extracted three times with dichloromethane (400 ml) and ether (200 ml). The organic layers are washed with brine, dried over anhydrous $MgSO_4$, concentrated and purified by column chromatography (hexane:ethyl acetate 200:1) to give 1.68 g of 4.4 in 90% yield (from 4.2).

Rf: 0.67 (hexane:ethyl acetate 4:1).

IR (film): 3307 (s); 2959 (m); 2116 (s); 1428 (s); 1112 (s); 702 (s); 739 (s) $cm^{-1}$.

$^1$H NMR (500 MHz, $CDCl_3$): δ7.69 (4H, m); 7.4 (6H, m); 3.74 (1H, dd, J=5.7, 9.6); 3.55 (1H, dd, J=7.6, 9.6); 2.66 (1H, ddf, J=2.3, 5.6, 7.6); 2.03 (1H, d, J=2); 1.23 (3H, d, J=6.8); 1.07 (9H, s) ppm.

EXAMPLE 24
Synthesis of 4.5

To a well stirred solution of B—Br-9-BBN (1M÷CHCl 8.04 ml, 8.04 mmol) in dichloromethane (12 ml) is added dropwise 4.4 (2.16 g; 6.6 mmol) in dichloromethane (24 ml) at 0° C. under nitrogen. The reaction mixture is stirred for 4 h at 0° C. Acetic acid (4.26 ml) is then added and the mixture is stirred for an additional hour at 0° C., followed by the addition of 51 ml of 3M NaOH in water and 8.52 ml of 30% hydrogen peroxide. After stirring for 30 min at room temperature (25° C.), the product is extracted with hexane three times and the organic layer is washed with water, aqueous $NaHCO_3$ and water again and finally dried over $MgSO_4$ (anh.). The residue obtained after concentration is purified by column chromatography (hexane:ethyl acetate 300:1) to give 2.4 g of 4.5 in 90% yield.

Rf: 0.6 (hexane:ethyl acetate 10:1).

IR (film): 2931 (m); 1625 (s); 1427 (s); 1112 (s); 887 (s); 823 (s); 739 (s);701 (s) $cm^{-1}$.

$^1$H NMR (500 MHz, $CDCl_3$): δ7.65 (4H, m); 7.42 (6H, m); 5.69 (1H, d, J=1.6); 5.49 (1H, d, J=1.6); 3.71 (1H, dd, J=6.9, 10); 3.56 (1H, dd, J=5.8, 10); 2.61 (1H, overlapped, J=6.9, 6.85, 5.87); 1.09 (3H, d, J=6.85); 1.05 (9H, s) ppm.

EXAMPLE 25
Synthesis of 4.8

To a solution of bromide 4.5 (520 mg, 1.29 mmol) in dry ether (2.5 ml) is added tert-butyllithium (2.6 mmol) rapidly in a portion at −120° C. (excess liquid $N_2$ in MeOH). To this solution is further added a freshly prepared solution of CuI (250 mg, 1.29 mmol)/HMPT (484 mg, 2.96 mmol) in ether (4.5 ml) at −120° C. The reaction mixture is allowed to warm gradually to −78° C., is further stirred for 1 h and then treated with freshly distilled $BF_3.OEt_2$ (310 mg, 2.2 mmol), followed by the dropwise addition of 3-methyl-cyclohexenone (116 mg, 1 mmol) in dry ether (2.5 ml). The reaction mixture is warmed to −20° C. and left at this temperature for 10 h. The above solution is poured into aqueous $NH_4Cl$/6N HCl (4:1 by volume) and extracted with ether (2×50 ml). The combined extracts are washed with 20% aquous $NH_4OH$ (2×30 ml), 2% aqueous HCl (30 ml) and water (30 ml) dried over anhydrous $MgSO_4$ and evaporated. The residue is purified by column chromatography (hexane:ethylacetate 10:1) and HPLC (hexane:ethyl acetate 4:1) to give 174 mg of 4.6 and its C13-epimer in 40% yield.

Rf: 0.32 (hexane:ethyl acetate 5:1).

To a solution of this mixture (35 mg, 0.08 mmol) in dry THF (1.5 ml) is added TBAF (1.1 M/THF, 0.3 ml, 0.32 mmol) at room temperature. After stirring for 2 h at room temperature the solvent is evaporated and the residue is purified by column chromatography (H:E 1:1) to give 14.1 mg of 4.7 with its C13-epimer. Careful separation with HPLC (hexane:ethyl acetate 6:4; two times) gives pure 4.7 next to its C 13-epimer (1:1).

Rf: 0.27 (hexane:ethyl acetate 1:1).

IR (film): 3386 (s, br); 2932 (m); 2253 (s); 1704 (s); 1590 (m); 1468 (s); 1384 (m); 1073 (s) $cm^{-1}$.

$^1$H NMR (360 MHz, $CDCl_3$): δ5.02 (1H, d, J=1.3); 4.94 (1H, s); 3.56 (1H, dd, J=6.3, 10.6); 3.45 (1H, dd, J=7.5, 10.6); 2.58 (1H, AB, d, J=14); 2.45 (1H, m); 2.30 (2H, m); 2.22 (1H, AB, d, J=14); 1.82 (2H, m); 1.61 (2H, m); 1.10 (3H, s); 1.08 (3H, d, J=6.8) ppm.

EXAMPLE 26

Synthesis of 6.2

To a stirred solution of 6.1 (1 g, 6.50 mmol) and sodium iodide (2.34 g, 15.60 mmol) in acetonitrile (12 ml) is added dropwise at 0° C. methyltrichlorosilane (1.84 ml, 15.60 mmol). After 2 hours reflux the mixture is cooled and water is added. Extraction with diethylether, followed by washing of the organic phase with aqueous sodium thiosulfate, water and brine, drying ($Na_2SO_4$) and concentrating in vacuo yielded the crude iodide which was purified on a silica column (pentane:ethyl acetate 8:2) to give 6.2 (1.58 g; 86.4%).

Rf: 0.21 (pentane:ethyl acetate 85:15).

UV: $\lambda_{max}$=254.

IR (film): 3302 (s); 2954 (s); 2866 (s); 1453 (m); 1365 (m); 1262 (m); 1183 (m); 1035 (s) $cm^{-1}$.

$^1$H NMR (360 MHz, $CDCl_3$): δ: 3.58 (1H, d, J=10.8); 3.43 (1H, d); 3.30 (1H, dd, J=9; J=3.5): 2.95 (1H, dd, J=11.5); 2.35–2.10 (2H, m); 1.61–1.05 (3H, m); 1.01 (3H, s); 0.98 (3H, s); 0.75 (3H, s) ppm.

EXAMPLE 27
Synthesis of 6.3
To a cooled solution (0° C.) of 6.2 (5 g, 17.73 mmol) in dichloromethane (50 ml) is added dropwise N,N-diisopropylethylamine (DIPEA, 6.96 ml, 3.99 mmol) and chloromethyl methyl ether (MOMCI, 1.98 ml, 26.65 mmol). After stirring at room temperature for 3 hours, the mixture is brought to pH 1–2 and extracted with diethylether (3×). The combined organic fractions are washed with brine and saturated sodium bicarbonate, dried ($Na_2SO_4$ anh.) and concentrated in vacuo. Purification by column chromatography (silica; hexane:acetone 95:5) yields 4.95 g (86%) of the MOM diethylether of 6.2. To a stirred solution of this intermediate (870 mg, 2.67 mmol) in tetrahydrofuran (6 ml) is added a solution of tetrabutylammonium fluoride (TBAF, 1 M in THF, 21.33 mmol, 21.33 ml). After stirring for 4 hours at room temperature water is added. Extraction with diethylether, drying of the organic phase ($MgSO_4$) and purification on a silica column (hexane:acetone 95:5) gives 465 mg pure 6.3 (88%).

Rf: 0.76 (hexane:acetone 9:1).

IR (film): 2966 (s); 2877 (s); 1651 (m); 1464 (m); 1369 (m); 1213 (w); 1151 (s); 1108 (s); 1049 (s) $cm^{-1}$.

$^1$H NMR: (360 MHz, $CDCl_3$): δ: 4.76 (2H, dd, J=2.2 Hz); 4.60 (2H, dd, J=6.4 Hz); 3.35 (3H, s); 3.33 (1H, d); 3.25 (1H, d, J=9.3 Hz); 2.43–2.37 (2H, m); 1.83–1.75 (1H, m); 1.48–1.38 (1H, m); 0.97 (3H, s); 0.94 (3H, s); 0.92 (3H, s) ppm.

EXAMPLE 28
Synthesis of 6.4 and 6.5
A solution of osmium tetroxide (0.67% in t.butanol, 0.184 mmol, 7 ml) is added dropwise to a mixture of 6.3 (372 mg, 1.88 mmol) and sodium periodate (998 mg, 4.7 mmol) in THF:water 1:1 (4 ml). After stirring for 30 hours at rom temperature, a saturated sodium thiosulfate solution in water (1 ml) is added and the resulting mixture is extracted with dichloromethane. Purification by column chromatography (silica; hexane:ethyl acetate 93:7) yields 244 mg (65%) of the ketone. A solution of this ketone (244 mg, 1.22 mmol) in tetrahydrofuran (1 ml) is added dropwise to a suspension of lithium aluminum hydride (47 mg, 1.22 mmol) in tetrahydrofuran (2 ml). After stirring at room temperature for 1 hour, sodium sulfate decahydrate is added and the resulting mixture is stirred for an additional 2 hours and subsequently filtered to remove the metal salts. The filtrate is concentrated in vacuo and purified by column chromatography (silica; hexane:ethyl acetate 85:15) to give 222 mg (90%) of a mixture of diastereomers 6.4 and 6.5.

Rf: 0.16 (hexane:ethyl acetate 8:2).

IR (film): 3426 (s, br); 2958 (s); 2876 (s); 1467 (m); 1369 (m); 1216 (m); 1151 (s); 1108 (s); 1046 (s) $cm^{-1}$.

$^1$H NMR: (360 MHz, $CDCl_3$): δ: 4.63 (2H:2, s); 4.59 (2H:2, s); 3.79 (1H:2, dd); 4.01 (1H:2, dd); 3.41 (1H:2, d); 3.30 (1H:2, d); 3.29 (1H:2, d); 3.25 (1H:2, d); 3.39 (3H:2, s); 3.36 (3H:2, s); 2.20–1.40 (4H, m); 1.00–0.85 (9H, 3×s) ppm.

EXAMPLE 29
Synthesis of 6.6
To a solution of 6.3 (1.552 g, 7.84 mmol) in tetrahydrofuran (35 ml) is added a solution of 9 borabicyclo[3.3.1] nonane (0.5 M in tetrahydrofuran, 15.7 ml, 7.85 mmol) and the resulting solution is stirred for 5 hours at 55° C. After cooling to room temperature, ethanol (4.71 ml) and a 6 M aqueous sodium hydroxide solution (1.57 ml, 9.42 mmol) are added, followed by dropwise addition at 0° C. of a 35% aqueous solution of hydrogen peroxide (3.68 ml). Stirring for 1 hour at reflux temperature, subsequent extraction of the water layer with diethylether, drying of the organic phase (Na$_2$SO$_4$ anh.) and solvent removal yields 2.8 g of a crude oil. Purification by column chromatography (hexane:acetone 8:2) and HPLC (silicagel; hexane:ethyl acetate 75:25) gives 6.6 (617 mg, 36%) next to the undesired epimer (864 mg, 51%)

Rf:0.25 (dichloromethane:methanol 9:1).

IR (film): 3418 (s, br); 2946 (s); 2875 (s); 1464 (s); 1368 (m); 1215 (m); 1150 (s); 1108 (s); 1047 (s) cm$^{-1}$.

$^1$H NMR: (500 MHz, CDCl$_3$): δ: 4.61 (2H, 2×d, J=6.5); 3.72 (1H, dd, J=5.6, 10.2); 3.52 (1H, dd, J=10.2, 9.3); 3.35 (3H, s); 3.34 (1H, d, J=9.15); 3.25 (1H, d); 2.10 (1H, ddd); 1.88 (2H, m); 1.65 (1H, m); 1.43 (1H, m); 1.35 (1H, m); 0.91 (3H, s); 0.90 (3H, s); 0.83 (3H, s) ppm.

EXAMPLE 30

Synthesis of 6.7

To a mixture of triphenylphosphine (1.46 g, 5.56 mmol), imidazole (378 mg, 5.56 mmol) and 6.6 (600 mg, 2.78 mmol) in diethylether:acetonitrile 3:1 (12 ml) is added at 0° C., portionwise, iodine (1.41 g, 5.56 mmol) and the resulting mixture is stirred in the dark for 3 hours at room temperature. Extraction with diethylether:hexane 1:1, washing of the collected organic fractions with brine, drying (Na$_2$SO$_4$ anh.) and solvent removal gives a pale yellow oil which is purified by column chromatography (silicagel; hexane:ethyl acetate 95:5) to yield 825 mg (91%) of the iodide. A solution of this ether (460 mg, 1.41 mmol) in methanol:tetrahydrofuran 3:1 (70 ml) is stirred in the presence of Amberlyst-15 for 72 hr at room temperature in the dark. Afterwards the Amberlyst-15 is filtered off and the filtrate is concentrated in vacuo and purified by column chromatography (silicagel; hexane:ethyl acetate 85:15 to 70:30) to give 6.7 (342 mg, 86%).

Rf: 0.20 (hexane:ethyl acetate 8:2).

IR (film): 3380 (s); 2963 (s); 2872 (m); 1452 (m); 1368 (m); 1264 (m); 1183 (m); 1028 (s) cm$^{-1}$.

$^1$H NMR: (500 MHz, CDCl$_3$): δ: 3.41 (2H, s br); 3.30 (1H, dd, J=9, 3.6); 2.98 (1H, dd, J=11.5); 2.35–2.27 (1H, m); 2.13–2.05 (1H, m); 1.81–1.73 (1H, m); 1.44–1.30 (3H, m); 0.89 (3H, s); 0.88 (3H, s); 0.71 (3H, s) ppm.

EXAMPLE 31

Synthesis of 6.8

To a suspension of copper(I) iodide (676 mg, 3.55 mmol) and zinc dust (928 mg, 14.18 mmol) in ethanol:water 7:3 (10 ml) are added methyl vinyl ketone (380 μl, 4.62 mmol) and 2 (1 g, 3.55 mmol). The reaction mixture is sonicated during 1 hour under an argon atmosphere followed by addition of more copper(I) iodide (338 mg, 1.775 mmol) and zinc dust (464 mg, 7.09 mmol). After another 35 minutes sonication, the mixture is filtered through celite and the copper- and zinc salts are washed with ethyl acetate. The filtrate is extracted with ethyl acetate, dried (anhydric magnesiumsulfate) and concentrated. Purification on a silica column (pentane:ethyl acetate 7:3) gives 510 mg 6.8 (64%).

Rf: 0.29 (pentane:ethyl acetate 85:15).

IR (film): 3420 (s); 2946 (s); 2869 (s); 1714 (s); 1454 (s); 1367 (s); 1231 (m); 1163 (s); 1024 (s) cm$^{-1}$.

$^1$H NMR: (360 MHz, CDCl$_3$): δ: 3.58 (1H, d, J$_{6,6'}$=10.7); 3.45 (1H, d); 2.50–2.35 (2H, m); 2.14 (3H, s); 1.96–1.84 (1H, m); 1.80–1.13 (8H, m); 0.98 (3H, s); 0.88 (3H, s); 0.70 (3H, s) ppm.

EXAMPLE 32

Synthesis of 6.10

To a solution of methyllithium (1.5 M in diethylether 11.6 ml, 17.34 mmol) is added dropwise a solution of 6.8 (490 mg, 2.17 mmol) in diethylether (5 ml) at −78° C. After stirring under an argon atmosphere for 2 hours, saturated ammonium chloride is added and the resulting mixture is extracted with diethylether, the organic phase dried (MgSO$_4$) and the solvent removed. Purification of the crude by column chromatography (silica; pentane:ethyl acetate 8:2) yields 455 mg of the white crystalline diol (85%). A solution of this diol (200 mg, 0.826 mmol) in dichloromethane (0.8 ml) is added to a mixture of dipyridine chromium(VI)oxide (1.066 g, 4.13 mmol) and dichloromethane. The mixture is stirred at room temperature; after two hours diethylether (5 ml) and celite are added. Filtration through silicagel-celite, washing with diethylether and solvent removal gives a residue which is purified on a silica column (pentane:ethyl acetate 8:2) and by HPLC (pentane:ethyl acetate 75:25). 70 mg of pure 6.10 is obtained (35%).

Rf: 0.24 (pentane:ethyl acetate 85:15).

IR (film): 3480 (s); 2964 (s); 1715 (s); 1470 (m); 1372 (m) cm$^{-1}$.

$^1$H NMR: (360 MHz, CDCl$_3$): δ: 9.64 (1H, s); 2.39–2.28 (1H, m); 2.04–1.92 (1H, m); 1.83–1.72 (1H, m); 1.53–1.23 (8H, m); 1.21 (6H, s); 1.03 (3H, s); 0.96 (3H, s); 0.75 (3H, s) ppm.

EXAMPLE 33

Synthesis of 6.12

A solution of n.butyllithium (2.5 M in hexane, 467 μl, 1.17 mmol) is added dropwise to a solution of (methoxymethyl)-triphenylphosphonium chloride (400 mg, 1.17 mmol) in tetrahydrofuran (4 ml) at −78° C. The resulting mixture is stirred for 20 minutes and subsequently a solution of 6.10 (70 mg, 291 μmol) in tetrahydrofuran (700 μl) is added dropwise. After stirring for 10 minutes, at −78° C., the mixture is allowed to warm to room temperature and stirred for an additional 21 hours. Addition of water, extraction with diethylether, drying (Na$_2$SO$_4$) and concentrating gives the crude enolether. To a solution of the enolether (65 mg, 243 μmol) in tetrahydrofuran (700 μl) is added a hydrochloric acid solution (2 M in THF, 66 μl). After 30 minutes the mixture is extracted with diethylether, the organic portions are washed with saturated sodium bicarbonate and brine and dried (Na$_2$SO$_4$). After removal of the solvent with a rotary evaporator the remaining oil is purified by column chromatography (silica; pentane:ethyl acetate 8:2); 25 mg pure 6.12 is obtained (45%).

Rf: 0.17 (pentane:ethyl acetate 8:2).

IR (film): 3440 (s); 2928 (m); 1715 (m); 1470 (w); 1380 (w) cm$^{-1}$.

$^1$H NMR: (500 MHz, CDCl$_3$): δ: 9.84 (1H, dd, J=4.1, 2.4); 2.31 (2H, dd); 1.99–1.90 (1H, m); 1.87–1.23 (1OH, m); 1.22 (6H, s); 0.98 (3H, s); 0.82 (3H, s); 0.68 (3H, s) ppm.

EXAMPLE 34

Synthesis of 6.9

To a suspension of copper(I)iodide (676 mg, 3.55 mmol) and zinc dust (928 mg, 14.18 mmol) in ethanol:water 7:3 (10 ml) are added ethyl vinyl ketone (458 μl, 4.61 mmol) and 6.2

(1 g, 3.55 mmol). The reaction mixture is sonicated during 1 hour under an argon atmosphere followed by addition of more copper(I)iodide (338 mg, 1.775 mmol) and zinc dust (464 mg, 7.09 mmol). After another 35 minutes of sonication, the mixture is filtered through celite and the copper and zinc salts are washed with diethylether in the sonicator. After drying on sodium sulfate, the filtrate is concentrated and purified on a silica column (pentane:ethyl acetate 85:15) to give 433 mg 6.9 (51%).

Rf: 0.29 (pentane:ethyl acetate 85:15).

IR (film): 3473 (s, br); 2940 (s); 2871 (s); 1712 (s); 1460 (s); 1376 (s); 1113 (s); 1028 (s) cm$^{-1}$.

$^1$H NMR: (200 MHz, CDCl$_3$): δ: 3.52 (2H, 2×d, J=10.6); 2.42 (2H, q, J=7.3); 1.98–1.14 (11H, m); 1.06 (3H, t, J=7.3); 0.98 (3H, s); 0.89 (3H, s); 0.70 (3H, s) ppm.

EXAMPLE 35
Synthesis of 6.11

To a solution of ethyl iodide (305 μl, 3.75 mmol) in diethylether (3.75 ml) is added tert.butyllithium (3.21 ml of a 2.34 M sol. in pentane, 7.5 mmol) at −78° C. and the resulting solution is stirred for 1 hour. Subsequently a solution of 6.9 (300 mg, 1.25 mmol) in dry diethylether (3 ml) is added dropwise. The mixture is stirred for 2 hours at −78° C. under an argon atmosphere and then brought to room temperature. Saturated ammonium chloride is added and the resulting mixture is extracted with diethylether and dichloromethane. The organic phase is dried (MgSO$_4$), filtered, concentrated and purified on a silica column (pentane:ethyl acetate 8:2) to yield 251 mg (74%) of the diol.

To a mixture of 4-methylmorpholine N-oxide (158 mg, 1.35 mmol), activated powdered molecular sieves 4 Å (450 mg) and the diol (243 mg, 0.9 mmol) in dichloromethane (1.8 ml) is added at 0° C. tetra(n.propyl)ammonium perruthenate (15.8 mg, 45 μmol) in portions. After 2 hours stirring at room temperature, the reaction mixture is filtered through silicagel, washed with dichloromethane and concentrated in vacuo. Purification by column chromatography (silica; pentane:ethyl acetate 85:15) gives 193 mg 6.11 (80%).

Rf: 0.20 (pentane:ethyl acetate 9:1).

IR (film): 3436 (s, br); 2965 (s); 2938 (s); 2877 (s); 1721 (s); 1460 (s); 1370 (m); 1266 (m); 1186 (m) cm$^{-1}$.

$^1$H NMR: (200 MHz, CDCl$_3$): δ: 9.65 (1H, s); 2.48–2.25 (1H, m); 2.09–1.90 (1H, m); 1.88–1.70 (1H, m); 1.65–1.20 (13H, m); 1.02 (3H, s); 0.97 (3H, s); 0.87 (6H, t, J=7.4 Hz); 0.76 (3H, s) ppm.

EXAMPLE 36
Synthesis of 6.13

To a solution of (methoxymethyl)triphenylphosphonium chloride (330 mg, 963 μmol) in diethylether (2.5 ml) is added n.butyllithium (2.5 M sol. in hexane, 347 μl, 866 μmol) at 0° C. After stirring for 10 minutes the red suspension is brought to room temperature, stirred 10 minutes and subsequently cooled again to −30° C. A solution of 6.11 (86 mg, 321 lmol) in diethylether (860 μl) is added dropwise and after ½ hour the cooling bath is removed and the mixture stirred at room temperature for 18 hours. Addition of water, followed by extraction with diethylether, drying (Na$_2$SO$_4$) and concentration in vacuo yields 200 mg of crude vinylether. After filtering through silicagel and evaporation of the solvent, the filtrate is diluted in tetrahydrofuran (1 ml) and treated with aqueous hydrochloric acid (2N sol. in tetrahydrofuran). After 30 min water is added and the mixture is extracted with diethylether, dried (Na$_2$SO$_4$) and filtered. The filtrate is concentrated in vacuo and purified on a silica column (pentane:ethyl acetate 9:1) and by HPLC (hexane:ethyl acetate 8:2) to give 30 mg (33%) of 6.13.

Rf: 0.26 (pentane:ethyl acetate 9:1).

IR (film): 3455 (m, br); 2965 (s); 2938 (s); 2876 (m); 1720 (s); 1460 (m); 1144 (m) cm$^{-1}$.

$^1$H NMR: (200 MHz, CDCl$_3$): δ: 9.8 (1H, dd, J=3, 3.5 Hz); 2.15 (2H, 2×d, J<1, 3, 3.5 Hz); 2.05–1.52 (2H, m); 1.52–1.4 (4H, q, J=7.5 Hz); 1.4–1.0 (6H, m); 0.99 (3H, s); 0.86 (6H, t, J=7.5 Hz); 0.81 (3H, s); 0.69 (3H, s) ppm.

EXAMPLE 37
Synthesis of 6.17(α+β) (R=Me)

A mixture of 6.4 and 6.5 (730 mg, 3.61 mmol)e potassium hydroxide (powdered, 400 mg, 7.22 mmol) and 1-chloro-3-methyl-2-butene (610 μl, 5.42 mmol) in toluene (8 ml) is sonicated during 30 minutes. After addition of a trace of 18-Crown-6 and more potassium hydroxide (200 mg, 3.61 mmol) the mixture is sonicated for an additional hour. Subsequently the mixture is filtered through a short pad of silicagel, the precipitate is washed with diethylether, the filtrate concentrated and purified by column chromatography (hexane:ethyl acetate 95:5→8:2) which yields 286 mg 6.17(α+β) (R=Me) (29%) and 450 mg of unreacted material.

Rf: 0.63 (hexane:ethyl acetate 8:2).

IR (film): 3015 (s); 1617 (m); 1420 (m); 1215 (s), 1015 (m); 923 (s) cm$^{-1}$.

$^1$H NMR: in accordance with structures of both epimers.

EXAMPLE 38
Synthesis of 6.18(α+β) (R=H)

A mixture of freshly powdered potassium hydroxide (700 mg, 12.5 mmol), 18-Crown-6 ether (50 mg, 193 mmol), 6.4 and 6.5 (700 mg, 3.47 mmol) and allyl bromide (644 μl, 7.62 mmol) in tetrahydrofuran (7 ml) is stirred for 48 hours at room temperature. The mixture is filtered through silicagel and the filtrate concentrated in vacuo. Purification by column chromatography (silica; hexane:ethyl acetate 95:5) yields 630 mg 6.18(α+β) (R=H) (75%).

Rf: 0.67 (hexane:ethyl acetate 8:2).

IR (film): 3079 (w); 2956 (m); 2875 (); 1 64 6 (w); 1465 (m); 1371 (m); 1150(s); 1106 (s); 1049 (s); 918(s) cm$^{-1}$.

$^1$H NMR: in accordance with structures of both epimers.

EXAMPLE 39
Synthesis of 6.19α (R=Me) and 6.19β (R=Me)

To a suspension of mercuric acetate (432 mg, 1.36 mmol) in water (1.35 ml) and tetrahydrofuran (1.35 ml) is added a solution of 6.17(α+β) (R=Me) (307 mg, 1.138 mmol) in tetrahydrofuran (2.7 ml); after a few minutes the color of the mixture becomes pale yellow. The mixture is stirred for 1 hour at room temperature and subsequently a 3M aqueous sodium hydroxide solution (1.35 ml) is added, immediately followed by addition of a sodium borohydride solution (1M in 3M sodium hydroxide, 0.68 ml). This yields a dark grey suspension which is filtered over a short pad of silicagel. The concentrated filtrate is purified by column chromatography (silica; hexane:ethyl acetate 8:2) to give 308 mg 19(α+β) (R=Me) (94%) of the tertiary alcohol. To a solution of this (288 mg, 1.0 mmol) in methanol:tetrahydrofuran 2:1 (90 ml) is added Amberlyst 15 (32 g). The resulting mixture is stirred for 55 h at room temperature and subsequently filtered through silicagel. The filtrate is concentrated in vacuo and purified by column chromatography (silica; hexane:ethyl acetate 6:4) to yield the diol (240 mg; 97%). To a mixture of 4-methylmorpholine N-oxide (NMMO, 157 mg, 1.348 mmol), activated powdered molecular sieves 4 Å (449 mg) and the diol (230 mg, 0.94 mmol) in dry dichloromethane (3 ml) is added portionwise at −10° C., solid tetra (n.propyl) ammonium perruthenate (TPAP, 15.8 mg, 45 lmol). After stirring for 1½ h at room temperature the mixture is filtered through celite and the residue washed with ethyl acetate. The dark colored filtrate is concentrated at the rotavapor and purified by column chromatography (silica; hexane:ethyl acetate 7:3). The two C-20 diastereomers 6.19α (R=Me; 90 mg, 40%) and 6.19p (R=Me; 60 mg, 26%) are separated by HPLC (hexane:acetone 92:8) and the relative configuration of both is established by NOE-experiments.

19α: Rf: 0.36 (hexane:acetone 75:25).

IR (film): 3444 (s, br); 2969 (s); 2875 (s); 1718 (s); 1466 (s); 1367 (s); 1161 (s); 1087 (s) cm$^{-1}$.

$^1$H NMR: (500 MHz, CDCl$_3$): δ: 9.65 (1H, s); 3.76–3.71 (1H, ddd); 3.55–3.49 (2H, m); 2.38–2.32 (1H, ddd); 2.12–2.04 (1H, m); 1.75–1.72 (2H, t); 1.72–1.68 (1H, m); 1.45–1.38 (1H, ddd); 1.23 (6H, s); 1.01 (3H, s); 0.99 (3H, s); 0.95 (3H, s) ppm.

19β: Rf: 0.41 (hexane:acetone 75:25).

IR (film): 3446 (s, br); 2964 (s); 2872 (s); 1718 (s); 1466 (s); 1384 (s); 1367 (s); 1154 (s); 1098 (s) cm$^{-1}$.

$^1$H NMR: (500 MHz, CDCl$_3$): δ: 9.61 (1H, s); 3.79–3.73 (1H, ddd, J=5.6, 5.7 Hz); 3.60–3.54 (1H, ddd); 3.50–3.45 (1H, t, J=7.3 Hz); 2.18–2.03 (2H, m); 1.77–1.74 (2H, t); 1.65–1.57 (2H, m); 1.52–1.45 (1H, m); 1.23 (6H, s); 1.09 (3H, s); 1.00 (3H, s); 0.90 (3H, s) ppm.

EXAMPLE 40

Synthesis of 6.20α (R=Et) and 6.20β (R=Et)

A solution of 6.18α,β (R=H) (600 mg, 2.48 mmol) and 9-borabicyclo [3.3.1]nonane (0.5 M in THF, 19.8 ml, 9.92 mmol) in tetrahydrofuran is stirred for 5 hours at 55° C. The mixture is brought to room temperature, ethanol (5.26 ml) and a 6M aqueous sodium hydroxide solution (1.75 ml, 9.92 mmol) are added and the mixture is subsequently cooled to 0° C. A 35% aqueous hydrogen peroxide solution (4.2 ml) is added slowly, followed by refluxing for 1 hour. Extraction with diethylether, drying (MgSO$_4$) and solvent evaporation yields a residue which is purified by column chromatography (silica; hexane:ethyl acetate 6:4) to give 615 mg of the alcohol (95%).

A mixture of this alcohol (220 mg, 0.846 mmol) and pyridinium dichromate (1.43 g, 5.08 mmol) in N,N-dimethylformamide (6ml) is stirred for 12 hours at 40° C. Water is added and the mixture extracted with diethylether. Drying of the organic pnase (MgSO$_4$) and concentration in vacuo yields a yellow oil which is diluted in diethylether. The solution is cooled at 0° C. and a solution of diazomethane in diethylether is added dropwise till complete methylation is observed by thin layer chromatography. Subsequently an equal volume of hexane is added and the organic phase is washed with water, dried (MgSO$_4$) and concentrated in vacuo. Purification by column chromatography (silica; hexane/ethyl acetate 8:2) and HPLC (hexane:ethyl acetate 9:1) yields 85 mg (35%) of the methylester.

A solution of this ester (90 mg, 0.31 mmol) in diethylether is added to ethylmagnesium iodide (1.3 mmol). The resulting mixture is stirred for 2 hours at room temperature and subsequently quenched with saturated ammonium chloride. Extraction with diethylether, drying of the organic fraction (MgSO$_4$) solvent removal and purification on silica (hexane:ethyl acetate 7:3) gives 90 mg (92%) of the tertiary alcohol.

To a solution of this alcohol (90 mg, 0.285 mmol) in methanol:tetrahydrofuran 3:1 (20 ml) is added Amberlyst 15 (7 g). After 72 hours stirring at room temperature the Amberlyst is filtered off, the filtrate is concentrated in vacuo and purified on a silica column (hexane:ethyl acetate 6:4) to yield 65 mg (84 %) of the diol.

To a solution of this diol (50 mg, 0.184 mmol) and triethylamine (211 μl, 1.84 mmol) in dimethyl sulfoxide:dichloromethane 1:1 (2 ml) is added portionwise sulfur trioxide pyridine complex (179 mg, 1.104 mmol). After 2 hours stirring, under nitrogen, at room temperature the mixture is filtered through silicagel and the filtrate, after solvent removal, purified by column chromatography (silica; hexane:acetone 9:1). HPLC (hexane:acetone 92:8) separation gives the two epimeric alcohols 6.20α (R=Et, 13 mg, 26%) and 6.20β (R=Et, 20 mg, 40%). The relative stereochemistry is established by NOE experiments.

6.20α: Rf: 0.32 (hexane:ethyl acetate 8:2).

IR (film): 3519 (s, br); 2966 (s); 2878 (s); 2728 (w); 1718 (s); 1462 (s); 1371 (m); 1264 (w); 1138 (s); 1089 (s) cm$^{-1}$.

$^1$H NMR: (500 MHz, CDCl$_3$): δ: 9.65 (1H, s); 3.71 (1H, m); 3.50 (2H, m); 2.39–2.31 (1H, m); 2.12–2.04 (1H, m); 1.75–1.67 (3H, m); 1.55–1.38 (6H, m); 1.01 (3H, s); 0.99 (3H, s); 0.95 (3H, s); 0.86 (6H, t) ppm.

6.20β: Rf: 0.35 (hexane:ethyl acetate 8:2).

IR (film): 3516 (s, br); 2962 (s); 2877 (s); 2716 (m); 1721 (s); 1463 (s); 1368 (m); 1139 (s); 1100 (s) cm$^{-1}$.

$^1$H NMR: (500 MHz, CDCl$_3$): δ: 9.61 (1H, s); 3.75 (1H, m); 3.54 (1H, m); 3.47 (1H, t); 2.17–2.03 (2H, m); 1.72 (2H, t); 1.65–1.42 (7H, m); 1.10 (3H, s); 1.00 (3H, s); 0.90 (3H, s); 0.86 (6H, t) ppm.

EXAMPLE 41

Synthesis of 621α (R=Me)

A solution of n.butyllithium (2.5 M in hexanes, 195 μl, 0.486 mmol) is added dropwise at −10° C. to a suspension of (methoxymethyl) triphenyl phosphonium chloride (233 mg, 0.680 mmol) in diethylether (1.8 ml). After 20 minutes the resulting red suspension is brought to room temperature, stirred for 10 minutes and then cooled again to −30° C. A solution of 6.19α (R=Me) (47 mg, 194 μmol) in diethylether (0.5 ml) is added dropwise, after stirring for ½ h at −30° C. the mixture is brought to room temperature and stirred for 15 hours. Work-up by filtration through silicagel, washing of the residue with diethylether and concentration of the filtrate yields 64 mg of a pale yellow oil which is diluted in tetrahydrofuran (1 ml). A solution of hydrochloric acid (2 N in tetrahydrofuran, 120 μl) is added and the resulting solution is stirred for 2 h at room temperature. Filtration through silicagel, concentration of the filtrate and purification on HPLC (hexane:acetone 9:1) give 6.21α (R=Me; 24 mg; 48%).

Rf: 0.21 (hexane:ethyl acetate 85:15).

¹H NMR: (360 MHz, CDCl₃): δ: 9.82 (1H, dd, J=2.2, 4 Hz); 3.79–3.72 (1H, dt, J=5.7, 9.5); 3.64–3.56 (1H, dd, J=5.6 Hz); 3.61–3.54 (1H, dt); 2.42–2.37 (1H, dd, J=2.2, 14.5 Hz); 2.33–2.27 (1H, dd, J=4, 14.5 Hz); 2.19–2.09 (1H, m); 1.99–1.89 (1H, m); 1.75 (2H, t); 1.66–1.54 (3H, m); 1.23 (6H, s); 1.00 (3H, s); 0.90 (3H, s); 0.83 (3H, s) ppm.

EXAMPLE 42

Synthesis of 6.21β (R=Me)

As described for 6.21α (R=Me; yield 36%).

Rf: 0.15 (hexane:ethyl acetate 85:15).

IR (film): 3452 (s, br); 2968 (s); 2877 (m); 1720 (s); 1468 (m); 1366 (m); 1155 (m); 1094 (s) cm⁻¹.

¹H NMR: (200 MHz, CDCl₃): δ: 9.84 (1H, dd, J=3.6 Hz); 3.81–3.42 (3H, m); 2.38–2.01 (4H, m); 1.80–1.55 (5H, m); 1.22 (6H, 2xs); 1.10 (3H, s); 0.88 (6H, 2×s) ppm.

EXAMPLE 43

Synthesis of 6.22α (R=Et)

A solution of n.butyllithium (2.5 M in hexane, 57 μl, 0.142 mmol) is added dropwise at −10° C. to a suspension of (methoxymethyl) triphenyl phosphoniumchloride (56 mg, 0.163 mmol) in diethylether (0.8 ml). After 10 minutes the resulting red suspension is brought to room temperature stirred for 10 minutes and then cooled again to −30° C. A solution of 6.20a α (11 mg, 40.7 μmol) in diethylether (0.2 ml) is added dropwise, after ½ hour at −30° C. the mixture is brought to room temperature and stirred for 15 hours. Work-up by filtration through silicagel, washing of the residue with diethylether and concentration of the filtrate yields 35 mg of a pale yellow oil which is diluted in tetrahydrofuran (1 ml). A solution of hydrochloric acid (2N in tetrahydrofuran, 150 μl) is added and the resulting solution is stirred for 2 h at room temperature. Filtration through silicagel, concentration of the filtrate and purification on HPLC (hexane:acetone 9:1) gives 3 mg (26%) of 6.22α.

Rf: 0.27 (hexane:ethyl acetate 8:2).

¹H NMR: (500 MHz, CDCl₃): δ: 9.81 (1H, t); 3.72 (1H, m); 3.52 (2H, m); 2.40 (1H, dd); 2.31 (1H, dd); 2.18–2.08 (1H, m); 1.99–1.90 (1H, m); 1.75–1.38 (9H, m); 1.01 (3H, s); 0.91 (3H, s); 0.87 (3H, s); 0.85 (6H, t) ppm.

EXAMPLE 44

Synthesis of 6.22β (R=Et)

As described for 6.22α (R=Et); yield 36%.

Rf: 0.29 (hexane:ethyl acetate 8:2).

IR (film): 3513 (s, br); 2963 (s); 2879 (m); 2732 (w); 1720 (s); 1463 (m); 1387 (m); 1094 (s) cm⁻¹.

¹H NMR: (500 MHz, CDCl₃): δ: 9.80 (1H, dd); 3.72 (1H, m); 3.49 (2H, m); 2.30 (1H, dd, J=14.3, 3.5 Hz); 2.21 (1H, dd, J=2.6 Hz); 2.15–2.08 (1H, m); 1.80–1.42 (10H, m); 1.10 (3H, s); 0.89 (3H, s); 0.87 (3H, s); 0.86 (6H, t) ppm.

EXAMPLE 45

Synthesis of 6.16

Starting from 6.7 as described for the synthesis of 6.13 starting from 6.3.

6.14: Rf: 0.26 (hexane:ethyl acetate 8:2).

¹H NMR: (360 MHz, CDCl₃): δ: 3.42 (2H, s, br); 2.42 (4H, m); 1.90–1.24 (9H, m); 1.05 (4H, t, J=7.3 Hz); 0.89 (3H, s); 0.80 (3H, s); 0.67 (3H, s) ppm.

6.15: Rf: 0.21 (hexane:ethyl acetate 8:2).

¹H NMR: (500 MHz, CDCl₃): δ: 9.65 (1H, s); 2.00 (2H, m); 1.65 (2H, m); 1.45 (4H, q); 1.40–1.05 (8H, m); 1.01 (3H, s); 0.93 (3H, s); 0.85 (6H, t); 0.71 (3H, s) ppm.

6.16: Rf: 0.26 (hexane:ethyl acetate 8:2).

IR (film): 3426 (s, br); 2935 (s); 1714 (m); 1650 (s); 1390 (m); 1112 (m) cm⁻¹.

¹H NMR: (500 MHz, CDCl₃): δ: 9.86 (1H, t, J=3.1 Hz); 2.29 (1H, dd, J=14.5 Hz); 2.24 (1H, dd); 1.91 (1H, m); 1.75 (1H, m); 1.66 (1H, m); 1.59 (1H, m); 1.45 (4H, q, J=7.6 Hz); 1.42–1.07 (8H, m); 1.05 (3H, s); 0.86 (6H, t); 0.80 (3H, s); 0.69 (3H, s) ppm

EXAMPLE 46

Synthesis of 6.24

To a solution of 6.2 (1.9 g, 6.7 mmol) in CH₂Cl₂ (120 ml) at 0° C., DIPEA (20 eq, 20 ml) is added. After stirring for 40 min at 0° C. MEMCl (8 eq, 6 ml) is added and stirring is continued for 2 h. The mixture is poured in a water-ether mixture. The organic phase is dried (MgSO₄). After filtration and evaporation the residue is purified by column chromatography (silicagel, diethylether:hexane 1:3) giving 6.23 (2.02 g, 80%).

Rf: 0.49 (diethylether:hexane 1:1).

IR (film): 3480, 3308, 1782, 1150, 1085cm⁻¹.

¹H NMR: (500 MHz, CDCl₃): δ: 4.688 and 4.671 (2×1H, J=6.7); 3.68 and 3.56 (2×2H, 2×m); 3.47 (1H, d, J=9.3), 3.39 (3H, s); 3.297 (1H, dd, J=3.3, 9.0); 3.281 (1H, d, J=9.4); 2.94 (1H, dd, J=9.0, 11.7); 2.28 (2H, dtd, J=3, 10, 12); 2.24 (1H, m); 0.99 (3H, s); 0.96 (3H, s); 0.72 (3H, s) ppm.

To a solution of 6.23 (1 g, 2.7 mmol) in DMF (160 ml), sodium nitrite (400 mg, 2 eq) and a catalytic amount of urea is added. After stirring for 2 days at r.t. the solution is poured in a ether-ice mixture. The ether phase is dried (MgSO₄). After filtration and evaporation the residue is purified by column chromatography (silicagel diethylether:hexane 1:6→1:3) giving the nitro compound (350 mg; 45%) with Rf=0.36 (diethylether:hexane 1:1).

To a solution of the nitro compound (345 mg, 1.2 mmol) in anhydrous MeOH (25 ml) NaOMe (98 mg, 1.3 eq), is added. After stirring for 30 min, the solution is cooled to −78° C. and a ozone flow (20 mmol/h) is passed through until the colour is deep blue (30 min), then the solution is flushed with nitrogen for 30 min at −78° C. followed by adding dimethylsulphide (3.5 ml).

The mixture is warmed to r.t. and after solvent evaporation an ether-brine mixture is added. The ether phase is dried (MgSO₄). After filtration, solvent evaporation and column chromatography (silicagel, nitromethane:benzene 1:14) gives 6.24 (215 mg, 70%).

Rf: 0.14 (nitromethane:benzene 1:14).

IR (film): 1717 cm⁻¹.

¹H NMR: (500 MHz, CDCl₃): δ: 9.76 (1H, d, J=2.24); 4.692 and 4.675 (2×1H, J=6.7); 3.69 and 3.56 (4H); 3.49 (1H, d, J=9.4); 3.39 (3H, s); 3.32 (1H, d, J=9.4); 2.69 (1H, td, J=2.2, 9.1); 2.11 (1H, m); 1.20 (3H, s); 1.02 (3H, s); 0.91 (3H, s) ppm.

EXAMPLE 47

Synthesis of 6.25

To a solution of n.butyllithium (500 μl, 2.4 M, 1.5 eq, in hexane) in THF (6 ml) at −78° C., under argon atmosphere, diisopropylamine (1.5 eq, 168 μl) is added. After stirring for 20 min at −78° C. triethyl-4-phosphonocrotonate (1.5 eq, 333 mg, 90%, 300 µl) is added dropwise. After stirring for 2 h at −78° C., a solution of 6.24 (215 mg, 833 µmol, 1 eq) in THF (5 ml) is added dropwise and stirring is continued for 2 h at −78° C. The mixture is then slowly warmed up to r.t. and is poured in an ether-brine mixture. The ether phase is dried (MgSO$_4$).

Filtration, evaporation and column chromatography (diethylether:hexane 1:4) gives the dienic ester (267 mg, 91% with Rf=0.39 (diethylether:hexane 1:1). To a solution of this product (267 mg, 754 µmol) in EtOAc (10 ml), a catalytic amount of palladium on carbon (10%) is added, after which the mixture is hydrogenated for 3 h (4 atm). Filtration over celite, addition of Et$_3$N (200 µl), evaporation and column chromatography (diethylether:hexane 1:14→1:6) gives the saturated product (215 mg, 80%, with Rf=0.53 (diethylether:hexane 1:1)).

To a solution of this (60 mg, 169 µmol) in CH$_2$Cl$_2$ (1200 µl), at −78° C., a solution of dimethylborobromide (±10 eq, 1 ml, 1.5 M in CH$_2$Cl$_2$:ClCH$_2$CH$_2$Cl 2:1) is added. After stirring for 1 h at −78° C., the mixture is transferred to a vigorously stirred mixture of THF (8 ml) and saturated NaHCO$_3$ solution (4 ml). The reaction flask is washed with dichloromethane (2×2 ml:) followed by addition of ether and brine. The organic phase is dried (MgSO$_4$). After filtration and evaporation and column chromatography (diethylether:hexane 1:3) 6.25 (42 mg, 93%) is obtained.

Rf: 0.38 (diethylether:hexane 1:1).

IR (film):1717 cm$^{-1}$.

$^1$H NMR: (500 MHz, CDCl$_3$): δ: 4.12 (2H, q, J=7.13); 3.57 (13H, br, d, J=10), 3.45 (1H, br, d, J=10); 2.29 (2H, m); 1.87 (1H, m); 1.73 (1H, qd, J=2, 10); 1.25 (3H, t, J=7.13); 0.98 (3H, s); 0.89 (3H, s); 0.71 (3H, s) ppm.

EXAMPLE 48

Synthesis of 6.26

To a solution of 6.25 (140 mg, 520 µmol) in CH$_2$Cl$_2$-DMSO (2.5 ml:5 ml), at −15° C., a solution of Et$_3$N (3 eq, 220 µl) and sulphur trioxide-pyridine complex (25 eq, 205 mg) in CH$_2$Cl$_2$-DMSO (1 ml:2 ml) is added dropwise. After stirring for 3 h between −10° C. and 4° C, the mixture is poured in an ether-brine. The organic phase is dried (MgSO$_4$). Filtration, evaporation, and column chromatography (silicagel, diethylether:hexane 1:9) gives the aldehyde (100 mg, 72% with Rf=0.60 (diethylether:hexane 1:1)). This aldehyde is transformed into 6.26 as described for 6.12 from 6.10 (yield 57%).

Rf: 0.50 (Et$_2$O:hexane 1:1).

$^1$H NMR: (500 MHz, CDCl$_3$): δ: 9.83 (1H, dd, J=2.48, 4.12); 4.13 (2H, q, J=7.13); 2.30 (4H, m); 1.93 (1H, m); 1.27 (3H, t, J=7.1), 0.95 (3H, s); 0.80 (3H, s); 0.68 (3H, s) ppm.

EXAMPLE 49

Synthesis of 6.27

Aldehyde 6.26 is coupled with 13.1 as described for analogue 11 from 6.12 (yield 91% with Rf 0.73, Et$_2$O:hexane 1:1).

$^1$H NMR: (360 MHz, CDCl$_3$): δ: 6.34 (1H, dd, J=11, 15); 5.92 (1H, d, J=11); 5.66 (dt, J=8,15); 5.20 (1H, br s); 4.87 (1H, br s); 4.39 (1H, t, J=5.5); 4.185 (1H, m); 4.13 (2H, q, J=7.14); 2.40 (1H, dd, J=3, 13); 2.30 (2H, m); 2.18 (1H, dd, J=7, 13); 1.26 (3H, t, J=7.14); 0.882 (9H, s); 0.866 (9H, s); 0.80 (3H, s); 0.78 (3H, s); 0.66 (3H, s); 0.07 (12H, s) ppm.

EXAMPLE 50

Synthesis of 6.29

To a suspension of copper(I)iodide (420 mg, 2.2 mmol) and zinc dust (600 mg, 9.2 mmol) in ethanol-water 7:3 (27 ml) are added trans-2,4-pentadianoic acid ethyl ester (270 µl, 1.93 mmol), and iodide 6.2 (420 mg, 1.5 mmol). The mixture is sonicated during 1 h under argon at 0° C. The mixture is filtered through celite and washed with EtOAc. The filtrate is extracted with EtOAc, dried (MgSO$_4$) and concentrated. Column chromatography (silica gel:diethyl ether:hexane 1:9→1:5) gives 6.28 (145 mg, 35%) and recovered 6.2 (145 mg, 35%).

Rf: 0.38 (diethyl ether:hexane 1:1).

$^1$H NMR: (500 MHz, CDCl$_3$): δ: 5.55 (2H, 2×dt, J=6, 15); 4.14 (2H, q, J=7.13); 3.58 (1H, br d, J=11); 3.45 (1H, br d, J=11); 3.02 (2H, d, J=6); 2.10 (1H, m); 1.90 (2H, m); 1.75 (1H, qd, J=3,10); 1.26 (3H, t, J=7.12); 0.98 (3H, s); 0.89 (3H, s); 0.72 (3H, s) ppm.

To a solution of 6.28 (40 mg, 142 µmol) in dry EtOAc (8 ml), a catalytic amount of Pd/C (10%) is added, after which the mixture is hydrogenated for 3 h (4 atm). Filtration over celite, addition of Et$_3$N (200 µl), evaporation and column chromatography (diethyl ether:hexane 1:4) gives 6.29 [32 mg, 80%, with Rf=0.36 (diethyl ether:hexane 1:1)].

$^1$H NMR: (500 MHz, CDCl$_3$): δ: 4.13 (2H, q, J=7); 3.58 (1H, d, J=10); 3.46 (1H, d, J=10); 2.30 (2H, t, J=7); 1.87 (1H, m); 1.72 (1H, qd, J=3, 10); 1.26 (3H, t, J=7); 0.99 (3H, s); 0.89 (3H, s); 0.71 (3H, s) ppm.

EXAMPLE 51

Synthesis of 10.2

A solution of 10.1 (3.44 g, 17.36 mmol), ethylene glycol (5.3 ml, 95 mmol) and pyridinium p-toluenesulfonate (500 mg, 1.99 mmol) in cyclohexane (190 ml) is refluxed for 3 h with continuous separation of water. After cooling to r.t., the solvent is evaporated, and the residue is dissolved in diethyl ether (300 ml). Washing with a saturated NaHCO$_3$-solution and brine, drying (Na$_2$SO$_4$), solvent evaporation and purification by column chromatography (silica gel hexanes:acetone 9:1) and HPLC (isooctane:acetone 95:5) gives 10.2 (3.6 g, 86%).

Rf: 0.20 (hexane:acetone 95:5).

IR (film): 2950; 2881; 1740; 1436; 1280; 1189 cm$^{-1}$.

$^1$H NMR: (500 MHz, CDCl$_3$): δ: 3.93 (4H, m); 3.65 (3H, s); 2.47 (1H, dd, J=14.45, 3.13); 2.06 (1H, tt, J=11.15, 3.31); 2.02 (1H, dd, J=14.42, 10.72); 1.63–1.52 (5H, m); 1.22 (1H, m); 0.911 (s), 0.898 (3H, s) ppm.

EXAMPLE 52

Synthesis of 10.3

To a stired solution of LDA (2M in hexane, 4.67 ml, 9.348 mmol) in THF (5.45 ml) at −30° C. is added a solution of 10.2 (1.510 g, 6.232 mmol) in THF (21.8 ml), and stirring is continued for 1 h. After cooling to −78° C., a mixture of 5-bromo-1-pentene (2.34 ml, 19.76 mmol) and hexamethylphosphoramide (5.5 ml, 31.16 mmol) is added; stirring is continued for 3 h. The mixture is allowed to come very slowly to r.t. and is then diluted with water and diethyl ether. Extraction of the water layer with diethyl ether, drying of the organic phase (Na$_2$SO$_4$, solvent evaporation and purification by column chromatography (silica gel:hexane:acetone 9:1) and HPLC (isooctane:acetone 97:3) yields 10.3 (1.81 g, 93%).

Rf: 0.24 (isooctane:acetone 97:3).

IR (film): 3076; 2950; 2881; 1732; 1641; 1435; 1186 cm$^{-1}$.

$^1$H NMR: (500 MHz, CDCl$_3$): δ: 5.76 (1H, ddt, J=17.10, 10.17, 6.65 (t)); 4.99 (1H, ddd, J=17.13, 1.82, 1.59); 4.94 (1H, m); 3.92 (4H, m); 3.65 (3H, s); 2.49 (1H, dt, J=11.61, 3.39 (t)); 2.03 (2H, m); 1.95 (1H, dt, J=12.87, 3.52(t)); 1.65–1.59 (3H, m); 1.57 (1H, m); 1.53 (1H, m); 1.51–1.40 (3H, m); 1.35–1.19 (3H, m); 0.961 (3H, s); 0.924 (3H, s) ppm.

EXAMPLE 53

Synthesis of 10.6

To a suspension of LiAlH$_4$ (332.5 mg, 8.762 mmol) in diethyl ether (165 ml) is added dropwise at 0° C. a solution of 10.3 (1.600 g, 5.154 mmol) in diethyl ether (82 ml); the mixture is stirred for 1 h at 0° C. and for 3 h at r.t. To the vigorously stirred mixture is then added, very slowly, a saturated Na$_2$SO$_4$-solution, until a white precipitate flocculates. The suspension is stirred for 1 h, the precipitate filtered over celite, and the solvent evaporated, yielding 10.4 (1.453 g, 99.8%).

Rf: 0.22 (hexane:acetone 8:2).

$^1$H NMR: (500 MHz, CDCl$_3$): δ: 5.79 (1H, ddt, J=17.10, 10.17, 6.64(t)); 4.99 (1H, ddd, J=17.14, 1.94, 1.61); 4.94 (1H, m); 3.92 (4H, m); 3.55 (1H, m); 3.40 (1H, m); 2.03 (2H, m); 1.77 (1H, dd, J=12.82, 3.55); 1.63 (1H, m); 1.57 (1H, dd, J=12.72, 3.67); 1.54–1.28 (12H, m); 0.978 (3H, s); 0.910 (3H, s) ppm.

To a solution of 10.4 (1.453 g, 5.145 mmol) in dichloromethane (25.7 ml) and triethylamine (3.9 ml, 20.58 mmol), a solution of TsCl (1.962 g, 10.29 mmol) in dichloromethane (15.4 ml), and a small amount of 4-dimethylaminopyridine are added at 0° C. After stirring for 20 h at r.t. the volume is reduced to 50%, followed by filtration of the precipitate. Complete evaporation of the solvent, and HPLC purification (hexane:acetone 85:15) gives 10.5 (2.126 g, 95%).

Rf: 0.25 (hexane:acetone 85:15).

To a solution of 10.5 (2.126 g, 4.870 mmol) in diethyl ether (250 ml) is added LiAlH$_4$ (3.69 g, 97.40 mmol) and the refluxed suspension is stirred for 5 h. After cooling to 0° C. a saturated Na$_2$SO$_4$-solution is carefully added until the grey precipitate has disappeared. A small excess of Na$_2$SO$_4$-solution is added and stirring is continued for 3 h. The precipitate is filtered over celite and is washed twice by suspending it in diethyl ether, followed by a new filtration. After evaporating the solvent, the residue is purified by HPLC (isooctane:ethyl acetate 98:2), giving 10.6 (1.14 g, 88%).

Rf: 0.20 (isooctane:ethyl acetate 98:2).

IR (film): 3076; 2949; 2869; 1641; 1464; 1090 cm$^{-1}$.

$^1$H NMR: (500 MHz, CDCl$_3$): δ: 5.81 (1H, ddt, J=17.17, 10.21, 6.63(t)); 4.99 (1H, ddd, J=17.02, 2.08, 1.58); 4.93 (1H, m); 3.92 (4H, m); 2.02 (2H, m); 1.64 (2H, m); 1.54 (2H, m); 1.52–1.33 (7H, m); 1.26 (2H, m); 0.971 (3H, s); 0.911 (3H, s); 0.907 (3H, d, J=6.83); 0.895 (1H, m) ppm.

EXAMPLE 54

Synthesis of 10.7

At −78° C., ozone is passed through a solution of 10.5 (565 mg, 2.121 mmol) in dichloromethane (16.8 ml) and a 2.5M solution of sodium hydroxide in methanol (4.24 ml), until a light blue color is retained. The reaction mixture is diluted with diethyl ether and water. After the temperature has raised to room temperature, the organic phase is washed with brine, dried (Na$_2$SO$_4$) and the solvent is evaporated. Purification of the residue by column chromatography (hexane:acetone 9:1) and HPLC (hexane:acetone 97:3) gives the ester (405 mg, 64%). A solution of this ester (400 mg, 1.340 mmol) and pyridinium p-toluenesulfonate (101 mg, mmol) in acetone 13.4 ml), and a few drops of water, is refluxed for 3 h. After cooling to r.t., the solvent is evaporated and the residue is dissolved in diethyl ether, followed by washing with a saturated NaHCO$_3$-solution and brine. Drying (Na$_2$SO$_4$), solvent evaporation and purification by column chromatography (silica gel:hexane:acetone 9:1), and HPLC (hexane:acetone 96:4), gives 10.7 (256 mg, 75%) next to 10.6 (83 mg, 21%).

Rf: 0.19 (hexane:acetone 93:7).

IR (film): 1739; 1705 (s); 1454; 1436; 1249 cm$^{-1}$.

$^1$H NMR: (500 MHz, CDCl$_3$): δ: 3.67 (3H, s); 2.49 (1H, dt, J=13.62(t), 6.39); 2.33–2.24 (3H, m); 2.03 (1H, ddd, J=12.90; 6.24; 3.29); 1.80–1.58 (4H, m); 1.56–1.47 (3H, m); 1.33 (1H, m); 1.11 (3H, s); 1.07 (3H, s); 1.02 (1H, m); 0.943 (3H, d, J 6.90) ppm.

EXAMPLE 55

Synthesis of Aldehydes 10.8 and 10.9

A. To a solution of FOSMIC (19.6 μl, 113.6 μmol) in diethyl ether (475 μl) is added at −60° C. a 2.5M solution of butyllithium in hexanes (52 μl, 130.5 μmol), and the resulting solution is stirred for 15 minutes. A solution of 10.7 (28.9 mg, 113.6 μmol) in diethyl ether (119 μl) is then added, and the mixture is allowed to come to 0° C. and stirring is continued for 1.5 h. After adding, carefully, a 37%-aquous HCl solution (200 μl) the mixture is vigorously stirred overnight. After diluting with diethyl ether, the water layer is extracted with diethyl ether and ethyl acetate, followed by washing the organic phase with brine and drying (Na$_2$SO$_4$). The solution is treated with diazomethane, the excess is destroyed by adding silica gel. Filtration, solvent evaporating and purification by column chromatography (silica gel:hexane:acetone 9:1) gives 10.8 and 10.9 (7.4:1 ratio; 17 mg, 64%). The mixture can be separated by HPLC (hexane:acetone 96:4).

Rf: 0.35 (hexane:acetone 9:1).

IR (film): 2934; 2863; 1739; 1719; 1438; 1374; 1248; 1171 cm$^{-1}$.

hu 1H NMR: (500 MHz, CDCl$_3$): δ: 9.80 (1H, d, J=2.89); 3.66 (3H, s); 2.29 (2H, m); 1.99 (1H, dt, J=12.53, 3.29(t)); 1.86 (1H, m); 1.74 (2H, m); 1.63–1.44 (4H, m); 1.39 (1H, m); 1.23 (2H, m); 1.17 (3H, s); 1.02 (1H, m) ppm.

B. A suspension of trimethylsulfonium iodide (107.0 mg, 0.514 mmol) and 2.5M solution of butyllithium (in hexane 132 μl, 0.29 mmol) in THF (6.2 ml) is stirred for 1 h at r.t. After cooling to 0° C., a solution of 10.7 (52.3 mg, 0.206 mmol) in THF (4.1 ml) is added and stirring is continued for 2 h. at. r.t. The mixture is diluted with dichloromethane, extracted with water and brine, dried (Na$_2$SO$_4$), and the solvent evaporated. The residue is purified by column chromatography (silica gel:hexane:acetone 9:1) and HPLC (hexane:acetone 96:4), yielding the two diastereoisomers 10.10 (17 mg, 33% ratio 6:4) and starting material 10.7 (18 mg, 33%).

Rf: 0.17 (hexane:acetone 96.5:3.5).

To a solution of 10.7 (17 mg, 63.34 μmol) in diethyl ether (3.2 ml) is added at 0° C. boron trifluoride diethyl etherate (40 μl, 324.6 μmol). The solution is stirred for 1 h at 0° C. and 12 h at r.t.; The mixture is poured in diethyl ether and washed with a saturated NaHCO$_3$-solution and brine. After evaporation of the solvent the residue is purified by column chromatography (silica gel:hexane:acetone 9:1), yielding a mixture of 10.8 and 10.9 (11 mg, 65%; ratio 1.6:1). The mixture can be separated by HPLC (hexane:acetone 96:4).

Rf: 0.38 (hexane:acetone 9:1).

IR (film): 2950; 2867; 1739; 1713; 1437 cm$^{-1}$.

$^1$H NMR: (500 MHz, CDCl$_3$): δ: 9.98 (1H, d, J=2.60); 3.67 (3H, s); 2.30 (2H, m); 2.01 (1H, m); 1.84 (1H, m); 1.77–1.64 (4H, m); 1.55–1.28 (6H, m); 1.18 (3H, s); 1.01 (3H, s); 0.941 (1H, m); 0.927 (3H, d, J=6.88) ppm.

EXAMPLE 56

Synthesis of 11.13

A solution of (−)-camphoric acid 11.12 (3 g, 15 mmol) in dry THF (45 ml) is added slowly to a stirred suspension of LiAlH$_4$ (1.9 g, 50 mmol) in dry Et$_2$O (40 ml); the mixture is refluxed for 4 h. After cooling to r.t., Na$_2$SO$_4$.10 H$_2$O is added. Filtering, solvent evaporation and crystallisation from EtOAc yields the diol (2.28 g, 88%).

A solution of the diol (0.54 g, 3.14 mmol) in vinyl acetate (10 ml) is treated for 66 h with SAM II lipase (300 mg) at 37° C.

Solvent evaporation and column chromatography (silicagel, pentane:EtOAc 8:2) yields monoacetate 11.13 (0;4 g, 60%).

Rf: 0.28 (pentane:EtOAc 8:2).

IR (film): 3440 (s, broad); 2962 (s); 2874 (m); 1739 (s); 1463 (m); 1369 (m); 1246 (s); 1144 (w); 1033 (s); 971 (w) cm$^{-1}$.

$^1$H NMR: (360 MHz, CDCl$_3$): δ: 4.08 (1H, dd, J=10.80); 3.98 (1H, dd, J=6.10, 8.20); 3.58 (1H, d, J=10.75); 3.46 (1H, d); 2.20 (1H, ddt, J=8.9); 2.03 (3H, s); 1.89 (1H, ddd), 1.58 (1H, dt); 1.35 (2H, 2); 1.01 (6H, s); 0.81 (3H, s) ppm.

EXAMPLE 57

Synthesis of 11.14

To 11.13 (317 mg, 1.48 mmol) and Et$_3$N (1.71 ml, 14.8 mmol) in CH$_2$Cl$_2$:DMSO (1:1; 8 ml) is added SO$_3$.pyridine complex (1.42 g, 8.88 mmol) After stirring for 3 h at r.t. the mixture is poured in H$_2$O and extracted with Et$_2$O. The organic layer is washed with 1 N HCl and with brine, dried (Na$_2$SO$_4$) and concentrated. Column chromatography (silicagel, pentane:EtOAc 9:1) gives the aldehyde (250 mg, 80%).

This aldehyde (190 mg, 0.90 mmol) in dry THF (2 ml) is added to lithio triethyl-4-phosphonoacetate (2.83 mmol; from phosphonoacetate and LDA) in dry THF (8 ml) at 0° C. After stirring for 12 h at 25° C., the mixture is washed with brine and dried (MgSO$_4$). Solvent evaporation yields crude acetate which is solvolysed with K$_2$CO$_3$ in EtOH at r.t. Filtration, solvent evaporation and column chromatography (silicagel; pentane:EtOAc 75:25) yields 11.14 (155 mg, 65%).

Rf: 0.31 (pentane:EtOAc 8:2).

IR (film): 3436 (s, broad); 2965 (s); 2870 (m); 1712 (s); 1636 (s); 1462 (s); 1369 (m); 1330 (m); 1253 (s); 1140 (s); 1007 (s); 882 (m); 832 (w) cm$^{-1}$.

$^1$H NMR: (500 MHz, CDCl$_3$): δ: 7.28 (1H, dd, J 10.5, 15.4); 6.18 (1H, d, J=15.5); 6.10 (1H, dd); 5.80 (1H, d); 4.19 (2H, q, J=7.2); 3.71 (1H, dd, J=10.3, 5.8); 3.53 (1H, dd, J=8.2); 2.13 (1H, m); 2.00 (1H, m); 1.94 (1H, m); 1.48 (1H, m); 1.41 (1H, m); 1.28 (3H, t); 1.01 (3H, s); 0.94 (3H, s); 0.68 (3H, s) ppm.

EXAMPLE 58

Synthesis of 11.16

A solution of 11.14 (17 mg, 0.064 mmol) in EtOAc (1 ml), and 5% Rh on Al$_2$O$_3$ (20 mg) is stirred at r.t. for 2 h under H$_2$ atmosphere. Filtration on silicagel, solvent evaporation and HPLC (pentane:EtOAc 7:3) purification gives 11.16 (16 mg, 90%).

Rf: 0.29 (pentane:EtOAc 75:25).

IR (film): 3385 (s, broad); 2941 (s); 2860 (m); 1735 (s); 1455 (s); 1371 (s); 1248 (s); 1152 (s); 1022 (s); 945 (m); 870 (w) cm$^{-1}$.

$^1$H NMR: (500 MHz, CDCl$_3$): δ: 4.12 (2H, q, J=7.1); 3.72 (1H, dd, J=10.2, 5.4); 3.50 (1H, dd, J=8.7); 2.30 (2H, t, J=7.4); 2.07 (1H), 1.88 (1H); 1.60 (2H, m); 1.53 (1H); 1.40 (1H); 1.38–1.18 (5H, m); 1.25 (3H, t); 0.89 (3H, s); 0.84 (3H, s); 0.68 (3H, s) ppm.

EXAMPLE 59

Synthesis of 11.18

A solution of 11.16 (10 mg, 0.037 mmol) in dry Et$_2$O (1 ml) and EtMgCl (2M sol. in Et$_2$O, 144 μl, 289 μmol) is stirred for 90 min at r.t. One drop of saturated NH$_4$Cl solution is then added. Filtration on silicagel, rincing with pentane:EtOAc (6:4), solvent concentration and HPLC (pentane:EtOAc 6:4) purification gives 11.18 (7.8 mg, 75%).

Rf: 0.20 (pentane:EtOAc 8:2).

IR (CH$_2$Cl$_2$): 3349 (s, broad); 2966 (s); 2936 (m); 2874 (m); 1457 (m); 1388 (m); 1374 (m); 1264 (w); 1094 (m); 1034 (m); 973 (w); 946 (w); 878 (w) cm$^{-1}$.

$^1$H NMR: (360 MHz, CDCl$_3$): δ: 3.72 (1H, dd, J=5.41, 0.1); 3.51 (1H, dd, J=8.7); 2.09 (1H, dddd, J=9.6); 1.90 (1H, dddd, J=13); 1.46 (4H, q, J=7.4); 1.65–1.15 (11H, m); 0.90 (3H, s); 0.86 (6H, t); 0.84 (3H, s); 0.69 (3H, s) ppm.

EXAMPLE 60

Synthesis of 11.17

From 11.16 and MeMgBr as described for 11.18 (yield 86%)

Rf: 0.37 (pentane:EtOAc 5:5).

IR (CH$_2$Cl$_2$): 3354 (s, broad); 2937 (s); 2868 (m); 1466 (s); 1375 (s); 1204 (w); 1150 (w); 1090 (w); 1040 (m); 1008 (m); 905 (w) cm$^{-1}$.

$^1$H NMR: (500 MHz, CDCl$_3$): δ: 3.72 (1H, dd, J=5.15, 9.85); 3.51 (1H, dd, J=9.3); 2.08 (1H, m); 1.89 (1H, m); 1.53 (1H, m), 1.50–1.15 (10H, m); 1.21 (6H, s); 0.90 (3H, s); 0.85 (3H, s); 0.69 (3H, s) ppm.

EXAMPLE 61

Synthesis of 11.19

To a solution of 11.17 (12 mg, 47 μmol), N-methyl morfoline oxide (8.5 m g, 72 μmol) and activated molecular sieves (4 Å; 24 mg) in CH$_2$Cl$_2$ (400 μl) is added tetra-n-propyl ammonium perruthenate (0.8 mg, 2.35 μmol). After stirring for 2 h at r.t. the mixture is filtered on silicagel. The residue is washed with pentane:EtOAc 5:5. Solvent evaporation and HPLC (pentane:EtOAc 85:15) purification gives 11.19 (8;3 mg, 70%).

Rf: 0.38 (pentane:EtOAc 8:2).

IR (CH$_2$Cl$_2$): 3421 (s, broad); 2966 (s); 2862 (m); 2718 (w); 1713 (s); 1466 (s); 1377 (s); 1133 (w); 905 (w) cm$^{-1}$.

$^1$H NMR: (500 MHz, CDCl$_3$): δ: 9.76 (1H, d, J=2.3); 2.70 (1H); 2.04 (1H), 1.75–1.21 (1H, m); 1.21 (6H, s); 1.09 (3H, s); 0.87 (3H, s); 0.84 (3H, s) ppm.

EXAMPLE 62

Synthesis of 11.20

From 11.18 as described for 11.19 from 11.17 (yield 78%).

Rf: 0.15 (hexane:ethyl acetate 85:15).

IR (film): 3442 (s, broad); 2938 (s); 2871 (m); 2720 (w); 1717 (s); 1457 (s); 1377 (s); 1262 (m); 1092 (m); 1031 (s); 947 (w); 877 (w) cm$^{-1}$.

$^1$H NMR: (500 MHz, CDCl$_3$): δ: 9.76 (1H, d, J=2.2); 2.70 (1H, ddd); 2.06 (1H, m); 1.74–1.59 (2H, m); 1.51 (1H, m); 1.46 (4H, q, J=7.5); 1.41 (1H, m); 1.39–1.20 (1H, m); 1.09 (3H, s); 0.87 (3H, s); 0.86 (6H, t); 0.84 (3H, s) ppm.

EXAMPLE 63

Synthesis of 11.23

To a stirred solution of LDA (2.11 mmol) THF (2 ml) is added at −78° C., a solution of 11.22 (0.58 g, 1.85 mmol) in THF (0.4 ml) over a period of 10 minutes. The resulting solution is warmed up slowly to r.t. After stirring at r.t. for 2 h the reaction mixture is cooled to −78° C. and PhNTf$_2$ (0.71 g, 2.0 mmol) in THF (2.5 ml) is added dropwise. The solution is warmed up slowly to 0° C. and stirred overnight. Water is added extraction with pentane, drying (MgO$_4$) and solvent evaporation and purification by column chromatography (silicagel, hexane:EtOAc 10:1) gives 11.23 (0.47 g, 65%).

Rf: 0.30 (hexane:EtOAc 10:1).

IR (film): 3750; 2973; 1417; 1209; 114 cm$^{-1}$.

$^1$H NMR: (500 MHz, CDCl$_3$): δ: 5.60 (1H, dd, J=6.86, 3.50); 4.90 (1H, q, J=5.3); 3.54 (1H, m); 3.48 (1H, m); 2.5 (1H, m); 2.3 (2H, m); 2.0 (2H, m); 1.8 (1H, m); 1.5–1.4 (10H, m); 1.33 (3H, d, J=5.28); 1.21 (3H, s); 1.19 (3H, s); 1.18 (3H, t, J=7.05); 1.05 (1H, m); 0.94 (3H, d, J=6;52); 0.76 (3H, s) ppm.

EXAMPLE 64

Synthesis of 11.24

Through a solution of 11.23 (400 mg, 0.83 mmol) and solid NaHCO$_3$ (112 mg, 1.3 mmol) in MeOH (200 ml) is passed a stream of ozone (18 mmol/h), generated by a WELSBACH generator, at −78° C. over a period of 30 min while the solution turned to deep blue. The solution is then flushed with nitrogen until the solution became colourless. NaBH$_4$ (1.0 g, 26 mmol) is added to the mixture at −78° C., after 15 min, another portion (1.0 g, 26 mmol) is added. The mixture is allowed to warm up slowly to r.t. and is stirred for 18 h. Sodium borohydride (2.0 g, 52 mmol) is added at −20° C. and the reaction mixture is stirred for 2 h and then slowly warmed up to r.t. MeOH is evaporated and saturated NH$_4$Cl solution is added. Extraction with CH$_2$Cl$_2$, drying (MgSO$_4$) and solvent evaporation gives 11.24 (300 mg, 91%).

Rf: 0.23 (hexane:EtOAc 2:1).

IR (film): 3397, 2970; 2348; 1713; 1416; 1209; 114; 904 cm$^{-1}$.

$^1$H NMR: (500 MHz, CDCl$_3$): δ: 4.90 (1H, q, J=5.3); 3.65 (3H, s); 3.64 (2H, m); 3.54 (1H, m); 3.48 (1H, m); 2.70 (1H, t, J=9.36); 2.0 (1H, m); 1.80 (1H, m); 1.70 (2H, m); 1.5–1.4 (7H, m); 1.30 (6H, m); 1.20 (10H, m); 1.10 (1H, m); 1.0 (3H, t, J=6.43); 0.80 (3H, s) ppm.

EXAMPLE 65

Synthesis of 11.26

To a solution of 11.24 (90 mg, 0.2 mmol) is added a solution of TsCl (167 mg, 0.87 mmol) in pyridine (2.5 ml). The mixture is stirred at −4° C. for 18 hrs. An ammonium acetate solution is added, extraction with CH$_2$Cl$_2$, drying (MgSO$_4$) and solvent evaporation gives a crude oil which is used in the next reaction. To LiAlH$_4$ (160 mg, 4.2 mmol) in dry THF (5 ml), is added 11.25 (460 mg, 0.11 mmol) in dry THF (5 ml) at 0° C. The mixture is refluxed for 36 h, then 10% HCl solution is carefully added until neutralization. Solvent evaporation and HPLC purification (hexane:EtOAc 1:1) gives 11.26 (31 mg, 61%).

Rf: 0.29 (hexane:EtOAc 1:1).

IR (film): 3855; 2957 cm$^{-1}$.

$^1$H NMR: (500 MHz, CDCl$_3$): δ: 3.72 (1H, dd, J=10.20, 4.70); 3.41 (1H, dd, J=10.20, 9.07); 1.92 (1H, m); 1.70 (2H, m); 1.60 (1H, s br); 1.56 (1H, m); 1.5–1.3 (12H, m); 1.25 (1H, m); 1.20 (6H, s); 1.04 (1H, m); 0.95 (3H, d, J=6.71); 0.85 (3H, t, J=7.15); 0.67 (3H, s) ppm.

EXAMPLE 66

Synthesis of 11.27

To a mixture of 11.26 (30 mg, 100 µmol), N-methylmorfolin oxide (1.66 eq, 166 µmol, 19 mg) and molecular sieves (54 mg, type 4 Å, 2 à 3µ) in CH$_2$Cl$_2$ (1.5 ml), tetrapropylammonium perruthenate (5 µmol, 1.8 mg) is added. After stirring for 1 h the greyblack suspension is purified by direct column chromatography (Et$_2$O:hexane 1:4→1:1) yielding 11.27 (15 mg, 50%).

Rf: 0.33 (Et$_2$O:hexane 1:1).

$^1$H NMR: (500 MHz, CDCl$_3$): δ: 9.69 (1H, d, J=3.31); 2.58 (td, J=3.3, 9.1); 1.98 (1H, m); 1.87 (1H, m); 1.22 (6H, s); 0.96 (3H, d, J=6.68); 0.92 (3H, t, J=7.2); 0.87 (3H, s) ppm.

EXAMPLE 67

Synthesis of 12.2

A mixture of 12.1 (75 mg, 0.268 mmol) and sodium methoxide (catalytic amount) in super dry methanol (1.5 ml) is stirred for 24 hrs at r.t. under Ar. The mixture is then filtered through silicagel, the filtrate concentrated in vacuo and separated by HPLC (silicagel; hexane:ethyl acetate 75:25) to yield the cis fused ketone (55 mg, 73%) next to the trans isomer (18 mg).

The cis ketone (50 mg, 0.179 mmol) and 1-(trimethylsilyl)imidazole (104 µl, 0.716 mmol) in dichloromethane (1.8 ml) is stirred for 3 hrs at room temperature. After solvent removal in vacuo, diethylether is added and the resulting precipitate is filtered off on a short silica pad. Concentration of the filtrate yields 73 mg of a crude product which is purified on HPLC silicagel;hexane:ethyl acetate 95:5) to give the protected alcohol 12.2 (50 mg, 79%).

Rf: 0.58 (hexane:ethyl acetate 85:15).

IR (film): cm$^{-1}$.2958 (s), 1710 (s), 1464 (m), 1379 (m), 1320 (w), 1249 (s), 1156 (m) cm$^{-1}$.

$^1$H NMR: (500 MHz, CDCl$_3$): δ: 2.31 (3H, m), 2.15 (1H, m), 1.95–1.70 (5H, m), 1.57 (1H, m), 1.43–1.25 (8H, m), 1.18 (6(+1)H, s), 1.04 (3H, s), 0.91 (3H, d), 0.10 (9H, s) ppm.

EXAMPLE 68

Synthesis of 12.5

A suspension of NaH (956 mg; 23.9 mmol) in anhydrous dimethyl sulfoxide (30 ml) is stirred at 65° C., under nitrogen, for 1.5 h, after which 3-ethoxyethyl-3-methyl-1-butyn (3.68 g; 23.9 mmol) is slowly added. A solution of the 12.3 (1.77 g; 4.84 mmol) in dry dimethylsulfoxide (10 ml) is then added and stirring is continued for 0.5 h at r.t. The reaction mixture is poured into an ice cold saturated $NH_4Cl$ solution. The aquous phase is extracted with ether, and the combined extracts are washed with brine, dried ($MgSO_4$) and evaporated under reduced pressure. The residue is purified by column chromatography (silicagel; hexane:ethyl acetate 8:2) to give 12.4 (1.24 g; 67% yield) of the product. A mixture of this alcohol (560 mg; 1.6 mmol) and pyridinium dichromate (1.8 g; 4.8 mmol) in dichloromethane (10 ml) is stirred for 2 hrs at r.t. The resulting ketone is directly purified by column chromatography (hexane: ethyl acetate 8:2); 467 mg (84%) is obtained.

A solution of this ketone (369 mg; 1.06 mmol) and a catalytic amount of sodium methoxide in dry methanol (10 ml) is stirred under nitrogen at r.t. for 12 hrs. The reaction mixture is filtered on silicagel, using methanol as the eluent. Evaporation under reduced pressure gave a residue that was purified on a silicagel column (ethyl acetate:hexane 2:8). Pure 12.5 (149 mg; 65%) is obtained upon separation by HPLC (ethyl acetate:hexane 2:8).

Rf: 0.48 (hexane:ethyl acetate 8:2).

IR (film): 3398, 2979, 2934, 2875, 2291, 2226, 1708, 1464, 1443, 1378, 1360, 1334, 1253, 1160, 1124, 1081, 1053 $cm^{-1}$.

$^1$H NMR: (200 MHz, $CDCl_3$): δ: 1.18 (3H, t); 3.67 (1H, dq, J=9.11 7.05 Hz); 3.49 (1H, dq, J=9.11, 7.10 Hz); 5.68 (1H, q, 5.24 Hz); 1.32 (3H, d, 5.24 Hz); 1.49 (3H, s); 1.43 (3H, s); 2.23 (2H, m); 1.06 (3H, d, 6.48 Hz); 1.06 (3H, s); 2.44 (1H, m) ppm.

EXAMPLE 69

Synthesis of 12.6

A solution of 12.4 (1.035 g; 3.1 mmol) and p-toluene sulfonic acid (295 mg; 1.55 mmol) in toluene (50 ml) is stirred at 60° C. for 1 h. The reaction mixture is then poured in saturated $NaHCO_3$ solution, extracted with diethylether, washed and dried ($MgSO_4$). Column chromatography (silicagel, hexane-ethyl acetate 85:15) of the residue, obtained upon filtration and solvent evaporation gives 12.6 (567 mg, 70%).

Rf: 0.45 (hexane:ethyl acetate 8:2).

IR (film): 3426, 2932, 2868, 2223, 1615, 1457, 1372, 1165 $cm^{-1}$.

$^1$H NMR: (500 MHz, $CDCl_3$): δ: 5.14 (1H, s, J=28.78 Hz); 5.20 (1H, s); 1.88 (3H, s); 2.34 (1H, d, J=3.41 Hz); 2.38 (1H, d, $J_{c'd}$=3.45 Hz, $J_{cc'}$=16.76 Hz); 1.06 (3H, d, J=6.56 Hz); 0.93 (3H, s); 4.08 (1H, m) ppm.

EXAMPLE 70

Synthesis of 12.7

A mixture of 12.6 (300 mg; 1.15 mmol), 3-chloroperoxybenzoic acid (497 mg, 80%; 2.31 mmol and $Na_2HPO_4$ (163 mg; 1.15 mmol) in dry THF (30 ml) is stirred at 0° C. under nitrogen atmosphere. After 3 days stirring, the mixture is diluted with ethyl acetate:hexane (1:1), washed with 10% $Na_2SO_3$ solution, with saturated $Na_2CO_3$ solution and with brine and is dried ($MgSO_4$). Filtration and removal of the solvents under reduced pressure, and column chromatography (silicagel;ethyl acetate:hexane 2:8) gives the epoxide (90 mg; 66%).

A mixture of this product (50 mg; 0.181 mmol) and pyridinium dichromate (203 mg; 0.54 mmol) in dichloromethane (4 ml) is stirred for 2 h at r.t. The reaction mixture is purified by column chromatography (hexane:ethyl acetate 8:2) to give the trans fused ketone (36 mg; 69%).

A solution of the ketone (80 mg; 0.328 mmol) and 1,8-diazabicyclo [5.4.0]undec-7-ene (76 mg; 0.500 mmol) in dichloromethane (2 ml) is stirred at r.t. for 3 days. The reaction mixture is poured in saturated $NH_4Cl$ solution, extracted with diethylether washed with saturated $NaHCO_3$ and brine, and dried ($MgSO_4$). The residue, after filtration and removal of the solvents, is purified on HPLC (ethyl acetate:hexane 15:85) and affords 12.7 (8 mg, 27%) next to the trans fused isomer (30 mg).

Rf: 0.24 (ethyl acetate:hexane 15:85).

IR (film): 3410, 2952, 2239, 1712, 1460, 1379, 1139, 1307, 1271, 1232, 1152, 1068 $cm^{-1}$.

$^1$H NMR: (200 MHz, $CDCl_3$): δ: 1.52 (3H, s); 2.95 (1H, d, 4.47 Hz); 2.71 (1H, d, 5.65 Hz); 1.05 (3H, s); 1.05 (3H, d, 6.5 Hz) ppm.

EXAMPLE 71

Synthesis of 12.10

Ozonolysis of vitamin $D_2$ (2 g; 5.05 mmol) in dichloromethane:methanol 50 ml, (1:1) is carried out at −78° C. Subsequent work-up with dimethylsulfide (8 ml) at −78° C. for 30 min and evaporation of the solvent gives crude 12.8. It is dissolved in tetrahydrofuran (30 ml) and 5% HCl (10 ml) is added under stirring. Stirring is continued at 30° C., under nitrogen, for 36 hrs. Evaporation of the solvent, addition of diethylether, washing with saturatted $NaHCO_3$ solution, drying ($MgSO_4$) and concentration in vacuo affords a residue. Flash chromatography (silicagel; hexane-:ethyl acetate 8:2) gives white crystalline 12.9 together with the 20-S-isomer 736 mg, 70%; 2.5:1 ratio). This mixture (200 mg; 0.96 mmol) in methanol (25 ml) is treated with $NaBH_4$ (73 mg, 1.92 mmol) at r.t., under $N_2$, for 20 min. A HCl solution (10%, 8 ml) is added, after stirring for 10 min, the methanol is evaporated. Addition of diethylether, washing with saturated $NaHCO_3$, drying ($MgSO_4$) evaporation and separation of the C-20 epimers (HPLC; hexane:ethyl acetate:methanol; 100:100; 1.5) yields 12.10 (140 mg; 69%).

Rf: 0.45 (hexane:ethyl acetate:methanol 5:4:1).

IR (film): 2795, 2703, 1719, 1700, 1380 $cm^{-1}$.

$^1$H NMR: (360 MHz, $CDCl_3$): δ: 0.86 (3H, d, J=6.75 Hz) 0.89 (s) and 1.02 (s) (3H), 3.30–3.94 (3H, m) ppm.

EXAMPLE 72

Synthesis of 12.12

A solution of 12.10 (170 mg, 0.8 mmol) and TsCl (229 mg, 1.20 mmol) in dry pyridine (10 ml) is kept at 0° C. for 13 hrs. The mixture is then poured in ice-water, extraction, washing ($NaHCO_3$ sat. solution) drying ($MgSO_4$) solvent evaproation and flash chromatography (silicagel; hexane-:ethyl acetate 6:4) gives 12.11 (163 mg, 56%). Reaction of 12.11 (160 mg, 0.44 mmol) with the anion of 3-ethoxyethyl- 1-butyn (2.2 ml) as described for 12.4, in example 61, gives after work-up and flash chromatography (silicagel;hexane:ethyl acetate 8:2) 86 mg (56%) of the product. A mixture of this alcohol (56 mg, 0.16 mmol) and pyridinium dichromate (241 mg, 0.64 mmol) in dry dichloromethane (7 ml) is stirred at r.t., under $N_2$ for 1 h. Direct flash chromatography (silicagel; hexane:ethyl acetate 8:2) gives 12.12 (39 mg; 70%).

Rf: 0.21 (hexane:ethyl acetate 9:1).
IR (film): 2231, 1708 $cm^{-1}$.
$^1$H NMR: (500 MHz, $CDCl_3$): δ: 0.95 (d, J=6.56 Hz) and 0.96 (d, J=6.67 Hz) (3H), 1.03 (3H, s), 1.18 (3H, m), 1.31 (3H, d, J=5.31 Hz), 1.42 (3H, s), 1.478 (s) and 1.482 (s) (3H), 3.43–3.69 (2H, m), 5.08 (1H, m) ppm.

EXAMPLE 73
Synthesis of 12.13

From 12.10 and 3-(ethoxy)-ethoxy-ethyl-1-pentyne as described for 12.12.

Rf: 0.35 (hexane:EtOAc ~9:1).
IR (film): 2234; 1708 $cm^{-1}$.
$^1$H NMR: (500 MHz, $CDCl_3$): δ: 5.10 (1H, q, J 5.21); 3.68 (1H, m); 3.48 (1H, m); 1.31 (3H, d, J=5.21); 1.17 (3H, dd, J=7.03, 7.03); 1.04 (3H, s); 0.97 (3H, d, J=6.63); 0.94 (6H, m) ppm.

EXAMPLE 74
Synthesis of 12.14

A mixture of 12.12 (19 gm, 0.055 mmol), 5% Rh/$Al_2O_3$ (8 mg) and EtOAc (2.5 ml) is stirred at r.t. uner $H_2$ (atmospheric pressure) for 1 h. The mixture is filtered through a short silica gel column (hexane:EtOAc 7:3). HPLC purification (hexane:EtOAc 9:1) gives 12.14 (17 mg, 89%).

Rf: 0.50 (hexane:EtOAc 8:2).
IR (film): 1708 $cm^{-1}$.
$^1$H NMR: (500 MHz, $CDCl_3$): δ: 4.86 (1H, q, J=5.33); 3.50 (2H, m); 1.26 (3H, d, J=5.33); 1.19 (3H, s); 1.17 (3H, dd, J=6.90, 6.90); 1.17 (3H, s); 1.02 (3H, s); 0.82 (3H, d, J=6.67) ppm.

EXAMPLE 75
Synthesis of 12.15

To a solution of LDA (0.50 mmol) in dry THF (3.5 ml) at −78° C., under $N_2$, triethyl 4-phosphonocrotonate (90%, 124 μl, 0.50 mmol) is added dropwise. Stirring is continued at −78° C. for 30 min. A solution of 12.9 (88 mg, 0.42 mmol) in dry THF (1.5 ml) is added dropwise. The reaction is stirred at −78° C. for 2 h, and then allowed to come to r.t. over 1 h. The mixture is diluted with ether, washed with brine, dried ($MgSO_4$), and evaporated. HPLC purification (hexane:EtOAc 88:12) gives 12.15 (110 mg, 85%).

Rf: 0.41 (hexane:EtOAc 8:2).
IR (film): 1708, 1639, 1616, 1004 $cm^{-1}$.
$^1$H NMR: (500 MHz, $CDCl_3$): δ: 7.23 (1H, dd, J=15.39, 11.00); 6.12 (1H, dd, J=15.19, 10.99); 5.93 (1H, dd, J=15.19, 9.66); 5.80 (1H, d, J=15.39); 4.20 (2H, m); 1.29 (3H, dd, J=7.08, 7.08); 0.96 (3H, d, J=6.65); 1.01 (3H, s) ppm.

EXAMPLE 76
Synthesis of 12.14

A mixture of 12.13 (67 mg, 0.23 mmol), 5% Rh/$Al_2O_3$ (30 mg) and EtOAc (4 ml) is stirred under $H_2$ (atmospheric pressure) at r.t. for 1.5 h. The mixture is then filtered through a short silica gel column (hexane:EtOAc 1:1). HPLC purification (hexane:EtOAc 88:12) gives 12.14 (63 mg, 93%).

Rf: 0.49 (hexane:EtOAc 8:2).
IR (film): 1735, 1707 $cm^{-1}$.
$^1$H NMR: (500 MHz, $CDCl_3$): δ: 4.12 (2H, q, J=7.20 Hz); 1.25 (3H, t, J=7.20 Hz), 1.02 (3H, s); 0.82 (3H, d, J=6.65) ppm.

EXAMPLE 77
Synthesis of 12.15

The Horner-Wittig coupling of 12.14 (60 mg, 0.19 mmol) with 13.2 (162 mg, 0.28 mmol), using n-BuLi (1.6 M solution in hexane, 175 μl, 0.28 mmol) as base, is carried out as described for 10. Flash chromatography (hexane:EtOAc 1:1) and HPLC separation (hexane:EtOAc 18:1) gives (80 mg, 62%).

Rf: 0.64 (hexane:EtOAc 9:1).

EXAMPLE 78
Synthesis of 12.17

From 12.8 by Horner-Wittig reaction as described for 12.15 from 12.9 followed by NaOEt-EtOH induced epimerization at r.t. for 21 h (overall yield 48%).

Rf: 0.28 (n.pentane:acetone 94:6).
IR (film): 2957 (s); 1713 (s); 1641 (s); 1463 (m); 1137 (s) $cm^{-1}$.
$^1$H NMR: (500 MHz, $CDCl_3$): δ: 7.21 (1H, dd, J=10.8, 15.3); 6.10 (1H, dd, J=10.8. 15.1); 5.99 (1H, dd, J=8.8, 15.1); 5.77 (1H, d, J=15.3); 4.19 (2H, q, J=7.1); 2.32 (4H, m); 2.15(1H, m); 1.92 (1H, m); 1.84 (1H, m); 1.75 (3H, m); 1.60 (2H, m); 1.44 (1H, m); 1.35 (1H, m); 1.29 (3H, t, J=7.1); 1.05 (3H, d, J=6.5); 1.04 (3H, s) ppm.

EXAMPLE 79
Synthesis of 12.18

From 12.17 as described for 12.16 from 12.15 (yield: 88%).

Rf: 0.35 (n.pentane:acetone 96:4).
IR (film): 2954 (s); 1733 (s); 1713 (s); 1380 (s); 1159 (s); 1097 (s) $cm^{-1}$.
$^1$H NMR: (500 MHz, $CDCl_3$): δ: 4.12 (2H, q, J=7.1); 2.31 (5H, m); 2.15 (1H, m); 1.91 (3H, m); 1.75 (2H, m); 1.56 (3H, m); 1.43–1.24 (6H, m); 1.25 (3H, t, J=7.1); 1.19 (1H, m); 1.03 (3H, s); 0.89 (3H, d, J=6.6) ppm.

EXAMPLE 80
Synthesis of Analogue 1

As described for 11 starting from 13.1 and 10-hydroxy-10-methyldecanal.

Rf: 0.40 (dichloromethane:methanol 9:1).
IR (film): 3374 (s); 3025 (w); 2969 (s); 2929 (s); 2853 (s); 1634 (m); 1466 (w); 1432 (w); 1366 (w); 1306 (w); 1266 (w); 1218 (w); 1149 (w); 1054 (w); 975 (w); 958 (w); 907 (w); 800 (w); 737 (w) $cm^{-1}$.
$^1$ H NMR: (360 MHz, $CDCl_3$): δ: 6.37 (1H, dd, J=11, 15 Hz); 6.03 (1H, d, J=11 Hz); 5.71 (1H, dt, J=15 Hz); 5.31 (1H, d, J=7 Hz); 4.99 (1H, d); 4.42 (1H, t, J=5.5 Hz); 4.20 (1H, m); 2.58 (1H, dd, J=13 Hz); 2.54 (1H, dd, J=4 Hz°; 2.06 (2H, dd, J=7 Hz); 1.96 (2H, t, J=5.51 Hz); 1.85–1.65 (3H, m); 1.50–1.15 (18H, m).

EXAMPLE 81
Synthesis of the Analogue 2

From 1.8 d as described for 13.

Rf: 0.37 (dichloromethane:methanol 88:12).

IR (film): 3368; 1610; 1374; 1049 cm$^{-1}$.

$^1$H NMR: (500 MHz, CDCl$_3$): δ: 6.31 (1H, d, J=11.2); 6.06 (1H, d, J=11.2); 4.15 (1H, bs); 4.13–4.04 (2H, m); 2.75–2.64 (2H, m); 2.49 (1H, dd, J=13.1, 3.8); 2.40 (1H, m); 2.28 (1H, dd, J=13.8, 7.9); 2.21 (1H, dd, J=13.5, 7.1); 2.15–0.70 (22H, ); 1.21 (6H, s); 0.9 (3H, d, J=6.73) ppm.

EXAMPLE 82
Synthesis of the Analogue 3

From 1.11d as described for 11.

Rf: 0.32 (acetone:hexane 4:6).

IR (film) 3356; 1441; 1378; 1215; 1144 cm$^{-1}$.

$^1$H NMR: (500 MHz, CDCl$_3$): δ: 6.37 (1H, d, J=11.4); 6.18 (1H, d, J=11.4); 5.32 (1H, bs); 5.02 (1H, s); 4.43 (1H, m); 4.21 (1H, m); 2.87 (1H, dm, J=13.6); 2.61 (1H, dd, J=3.4 Hz, J=13.2 Hz); 2.30 (1H, dd, J=7.3, 13.2); 2.01–1.93 (2H, m); 1.25 (6H, s, 20% 20-epi); 1.21 (6H, s); 0.87 (3H, d, J=6.7); 0.76 (3H, d, J=6.6, 20% 20-epi) ppm.

EXAMPLE 83
Synthesis of the Analogue 4

To a solution of 13.1 (76 mg, 0.13 mmol) in THF (2 ml) was added dropwise n-butyllithium (52 μl, 0.13 mmol, 2.5M solution in hexane) at −78° C. under nitrogen atmosphere. The formed dark red solution was stirred for 1 hour at −78° C. after which a solution of 2.5 (25 mg, 0.065 mmol) in THF (1 ml) was added. The red solution was stirred at −78° C. for 1 hour and was then warmed up to room temperature. The reaction mixture was immediately filtered through a silica gel column (EtOAc:Hex 1:30) and the crude product (74 mg) was further purified by HPLC (EtOAc:Hex 1:200) yielding 45.0 mg (92%) of coupling product.

A solution of coupling product (45.0 mg, 0.06 mmol) and TBAF (1.27 ml, 1.27 mmol, 1M solution in THF) in THF (3 ml) was stirred at room temperature (25–30° C.) for 39 hours. The reaction mixture was immediately filtered through a silica gel column (MeOH:CH$_2$Cl$_2$ 1:20) and the crude product (59 mg) was separated by HPLC (MeOH:CH$_2$Cl$_2$ 1:16) to give 4 (19.1 mg, 78%). A product (8.3 mg), that was not identified, was also obtained.

Rf: 0.21 (dichloromethane:methanol 1:20).

IR (film): 3378 (s); 2954 (s); 1643 (w); 1453, 1383 (s); 1264 (s); 1142 (w); 1057 (s); 742 (s) cm$^{-1}$.

$^1$H NMR: (500 MHz, CDCl$_3$): δ: 6.32 (1H, d, J=11.2 Hz); 6.05 (1H, d, J=11.2 Hz); 5.32 (1H, m); 4.98 (1H, m); 4.45 (1H, m); 4.20 (1H, m); 3.30 (1H, m); 2.60 (1H, dd, J=3.9, 13.2 Hz); 2.42 (1H, m); 2.30 (1H, dd, J=7.4, 13.2 Hz); 2.24 (2H, m); 1.96 (2H, m); 1.79 (1H, d, J=13.1 Hz); 1.65 (6H, m); 1.47 (2H, m); 1.25 (1H, m); 0.90 (3H, d, J=6.6 Hz); 0.89 (6H, dd, J=6.8 Hz); 0.75 (3H, s); 0.74 (3H, d, J=7.2 Hz).

EXAMPLE 84
Synthesis of analogue 5 and Previtamin 56

To a solution of 13.1 (110 mg, 0.188 mmol) in THF (3 ml) was added dropwise n-butyllithium (76 μl, 0.188 mmol, 2.5M solution in hexane) at −78° C. under nitrogen atmosphere. The formed dark red solution was stirred for 1 hour at −78° C. after which a solution of the 2.7 (36 mg, 0.094 mmol) in THF (1 ml) was added. The red solution was stirred at −78° C. for 1 hour and was then slowly warmed up to room temperature. The reaction mixture was immediately filtered through a silica gel column (EtOAc:Hex 1:20) and the crude product (117 mg) was further purified by HPLC (EtOAc:Hex 1:200) yielding 66.0 mg (93%) of coupling product.

A solution of coupling product (65.0 mg, 0.087 mmol) and TBAF (2.61 ml, 2.61 mmol, 1M solution in THF) in THF (8 ml) was stirred at 30–40° C. for 40 hours. The reaction mixture was immediately filtered through a silica gel column (MeOH:CH$_2$Cl$_2$ 1:20) and the crude product (82 mg) was separated again by HPLC (MeOH:CH$_2$Cl$_2$ 1:20) to give 5 (23.3 mg, 66%) and 56 (4.2 mg, 12%).

5: Rf: 0.15 (dichloromethane:methanol 1:20).

IR (film): 3385 (s); 2956 (s); 1642 (w); 1450, 1383 (s); 1056, 909 (s); 734 (m) cm$^{-1}$.

$^1$H NMR: (500 MHz, CDCl$_3$): δ: 6.32 (1H, d, J=11.2 Hz); 6.06 (1H, d, J=11.2 Hz); 5.31 (1H, d, J=2.2 Hz); 4.99 (1H, d, J=2.2 Hz); 4.42 (1H, m); 4.21 (1H, m); 3.31 (1H, m); 2.60 (1H, dd, J=3.9, 13.2 Hz); 2.42 (1H, m); 2.29 (1H, dd, J=7.4, 13.1 Hz), 2.02 (4H, m); 1.80 (1H, d, J=13.0 Hz); 1.65 (5H, m); 1.45 (4H, m); 0.90 (3H, d, J=6.6 Hz); 0.89 (6H, dd, J=6.6 Hz); 0.75 (3H, s); 0.74 (3H, d, J=7.2 Hz).

56: Rf: 0.15 (dichloromethane:methanol 20:1).

IR (film): 3384 (s), 2956, 2863 (s), 1640 (w), 1453, 1383 (s), 1056, 908 (s) cm$^{-1}$.

$^1$H NMR: (500 MHz, CDCl$_3$): δ: 5.89 (1H, d, J=12.2 Hz); 5.68 (1H, d, J=13.0 Hz); 5.65 (1H, br s); 4.18 (1H, br s); 4.10 (1H, m); 3.33 (1H, m); 2.43 (1H, dd, J=4.5, 16.8 Hz); 2.10 (2H, m); 2.00 (2H, m); 1.72 (3H, s); 1.71 (2H, m); 1.60 (4H, m); 1.45 (3H, m); 1.33 (2H, m); 0.92 (3H, d, J=6.8 Hz); 0.90 (3H, d, J=6.6 Hz); 0.88 (3H, d, J=5.9 Hz); 0.80 (3H, s); 0.77 (3H, d, J=7.2 Hz).

MS (m/z): 404 (5), 387 (6), 386 (4), 229 (30), 211 (30), 95 (40).

EXAMPLE 85
Synthesis of 6

To a solution of 13.2 (57 mg, 0.099 mmol) in THF (2 ml) was added dropwise n-butyllithium (40 μl, 0.099 mmol, 2.48M solution in hexane) at −78° C. under nitrogen atmosphere. The formed dark red solution was stirred for 1 hour at −78° C. after which a solution of 2.7 (19 mg, 0.049 mmol) in THF (1.5 ml) was added. The red solution was stirred at −78° C. for 1 hour and was then slowly warmed up to room temperature. The reaction mixture was immediately filtered through a silica gel column (EtOAc:Hex 1:20) and the crude product 44 mg was further purified by HPLC (EtOAc:Hex 1:140) yielding 32.0 mg (88%) of coupling product.

A solution of coupling product (32.0 mg, 0.043 mmol) and TBAF (1.96 ml, 1.96 mmol, 1M solution in THF) in THF (4 ml) was stirred at 30–45° C. for 40 hours. The reaction mixture was immediately filtered through a silica gel column (MeOH:CH$_2$Cl$_2$ 1:20) and the crude product (17 mg) was separated again by HPLC (MeOH:CH$_2$Cl$_2$ 1:20) to give a 4/1 mixture of E- and Z-isomers (15.5 mg, 91%).

This mixture was separated again on a special HPLC column (RSiL CN, 10 micron; 5.0 ml/min; 5.0 mg/500 μl/shot) with eluent Hex:i.PrOH:CH$_3$C N 89:10:1 to give 13.2 mg of analogue 6 (E-isomer) and 2 mg of Z-isomer. The separation was not easy and both were separated several times.

IR (film): 3380 (s); 2957 (s); 1616 (w); 1452, 1381 (m); 1047 (s); 736 (m) cm$^{-1}$.

$^1$H NMR: (CDCl3): δ6.26 (1H, d, J=11.2); 5.94 (1H, d, J=11.2); 4.08 (2H, m); 3.33 (1H, m); 2.64 (1H, dd, J=3.8, 13.3); 2.48 (1H, dd, J=3.7, 13.3); 2.43 (1H, m); 2.29 (1H, dd, J=7.7, 13.4); 2.18 (1H, dd, J=6.7, 13.3); 2.07 (1H, d, J=13.0); 2.00 (1H, m); 1.88 (2H, m); 1.86 (1H, d, J=13.1); 0.93 (3H, d, J=6.3); 0.91 (3H, d, J=6.4); 0.89 (3H, d, J=6.5); 0.79 (3H, d, J=7.8); 0.87 (3H, s) ppm.

MS (m/z): 392 (M.$^+$, 5); 374 (8); 308 (10); 235 (50); 217 (40); 55 (100).

EXAMPLE 86
Synthesis of Analogue 7

As described for 11.

IR (film): 3380 (s); 2939 (s); 1625 (w); 1452, 1383 (m); 909 (m) cm$^{-1}$.

$^1$H NMR: (CDCl3): δ66.32 (1H, d, J=11.2); 6.04 (1H, d, J=11.2); 5.32 (1H, t, J=1.4); 4.99 (1H, m); 4.43 (1H, m); 4.22 (1H, m); 2.60 (1H, dd, J=3.9, 13.2); 2.43 (1H, dt, J=13.7, 5.1); 2.29 (1H, dd, J=7.4, 13.2);2.03 (1H, m); 2.02 (1H, d, J=13.1); 1.96 (2H, m); 1;80 (1H, d, J=13.0); 1.21 (6H, s); 0.89 (3H, d, J=6.8); 0.75 (3H, s); 0.73 (3H, d, J=6.3) ppm.

MS (m/z): 404 (M.$^+$, 1%).

EXAMPLE 87
Synthesis of Analogue 8

As described for 13.

UV: λ$_{max}$=249.5 nm.

IR (film): 3382 (s); 2935 (s); 1615 (w); 1454, 1380 (m); 1048 (m); 909, 734 (s) cm$^{-1}$.

$^1$H NMR: (CDCl3): δ6.26 (1H, d, J=11.2); 5.94 (1H, d, J=11.2); 4.09 (2H, m); 2.67 (1H, dd, J=3.8, 13.3); 2.49 (1H, dd, J=3.8, 13.3); 2.43 (1H, m); 2.29 (1H, dd, J=7.6, 13.3); 2.19 (1H, dd, J=6.7, 13.2); 2.04 (1H, d, J=13.0 Hz); 2.00 (1H, m); 1.90 (1H, m); 1.86 (1H, m); 1.84 (1H, d, J=13.0 Hz); 1.70 (1H, m); 1.56 (3H, m); 1.21 (6H, s); 0.89 (3H, d, J=6.9); 0.77 (3H, d, J=7.3); 0.76 (3H, s) ppm.

EXAMPLE 88
Synthesis of Analogue 9

As described for 11.

Rf: 0.30 (dichloromethane:methanol 1:20).

IR (film): 3386 (s); 2932, 2874 (s); 1640 (w); 1456, 1475 (s); 1141, 1053 (s); 816 (m) cm$^{-1}$.

$^1$H NMR: (500 MHz, CDCl$_3$): δ: 6.32 (1H, d, J=11.3 Hz); 6.10 (1H, d, J=11.3 Hz); 5.25 (1H, d, J=1.7 Hz); 5.05 (1H, d, J=2.2 Hz); 4.40 (1H, m); 4.24 (1H, m); 3.65 (2H, m); 3.46 (2H, m); 2.62 (1H, dd, J=4.1, 12.8 Hz); 2.47 (1H, m); 2.25 (1H, dd, J=10.8, 12.3 Hz); 2.12 (2H, m); 2.02 (1H, m); 1.80 (3H, m); 1.70 (3H, m); 1.55 (4H, m); 1.35 (2H, m); 1.23 (6H, s); 0.8 (3H, s).

EXAMPLE 89
Synthesis of Analogue 10

As described for 11. Both epimers could be separated by HPLC (silica:ethyl acetate:pentane 15:85) on the stage of the TBMBS ethers. The respective structures were proven bij NOE measurements.

Rf: 0.36 (dichloromethane:methanol 7:1).

10α: Rf: 0.20 dichloromethane:methanol 92:8).

IR (film): 3324, 2986, 2880, 1455, 1414, 1378, 1260, 1130 cm$^{-1}$.

$^1$H NMR: (MHz, CDCl3): δ: 6.45 (1H, dd, J=11, 15 Hz); 6.05 (1H, d, J=11 Hz); 5.71 (1H, dt, J=7.5 and 15 Hz); 5.30 (1H, m); 5.00 (1H, d, J=4.5 Hz); 4.98 (1H, m); 4.42 (1H, m); 4.21 (1H, m); 3.80 (1H, d, J=8.2 Hz); 3.50 (1H, d, J=8.2 Hz); 3.48 (1H, s); 2.58 (1H, dd, J=4, 13.2 Hz); 2.35 (2H, d, J=7.5 Hz); 2.28 (1H, dd, J=7.2,13.2 Hz); 1.95 (2H, t, J=5.5 Hz); 1.7–1.5 (4H, m); 1.48 (4H, q, J=7.5 Hz); 1.43 (2H m); 1.25 (3H, s); 0.85 (6H, t, J=7.5 Hz).

10β: $^1$H NMR: (500 MHz, CDCl3): δ: 6.46 (1H, dd, J=11, 15 Hz); 6.05 (1H, d, J=11 Hz); 5.69 (1H, dt, J=7.5,15 Hz); 5.31 (1H, t, J=1.5 Hz); 5.00 (1H, t, J=4.7 Hz); 4.98 (1H, m); 4.45 (1H, m); 4.21 (1H, m); 3.67 (1H, d, J=8 Hz); 3.62 (1H, d, J=8 Hz); 2.58 (1H, dd, J=3.4, 13.3 Hz); 2.40 (1H, dd, J=7.5, 14 Hz); 2.35 (1H, dd, J=7.5, 14 Hz); 2.28 (1H, dd, J=7, 13.3 Hz); 1.97 (2H, t, J=5.5 Hz); 1.75–1.55 (4H, m); 1.47 (4H, q, J=7.5 Hz); 1.43 (2H, m); 1.27 (3H, s); 0.85 (6H, t, J=7.5 Hz).

EXAMPLE 90
Synthesis of Analogue 11

To a solution of dry A-ring phosphine oxide 13.1 (87 mg, 150 μmol) in tetrahydrofuran (1.4 ml) is added a n.butyl-lithium solution (2.5 M in hexane, 57 μl, 142.5 μmol) at −78° C. After stirring, the resulting red suspension for 1 hour, a solution of 6.12 (12 mg, 47.2 μmol) in tetrahydrofuran (0.5 ml) is added dropwise. The reaction mixture is stirred for 1 hour at −78° C. and then the cooling bath is removed. Water is added slowly till the orange colour has completely disappeared and the tetrahydrofuran is removed. After addition of diethylether and saturated sodium bicarbonate, the aqueous layer is extracted several times with diethylether. The collected organic phases are filtered through silicagel, the filtrate concentrated in vacuo and the remaining oil purified by HPLC (pentane:ethyl acetate 8:2) to give 24 mg (82%) of the coupled product.

To a solution of this (24 mg, 38.8 μmol) in tetrahydrofuran (0.5 ml) is added a tetra (n.butyl)ammoniumfluoride solution (1 M in THF, 311 μl, 311 μmol) and the resulting mixture is stirred at room temperature under an argon atmosphere in the dark for 87 hours. After evaporation of the THF, the residue is purified on a silica column (dichloromethane:methanol 9:1) and HPLC (CH$_2$Cl$_2$:MeOH 94:6) to yield 15 mg (98%) of 11.

Rf: 0.16 (dichloromethane:methanol 9:1).

IR (film): 3354 (s); 2966 (s); 2936 (o); 2869 (m); 1635 (w); 1468 (m); 1377 (s); 1366 (s); 1265 (m); 1215 (m); 1152 (s); 1056 (s); 976 (m) cm$^{-1}$.

$^1$H NMR: (360 MHz, CDCl$_3$): δ: 6.36 (1H, dd, J=11 Hz, J=15 Hz); 6.15 (1H, d, J=11 Hz); 5.77 (1H, dt, J=15 Hz, J=7.5 Hz); 5.31 (1H, d, J<1); 5.00 (1H, d); 4.43 (1H, t, J=5.5); 4.21 (1H, m); 2.57 (1H, dd, J=13, 3.7 Hz); 2.27 (1H, dd, J=7); 2.10–1.71 (7H, m); 1.60–1.25 (10 H, m); 1.21 (6H, s); 0.82 (3H, s); 0.78 (3H, s); 0.66 (3H, s).

EXAMPLE 91
Synthesis of Analogue 12

As described for 11.

Rf: 0.25 (dichloromethane:methanol 95:5).

IR (film): 3374 (s, br); 2965 (s); 2938 (s); 2876 (m); 1631 (m); 1460 (m); 1057 (s); 976 (m); 935 (s); 909 (s) cm$^{-1}$.

$^1$H NMR: (200 MHz, CDCl$_3$): δ: 6.36 (1H, dd, J 10.7, 15 Hz); 6.05 (1H, d, J=10.7 Hz); 5.76 (1H, dt, J=15, 7.5 Hz);

5.31 (1H, d); 4.99 (1H, d); 4.43 (1H, t, J=5.6 Hz); 4.21 (1H, m); 2.58 (1H, dd, J=7, 13.2 Hz); 2.25 (1H, dd, J=3.7, 13.2 Hz); 2.06–2.00 (1H, m); 2.00–1.92 (2H, t); 1.84–1.54 (5H, m); 1.53–1.38 (6H, m); 1.38–1.00 (8H, m); 0.87 (6H, t); 0.83 (3H, s); 0.79 (3H, s); 0.66 (3H, s).

EXAMPLE 92

Synthesis of Analogue 13

To a solution of 13.2 (76 mg, 133 μmol) in tetrahydrofuran (1.3 ml) is added a n.butyllithium solution (2.5M in hexane, 51 μl, 127 μmol) at −75° C. After stirring the resulting red suspension during 1 h, a solution of 6.13 (13 mg, 46 μmol) in tetrahydrofuran (0.5 ml) is added dropwise. The reaction mixture is stirred for 1 h at −75° C. and subsequently the cooling bath is removed. After addition of ethyl acetate (2 ml) and saturated sodium bicarbonate (2 ml) the aqueous layer is extracted several times with ethyl acetate. The collected organic phases are filtered through silicagel, the filtrate concentrated in vacuo and the remaining oil purified by HPLC (pentane:ethyl acetate 95:5) to give 11 mg (38%) of the coupled product.

To a solution of this (11 mg, 17 μmol) in methanol (2.5 ml) and tetrahydrofuran (2.5 ml) is added Amberlyst-15 (1.6 9) and the resulting mixture is stirred at room temperature under argon in the dark for 9 h. The mixture is filtered through silicagel. The Amberlyst-15 is washed several times with methanol and filtered through silicagel. The filtrate is concentrated in vacuo and the remaining oil purified by HPLC (dichloromethane:methanol 95:5) to give 13 (6 mg, 86%).

Rf: 0.19 (dichloromethane:methanol 95:5).

UV: $\lambda_{max}$240,9 nm; ($\epsilon$=32.535,7).

IR (film): 3443 (s, br); 2913 (w), 1518 (m); 1433 (s); 1256 (w); 1087 (w), 1024 (w) cm$^{-1}$.

$^1$H NMR: (500 MHz, CDCl$_3$): δ: 6.26 (1H, dd, J=10.8, 14.9 Hz); 6.05 (1H, d, J=10.8 Hz); 5.72 (1H, dt, J=15, 7.7 Hz); 4.12–4.08 (2H, m); 2.54 (1H, dd, J=13.5, 3.9 Hz); 2.47 (1H, dd, J=13.1, 3.5 Hz); 2.3 (1H, dd, J=13.3, 7.6 Hz); 2.15 (1H, dd, J=13.3, 6.9 Hz); 2.1 (1H, dd, J=13.3, 7.1 Hz); 2.03 (1H, dd, J=13.6, 8.4 Hz); 1.8–1.9 (3H, m); 1.75 (1H, m); 1.64–1.5 (3H, m); 1.48–1.4 (4+2, q+m); 1.4–1 (7H, m); 0;87 (6H, t, J=7.4 Hz); 0.84 (3H, s); 0.79 (3H, s); 0.67 (3H, s).

EXAMPLE 93

Synthesis of Analogue 14

The coupling of 6.21α with 13.1 is carried out as described for 6.12. Cleavage of the silyl ether is however performed upon stirring a methanolic solution in the presence of Amberlyst 15 for 4 h at room temperature. After filtration the compound 14 is purified by HPLC (dichloromethane:methanol 95:5).

Rf: 0.40 (dichloromethane:methanol 9:1).

IR (film): 3386 (s); 2969 (s); 1641 (w); 1468 (m); 1366 (s); 1154 (m); 1058 (s); 978 (m) cm$^{-1}$.

$^1$H NMR: (500 MHz, CDCl$_3$): δ: 6.37 (1H, dd, J=10.8, 15.1 Hz); 6.04 (1H, d, J=10.8 Hz); 5.71 (1H, dt, J=15.1 Hz, J=7.5 Hz); 5.30 (1H, d, J<1); 4.98 (1H, d); 4.42 (1H, m); 4.21 (1H, m); 3.75 (1H, dt); 3.61–3.55 (2H, m); 2.56 (1H, dd, J=13.2, 3.9 Hz); 2.25 (1H, dd, J=7.3 Hz); 2.11–1.90 (4H, m); 1.81–1.30 (9H, m); 1.24 (6H, s); 0.89 (3H, s); 0.83 (3H, s); 0.81 (3H, s).

EXAMPLE 94

Synthesis of Analogue 15

As described for 14 starting from 6.22α.

Rf: 0.59 (dichloromethane:methanol 9:1).

IR (film): 3380 (s, br); 2964 (s); 1632 (w); 1462 (s); 1376 (s); 1262 (m); 1067 (s) cm$^{-1}$.

$^1$H NMR: (500 MHz, CDCl$_3$): δ: 6.37 (1H, dd, J=10.8, 15.1 Hz); 6.04 (1H, d); 5.71 (1H, dt, J=7.5 Hz); 5.30 (1H, d); 4.98 (1H, d); 4.42 (1H, m); 4.21 (1H, m); 3.71 (1H, m); 3.60–3.46 (2H, m); 2.57 (1H, dd, J=13.4, 3.7 Hz); 2.25 (1H, dd, J=7.4 Hz); 2.11–1.9 (4H, m); 1.73–1.65 (3H, m); 1.60–1.20 (10H, m); 0.89 (3H, s); 0.87 (6H, t); 0.83 (3H, s); 0.81 (3H, s).

EXAMPLE 95

Synthesis of Analogue 16

As described for 14 starting from 6.16.

Rf: 0.27 (dichloromethane:methanol 95:5).

IR (film): 3380 (s, br); 2966 (s); 1616 (w); 1551 (m); 1422 (s); 1278 (s); 1156 (m) cm$^{-1}$.

$^1$H NMR: (360 MHz, CDCl$_3$): δ: 6.35 (1H, dd, J=10.9, 15.2 Hz); 6.07 (1H, d, J=10.9 Hz); 5.76 (1H, dt); 5.31 (1H, d, J<1); 5.00 (1H, d); 4.44 (1H, t, J=5.8 Hz); 4.22 (1H, m); 2.57 (1H, dd, J=13.3, 3.6 Hz); 2.27 (1H, dd, J=6.8 Hz); 2.10–1.50 (11H, m); 1.45 (4H, q, J=7.5 Hz); 1.42–1.00 (7H, m); 0.86 (6H, t, J=7.5 Hz); 0.80 (3H, s); 0.78 (3H, s); 0.67 (3H, s).

EXAMPLE 96

Synthesis of Analogue 17

As described for 11.

Rf: 0.31 (dichloromethane:methanol 9:1).

IR (film): 3384 (s); 2968 (s); 1631 (m); 1467 (s); 1365 (s); 1265 (m); 1154 (m); 1090 (s); 1056 (s) cm$^{-1}$.

$^1$H NMR: (500 MHz, CDCl$_3$): δ: 6.35 (1H, dd, J=10.6, 15 Hz); 6.05 (1H, d, J=10.6); 5.73 (1H, dt, J=15, 7.5 Hz); 5.31 (1H, d); 4.99 (1H, d, J~1); 4.43 (1H, t, J=5.5 Hz); 4.22 (1H, m); 3.75 (1H, m); 3.55 (1H, m) 3.48 (1H, m); 2.57 (1H, dd); 2.27 (1H, dd); 2.00 (4H, m); 1.75 (2H, t, J=5.6 Hz); 1.83–1.20 (7H, m); 1.25 (6H, s); 0.88 (3H, s); 0.86 (3H, s); 0.83 (3H, s).

EXAMPLE 97

Synthesis of Analogue 18

As described for 14 starling from 6.22β.

Rf: 0.54 (dichloromethane:methanol 9:1).

IR (film): 3380 (s, br); 2964 (s); 2875 (s); 1632 (w); 1462 (s); 1364 (m); 266 (m); 1091 (s); 1065 (s) cm$^{-1}$.

$^1$H NMR: (500 MHz, CDCl$_3$): δ: 6.35 (1H, dd, J=10.7, 15.1 Hz); 6.05 (1H, d, J=10.7 Hz); 5.72 (1H, dt, J=7.5 Hz); 5.31 (1H, d); 4.99 (1H, d); 4.43 (1H, m); 4.22 (1H, m); 3.71 (1H, dt); 3.55–3.45 (2H, m); 2.57 (1H, dd, J=13.3, 3.7 Hz); 2.28 (1H, dd, J=7.0 Hz); 2.02–1.90 (4H, m); 1.72 (2H, t); 1.61–1.43 (11H, m); 0.87 (3H, s); 0.85 (3H, s); 0.84 (6H, t); 0.83 (3H, s).

EXAMPLE 98

Synthesis of the Analogue 19

To a solution of 6.27 (12 mg, 19 μmol) in THF (1 ml), at −5° C., a solution of MeMgBr (50 μl 3M in Et$_2$O, 8 eq) is added dropwise. After warming overnight to r.t. the mixture is poured in an ice-ammoniumchloride solution-ether mixture. The organic phase is dried (MgSO$_4$). Filtration, evaporation and column chromatography (diethyl ether:hexane 1:9→1:4) gives the bis silylated analogue (10 mg, 82%). TBAF deprotection as described for analogue 11 gives 19 (5 mg, 80%).

Rf: 0.27 (MeOH:CH$_2$Cl$_2$ 1:19).

$^1$H NMR: (500 MHz, CDCl$_3$): δ: 6.36 (1H, dd, J=10.8, 15.2); 6.05 (1H, 10.8); 5.76 (1H, dt, J=7.7, 15.1); 5.31 (1H, dd, J=1,2); 5.00 (1H, br s); 4.43 (1H, t, J 5.7); 4.22 (1H, m); 2.57 (1H, dd, J=3.8, 13.3); 2.26 (1H, dd, J=7.5, 13.3); 1.21 (6H, s); 0.82 (3H, s); 0.78 (3H, s); 0.66 (3H, s) ppm.

EXAMPLE 99

Synthesis of the Analogue 20

From 6.27 with EtMgBr as described for 19 (yield 50%).

Rf: 0.29 (MeOH:CH$_2$Cl$_2$ 1:19).

$^1$H NMR: (500 MHz, CDCl$_3$): δ: 6.36 (1H, dd, J=10.8, 15.1); 6.06 (1H, d=10.8); 5.76 (1H, dt, J=7.5, 15.1); 5.31 (1H, dd, J=1, 2); 5.00 (1H, br s); 4.43 (1H, t, J=5.5); 4.22 (1H, m); 2.57 (1H, dd, J=3.6, 13.2); 2.26 (1H, dd, J=7.2, 13.3); 1.46 (4H, q, 7.5); 0.86 (6H, t, J=7.5); 0.82 (3H, s); 0.78 (3H, s); 0.66 (3H, s) ppm.

EXAMPLE 100

Synthesis of 21

From 6.30 as described for 19 from 6.26 (yield 48%).

Rf: 0.16CH$_2$Cl$_2$: (MeOH 1:19).

$^1$H NMR: (500 MHz, CDCl$_3$): δ: 6.36 (1H, dd, J=10.8, 15.1); 6.06 (1H, d=10.8); 5.76 (1H, dt, J=7.5, 15.1); 5.31 (1H, dd, J=1, 2); 5.00 (1H, br s); 4.43 (1H, t, J=5.5); 4.22 (1H, m); 2.57 (1H, dd, J=3.6, 13.2); 2.26 (1H, dd, J=7.2, 13.3); 1.46 (4H, q, 7.5); 0.86 (6H, t, J=7.5); 0.82 (3H, s); 0.78 (3H, s); 0.66 (3H, s) ppm.

EXAMPLE 101

Synthesis of Analogue 22

As described for 11.

Rf: 0.30 (dichloromethane:methanol 1:20).

IR (film): 3389 (s); 2932 (s); 1632 (w); 1462, 1366 (m); 1089, 1057 (s); 736 (m) cm$^{-1}$.

$^1$H NMR: (500 MHz, CDCl$_3$): δ: 6.38 (1H, dd, J=10.7, 15.1 Hz); 6.04 (1H, d, J=10.7 Hz); 5.72 (1H, m); 5.30 (1H, s); 4.98 (1H, s); 4.41 (1H, m); 4.21 (1H, m); 3.73 (1H, m); 3.66 (1H, m); 3.38 (1H, m); 2.58 (1H, m); 2.27 (1H, m); 1.97 (4H, m); 1.73 (2H, m); 1.60 (4H, m); 1.40 (2H, m); 1.22 (6H, s); 0.87 (3H, s).

EXAMPLE 102

Synthesis of Analogue 23

As described for 11.

Rf: 0.21 (dichloromethane:methanol 1:17).

IR (film): 3384, 2932 (s); 1630 (w); 1455, 1365 (m); 1265, 1152 (m); 1089, 1054 (s); 909, 734 (s) cm$^{-1}$.

$^1$H NMR: (500 MHz, CDCl$_3$): δ: 6.38 (1H, m); 6.05 (1H, d, J=10.8 Hz); 5.70 (1H, m); 5.28 (1H, s); 4.95 (1H, s); 4.41 (1H, m); 4.21 (1H, m); 3.70 (2H, m); 3.41 (1H, m); 2.55 (1H, m); 2.25 (1H, m); 2.15 (2H, m); 2.00 (4H, m); 1.72 (4H, m); 1.60 (2H, m); 1.40 (2H, m); 1.21 (6H, s); 1.10 (2H, m); 0.89 (3H, s).

EXAMPLE 103

Synthesis of Analogue 24

As described for 11.

Rf: 0.29 (dichloromethane:methanol 1:20).

IR (film): 3421 (m); 2931 (s); 1637 (w); 1458, 1379 (m); 1085 (s); 911 (s); 935 (s) cm$^{-1}$.

$^1$H NMR: (500 MHz, CDCl$_3$): δ: 6.38 (1H, m); 6.04 (1H, d, J=10.8 Hz); 5.70 (1H, m); 5.30 (1H, m); 4.98 (1H, s); 4.40 (1H, m); 4.20 (1H, m); 3.58 (1H, m); 3.53 (1H, m); 3.43 (1H, m); 2.92 (1H, m); 2.55 (1H, m); 2.25 (1H, m); 2.08 (1H, m); 1.98 (4H, m); 1.80 (3H, m); 1.60 (1H, m); 1.40 (3H, m); 1.32 (3H, s); 1.28 (3H, s); 0.90 (3H, s).

EXAMPLE 104

Synthesis of Analogue 25

As described for 11.

Rf: 0.30 (dichloromethane:methanol 1:20).

IR (film): 3401 (s); 2924 (s); 1633 (w); 1453, 1374 (m); 1164, 1054 (s); 738 (s) cm$^{-1}$.

$^1$H NMR: (500 MHz, CDCl$_3$): δ: 6.39 (1H, m); 6.06 (1H, d, J=10.8 Hz); 5.70 (1H, m); 5.32 (1H, t, J=1.6 Hz); 5.00 (1H, m); 4.43 (1H, m); 4.21 (1H, m); 2.55 (1H, m); 2.25 (1H, m); 2.15 (1H, dd, J=8.2, 14.0 Hz); 2.00 (5H, m); 1.90 (2H, m); 1.60 (4H, m); 1.49 (6H, s); 1.40 (2H, m); 1.10 (1H, m); 0.87 (3H, s).

EXAMPLE 105

Synthesis of Analogue 26

As described for 11.

Rf: 0.36 (dichloromethane:methanol 7:1).

$^1$H NMR: (500 MHz, CDCl$_3$): δ: 6.39 (1H, dd, 10.8, 15.2 Hz); 6.04 (1H, d, 10.8 Hz); 5.68 (1H, dt, 7, 15 Hz); 5.31 (1H, dd, 1, 2 Hz); 4.99 (1H, d, 1 Hz); 4.43 (1H, m); 4.22 (1H, m); 3.72 (1H, ddd, 5, 7, 9.5 Hz); 3.66 (1H, ddd, 5, 7, 9.5 Hz); 3.27 (1H, dt, 4, 11 Hz); 2.57 (1H, dd, 3.7, 13.3 Hz); 2.27 (1H, dd, 7.0, 13.4 Hz); 1.24 (6H, s); 0.76 (3H, d, 7.02 Hz).

EXAMPLE 106

Synthesis of Analogue 27

As described for 11.

Rf: 0.23 (dichloromethane:methanol 9:1).

IR (film): 3382 (s); 2930 (s); 1632, 1445, 1359, 1261, 1153, 1091 cm$^{-1}$.

$^1$H NMR: (360 MHz, CDCl$_3$): δ: 6.37 (1H, dd, 10.8, 15.1 Hz); 6.03 (1H, d, 10.8 Hz); 5.66 (1H, dt, 7.5, 15.1 Hz); 5.30 (1H, br s); 4.98 (1H, br s); 4.43 (1H, m); 4.21 (1H, m); 3.87 (1H, ddd, 4.5, 7, 9 Hz); 3.53 (1H, ddd, 5, 7, 9 Hz); 2.90 (1H, m); 2.80 (1H, td, 4, 10 Hz); 2.57 (1H, dd, 3.6, 13.3 Hz); 2.31 (1H, m); 2.25 (1H, dd, 7.4, 13.3 Hz); 2.10 (1H, m); 1.24 (6H, s); 1.01 (3H, d, 6.03 Hz).

EXAMPLE 107

Synthesis of Analogue 28

As described for 11.

Rf: 0.26 (dichloromethane:methanol 9:1).

IR (film): 3384 (s); 2929 (s); 3026, 1631, 1443, 1363, 1261, 1218 cm$^{-1}$.

$^1$H NMR: (360 MHz, CDCl$_3$): δ: 6.35 (1H, dd, 10.8, 15.2 Hz); 6.02 (1H, d, 10.8 Hz); 5.67 (1H, dt, 7, 15 Hz); 5.29 (1H, d, 1 Hz), 4.97 (1H, d, 1 Hz), 4.42 (1H, m); 4.21 (1H, m); 3.84 (1H, ddd, 4, 7, 9 Hz); 3.49 (1H, ddd, 4, 7, 9 Hz); 3.36 (1H, W1/2, 8 Hz, m); 2.56 (1H, dd, 4,13 Hz); 2.25 (1H, dd, 7, 13 Hz); 2.19 (1H, m); 1.25 (6H, s); 0.98 (3H, d, 6.7 Hz).

EXAMPLE 108

Synthesis of Analogue 29

As described for 11.

Rf: 0.38 (dichloromethane:methanol 9:1).

IR (film): 3357, 2926, 2857, 1366, 1056, 975, 908, 801, 734 cm$^{-1}$.

$^1$H NMR: (500 MHz, CDCl$_3$): δ: 6.34 (1H, dd, J=15.2, 11.0 Hz); 6.04 (1H, d, J=10.9 Hz); 5.67 (1H, ddd, J=15.1, 8.5, 6.0 Hz); 5.31 (1H, bs); 4.99 (1H, bs); 4.43 (1H, m); 4.21 (1H, m); 2.57 (1H, dd, J=13.2, 3.62 Hz); 2.36 (1H, dd, J=13.8, 5.8 Hz); 2.26 (1H, dd, J=13.4, 7.2 Hz); 1.95 (2H, m); 1.70–1.44 (12H, m); 1.42–1.36 (2H, m); 1.27–1.14 (2H, m); 1.20 (6H, s); 1.05–0.87 (2H, m); 0.23 (3H, s); 0.62 (3H, s).

EXAMPLE 109

Synthesis of Analogue 30

As described for 11.

Rf: 0.29 (dichloromethane:methanol 13:1).

IR (film): 3370 (s); 3082, 3045, 2964 (s), 1602, 1581, 1460, 1291 cm$^{-1}$.

$^1$H NMR: (500 MHz, CDCl$_3$): δ: 7.20 (1H, t, 7.96 Hz); 6.90 (1H, ddd, 0.8, 1.5, 8 Hz); 6.86 (1H, dd, 1.6, 2.2 Hz); 6.71 (1H, ddd, 0.7, 2.1, 8 Hz); 6.43 (1H, dd, 10.7, 15.5 Hz); 6.08 (1H, d, 10.7 Hz); 5.89 (1H, d, 15.5 Hz); 5.31 (1H, dd, 1.4, 1.8 Hz); 5.00 (1H, br s); 4.44 (1H, dd, 5, 7 Hz); 4.23 (1H, m); 3.96 (2H, t, 6.4 Hz); 2.57 (1H, dd, 3.73, 13.4 Hz); 2.28 (1H, dd, 6.9, 13.4 Hz); 1.978 (1H, dd, 5, 7 Hz); 1.962 (1H, ddd, 0.6, 4, 8 Hz); 1.50 (4H, q, 7.52 Hz); 1.39 (6H, S); 0.88 (6H, t, 7.52 Hz).

EXAMPLE 110

Synthesis of Analogue 31

After protection of the tertiary alcohol as trimethylsilyl ether the appendage of the nor A-ring is done as usual. After removal of the silyl ether protective groups (TBAF, THF) the mixture is purified by column chromatography (silica gel; dichloromethane:methanol 24:1) leading to a mixture of the E-analogue 31 and its Z-isomer at 7,8 (ratio 2:1).

Rf: 0.20 (CH$_3$OH:CH$_2$Cl$_2$ 1:19).

$^1$H NMR: E-isomer (CDCl$_3$): δ 6.25 (1H, d, J=11.2); 5.94 (1H, d, J=11.3); 4.10 (1H, m); 4.05 (1H, m); 2.81 (1H, m); 2.69 (1H, dd, J=3.8, 13.2); 2.25 (1H, dd, J=7.8, 13.3); 1.20 (6H, s); 0.67 (3H, s).

$^1$H NMR: Z-isomer (CDCl$_3$): δ6.22 (1H, d, J=11.1); 6.08 (1H, d, J=11.1); 4.10 (1H, m); 4.05 (1H, m); 2.39 (1H, dd, J=6.7, 13.4); 1.20 (6H, s); 0.67 (3H, s).

EXAMPLE 111

Synthesis of Analog 32

As described for 11. Obtained together with the 7-Z-isomer (1:1).

Rf: 0.43 (dichloromethane:methanol 94:6).

IR (film): 3356–2924; 1436; 1374, 1205; 1144; 1054 cm$^{-1}$.

$^1$H NMR: (500 MHz, CDCl$_3$): δ: 6.30–6.29 (1H, 2xd, J=11.35, 11.11); 6.17–6.14 (1H, 2xd, J=11.51–11.46); 5.48 (1H, m); 5.33 (1H, m); 5.00 (1H, dpp s); 4.43 (1H, m); 4.22 (1H, m); 3.94 (1H, m); 2.60 (1H, d m, J=13); 2.35–2.15 (4H, m); 2.50–2.36 (2H, m); 1.23 (6H, 2xs); 2.12–1.91 (5H, m); 1.88–1.79 (2H, m); 1.71–1.45 (7H, m) ppm.

EXAMPLE 112

Synthesis of Analogue 33

As described for 11. Obtained together with the 7-Z-isomer (6:4).

Rf: 0.31 (dichloromethane:methanol 94:6).

IR (film): 3367, 2936, 2865, 1433, 1363, 1308, 1217, 1152 cm$^{-1}$.

$^1$H NMR: (500 MHz, CDCl$_3$): δ: 6.25 (1H, 2xd, J=11.55, 11.65); 6.18 (1H, 2xd, J=11.37, 11.36); 5.32 (1H, b s); 4.99 (1H, b s); 4.43 (1H, m; 4.21 (1H, m); 3.99 (1H, ddd, J=7.2, 5.1, 5.1); 3.93 (1H, ddd, J=5.7, 4.9, 4.9); 3.85 (1H, m); 3.77 (1H, m); 2.60 (1H, dd, J=13.18, 3.79); 2;49 (1H, dd, J=6.0, 14.1); 2.45–1.23 (20H, m); 1.20 (6H, 2xs) ppm.

EXAMPLE 113

Synthesis of Analogue 34

As described for 11. Obtained together with the 7-Z-isomer (6:4).

Rf: 0.3 (dichloromethane:methanol 94:6).

IR (film): 3371, 2929, 2865, 1428, 1360, 1298, 1152, 1049, 974 cm$^{-1}$.

$^1$H NMR: (500 MHz, CDCl$_3$): δ: 6.18 (1H, 2xd, J=11.36, 11.46); 6.08 (1H, 2xd, J=11.35, 11.5); 5.65 (2H, m); 4.10 (2H, m); 4.05 (H, m); 3.95 (1H, m); 3.90 (1H, m); 3.83 (1H, m); 2.71 (1H, dd, J=13.25, 3.75); 2.59 (1H, dd, J=13.6, 3.6); 2.52–1.56 (17H, m); 1.31 (3H, s); 1.29 (3H, s); 1.21 (1H, m) ppm.

EXAMPLE 114

Synthesis of Analogue 35

As described for 11. Obtained together with the 7-Z-isomer (1:1).

Rf: 0.30 (dichloromethane:methanol 94:6).

$^1$H NMR: (500 MHz, CDCl$_3$): δ: 6.21 (1H, 2xd, J=9.32, 9.7); 6.08 (1H, 2xd, J=11.1, 11.71); 4.2–4.0 (4H, m); 2.62 (1H, d m, J=11.7); 2.49 (1H, dm, J=16.2) ppm.

EXAMPLE 115

Synthesis of Analogue 36

As described for 11. Obtained together with the 7-Z-isomer (1:1).

Rf: 0.26 (dichloromethane:methanol 94:6).

IR (film) 3390, 2925, 2855, 1458, 1361, 1172, 1051 cm$^{-1}$.

$^1$H NMR: (500 MHz, CDCl$_3$): δ: 6.28 (1H, 2xd, J=11.22, 11.38 Hz); 6.18 (1H, 2xd, J=11.95, 11.17 Hz); 5.33 (1H, appd, J=1.45 Hz); 5.0 (1H, m); 4.44 (1H, m); 4.21 (1H, m); 4.13 (1H, m); 4.04 (1H, m); 1.60 (1H, dm, J=12.80 Hz); 2.40 (5H, m); 2.20 (5H, m); 2.10 (4H, m); 1.92 (4H, m); 1.85 (12H, m); 1.40 (12H, m); 1.25 (6H, 2xs); 1.21 (6H, 2xs).

EXAMPLE 116

Synthesis of the Analogue 37

From 11.19 as described for analogue 11.

Rf: 0.48 (CH$_2$Cl$_2$:MeOH 9:1).

IR (CH$_2$Cl$_2$): 3343 (br, s); 2962 (s); 2861 (m); 1640 (w); 1558 (w); 1456 (s); 1375 (s); 1261 (m); 1057 (s) cm$^{-1}$.

$^1$H NMR: (500 MHz, CDCl$_3$): δ: 6.34 (1H, dd, J=10.8, 15.1); 6.08 (1H, d, J=10.8); 5.65 (1H, dd, J=15.1, 8.6); 5.32 (1H, d, J=1); 5.01 (1H, d);4.42 (1H, m); 4.21 (12H, m); 2.58 (1H, dd, J=13.1, 3.9); 2.47 (1H); 2.27 (1H, dd, J=7.6); 1.99 (1H, m); 1.95 (1H, m) 1.76 (1H, m); 1.60–1.20 (14H, m); 1.21 (6H, s); 0.84 (3H, s); 0.76 (3H, s); 0.67 (3H, s) ppm

EXAMPLE 117

Synthesis of the Analogue 38

From 11.20 as described for analogue 11.

Rf: 0.19 ($CH_2Cl_2$:MeOH 95:5).

IR ($CH_2Cl_2$): 3380 (s); 2960 (s); 2939 (s); 2872 (m); 1633 (m); 1454 (s); 1374 (s); 1253 (m); 1092 (s); 1054 (s) $cm^{-1}$.

$^1$H NMR: (500 MHz, $CDCl_3$): δ: 6.34 (1H, dd, J 10.8, 15.1); 6.08 (1H, d); 5.65 (1H, dd, J=8.5); 5.32 (1H, d, J=1); 5.01 (1H, d); 4.42 (1H, m); 4.22 (1H, m); 2.58 (1H, dd, J=13.2, 4.0); 2.47 (1H, dd); 2.27 (1H, dd, J=7.6); 2.23–1;90 (2H, m); 1.76 (1H, m); 1.60–1.50 (5H, m); 1.46 (4H, q, J=7.5); 1.50–1.38 (4H, m); 1.35–1.15 (5H, m); 0.86 (6H, t); 0.84 (3H, s); 0.76 (3H, s); 0.67 (3H, s) ppm.

EXAMPLE 118

Synthesis of the Analogue 39

From 11.21 as described for analogue 11.

Rf: 0.20 ($CH_2Cl_2$:MeOH 95:5).

IR ($CH_2Cl_2$): 3402 (s); 2967 (s) 2872 (m); 1634 (w); 1422 (m); 1373 (m); 1265 (s); 1138 (w) $cm^{-1}$.

$^1$H NMR: (500 MHz, $CDCl_3$): δ: 6.35 (1H, dd, J=10.8, 15.1); 6.21 (1H, dd, J=10.8, 15.5); 6.07 (1H, d); 5.96 (1H, dd, J=15.5); 5.75 (2H, 2×d); 5.63 (1H, dd, J=8.6); 5.31 (1H, d, J=<1); 5.01 (1H, d); 4.44 (1H, m); 4.22 (1H, m); 2.57 (1H, dd); 2.50 (1H, dd, J=8.9); 2.26 (1H, dd); 2.02–1.83 (4H, m); 1.55 (m); 1.45 (m); 1.34 (6H, s); 0.98 (3H, s); 0.77 (3H, s); 0.65 (3H, s) ppm.

EXAMPLE 119

Synthesis of the Analogue 40

From 11.27 as described for analogue 11. Also the 7,8-Z-isomer 40Z is formed (ratio 34:34' 4:1). They can be separated y column chromatography on silver nitrate impregnated silica gel (eluens MeOH:CH2Cl2 1:24→1:6).

40: Rf: 0.14 (MeOH:$CH_2Cl_2$ 1:14 on $AgNO_3$-silica gel).

$^1$H NMR: (500 MHz, $CDCl_3$): δ: 6.30 (1H, dd, J=10.8, 15.2); 6.08 (1H, d, J=10.8); 5.60 (1H, dd, J=8.8, 15.2); 5.30 (1H, br s); 4.98 (1H, d, J=1.8); 4.43 (1H, m); 4.20 (1H, m); 2.58 (1H, dd, J=4.0, 13.0); 2.3 (1H, q, J=9); 2.25 (1H, J=8.3, 13.0); 2.05 (1H, m); 1.88 (1H, ddd, J=3.8. 8.3, 13); 1.78 (1H, m); 1.21 (6H, s); 0.93 (2H, t, J=7); 0.94 (3H, d, J=7.0); 0.85 (3H, t, J=6.6); 0.65 (3H, s) ppm.

40Z: Rf: 0.10 (MeOH:$CH_2Cl_2$ 1:14 on $AgNO_3$-silica gel).

$^1$H NMR: (500 MHz, $CDCl_3$): δ: 6.35 (1H, t, J=11); 6.26 (1H, d, J=12.5); 5.33 (1H, dd, J=1, 2); 5.28 (1H, t, J=11); 5.01 (1H, br s);4.43 (1H, m); 4.22 (1H, m); 2.84 (1H, q, J=9); 2.59 (1H, dd, J=4.1, 13.2); 2.31 (1H, dd, J=6.9, 13.4); 1.97 (1H, ddd, J=4, 8, 1.2); 1.82 (1H, m); 1.22 (6H, s); 0.96 (3H, d, J=6.7); 0;94 (3H, t, J=7.3); 0.84 (2H, t, J=6.5); 0.70 (3H, s) ppm.

EXAMPLE 120

Synthesis of Analogue 41

As described for 11.

Rf: 0.37 (dichloromethane:methanol 9:1).

IR (film): 3376 (s, br), 2934 (s), 2242 (w), 1631 (w), 1461 (s), 1381 (m), 1056 (s), 958 (m), 911 (s) $cm^{-1}$.

$^1$H NMR: (360 MHz, $CDCl_3$): δ: 6.41–6.30 (1H, m); 6.10–6.00 (1H, m); 5.70–5.59 (1H, m); 5.31 (1H, d); 5.00 (1H, s, br); 4.44 (1H, m); 4.22 (1H, m);2.60–2.52 (1H, m); 2.30–2.00 (4H, m); 1.96 (2H, t); 1.90–1.10 (14H, m); 1.05 (6H, t); 0.95–0.80 (6H, m).

EXAMPLE 121

Synthesis of Analogue 42

As described for 11

Rf: 0.28 (dichloromethane:methanol 9:1).

IR (film): 3382 (s), 2925, 1660, 1455, 1261, 1055 $cm^{-1}$.

$^1$H NMR: (360 MHz, $CDCl_3$): δ: 7.12 (1H, dd, 11.2, 15.5 Hz); 6.30 (1H, d, 15.5 Hz); 6.19 (1H, d, 3.3 Hz); 6.18 (1H, d, 11 Hz); 6.17 (1H, d, 3.3 Hz); 6.06 (1H, dt, 1, 11 Hz); 5.50 (1H, ddd, 7, 8, 11 Hz); 5.27 (1H, d, 2 Hz); 5.05 (1H, d, 2 Hz); 4.42 (1H, m, W1/2 11 Hz); 4.25 (1H, m, W1/2 19 Hz); 2.91 (1H, m); 2.64 (1H, dm, 13 Hz); 2.44 (2H, m); 2.31 (1H, dd, 8.5, 13 Hz); 1.83 (1H, ddd, 4, 9, 13 Hz); 0.88 (3H, t, 7.5 Hz); 0.86 (3H, t, 8 Hz).

EXAMPLE 122

Synthesis of Analogue 43

As described for 13.

Rf: 0.39 (dichloromethane:methanol 9:1).

IR (film): 3377 (s, br), 2931 (s), 1610 (w), 1454 (s), 1376 (s), 1265 (s), 1214 (w), 1152 (w), 1049 (s), 976 (m) $cm^{-1}$.

$^1$H NMR: (500 MHz, $CDCl_3$): δ: 6.26 (1H, d, J=11.2); 6.04 (1H, d); 4.09 (2H, m); 2.69 (1H, dd, J=3.8, 13.3 Hz); 2.47 (2H, m); 2.29 (1H, dd, J=13.3, 7.8 Hz); 2.21–2.07 (3H, m); 1.91 (1H, m); 1.85 (2H, m); 1.73–1.30 (17H, m); 1.23 (6H, s); 1.05 (1H, m); 0.93 (3H, s); 0.88 (3H, d, J=6.6 Hz);

EXAMPLE 123

Synthesis of Analogue 44

As described for 13.

Rf: 0.062 (ethyl acetate:hexane 5:95).

IR (film): 3379, 2927, 2291, 3224, 1608, 1452, 1374, 1261, 1125, 1087.3, 1044 $cm^{-1}$.

$^1$H NMR: (360 MHz, $CDCl_3$): δ: 4.10 (2H, dddd); 6.25 (1H, d, J=11.3 Hz); 6.05 (1H, d, J=11.4 Hz); 0.95 (3H, s); 1.03 (3H, d, J=6.49 Hz); 1.50 (6H, s); 2.49 (1H, dd, J=13.4, 3.55 Hz); 2.69 (1H, dd, J=13.3, 3.83 Hz).

EXAMPLE 124

Synthesis of Analogue 45

As described for 13.

Rf: 0.24 (dichloromethane:methanol 4:96).

IR (film): 3422, 2976, 1642, 1451, 1267, 1088, 1048, 880 $cm^{-1}$.

$^1$H NMR: (500 MHz, $CDCl_3$): δ:: 1.53 (3H, s); 2.97 (1H, d, J=5.55 Hz); 2.73 (1H, d, J=5.54 Hz); 1.04 (3H, d, J=5.17 Hz); 0.95 (3H, s); 6.25 (1H, d, J=11.38 Hz); 6.04 (1H, d, J=11.30 Hz); 4.00 (2H, m).

EXAMPLE 125

Synthesis of Analogue 46

As described for 13.

Rf: 0.17 (dichloromethane:methanol 95:5).

IR (film): 3360, 3040, 2233, 1647, 1611, 811 $cm^{-1}$.

$^1$H NMR: (500 MHz, $CDCl_3$): δ: 0.93 (3H, s); 0.94 (3H, d, J=7.81 Hz); 1.49 (6H, s); 4.09 (2H, m); 6.04 (1H, d, J=11.11 Hz); 6.25 (1H, d, J=11.11 Hz).

EXAMPLE 126

Synthesis of the Analogue 47

From 12.14 as described for analogue 13.

Rf: 0.24 ($CH_2Cl_2$:MeOH 95:5).

UV (MEOH) $λ_{max}$=249 nm.

IR (film): 3360; 3036; 1649; 1610; 811 $cm^{-1}$.

¹H NMR: (500 MHz, CDCl₃): δ: 6.26 (1H, d, J=11.31); 6.03 (1H, d, J=11.31); 4.09 (2H₁ m); 1.21 (6H, s); 0.92 (3H, d) 0.84 (3H, d, J=6.61) ppm.
MS: m/z 386 (3); 353 (1; 303 (1); 45 (100).

EXAMPLE 127
Synthesis of the Analogue 48
From 12.13 as described for 13.
Rf: 0.31 (CH₂Cl₂:MeOH 95:5).
IR (film): 3361; 3036; 2236; 1612; 811 cm⁻¹.
¹H NMR: (500 MHz, CDCl₃): δ: 6.25 (1H, d, J=1t04); 6.04 (1H, d, J=11.04 Hz); 4.10 (2H, m); 1.02 (6H, t, J=7.37); 0.95 (3H, d, J=6.71); 0.93 (3H, s) ppm.

EXAMPLE 128
Synthesis of the Analogue 49
From 12.15 and 13.2 as described for 19 from 6.26.
Rf: 0.17 (CH₂Cl₂:MeOH 95:5).
IR (film): 3364; 3026; 1599; 990; 810 cm⁻¹.
¹H NMR: (500 MHz, CDCl₃): δ: 6.26 (1H, d, J=11.20); 6.16 (1H, dd, J=15.44, 0.30); 6.04 (1H, d, J=11.20 ); 5.95 (1H, dd, J=15.29, 10.30); 5.70 (1H, d, J=15.44); 5.58 (1H, dd, J=15.28, 8.22); 4.08 (2H, m); 1.34 (6H, s); 0.96 (3H, d, J=6.70); 0.93 (3H, s) ppm.

EXAMPLE 129
Synthesis of the Analogue 50
From 12.15 as described for 20 from 6.26.
Rf: 0.26 (CH₂Cl₂:MeOH ~95:5).
¹H NMR: (500 MHz, CDCl₃): δ: 6.26 (1H, d, J=11.16); 6.16 (1H, dd, J=15.46, 10.32); 6.04 (12H, d, J=11.16); 5.97 (1H, d,d J=15.24, 10.32); 5.57 (1H, dd, J=15.24, 8.07); 5.52 (1H, d, J=15.46); 4.09 (2H, m); 0.98 (3H, d, J=6.71); 0.94 (3H, s); 0.87 (6H, dd, J=7.44, 7.44) ppm.

EXAMPLE 130
Synthesis of the Analogue 51
From 12.16 as described for 19 from 6.26.
Rf: 0.17 (CH₂Cl₂:MeOH ~95:5).
IR (film): 3360; 3036; 1610; 811 cm⁻¹.
¹H NMR: (360 MHz, CDCl₃): δ: 6.26 (1H, d, J=11.09); 6.03 (1H, d, J=11.09); 4.08 (2H, m); 1.20 (6H, s); 0.92 (3H, s); 0.82 (3H, d, J=6.48) ppm.
MS: m/z 400 (29); 382 (10); 303 (4); 275 (11); 257 (12); 59 (100).

EXAMPLE 131
Synthesis of the Analogue 52
From 12.16 as described for 20 from 6.26.
Rf: 0.28 (CH₂Cl₂:MeOH ~95:5).
IR (film) 3364; 3037; 1611; 811 cm⁻¹.
¹H NMR: (360 MHz, CDCl₃): δ: 6.26 (1H, d, J=10.98); 6.03 (1H, d, J=10.98); 4.08 (2H, m); 1.45 (4H, q, J=7.40); 0.92 (3H, s); 0.85 (6H, t, J=7.40); 0.82 (3H, d, J=6.55) ppm.
MS: m/z428 (34); 381 (11); 299 (6); 45 (100).

EXAMPLE 132
Synthesis of the Analogue 53
From 12.17 as described for 19 from 6.26.
Rf: 0.20 (CH₂Cl₂:MeOH ~95:5).
IR (film): 3370 (s, br); 3051 (w); 2970 (m); 1607 (m); 1263 (s); 1095 (s) cm⁻¹.
¹H NMR: (500 MHz, CDCl₃): δ: 6.23 (2H, m); 5.99 (2H, m); 5.73 (1H, d, J=15.5): 5.65 (1H, dd, J=8.5, 15.35); 4.10 (1H, m); 4.06 (1H, m); 2.69 (1H, m); 2.48 (3H, m); 2.26 (1H, dd, J=5.0, 13.0); 2.15 (2H, m); 1.91 (1H, m); 1.83 (3H, m); 1.72 (1H, m); 1.62–1.44 (4H, m); 1.35 (6H, 2s); 1.25 (3H, m); 0.99 (3H, d, J=6.8); 0.94 (3H, s) ppm.

EXAMPLE 133
Synthesis of the Analogue 54
From 12.18 as described for 19 from 6.26.
Rf: 0.19 (CH₂Cl₂:MeOH ~95:5).
IR (CH₂Cl₂): 3372 (s); 2928 (s); 1620 (w); 1462 (m); 1374 (s); 1019 (s); 974 (m) cm⁻¹.
¹H NMR: (500 MHz, CDCl₃): δ: 6.26 (1H, d, J=11.3); 6.04 (1H, d. J=11.3); 4.09 (2H, m); 2.69 (1H, dd, J=3.8, 13.2); 2.47 (3H, m); 2.30 (1H, dd, J=7.7, 13.3); 2.19 (1H, dd, J=16.4, 13.2); 2.10 (1H, m); 1.90 (1H, m); 1.84 (2H, m); 1.70 (1H, m); 1.62–1.23 (19H, m); 1.22 (6H, s); 0.93 (3H, s); 0.87 (3H, d, J=6.6) ppm.
MS: m/z

EXAMPLE 134
Synthesis of the Analogue 55
From 12.18 as described for 20 from 6.26.
Rf: 0.19 (CH₂Cl₂:MeOH ~95:5).
IR (film): 3383 (s, br); 2927 (s); 161 0 (m); 1046 (s); 974 (m) cm⁻¹.
¹H NMR: (500 MHz, CDCl₃): δ: 6.26 (1H, d, J=11.2); 6.04 (1H, d, J=11.2); 2.46 (2H, m); 2.29 (1H, dd, J=7.7, 13.2); 2.19 (1H, dd, J=6.5, 13.3); 2.10 (2H, m); 1.91 (1H, m); 1.84 (2H, m); 1.70 (1H, m); 1.62–1.50 (6H, m); 1.47 (4H, q, J=7.5); 1.50–1.17 (13H, m); 0.92 (3H, s); 0.86 (6H, t, J=7.5); 0.86 (3H, d, J=6.5) ppm.

EXAMPLE 135
Synthesis of the Analogue 56
From 10.8 as described for 19 from 6.26.
Rf: 0.26 (hexane:acetone 6:4)
IR (film): 3388, 2927, 1634, 1464, 1367, 1058, 909, 734 cm⁻¹.
¹H NMR: (500 MHz, CDCl₃): δ: :6.31 (1H, dd, J=15.16, 10.81); 6.05 (1H, d, J=10.84); 5.65 (1H, dd, J=15.15, 8.97); 5.30 (1H, m); 4.99 (1H, m); 4.43 (1H, m); 4.22 (1H, m); 2.58 (1H, dd, J=13.32, 3.88); 2.16 (1H, dd, J=13.15, 7.11); 2.00 (1H, m); 1.94 (1H, m); 1.77–1.71 (3H, m); 1.54–1.24 (m); 1.21 (6H, s); 0.896 (3H, d, J=7.58); 0.889 (3H, s); 0.740 (3H, s) ppm.

EXAMPLE 136
Synthesis of the Analogue 57
From 10.9 as described for 19 from 6.26.
Rf: 0.26 (hexane:acetone 6:4)
IR (film): 3387, 2934, 2865, 1634, 1454, 1366, 1057, 736 cm⁻¹.
¹H NMR: (500 MHz, CDCl₃): δ: :6.34 (1H, dd, J=14.98, 10.65); 6.07 (1H, d, J=10.86); 6.05 (1H, dd, J=15.11, 9.62); 5.31 (1H, m); 4.99 (1H, m); 4.44 (1H, m); 4.23 (1H, m); 2.57 (1H, d, J=13.14, 3.78); 2.28 (1H, dd, J=13.18, 6.69); 1.97 (2H, m); 1.88 (1H, m); 1.78 (1H, m); 1.65 (1H, m); 1.53–1.24 (m); 1.21 (6H, s); 0.958 (3H, s); 0.906 (3H, d); 0.830 (3H, s) ppm.

EXAMPLE 137
Synthesis of 16.3
A suspension of (–)-quinic acid (16.1 47.5 g, 0.24 mol) and TsOH (200 mg) in toluene (400 ml) is refluxed and the H$_2$O formed is removed with a Dean-Stark apparatus. After 12 h, the mixture is filtered and dried (Na$_2$SO$_4$). Solvent evaporation gives crude 16.2 (42 g, 99%) which is used as such in the next step.

A mixture of 16.2 (1.1 g, 6.3 mmol), t-butyldimethylsilyl chloride (1.09 g, 7.24 mmol), DMAP (13 mg, 0.11 mmol) and imidazole (549 mg, 8.08 mmol) in DMF (5.8 ml) is stirred for 12 h at r.t. under nitrogen. The mixture is diluted with Et$_2$O, quenched with H$_2$O and extracted with Et$_2$O. The organic layer is washed with brine, dried (Na$_2$SO$_4$), filtered and concentrated. Column chromatography (silicagel; hexane:EtOAc 2:1) and HPLC separation (CH$_2$Cl$_2$:MeOH, 97:3) gives 16.3 (1.16 g, 66%). M.p. 94–96° C.

Rf: 0.29 (hexane:EtOAc 2:1).

IR (film): 3480, 3308, 1782, 1150, 1085 cm$^{-1}$.

$^1$H NMR: (500 MHz, CDCl$_3$): δ: 4.87 (1H, dd, J=4.9, 6.0); 3.97 (1H, dd, J=4.4, 4.9); 3.89 (1H, ddd, J=4.4, 7.0, 10.8); 2.97 (1H, s, D$_2$O exchangeable), 2.79 (1H, s, D$_2$O exchangeable); 2.62 (1H, d, J=11.6); 2.29 (1H, ddd, J=2.8, 6.0, 11.6); 2.02 (1H, ddd, J=2.8, 1.0, 12.1); 1.97 (1H, dd, J=10.8, 12.1); 0.91 (9H, s);0.10 (6H, s) ppm.

EXAMPLE 138
Synthesis of 16.5

A mixture of 16.3 (8.43 g, 29.2 mmol), 1,1-thiocarbonyidiimidazole (28.3 g, 0.154 mol) and DMAP (203 mg, 1.67 mmol) in dichloroethane (80 ml) is refluxed for 3 days. The solution is decanted and the residue is washed with warm CH$_2$Cl$_2$. Evaporation of the combined organic phases and chromatography (silicagel; hexane:EtOAc 1:4) gives 16.4 (12.9 g, 87%). Tributyltin hydride (0.42 ml, 1.58 mmol) is added dropwise to a solution of 16.4 (200 mg, 0.395 mmol) and AIBN (8 mg) in degassed dry toluene (5 ml). After reflux for 5 h, the solvent is evaporated. Column chromatography (silicagel; hexane:EtOAc 5:1) gives 16.5 (56 mg, 55%). M.p. 52–54° C.

Rf: 0.60 (hexane:EtOAc 2:1).

IR (film): 1777, 1259, 1124, 838, 776 cm$^{-1}$.

$^1$H NMR: (500 MHz, CDCl$_3$): δ: 4.84 (1H, dd, J=5.7, 5.0); 4.03 (1H, ddd, J=6.5, 6.4, 9.6, 9.6); 2.68 (1H, m); 2.41 (1H, ddddd, J=1.9, 2.0, 5.0, 6.5, 13.4); 2.35 (1H, dddd, J=1.9,2.0, 5.7; 11.5); 2.24 (1H, ddddd, J=2.0, 2.0, 4.9, 6.4, 12.7); 1.81 (1H, d, J=11.5); 1.58 (1H, m); 1.52 (1H, dd, J=9.6, 13.4); 0.88 (9H, s); 0.05 (6H, s) ppm.

EXAMPLE 139
Synthesis of 16.6

A 30% solution of NaOMe in dry MeOH (3.7 ml, 19.47 mmol) is added to 16.5 (2.49 g, 9.73 mmol) in dry MeOH (40 ml) at 0° C. under nitrogen. After stirring for 1 h at 0° C., saturated NH$_4$Cl solution (40 ml) is added and the solution is neutralized with 2 N HCl. The mixture is extracted with CH$_2$Cl$_2$, the combined organic layer is washed with brine, dried (MgSO$_4$). Filtration, solvent evaporation and filtration over a short pad of silicagel (hexane:EtOAc 2:1) gives pure 16.6 (2.8 9, 100%).

Rf: 0.28 (hexane:EtOAc 2:1).

IR (film): 3385, 1739, 1257, 1039, 837, 778 cm$^{-1}$.

$^1$H NMR: (500 MHz, CDCl$_3$): δ: 4.24 (1H, s); 4.04 (1H, m); 3.70 (3H, s); 2.85 (1H, dddd, J=3.67, 3.67, 11.95, 11.95); 2.22 (1H, m); 1.98 (1H, m); 1.85 (1H, m); 1.32–1.57 (3H, m); 0.90 (9H, s); 0.08 (6H, s) ppm.

EXAMPLE 140
Synthesis of 16.7

A mixture of 16.6 (2.77 g, 9.63 mmol), p-bromophenyl sulphonyl chloride (4.00 g, 15.6 mmol), DMAP (30 mg, 0.25 mmol) in anhydrous pyridine (4.6 ml) and chloroform (1.8 ml) is stirred for 1.5 h at 0° C., and 12 h at r.t. Water and ether is added. The mixture is extracted with ether. The combined organic phase is washed successively with 2% HCl solution, saturated NaHCO$_3$ solution and water and is dried (MgSO$_4$). Filtration, concentration and chromatography (silicagel; hexane:EtOAc 5:1) gives 16.7 (4.88 g, 100%).

M.p. 62–64° C.

Rf: 0.57 (hexane:EtOAc 2:1).

IR (film): 1737, 1577, 1369, 1188, 1049, 967, 822 cm$^{-1}$.

$^1$H NMR: (500 MHz, CDCl$_3$): δ: 7.73 (4H, m); 4.72 (1H, dddd, J=4.52, 4.52, 11.29, 11.29); 4.19 (1H, m); 3.69 (3H, s); 2.81 (1H, dddd, J=3.64, 3.64, 12.47, 12.47); 2.31 (1H, m); 1.86 (1H, m); 1.60 (1H, m); 1.43–1.52 (3H, m); 0.83 (9H, s); 0.02 (3H, s); –0.02 (3H, s) ppm.

EXAMPLE 141
Synthesis of 16.8

To a stirred solution of 16.7 (4.64 g, 9.15 mmol) in anhydrous t-BuOH (30 ml) is added dropwise a 1 M solution of t-BuOK in t-BuOh (10.6 ml, 10.6 mmol) at 50° C., under N$_2$. The resulting mixture is refluxed for 1 h. saturated NH$_4$Cl solution (20 ml), brine (10 ml) and water (5 ml) are added. The mixture is extracted with ether. The combined organic phase is dried (MgSO$_4$), filtered, and the solvent is evaporated below 18° C. Chromatography (silicagel; ether-:pentane 5:95) gives 16.8 (1.63 g, 71%).

Rf: 0.48 (hexane:EtOAc 5:1).

IR (film) 1727, 1371, 1256, 1114, 1097, 838 cm$^{-1}$.

$^1$H NMR: (500 MHz, CDCl$_3$): δ: 3.93 (1H, m); 3.66 (3H, s); 2.20 (1H, dd, J=7.2, 12.9); 2.14 (1H, dd, J=8.2, 12.9); 2.07 (1H, dd, J=7.1, 12.0); 1.81 (1H, m); 1.77 (1H, m); 1.29 (1H, dd, J=5.0, 8.5); 0.87 (9H, s); 0.67 (1H, dd, J=5.0, 5.0); 0.02 (6H, s).

MS: m/z 239 (10, 213 (100), 199 (9), 167 (35), 149 (39), 125 (20), 111 (18), 89 (96), 45 (98) ppm.

EXAMPLE 142
Synthesis of 16.9

To a stirred solution of 16.8 (570 mg, 2.11 mmol) in anhydrous toluene (25 ml) is added dropwise a solution of diisobutylaluminum hydride (5.28 ml, 5.28 mmol) 1 M in hexane at –78° C., under N$_2$. Stirring is continued for 2 h at –78° C. The reaction is quenched with a 2 N solution of potassium sodium tartrate (25 ml). The stirring is continued overnight while the temperature gradually came to r.t. The mixture is extracted with CH$_2$Cl$_2$, dried (MgSO$_4$) and evaporated. Chromatography (silicagel; hexane:EtOAc 4:1), purification gives 16.9 (500 mg, 98%).

Rf: 0.30 (hexane:EtOAc 4:1).

IR (film) 3328, 1256, 1115, 1094, 1032, 904, 775 cm$^{-1}$.

$^1$H NMR: (500 MHz, CDCl$_3$): δ: 4.03 (1H, m); 3.62 (1H, dd, J=5.1, 11.1); 3.51 (1H, dd, J=5.1, 11.1); 2.05 (1H, dd, J=6.4, 12.6 Hz); 1.92 (1H, dd, J=6.4, 12.6); 1.75–1.84 (2H, m); 1.18 (1H, ddd, J=4.2, 4.2, 8.4); 0.89 (9H, s); 0.51 (1H, dd, J=5.1, 8.4); 0.02 (6H, s); 0.38 (1H, dd, J=4.2, 4.2) ppm.

EXAMPLE 143

Synthesis of 16.10

To a stirred solution of 16.9 (480 mg, 1.98 mmol) in dichloromethane (20 ml) is added PCC (750 mg, 3.4 9 mmol) at r.t. under nitrogen. After 2 h stirring, the mixture is filtered over celite, which is washed with dichloromethane. The combined filtrate is washed successively with brine, $NaHCO_3$ solution and brine. Drying ($Na_2SO_4$), filtration and chromatography (silicagel, ether:pentane 1:9) gives 16.10 (430 mg, 90%).

Rf: 0.40 (hexane:EtOAc 9:1).

IR (film): 1706, 1256, 1121, 1072, 838, 778 $cm^{-1}$.

$^1$H NMR: (500 MHz, $CDCl_3$): δ: 8.90 (1H, s); 4.04 (1H, m); 2.17 (1H, ddd, J=1.1, 8.0, 13.0); 2.13 (1H, dd, J=7.2, 13.0); 2.10 (1H, dd, J=7.2, 13.0); 1.93 (1H, ddd, J=5.1, 5.3, 8.8); 1.80 (1H, ddd, J=5.1, 8.0, 13.0); 1.35 (1H, dd, J=5.6, 8.8); 0.97 (1H, dd, J=5.3, 5.6); 0.88 (9H, s);0.04 (6H, s) ppm.

EXAMPLE 144

Synthesis of 16.11

To a suspension of t-BuOK (352 mg, 3.14 mmol) in dry THF (2 ml) is added dropwise a solution of dimethyl diazomethyl phosphonate (219 mg, 1.45 mmol) in dry THF (2 ml) at −78° C., under nitrogen. After 10 min, a solution of 16.10 (290 mg, 1.21 mmol) in dry THF (2 ml) is added dropwise at −78° C. Stirring is continued, at −78° C. for 4 hrs, at −15° C. for 8 hrs, and at r.t. for 5 hrs. Water is added, followed by extraction with dichloromethane and drying ($MgSO_4$). Filtration, solent evaporation below 18° C. and chromatography (silicagel:pentane, then ether:pentane 1:9) gives 16.11 (254 mg, 89%) as a colorless oil.

Rf: 0.69 (hexane:EtOAc 9:1).

IR (film): 3467, 3315, 2113, 1111, 1095, 836, 776 $cm^{-1}$.

$^1$H NMR: (500 MHz, $CDCl_3$): δ: 3.84 (1H, m); 2.28 (1H, J=7.1, 12.5); 2.05 (1H, dd, J=7.1, 12.7); 1.92 (1H, s); 1.90 (1H, ddd, J=1.0, 8.3, 12.5); 1.83 (1H, ddd, J=4.9, 8.1, 12.7); 1.60 (1H, ddd, J=4.9, 4.9, 8.3); 0.88 (9H, s); 0.81 (1H, dd, J=4.9, 8.1 Hz); 0.55 (1H, dd, J=4.9, 4.9); 0.01 (6H, s) ppm.

EXAMPLE 145

Synthesis of 16.12

Sodium hexamethyldisilazide (1M in THF, 5.2 ml, 5.2 mmol) is added to (bromomethylene)triphenyl phosphonium bromide (2.35 g, 5.4 mmol) in dry THF (7 ml) at −68° C. After 1 h, a solution of 12.2b (357 mg, 0.91 mmol) in 2 ml of THF is added. After stirring for 1 h, the mixture is allowed to reach r.t. and is stirred overnight. Filtration through a short pad of celite, washing with hexane and concentration affords an oily residue which is chromatographed (silica gel, hexane) to provide (E)- and (Z)-16.12 (in 3:1 ratio) in a combined yield of 56% (237 mg).

Rf: 0.41 (hexane).

IR (film): 2955, 2874, 1622, 1462, 1380, 1235, 1043, 743 $cm^{-1}$.

$^1$H NMR: (500 MHz, $CDCl_3$): δ: 5.87 (1H, br s); 2.50 (1H, ddd, J=4.6, 4.8, 14.5); 2.22 (1H, dd, J=8.1, 9.7); 2.10 (1H, m); 1.86 (1H, m); 1.28 (3H, s); 1.20 (6H, s); 0.94 (9H, t, J=8.0); 0.87 (3H, d, J=5.5); 0.56 (6H, q, J=8.0) ppm.

MS m/z: 115 (17); 103 (89).

EXAMPLE 146

Synthesis of 16.15

To a stirred solution of 16.12 (51 mg, 0.11 mmol) in ether (0.6 ml) is added dropwise a solution of t-butyllithium (1.7 M in n-pentane, 0.16 ml, 0.27 mmol) at −78° C., under argon and stirring is continued for 50 min. Then a solution of 16.10 (12 mg, 0.05 mmol), in diethyl ether (0.2 ml) is dropwise added. The mixture is stirred 1 h at −78° C. and is quenched with saturated aqueous $NH_4Cl$ (2 ml) and extracted with $Et_2O$ and EtOAc. The combined organic phase is dried ($MgSO_4$), concentrated, filtered over a short silica gel pad (EtOAc:hexane 1:6) and purified by HPLC (silica gel; EtOAc:hexane 1:9) to give an epimeric mixture (in a ratio of 6:4) of (E)-16.15 (11 mg) and (Z)-16.15 (3.5 mg) in a combined yield of 46%.

Rf: 0.59 (EtOAc:hexane 1:6).

IR (film) 3394, 2954, 2876, 1465, 1390, 1383, 1092, 1043 $cm^{-1}$.

$^1$H NMR: (500 MHz, $CDCl_3$): δ: 5.14 (1H, 2×d, J=8.5, 8.7); 4.42 (1H, d, J=7.7, min); 4.23 (1H, d, J=8.5, maj.); 4.02 (1H, m); 1.20 (3H, s); 0.94 (12H, t, J=8.0, superposed with s); 0.87 (12H, s+d, superposed); 0.56 (6H, q, J=8.0); 0.28 (1H, dd, J=4.4, 4.6, min); 0.23 (1H, dd, J=4.4, 4.6 maj.); 0.02 (6H, 2×s); ppm.

EXAMPLE 147

Synthesis of 16.13

To a stirred solution of 16.11 (22 mg, 0.093 mmol) in dry THF (4 ml) at −50° C., n-butyllithium (1.6 M solution in n-hexane, 0.14 ml, 0.23 mmol), is added. After stirring for 1 h 12.2b (40 mg, 0.10 mmol) in dry THF (1 ml) is added. The temperature was allowed to reach r.t. and stirring was continued for 30 min. Quenching with water, extraction with $Et_2O$, usual work-up and HPLC purification (silica gel; EtOAc:hexane 1:20) provide 16.13 (22 mg, 55% based on the recovered 12.2, 15 mg) as a single diastereomer.

Rf: 0.52 (EtOAc:hexane 1:9).

IR (film): 3477, 2953, 2875, 2226, 1463, 1380, 1253, 1093 $cm^{-1}$.

$^1$H NMR: (500 MHz, $CDCl_3$): δ: 3.83 (1H, J=7.7, 7.8, 15.2); 2.23 (1H, dd, J=7.1, 12.5); 2.03 (1H, dd, J=7.1, 12.6); 1.20 (6H, s); 0.99 (3H, s); 0.94 (9H, t, J=8.0); 0.88 (3H, d, J=6.6); 0.85 (9H, s); 0.73 (1H, dd, 5.0, 8.3); 0.56 (6H, q, d=8.0); 0.52 (1H, dd, J=4.9, 4.9); 0.0 (6H, s) ppm.

EXAMPLE 148

Synthesis of 16.14

Alcohol 16.13 (18 mg, 29 μmol) is refluxed in THF (5 ml) in the presence of $LiAlH_4$ (4 mg) and sodium methoxide (4 mg). After 2 h, the mixture is cooled, quenched with saturated $NH_4Cl$ and extracted with $Et_2O$. Usual work-up followed by chromatographic purification (silica gel, EtOAc:hexane 1:25) gives 16.14 (9 mg, 50%).

Rf: 0.43 (EtOAc:hexane 1:9).

IR (film) 3508, 2930, 2872, 2463, 1380, 1256, 1093, 837 $cm^{-1}$.

$^1$H NMR: (500 MHz, $CDCl_3$): δ: 5.34 (2H, s); 3.95 (1H, m); 2.06 (2H, m); 1.27 (3H, s); 1.19 (6H, s); 0.94 (9H, t, J=8.0); 0.93 (3H, d, J=6.0); 0.87 (9H, s); 0.55 (6H, q, J=8.0); 0.07 (1H, dd, J=3.2, 3.4); 0.02 (6H, 2×s) ppm.

EXAMPLE 149

Synthesis of Analogue 43 a) From 16.15:

A mixture of (E)-16.15 (10 mg, 0.016 mmol), PTSA (0.9 mg), water (0.4 ml) and 1,4-dioxane (1;5 ml) is stirred for 6 h at 63° C. The mixture is treated with sat. NaHCO$_3$ (1.5 ml) and extracted with CH$_2$Cl$_2$. The combined organic phase is dried (MgSO$_4$), concentrated, filtered over a short silica gel column (acetone:hexane 4:6) and purified by HPLC (silica gel; MeOH:CH$_2$Cl$_2$ 5:95) giving 43 (5.0 mg, 78%).

b) From 16.14:

As described from 16.15; yield 40% next to the 7-Z-isomer (ratio 3:1).

What we claim is:

1. A compound of the formula I:

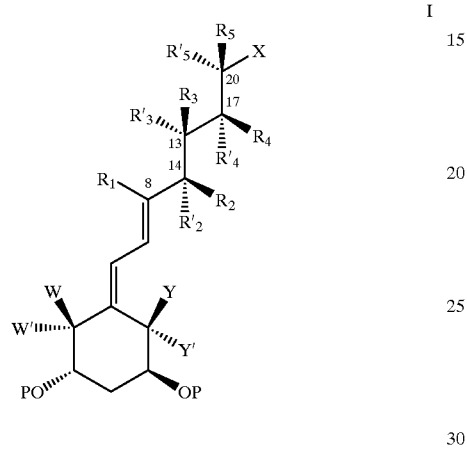

I in which

P is hydrogen or alkyl;

Y and Y' are each hydrogen or, when taken together, represent a group =CH$_2$;

W and W' are each hydrogen;

X is selected from the group consisting of a hydroxyalkyl, a hydroxyalkoxy, an alkoxy optionally comprising an epoxide function, a hydroxygen a hydroxyalkadiene, a hydroxyalkyne and isomeric forms thereof; and a) either $R_1$ and $R_3$ or $R'_3$ form a saturated 5- or 6-membered carbocyclic ring and $R_2$, $R'_2$, $R_3$ or $R'_3$, $R_4$, $R'_4$, $R_5$ and $R'_5$ are each Independently hydrogen or alkyl; or b) $R_2$ or $R'_2$ and $R_4$ or $R'_4$ form a saturated 5- or 6-membered carbocyclic ring, and $R_1$, $R_2$ or $R'_2$, $R_3$, $R'_3$, $R_4$ or $R'_4$, $R_5$ and $R'_5$ are each independently hydrogen or alkyl; or c) $R_3$ or $R'_3$ and $R_5$ or $R'_5$ form a saturated or unsaturated 5- or 6-membered carbocyclic ring, and $R_1$, $R_2$, $R'_2$, $R_3$ or $R'_3$, $R_4$, $R'_4$, and $R_5$ or $R'_5$ are each independently hydrogen or alkyl; or d) $R_3$ or $R'_3$ taken at the same time with $R_1$ and $R_5$ or $R'_5$ form a saturated 8- or 12-membered carbobicyclic ring, and $R_2$, $R'_2$, $R_3$ or $R'_3$, $R_4$, $R'_4$, and $R_5$ or $R'_5$ are each independently hydrogen or alkyl.

2. The compound according to claim 1, wherein

P is hydrogen;

Y and Y', taken together, form a =CH$_2$ group;

$R_1$, $R_2$, $R'_4$, $R_5$ and $R'_5$ are each hydrogen; and

X is a group hydroxyalkyne.

3. The compound according to claim 2, wherein X is a group —CH$_2$—C≡C—C(C$_2$H$_5$)$_2$(OH).

4. The compound according to claim 1, wherein $R_1$ and $R'_3$ taken together form a carbocyclic C-ring as shown in IIIa1 and IIIa2, respectively, or a diastereoisomer of IIIa1 and IIIa2:

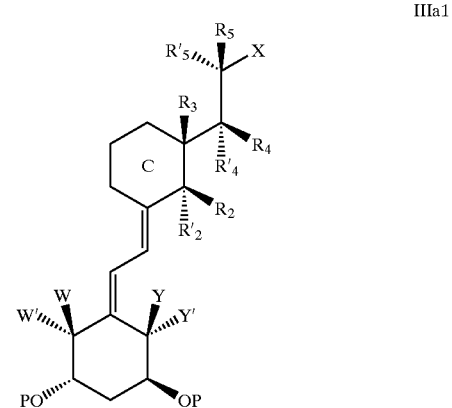

IIIa1

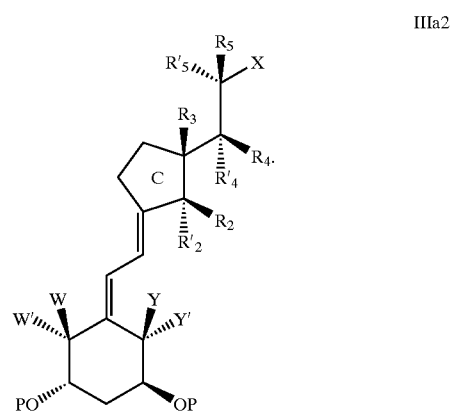

IIIa2 in which ring C may be saturated, unsaturated or substituted.

5. The compound according to claim 1, wherein $R_2$ and $R_4$ taken together form a carbocyclic D-ring as shown in IIIb1 and IIIb2, respectively, or a diastereoisomer of IIIb1 and IIIb2:

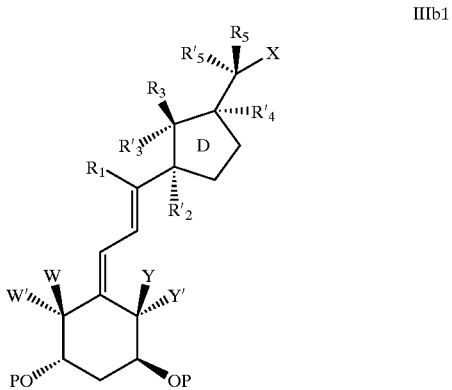

IIIb1

-continued

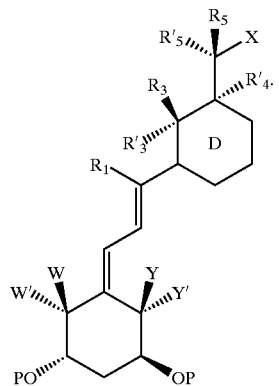

IIIb2 in which ring D may be saturated, unsaturated or substituted.

6. The compound according to claim 1, wherein R'$_3$ and R'$_5$ taken together form a carbocyclic E-ring as shown in IIIc1 and IIIc2, respectively, or a diastereoisomer of IIIc1 and IIIc2:

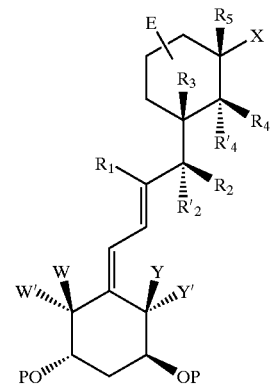

IIIc1

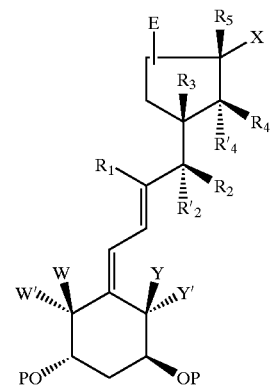

IIIc2 in which ring E may be saturated, unsaturated or substituted.

7. The compound according to claim 1, wherein R'$_3$ taken together at the same time with R$_1$ and R'$_5$ form a bicyclic CE-ring system as shown in IIIe1 and IIIe2, respectively, or a diastereoisomer of IIIe1 and IIIe2:

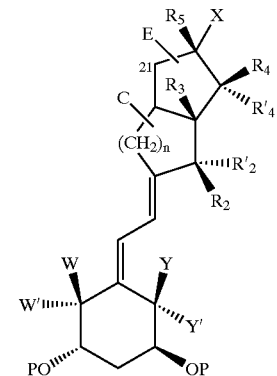

IIIe1

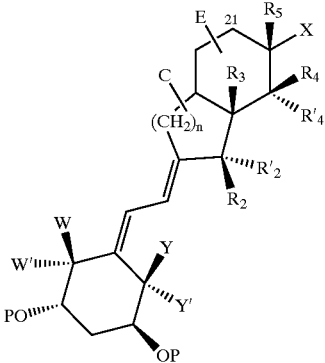

IIIe2 in which:

n is 1, 2, 3, or 4, and rings C and/or E is optionally saturated, unsaturated or substituted.

8. The compound according to claim 7, wherein X is hydrogen, lower alkyl, hydroxy or a functional group derived therefrom.

9. The compound according to claim 4, having one of the following structures:

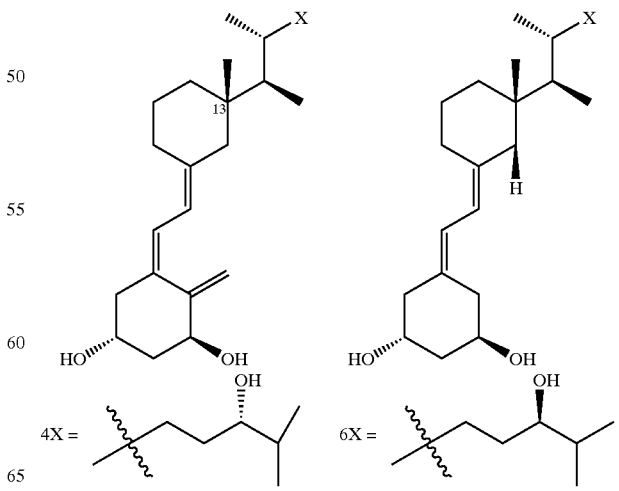

-continued

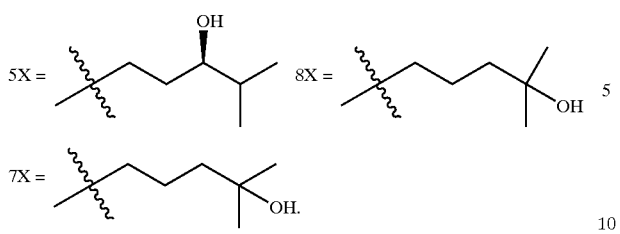

10. The compound according to claim 5, having one of the following structures:

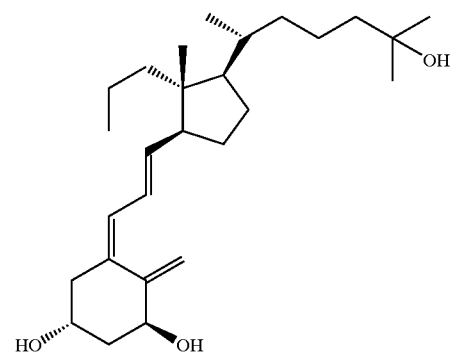

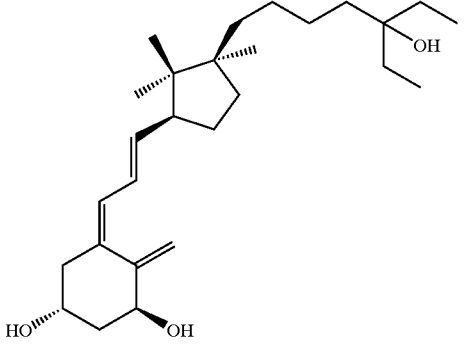

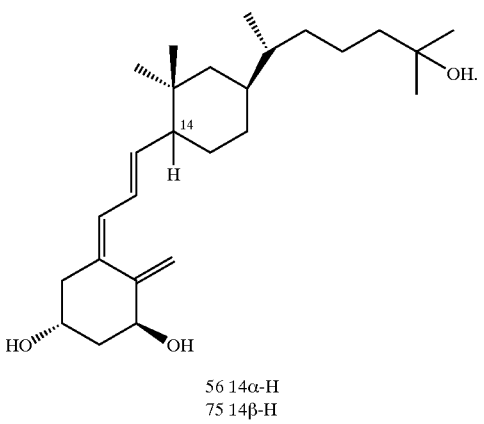

56 14α-H
75 14β-H

11. The compound according to claim 6, having one of the following structures:

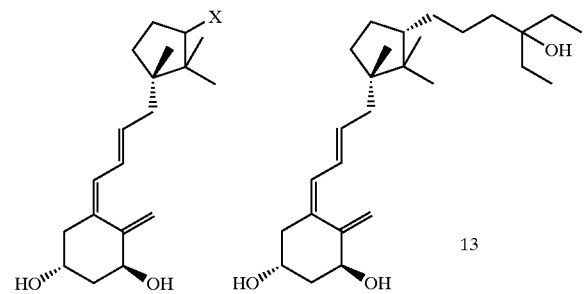

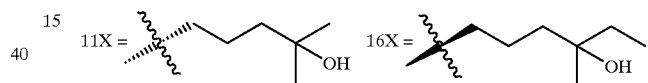

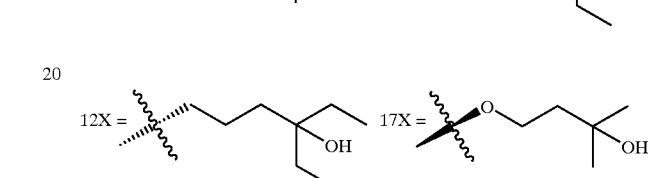

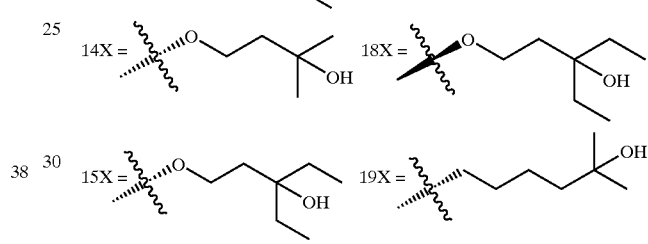

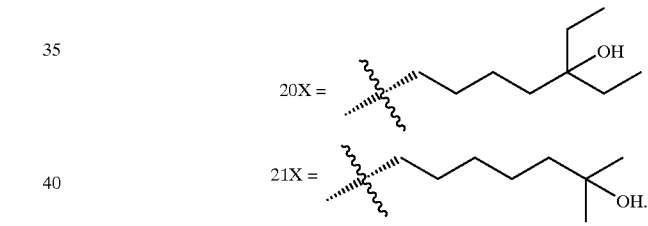

12. A pharmaceutical preparation comprising a therapeutically effective amount of a compound of claim 1 and a pharmaceutically and/or veterinarily acceptable carrier or diluent.

13. A pharmaceutical preparation comprising a therapeutically effective amount of a compound of claim 4, and a pharmaceutically and/or veterinarily acceptable carrier or diluent.

14. A pharmaceutical preparation comprising a therapeutically effective amount of a compound of claim 3 and a pharmaceutically and/or veterinarily acceptable carrier or diluent.

15. A pharmaceutical preparation comprising a therapeutically effective amount of a compound of claim 2 and a pharmaceutically and/or veterinarily acceptable carrier or diluent.

* * * * *